US008618356B2

(12) United States Patent
Doblin et al.

(10) Patent No.: US 8,618,356 B2
(45) Date of Patent: Dec. 31, 2013

(54) POLYSACCHARIDE SYNTHASES (H)

(76) Inventors: Monika Susanne Doblin, Moonee Ponds (AU); Filomena Angela Pettolino, Reservoir (AU); Antony Bacic, Eaglemont (AU); Stephen Alan Jobling, Nicholls (AU); Geoffrey Bruce Fincher, Hazelwood Park (AU); Rachel Anita Burton, Panorama (AU)

( * ) Notice: Subject to any disclaimer, the term of this patent is extended or adjusted under 35 U.S.C. 154(b) by 8 days.

(21) Appl. No.: 12/810,227

(22) PCT Filed: Dec. 24, 2008

(86) PCT No.: PCT/AU2008/001906
§ 371 (c)(1),
(2), (4) Date: Nov. 29, 2010

(87) PCT Pub. No.: WO2009/079714
PCT Pub. Date: Jul. 2, 2009

(65) Prior Publication Data
US 2011/0107467 A1 May 5, 2011

(30) Foreign Application Priority Data
Dec. 24, 2007 (AU) ................. 2007907071

(51) Int. Cl.
*A01H 5/00* (2006.01)
*A01H 15/00* (2006.01)
*C12N 15/82* (2006.01)
*C12N 15/80* (2006.01)
*C12N 1/14* (2006.01)
*C12N 1/00* (2006.01)

(52) U.S. Cl.
USPC .......... 800/284; 800/298; 435/468; 435/419; 435/471; 435/254.11

(58) Field of Classification Search
None
See application file for complete search history.

(56) References Cited

U.S. PATENT DOCUMENTS

| | | | |
|---|---|---|---|
| 2004/0123343 A1 | 6/2004 | La Rosa et al. | |
| 2006/0123505 A1 | 6/2006 | Kikuchi et al. | |
| 2006/0143729 A1* | 6/2006 | Alexandrov et al. | 800/278 |
| 2007/0016976 A1 | 1/2007 | Katagiri et al. | |

FOREIGN PATENT DOCUMENTS

| | | |
|---|---|---|
| EP | 0236124 B1 | 9/1987 |
| WO | WO 03000898 A1 | 1/2003 |
| WO | 2007/014433 A1 | 2/2007 |
| WO | WO2007/014433 * | 2/2007 |

OTHER PUBLICATIONS

Liepman et al (PNAS, Feb. 2005. (102)6 p. 2221-2226).*
Hazen et el (Plant Physiol. 128 (2), 336-340 (2002).*
Liepman et al (PNAS, 2005, 102(6) p. 2221-2226).*
Hunter et al (Plant Biology 2005, Meeting of the American Society of Plant Biologists, abstract 420, p. 177).*
Burton (Science, 2006 vol. 311 p. 1940-1942).*
NCBI Reference Sequence: XP_003543393.1.*
International Search Report for PCT/AU2008/001906, dated Jan. 30, 2009.
Hunter, C.T. et al., "Analyses of Mu-induced knockout mutations in cell wall biosynthetic genes of maize identified through reverse genetics", Plant Biology 2005, Meeting of the American Society of Plant Biologists, abstract 420, p. 177.
Hazen S.P. et al., "Cellulose synthase-like genes of rice", Plant Physiology, 2002, vol. 128, pp. 336-340. Table 1. See Also: Genbank accession No. AF435646, Oryza sativa CSLH1 mRNA, nucleic acid sequence, 2003. Genbank accession No. AAL38531, CSHL1 [Oryza sativa]; amino acid sequence, 2003.
Supplementary European Search Report issued in EP Patent Application No. 08864071.9, dated Mar. 14, 2011.
Liepman et al., "Expression of cellulose synthase-like (Cs1) genes in insect cells reveals that Cs1A family members encode mannan synthases," *PNAS USA*, 102(6):2221-2226 (2005).
Buckeridge et al., "The Mechanism of Synthesis of a Mixed-Linkage (1→3), (1→4) β-D-Glucan in Maize. Evidence for Multiple Sites of Glucosyl Transfer in the Synthase Complex," *Plant Physiology*, 120(4):1105-1116 (1999).
Urbanowicz et al., "Topology of the Maize Mixed Linkage (1→3), (1→4)-β-D-Glucan Synthase at the Golgi Membrane," *Plant Physiology*, 134:758-768 (2004).
Buckeridge et al., "Insight into multi-site mechanisms of glycosyl transfer in (1→4)β-D-glycans provided by the cereal mixed-linkage (1→3), (1→4)β-D-glucan synthase," *Phytochemistry*, 57(7):1045-1053 (2001).
Meikle et al., "The β-Glucan Synthase from *Lolium multiflorum*," *Journal of Biological Chemistry*, 266(33):22569-22581 (1991).
Gibeaut et al., "Synthesis of (1→3), (1→4)-β-D-glucan in the Golgi apparatus of maize coleoptiles," *PNAS USA*, 90:3850-3854 (1993).

* cited by examiner

*Primary Examiner* — Anne Kubelik
*Assistant Examiner* — Lee A Visone
(74) *Attorney, Agent, or Firm* — Heslin Rothenberg Farley & Mesiti P.C.; Andrew K. Gonsalves, Esq.

(57) ABSTRACT

The present invention relates generally to polysaccharide synthases. More particularly, the present invention relates to (1,3;1,4)-β-D-glucan synthases. The present invention provides, among other things, methods for influencing the level of (1,3;1,4)-β-D-glucan produced by a cell and nucleic acid and amino acid sequences which encode (1,3;1,4)-β-D-glucan synthases.

15 Claims, 34 Drawing Sheets

FIGURE 10

| DNA id. | | HvCslH1 | | OsCslH1 | | OsCslH2 | | OsCslH3 | |
|---|---|---|---|---|---|---|---|---|---|
| Prt id. | Prt sim. | | | | | | | | |
| HvCslH1 | | 100% | | | | | | | |
| | | | | | | | | | |
| OsCslH1 | | 74 | | 100% | | | | | |
| | | 69 | 83 | | | | | | |
| OsCslH2 | | 68 | | 72 | | 100% | | | |
| | | 62 | 76 | 65 | 78 | | | | |
| OsCslH3 | | 71 | | 76 | | 71 | | 100% | |
| | | 62 | 74 | 64 | 76 | 58 | 70 | | |

FIGURE 11

```
HvCslH1    -----MAGG------------------------KKLQERVALAR---TAWMLADFAILFL  28
OsCSLH3    -----MAAASGEKEEE----------------EKKLQERAPIRR---TAWMLANFVVLFL  36
OsCSLH1    -----MEAAARGN-------------------KKLQERVPIRR---TAWRLADLAILFL  32
OsCSLH2    MAVVAAAAATGSTTRSGGGGGEGTRSGRKKPPPPPLQERVPLGRRAAWAWRLAGLAVLLL  60
                    ..                         ****..: *     ** **.::.:*:*

HvCslH1    LLAIVARR--AASLRER---GGTWL-AALVCEAWFAFVWILNMNGKWSPVRFDTYPDNLA  82
OsCSLH3    LLALLVRRATAADAEERGVGGAAWR-VAFACEAWFAFVWLLNMNNAKWSPARFDTYPENLA  95
OsCSLH1    LLALLLHR----VLHDS---GAPWRRAALACEAWFTFMWLLNVNAKWSPVRFDTFPENLA  85
OsCSLH2    LLALLALRLLRHHGGAGG-DAGVWR-VALVCEAWFAALCALNVSAKWSPVRFVTRPENLV  118
           ***::   *           ..  *  .*:.*****:  :  **:..****.** * *:**.

HvCslH1    NR------------------------MEELPAVDMFVTTADPALEPPLITVNTVLSLL  116
OsCSLH3    GRCGAAHRPRKSSCISGHLDLMRRQCALMQDRRAAGGRHVRDDGGPGARAAGGDGEQGAL  155
OsCSLH1    ER------------------------IDELPAVDMFVTTADPVLEPPLVTVNTVLSLL  119
OsCSLH2    AEG---------------RTPSTTAAEYGELPAVDMLVTTADPALEPPLVTVNTVLSLL  162
                                       :  *..   . *    .       :   . *

HvCslH1    ALDYPDVG---------KLACYVSDDGCSPVTCYALREAAKFAGLWVPFCKRHDVAVRAP  167
OsCSLH3    AARRRLLPGRRRRRRRRRLACYVSDDGCSPVTYYALREAAGFARTWVPFCRRHGVAVRAP  215
OsCSLH1    ALDYPAAG--------EKLACYVSDDGCSPLTCYALREAARFARTWVPFCRRHGVAVRAP  171
OsCSLH2    ALDYPRAG--------ERLACYVSDDGCSPLTCHALREAAGFAAAWVPFCRRYGVAVRAP  214
            *               :*************:* :****** **  *****:*:.******

HvCslH1    FMYFSS--TPEVGTGTADHEFLESWALMKSEYERLASRIENADEGSIMRDSGDE-FAEFI  224
OsCSLH3    FRYFAS--APEFGP--ADRKFLDDWTFMKSEYDKLVRRIEDADETTLLRQGGGE-FAEFM  270
OsCSLH1    FRYFSS--TPEFGP--ADGKFLEDWTFMKSEYEKLVHRIEDADEPSLLRHGGGE-FAEFL  226
OsCSLH2    FRYFSSSSSPESGG-PADRKFLDDWTFMKDEYDKLVRRIKNTDERSLLRHGGGEFFAEFL  273
           * **:*  :** *   ** *  :**:.*::**.**::*. **:::** :::*...*.*  ****:

HvCslH1    DAERGNHPTIVKVLWDN-SKSKVGE--GFPHLVYLSREKSPRHRHNFQAGAMNVLTRVSA  281
OsCSLH3    DAKRTNHRAIVKVIWDNNSKNRIGEEGGFPHLIYVSREKSPGHHHHYKAGAMNALTRVSA  330
OsCSLH1    DVERGNHPTIIKVLWDN-NRSRTGD--GFPRLIYVSREKSPNLHHHYKAGAMNALTRVSA  283
OsCSLH2    NVERRNHPTIVK----------------------------------------TRVSA  290
           : .:*  ** **  :*:*                                        *****

HvCslH1    VMTNAPIMLNVDCDMFANNPQVALHAMCLLLGFDDEIHSGFVQVPQKFYGGLKDDPFGNQ  341
OsCSLH3    VMTNAPIMLNVDCDMFANDPQVVLHAMCLLLGFDDEISSGFVQVPQSFYGDLKDDPFGNK  390
OsCSLH1    LMTNAPFMLNLDCDMFVNNPRVVLHAMCLLLGFDDEISCAFVQTPQKFYGALKDDPFGNQ  343
OsCSLH2    VMTNAPIMLNMDCDMFVNNPQAVLHAMCLLLGFDDEASSGFVQAPQRFYDALKDDPFGNQ  350
           :*****:***:*****.*:*:..**************  .. ***.** **. ********:

HvCslH1    MQVITKKIGGGIAGIQGMFYGGTGCFHRRKVIYGMPPPDTVK--HETRGSPSYKELQVRF  399
OsCSLH3    LEVIYK---------GLFYGGTGCFHCRKAIYGIEPDSIVVGREGAAGSPSYKELQFKF  440
OsCSLH1    LEVSLMKVGRGIAGLQGIFYCGTGCFHRRKVIYGMRTG-----REGTTGYSSNKELHSKF  398
OsCSLH2    MECFFKRFISGVQGVQGAFYAGTGCFHRRKAVYGVPPNFNGAEREDTIGSSSYKELHTRF  410
           ::              * ** ****** **.:**:  .      .  : *  .* ***: :*

HvCslH1    GSSKVLIESSRNIISGDLLARPTVDVSSRIEMAKQVGDCNYEAGTCWGKEIGWVYGSMTE  459
OsCSLH3    ESSEELKESARYIISGDMSGEPIVDISSHIEVAKEVSSCNYESGTHWGLEVGWAYGSMTE  500
OsCSLH1    GSSNNFKESARDVIYGNLSTEPIVDISSCVDVAKEVAACNYEIGTCWGQEVGWVYGSLTE  458
OsCSLH2    GNSEELNESARNIIW-DLSSKPMVDISSRIEVAKAVSACNYDIGTCWGQEVGWVYGSLTE  469
            .*: : **:* :*    ::    .* **:**   :::**  *,  ***: ** ** *:**.****:**

HvCslH1    DILTGQRIHAAGWKSALLDTNPPAFLGCAPTGGPASLTQFKRWATGVLEILISRNSPILG  519
OsCSLH3    DILTGQRIHAAGWRSAKLETEPPAFLGCAPTGGPACLTQFKRWATGLFEILISQNNPLLL  560
OsCSLH1    DVLTGQRIHAAGWRSTLMEIEPPAFMGCAPNGGPACLTQLKRWASGFLEILISRNNPILT  518
OsCSLH2    DILTGQRIHAMGWRSVLMVTEPPAFMGSAPIGGPACLTQFKRWATGQSEIIISRNNPILA  529
           *:********  **:*.  :  :****:*.** ****.***:****:*  **:**:*.*:*

HvCslH1    TIFQRLQLRQCLGYLIVEAWPVRAPFELCYALLGPFCLLTNQSFLPTASDEGFRIPVALF  579
OsCSLH3    SIFKHLQFRQCLAYLTLYVWAVRGFVELCYELLVPYCLLTNQSFLSKASENCFNITLALF  620
OsCSLH1    TTFKSLQFRQCLAYLHSYVWPVRAPFELCYALLGPYCLSNQSFLPKTSEDGFYIALALF  578
OsCSLH2    TMFKRLKFRQCLAYLIVLGWPLRAPFELCYGLLGPYCILTNQSFLPKASEDGFSVPLALF  589
           : *: *::***.**  .    *:   .**** ** ** *:*:*:*****..:*:: *  :.:***
```

FIGURE 11 (Cont.)

```
HvCslH1     LSYHIYHLMEYKECGLSARAWWNNHRMQRITSASAWLLAFLTVILKTLGLSETVFEVTRK 639
OsCSLH3     LTYNTYNFVEYMECGLSVRAWWNNHRMQRIISASAWLLAFFTVLLKTIGLSETVFEVTRK 680
OsCSLH1     IAYNTYMFMEFIECGQSARACWNNHRMQRITSASAWLLAFLTVILKTLGFSETVFEVTRK 638
OsCSLH2     ISYNTYNFMEYMACGLSARAWWNNHRMQRIISVSAWTLAFLTVLLKSLGLSETVFEVTGK 649
            ::*:  *  ::*:   ** *.** ********  *.***  ***:**:**::********  *

HvCslH1     ESSTSDGGAGTDEADPGLFTFDSAPVFIPVTALSVLNIVALAVGAWRAVIGTAAVVHGGP 699
OsCSLH3     EKSTSDGNGQNDEVDPERFTFDASPVFIPVTALTMLNIVAITIGTWRAVFGTTEDVPGGP 740
OsCSLH1     DKSTSDGDSNTDEPEPGRFTFDESTVFIPVTALAMLSVIAIAVGAWRVVLVTTEGLPGGP 698
OsCSLH2     DKSMSDDDDNTDGADPGRFTFDSLPVFIPVTALAMLNIVAVTVGACRVAFGTAEGVPCAP 709
            :.* **..  .*  :*  ****  .********::*.::*:::*: *..: *:  :  .*

HvCslH1     GIGEFVCCGWMVLCFWPFVRGLVS-RGKHGIPWSVKVKAGLIVAAFVHLCTRN 751
OsCSLH3     GISEFMSCGWLLLCLLPFVRGLVG-KGSYGIPWSVKLKASLLVALFLFCSNRN 792
OsCSLH1     GISEFISCGWLVLCFMPLLRGLVG-SGRYGIPWSIKMKACLLVAIFLLFCKRN 750
OsCSLH2     GIGEFMCCGWLVLCFFPFVRGIVWGKGSYGIPWSVKLKASLLVAMFVTFCKRN 762
            **.**:.***:.***: *::**:*     *  :*****:*:** *:** *:   ..**
```

FIGURE 17

```
                   10        20        30        40        50        60        70        80        90
              ....|....|....|....|....|....|....|....|....|....|....|....|....|....|....|....|....|....|
HvCslH1       ------------------------------------------------------------------------------------------
HvCslH1Him    --GAGCTGTGTTCGTGGAGCCTAGCTAGTCTGCTACTGCTACTGCTGGCTAGTGGCTAC...----------------------........
HvCslH1g      ------------------------------------------------------------------------------------------
HvCslH1gHim   --GAGCTGTGTTCGTGGAGCCTAGCTAGTCTGCTACTGCTACTGCTGGCTAGTGGCTAC...----------------------........
TaCslH1-1     --------------------------------------------------------CTG---------------------CTCTCGGC
TaCslH1-2     ------------------------------------------------------------...,.-------------------.......
TaCslH1-3     GGAAATGCACCGAGCAGAGGTTAGTTTATCCGGTCTTTATAAATGCACTCTGTGGTGTTG..CTAGCTAGCTAGTCTGCTAC........

100       110       120       130       140       150       160       170       180
              ....|....|....|....|....|....|....|....|....|....|....|....|....|....|....|....|....|....|
HvCslH1       -------...............G........C......C................C......T....
HvCslH1Him    .A.....................G........C......C................C......T....
HvCslH1g      -------...............G........C......C................C......T....
HvCslH1gHim   .A....................C........G........................C......T....
TaCslH1-1     CGCGGCCATGGCGGGCGGCAAGAAGCTGCACGAGAGGGTCGCCCTGGGGAGAACTGCGTGGATGCTGGCCGACTTCGTGATCCTCCTCCT
TaCslH1-2     .A....................................G........C..G.GC..................T....
TaCslH1-3     ..............................G...................................................

190       200       210       220       230       240       250       260       270
              ....|....|....|....|....|....|....|....|....|....|....|....|....|....|....|....|....|....|
HvCslH1       ..........A...........C......C...............T...................................
HvCslH1Him    ..........A...........C......C...............T...................................
HvCslH1g      ..........A...........C......C...............T...................................
HvCslH1gHim   ..........A...........C......C...............T...................................
TaCslH1-1     CCTCCTCGCCCTCGTGGCCCGCCCCGCCGCGTCGCTCGGGGAGCGCGGCGGGACGTGGCTGGCCGCGCTCCTCTGCGAGGCGTGGTTCGC
TaCslH1-2     .C...........................................................A...................
TaCslH1-3     ..................................................................................

280       290       300       310       320       330       340       350       360
              ....|....|....|....|....|....|....|....|....|....|....|....|....|....|....|....|....|....|
HvCslH1       .....G................................................C......G..A....-------------
HvCslH1Him    .....G................................................C......G..A....-------------
HvCslH1g      .....G................................................C......G..A...........CT
HvCslH1gHim   .....G................................................C......G..A...........CT
TaCslH1-1     CTTCGCCTGGATCCTCAACATGAACGGCAAGTGGAGCCCCGTCCGGTTCGACACCTACCCCGAGAACCTCTCCCACAGGTACGTACGTTC
TaCslH1-2     .....G............................................................................
TaCslH1-3     ........................................................C.........................

370       380       390       400       410       420       430       440       450
              ....|....|....|....|....|....|....|....|....|....|....|....|....|....|....|....|....|....|
HvCslH1       ------------------------------------------------------------------------------------------
HvCslH1Him    ------------------------------------------------------------------------------------------
HvCslH1g      AC..A.GT..CC..G..G.C.AG.C-CCAC.A.G.T.ACC.C.A..A....C..AAATT..G.T.AGC.A..........A......
HvCslH1gHim   AC..A.GT..CC..G..G.C.AG.C-CCAC.A.G.T.ACC.C.A..A....C..AAATT..G.T.AGC.A..........A......
TaCslH1-1     TTGTGCACACTAACTGCAAAATAATGTTGACCTACAGCCTCGTTGCAGCTTCTTC----CTTAAACTGTGTCGTGTCTGTGATGATTTTGC
TaCslH1-2     ........................................A.......----......G...................
TaCslH1-3     ........................................A.......----...........................

460       470       480       490       500       510       520       530       540
              ....|....|....|....|....|....|....|....|....|....|....|....|....|....|....|....|....|....|
HvCslH1       ---.A...........................C.................T.............................
HvCslH1Him    ---.A...........................C.................T.............................
HvCslH1g      ....A...........................C.................T.............................
HvCslH1gHim   ....A...........................C.................T.............................
TaCslH1-1     TAGGCTGGAGGAGCTCCGGCGGGTGGACATGTTCCTCACGACGGGCGGACCCGCGCCTGGAGCCCCGCGTTGATCACGGTGAACACCGTGCT
TaCslH1-2     ....A....A.....................................................................
TaCslH1-3     ....A..........................................A..............................

550       560       570       580       590       600       610       620       630
              ....|....|....|....|....|....|....|....|....|....|....|....|....|....|....|....|....|....|
HvCslH1       ............................................T...................................
HvCslH1Him    ............................................T...................................
HvCslH1g      ............................................T...................................
HvCslH1gHim   ............................................T...................................
TaCslH1-1     CTCGCTGCTCGCCCTGGACTACCCGGACGTCGGCAAGCTGGCGTGCTACGTCTCCGACGACGGCTGCTCCCCGGTGACGTGCTACGCGCT
TaCslH1-2     ..................C.....................................CT.........T.T..
TaCslH1-3     ........................G........................C..............................
```

FIGURE 17 (Cont.)

```
                    640       650       660       670       680       690       700       710       720
                 ....|....|....|....|....|....|....|....|....|....|....|....|....|....|....|....|....|....|
HvCslH1          ...T................G........G.C..T............C.C.......C.........A...................
HvCslH1Him       ...T................G........G.C..T............C.C.......C.........A...................
HvCslH1g         ...T................G........G.C..T............C.C.......C.........A...................
HvCslH1gHim      ...T................G........G.C..T............C.C.......C.........A...................
TaCslH1-1        GCGCGAGGCCGCCAAGTTCGCCAGCCTCTGGATTCCCTTCTGCAAGAGGTATGACGTTGGTGTGAGGGCCCCTTTCATGTACTTCTCTTC
TaCslH1-2        .......................G................C.C............................................
TaCslH1-3        ....................G........G......T..........C.C.....................................

730       740       750       760       770       780       790       800       810
                 ....|....|....|....|....|....|....|....|....|....|....|....|....|....|....|....|....|....|
HvCslH1          .A..............A..C.............................G..........--------------------------
HvCslH1Him       .A..............A..C.............................G..........--------------------------
HvCslH1g         .A..............A..C.............................G.....................A...........G...
HvCslH1gHim      .A..............A..C.............................G.....................A...........G...
TaCslH1-1        CGCGCCGGAGGTTGGCACCGGTACAGCCGACCACGAGTTCCTGGAAAGCTGGGCACTCATGAAGGTTAGGCGCC-ATGGTGACCATTTCA
TaCslH1-2        ................A........T...........................................C..C..---...A..TG..G...
TaCslH1-3        ................A...A....T...........................................T.....-......T...GC.G 820       830       840       850       860       870       880       890       900
                 ....|....|....|....|....|....|....|....|....|....|....|....|....|....|....|....|....|....|
HvCslH1          -------------------------------------------------------------------G...........GA..
HvCslH1Him       -------------------------------------------------------------------G...........GA..
HvCslH1g         ....A.AAA........................A........G....T..................G...........GA..
HvCslH1gHim      ....A.AAA........................A........G....T..................G...........GA..
TaCslH1-1        GTTTCC---ATAATGTCTGGTCGTCCATCGTCGCCATGACCATGCATCTTCCTCGTGTACGTGTGACTTTCAGACCGAATATGAGAAGCT
TaCslH1-2        ....---...........A.................T..................G....................
TaCslH1-3        ....--------........A.................-..............C.C................

910       920       930       940       950       960       970       980       990
                 ....|....|....|....|....|....|....|....|....|....|....|....|....|....|....|....|....|....|
HvCslH1          A........A...............T....G.....A.........A........C................
HvCslH1Him       A........A...............T....G.....A.........A........C................
HvCslH1g         A........A...............T....G.....A.........A........C................
HvCslH1gHim      A........A...............T....G.....A.........A........C................
TaCslH1-1        GGCCAGCCGGATCGAGAACGCCGACGAGGTCTCCATTCTGCGTGACGGCGGCGAAGAGTTCGCCGAGTTCATCGACCCCGAGCGCGGGAA
TaCslH1-2        ....C........-...-...........-.........................C................
TaCslH1-3        ....C................G.A.A...A.........................C................

1000      1010      1020      1030      1040      1050      1060      1070      1080
                 ....|....|....|....|....|....|....|....|....|....|....|....|....|....|....|....|....|....|
HvCslH1          ..............-------------------------------------------------------------------
HvCslH1Him       ..............-------------------------------------------------------------------
HvCslH1g         .................................TGTCCATGCATG........A.........A..........A..........GT
HvCslH1gHim      .................................TGTCCATGCATG........A.........A..........A..........GT
TaCslH1-1        CCATCCTACCATCGTTAAGGTCGCCGGCACTGACCA-----------TGTCCATGTACATCGTGTCATGCCAAACGCGTAGCAAATCC--
TaCslH1-2        ...................T.........TATC----CACG.....................G..........A.....G......--
TaCslH1-3        .................GT..........TGTT----CATT.....................G..........A............--

1090      1100      1110      1120      1130      1140      1150      1160      1170
                 ....|....|....|....|....|....|....|....|....|....|....|....|....|....|....|....|....|....|
HvCslH1          ----------------------------------------.....G.....................TG................
HvCslH1Him       ----------------------------------------.....G.....................TG................
HvCslH1g         ...................TT.G.CCC............G..........................TG................
HvCslH1gHim      ...................TT.G.GCC............G..........................TG................
TaCslH1-1        GTCTCGTGCTAATATCGTCACGGTTAACCT-GTGTGAGTTCAGGTTCTCTGGGATAACAGCAAGAGCAAAGCAGGGGAAGGATTCCCACA
TaCslH1-2        ..............................-..C...................A.....A....T..........
TaCslH1-3        ...................T..-..C............C......................A.........

1180      1190      1200      1210      1220      1230      1240      1250      1260
                 ....|....|....|....|....|....|....|....|....|....|....|....|....|....|....|....|....|....|
HvCslH1          ..............................................C...T........---------------------
HvCslH1Him       ....................................................T........---------------------
HvCslH1g         ..............................................C...T..........................TCG
HvCslH1gHim      ....................................................T..........................TCG
TaCslH1-1        TCTGGTGTACCTCTCTCGAGAGAAAAGCCCCAGACATCGCCACAACTTCAAGGCCGGTGCCATGAATGTTCGGTGAGCACTCTCTTGTA
TaCslH1-2        ........GA..................T.....T..........................................C..
TaCslH1-3        .................T..........................................................C..
```

FIGURE 17 (Cont.)

```
                    1270      1280      1290      1300      1310      1320      1330      1340      1350
               ....|....|.... ....|....|....|....|....|....|....|....|....|....|....|....|....|....|....|
HvCs1H1        ------------------------------------------------------------------------------------------
HvCs1H1Him     ------------------------------------------------------------------------------------------
HvCs1H1g       .T..AC........G.....C......--..........G.....----------------------------------CCA.AT..
HvCs1H1gHim    .T..AC........G.....C......--..........G.....----------------------------------CCA.AT..
TaCs1H1-1      CACA---ACAGTGTTTCACTGGTAATCAGTGTGTCACACAAACAGCACAATAAGTGGCAGTTGAAAGTTCAGACATGTGTACAATGCGCTT
TaCs1H1-2      .T..AT........G....AC....................A.--........A.A....C......GCT...C..G.CA.AT..
TaCs1H1-3      .T..AT...A....G....AC....................A.--........A.A.A.........G---.C.TG.CA.TT..

1360      1370      1380      1390      1400      1410      1420      1430      1440
               ....|....|.... ....|....|....|....|....|....|....|....|....|....|....|....|....|....|....|
HvCs1H1        ----------------------------------------------------A...................C................
HvCs1H1Him     ----------------------------------------------------A...................C................
HvCs1H1g       T..------------.C........T.A.........................A...................C................
HvCs1H1gHim    T..------------.C........T.A.........................A...................C................
TaCs1H1-1      GATAATTTGCAAGCAAATAATTAAGCTGAGCGTTTCGTGGTGCAGACAAGGGTGTCGGCCGTGATGACCAACGCTCCAATCATGCTGAAT
TaCs1H1-2      ...------------.C...............A............................................G..........
TaCs1H1-3      ...------------.C...............A............................................G..........

1450      1460      1470      1480      1490      1500      1510      1520      1530
               ....|....|.... ....|....|....|....|....|....|....|....|....|....|....|....|....|....|....|
HvCs1H1        ..............T...........A..............A...............................................
HvCs1H1Him     ..............T...........A..............A...............................................
HvCs1H1g       ..............T...........A..............A...............................................
HvCs1H1gHim    ..............T...........A..............A...............................................
TaCs1H1-1      GTGGACTGCGACATGTTCGCCAACAACCCGCAGGTCGCCCTGCACGCGATGTGCCTCCTGTTGGGGTCGACGACGAGATCCACAGCGGG
TaCs1H1-2      .......T.................A................................................................
TaCs1H1-3      ..........................A................................................................

1540      1550      1560      1570      1580      1590      1600      1610      1620
               ....|....|.... ....|....|....|....|....|....|....|....|....|....|....|....|....|....|....|
HvCs1H1        .......A.T.....................C..T.............................-------------
HvCs1H1Him     .......A.T.....................C..T.............................-------------
HvCs1H1g       .......A.T.....................C..T..........................................
HvCs1H1gHim    .......A.T.....................C..T..........................................
TaCs1H1-1      TTCGTCCAGGCGCCACAGAAGTTCTACGGTGGCCTCAAGGATGACCCCTTTGGCAACCAGATGCAGGTTATAACCAAGGTACTACATATG
TaCs1H1-2      ..............................................................................
TaCs1H1-3      ..................C...........................................................

1630      1640      1650      1660      1670      1680      1690      1700      1710
               ....|....|.... ....|....|....|....|....|....|....|....|....|....|....|....|....|....|....|
HvCs1H1        ------------------------------------------------------------------------------------------
HvCs1H1Him     ------------------------------------------------------------------------------------------
HvCs1H1g       ..............C....C..C....TGTGC.........---------------A...............T..........G......
HvCs1H1gHim    ..............C....C..C....TGTGC.........---------------A...............T..........G......
TaCs1H1-1      CATGTGCACAAGTGCTGTTGTGGTAGTGC-----ACCACT-------------AGGGTAGTGTTACACTTGCACTCGTTTTTCTGGCAT
TaCs1H1-2      ......................------.....----------------................................
TaCs1H1-3      ------..........C.......T..A.TGTT-..AGT.TTTTTTTTGCAGCGAT.................T...............

1720      1730      1740      1750      1760      1770      1780      1790      1800
               ....|....|.... ....|....|....|....|....|....|....|....|....|....|....|....|....|....|....|
HvCs1H1        ------........AA...............TG..........................A.....T......
HvCs1H1Him     ------........AA...............TG..........................A.....T......
HvCs1H1g       ..............AA...............TG..........................A.....T......
HvCs1H1gHim    ..............AA...............TG..........................A.....T......
TaCs1H1-1      GTTCAGAAAATTGGAGGTGGGCTCGCCGGGATCCAAGGCACCTTCTACGGCGGCACGGGCTGTTTCACCGCAGGAAGGTCATCTACGGC
TaCs1H1-2      ..............................................................T......
TaCs1H1-3      ............C..................TG..........G..A........A.G......A.....T......

1810      1820      1830      1840      1850      1860      1870      1880      1890
               ....|....|.... ....|....|....|....|....|....|....|....|....|....|....|....|....|....|....|
HvCs1H1        ........A..T.........A..........-------------------------------------------
HvCs1H1Him     ........A..T.........A..........-------------------------------------------
HvCs1H1g       ........A..T.....C...A.........---.C........A..AC.....T.......A.G.........G....-
HvCs1H1gHim    ........A..T.........A.........---.C........A..AC.....T.......A.G.........G....-
TaCs1H1-1      ATGCCGCCTCCGGACACCGTCAAGCACGAGACAAGAGGTAATAAAACTGGGCACGCACAAGATGAGATCATCCGACGTAAATTGAAGTAT
TaCs1H1-2      ......................................A..A.........G-..G.............G.....
TaCs1H1-3      G........A..A...........A.......TG.A...........A..A.........G.........G.....
```

FIGURE 17 (Cont.)

```
                    1900      1910      1920      1930      1940      1950      1960      1970      1980
                ....|....|....|....|....|....|....|....|....|....|....|....|....|....|....|....|....|....|
HvCslH1         ----------------------------------------------------------------..........................
HvCslH1Him      --------------------------------------------------------------------------................
HvCslH1g        --------------------------------.T........TAAG......T.....................................
HvCslH1gHim     --------------------------------T..T........TAAG......T..................................
TaCslH1-1       TTGGTCAGTGCATTTCAGTTCGACTAGGGC-ATATCAAATGGC----TGTTCTCAATTTGCCAGGTTCACCATCTTACAAGGAGCTGCAA
TaCslH1-2       ....C.........................................----.T.....................................
TaCslH1-3       ..............G.................A.C............----...C.................................G 1990      2000      2010      2020      2030      2040      2050      2060      2070
                ....|....|....|....|....|....|....|....|....|....|....|....|....|....|....|....|....|....|
HvCslH1         .T..G................T...................................A.....................T...G.....
HvCslH1Him      .T..G................T...................................A.....................T...G.....
HvCslH1g        .T..G................T...................................A.....................T...G.....
HvCslH1gHim     .T..G................T...................................A.....................T...G.....
TaCslH1-1       GCCAAGTTTGGGAGCTCAAAGGAGTTGATCGAATCATCTAGGAACATCATCTCAGGGGACCTGCTCGCTAGACCAACCGTAGATATATCG
TaCslH1-2       ..........................................................A.............................A
TaCslH1-3       ..........................................................A....................T.....

2080      2090      2100      2110      2120      2130      2140      2150      2160
                ....|....|....|....|....|....|....|....|....|....|....|....|....|....|....|....|....|....|
HvCslH1         .....CA...............C.....T....................G........A.G.---------------------
HvCslH1Him      .....CA...............C.....T....................G........A.G.---------------------
HvCslH1g        .....CA...............C.....T....................G........A.G.---------------------
HvCslH1gHim     .....CA...............C.....T....................G........A.G..A...........AC.T.....
TaCslH1-1       AGTCGTGTCGAAATGGCAAAACAAGTAGGCGACTGCAACTATGAGGCTGGCACATGTTGGGGCCAAGAGGTGTGCTTAGCT-TC-GTTGC
TaCslH1-2       .....G................................................................-.-.....
TaCslH1-3       .....C...........................................G......A...........-..C.....

2170      2180      2190      2200      2210      2220      2230      2240      2250
                ....|....|....|....|....|....|....|....|....|....|....|....|....|....|....|....|....|....|
HvCslH1         -----------------------------------------------------------------------------
HvCslH1Him      -----------------------------------------------------------------------------
HvCslH1g        -----------------------------------------------------------------------------
HvCslH1gHim     ..........C............AT.T........T....T.......G..............----.......
TaCslH1-1       CGTATTTTTGCAGGTTTTGCTACAGTACGGCCACATCTACACACACCTTCTGCAGTTTCTCTCTA-TTACAGTTTCTTCC----ATGTATTT
TaCslH1-2       ..................................A..........................----..C.....
TaCslH1-3       ...............AT.T...A......A..........................G...........ATAT..A.....

2260      2270      2280      2290      2300      2310      2320      2330      2340
                ....|....|....|....|....|....|....|....|....|....|....|....|....|....|....|....|....|....|
HvCslH1         ------....T..............A..............A..............T...............A............
HvCslH1Him      ------....T..............A..............A.......T......T...............A............
HvCslH1g        ------....T..............A..............A..............T...............A............
HvCslH1gHim     ..........T..............A..............A..............T...............A............
TaCslH1-1       TTGCAGATTGGGTGGGTCTATGGATCAATGACAGAGGACATTTTGACCGGTCAACGGATCCAGCGGCGGGTTGGGAATCGGCCTTGTTG
TaCslH1-2       ...................................................G........A............
TaCslH1-3       ..........C....................................C........G.TG........T..........A....

2350      2360      2370      2380      2390      2400      2410      2420      2430
                ....|....|....|....|....|....|....|....|....|....|....|....|....|....|....|....|....|....|
HvCslH1         .....A.............T.........................G......G.......................G.....
HvCslH1Him      .....A.............T.........................G......G.......................G.....
HvCslH1g        .....A.............T.........................G......G.......................G.....
HvCslH1gHim     .....A.............T.........................G......G.......................G.....
TaCslH1-1       GACACCGACCCACCGGCATTCCTGGGATGTGCTCCGACCGGTGGACCAGCCAGCTTGACCCAGTTCAAGAGATGGGCAACAGGGCTTCTG
TaCslH1-2       ....................T............A..G..G..G..T.......................
TaCslH1-3       ........G....................................G.......................

2440      2450      2460      2470      2480      2490      2500      2510      2520
                ....|....|....|....|....|....|....|....|....|....|....|....|....|....|....|....|....|....|
HvCslH1         ........................T................C.AC............................C..G
HvCslH1Him      ........................T................C.AC............................C..G
HvCslH1g        ........................T................C.AC............................C..G
HvCslH1gHim     ........................T................C.AC............................C..G
TaCslH1-1       GAGATACTCATCAGCCGGAACAGCCCCATCCTCGGCACCATCTTCAAGGGCCTCCAACTCCGGCAATGCCTTGGCTATCTCATCGTAGAC
TaCslH1-2       ........................................G.C............................CA..
TaCslH1-3       ..............A.........G.................CGAC...............C..............A
```

```
                 3160      3170      3180      3190      3200      3210      3220      3230      3240
             ....|....|....|....|....|....|....|....|....|....|....|....|....|....|....|....|....|
HvCslH1      ................A.........................................G...................C..G..
HvCslH1Him   ................A.........................................G...................C..G..
HvCslH1g     ................A.........................................G...................C..G..
HvCslH1gHim  ................A.........................................G...................C..G..
TaCslH1-1    TCATGGTGGCCCGGGCGTCGGAGAGTTCGTGTGCTGTGGCTGGATGGTGTTGTGCTTCTGGCCATTCGTGAGAGGGCTTGTCAGTAGTGG
TaCslH1-2    ................A.............................C.............G...A...............C.....
TaCslH1-3    ................A....G...........................C....C..............G.........C..G..

3250      3260      3270      3280      3290      3300      3310      3320      3330
             ....|....|....|....|....|....|....|....|....|....|....|....|....|....|....|....|....|
HvCslH1      ....C....A.............C....A...........T.........................................--------
HvCslH1Him   ....C....A.............C....A...........T.........................................--------
HvCslH1g     ....C....A.............C....AA..........T.........................................G
HvCslH1gHim  ....C....A.............C....A...........T.........................................------
TaCslH1-1    AAAGTATGGGATCCCGTGGAGTGTCAGGGTGAAGGCTGGGTTGATTGTGGCTGCGTTCCTGCACCTCTGCACAAGGAACTAACCGGCCG-
TaCslH1-2    ...........................................................................................G.-
TaCslH1-3    ........A................................T..........................A.................G.-

3340      3350      3360      3370      3380      3390      3400      3410      3420
             ....|....|....|....|....|....|....|....|....|....|....|....|....|....|....|....|....|
HvCslH1      ------------------------------------------------------------------------------------------
HvCslH1Him   ------------------------------------------------------------------------------------------
HvCslH1g     GCTGGCCATCGAAATATTGGAAGCGTAATTTTAGTTCTACCATGGAACATGTAACGAAGACTCAAGCAGGAATTAAAGCGTGTTATTAA
HvCslH1gHim  ------------------------------------------------------------------------------------------
TaCslH1-1    ------------------------------------------------------------------------------------------
TaCslH1-2    ------------------------------------------------------------------------------------------
TaCslH1-3    ------------------------------------------------------------------------------------------

3430      3440      3450      3460      3470      3480
             ....|....|....|....|....|....|....|....|....|....|....|....
HvCslH1      ------------------------------------------------------------
HvCslH1Him   ------------------------------------------------------------
HvCslH1g     AGGAAGTTTGACCCAATGTATCTATCTATCTCTCCCAATCTCTCTCAATAATAAAGCAAAT
HvCslH1gHim  ------------------------------------------------------------
TaCslH1-1    ------------------------------------------------------------
TaCslH1-2    ------------------------------------------------------------
TaCslH1-3    ------------------------------------------------------------
```

FIGURE 19
A
B
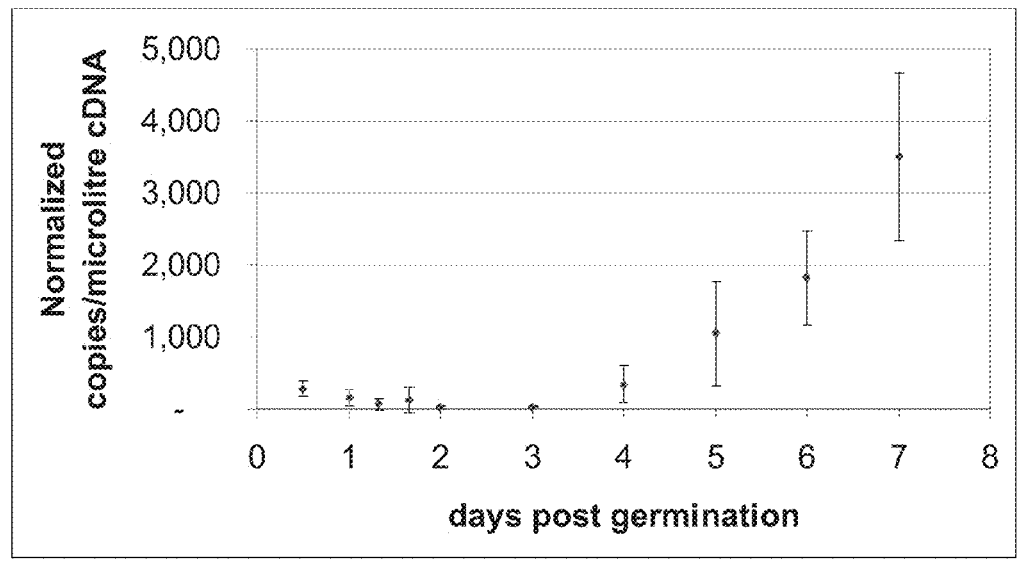

FIGURE 27

| Seq-> | HvCslH1 | | HvCslH1(Him) | | TaCslH1-3 | | TaCslH1-1 | | TaCslH1-2 | |
|---|---|---|---|---|---|---|---|---|---|---|
| HvCslH1 | 100 | | 99.9 | | 93.7 | | 93.8 | | 93.4 | |
|  | 100 | 100 | 100 | 100 | 93.1 | 97.3 | 92.8 | 97.6 | 92.6 | 97.7 |
| HvCslH1(Him) |  |  | 100 | | 93.8 | | 93.9 | | 93.5 | |
|  |  |  | 100 | 100 | 93.1 | 97.3 | 92.8 | 97.6 | 92.6 | 97.7 |
| TaCslH1-3 |  |  |  |  | 100 | | 95.3 | | 95.2 | |
|  |  |  |  |  | 100 | 100 | 94.3 | 98.1 | 94.0 | 98.3 |
| TaCslH1-1 |  |  |  |  |  |  | 100 | | 96.1 | |
|  |  |  |  |  |  |  | 100 | 100 | 95.1 | 99.1 |
| TaCslH1-2 | DNA % identity | |  |  |  |  |  |  | 100 | |
|  | aa % id | aa % sim |  |  |  |  |  |  | 100 | 100 |

SEQUENCE LISTING

```
<160> NUMBER OF SEQ ID NOS: 80

<210> SEQ ID NO 1
<211> LENGTH: 2256
<212> TYPE: DNA
<213> ORGANISM: Hordeum vulgare

<400> SEQUENCE: 1
atggcgggcg gcaagaagct gcaggagagg gtcgccctgg cgagaaccgc gtggatgctg       60
gccgacttcg cgatcctctt cctcctcctc gccatcgtgg cccgccgcgc cgcctcgctc      120
cgggagcgcg gcgggacgtg gttggcggcg ctcgtctgcg aggcgtggtt cgccttcgtg      180
tggatcctca acatgaacgg caagtggagc cccgtccggt cgacaccta ccccgacaac       240 ctcgccaaca ggatggagga gctcccgggg gtggacatgt tcgtcacgac cgcggacccg      300
gcgctggagc ctccgttgat cacggtgaac acggtgctct cgctgctcgc cctggactac      360
ccggacgtcg gcaagctggc gtgctacgtc tctgacgacg gctgctcccc ggtgacgtgc      420
tacgcgctgc gtgaggccgc caagttcgcc ggcctctggg tccctttctg caagaggcac      480
gacgttgctg tgagggcccc attcatgtac ttctcttcca cgccggaggt tggcacaggc      540
acagccgacc acgagttcct ggaaagctgg gcgctcatga agagcgaata tgagagacta      600
gccagccgaa tcgagaacgc cgatgagggc tccattatgc gtgacagcgg cgacgagttc      660
gccgagttca tcgacgccga gcgcgggaac catcctacca tcgttaaggt tctgtgggat      720
aacagcaaga gcaaagtggg ggaaggattc ccacatctgg tgtacctctc tcgagagaaa      780
agccccagac atcgccacaa cttccaggct ggtgccatga atgttctgac aagggtgtca      840
gccgtgatga ccaacgctcc catcatgctg aatgtggact gcgacatgtt cgccaacaat      900
ccgcaggtcg ccctacacgc gatgtgcctc ctattggggt cgacgacga gatccacagc      960 gggttcgtcc aagtgccaca gaagttctac ggtggcctca aggacgatcc ctttggcaac     1020
cagatgcagg ttataaccaa gaaaattgga ggtggaatcg ccgggatcca aggcatgttc     1080
tacggcggca cgggctgttt tcaccgcagg aaagtcattt acggcatgcc gccacctgac     1140
accgtcaaac acgagacaag aggttcacca tcttacaagg agctgcaagt caggtttggg     1200
agctcaaagg tgttgatcga atcatctagg aacatcatct caggagacct gctcgctaga     1260
ccaaccgttg atgtatcgag tcgcatcgaa atggcaaaac aagtcggcga ttgcaactat     1320
gaggctggca cgtgttgggg caaggagatt ggttgggtct atggatcaat gacagaagac     1380
attttgaccg gacaacggat ccatgcggcg ggttggaaat cggccttgtt ggacaccaac     1440
ccaccggcat tcttgggatg tgctccgacc ggggaccgg ccagcttgac ccagttcaag      1500
agatgggcaa caggggttct ggagatactc atcagccgga acagccctat cctcggcacc     1560
atcttccaac gcctccaact ccggcaatgc cttggctatc tcatcgtcga ggcgtggccc     1620
gtgagggcgc ctttcgagct gtgctatgca ctattgggac ctttctgcct tctcacaaac     1680
cagtccttct tgccaacggc atcggatgaa ggttttcgca tcccagtagc tctattcttg     1740
agttaccaca tataccactt gatggagtac aaggagtgcg gctctctgc ccgcgcctgg      1800 tggaacaacc acaggatgca acgcatcacc tcggcctccg cctggctcct cgccttcctc     1860
accgtgatcc tcaagacact agggctctct gagaccgtgt tcgaggtcac ccgcaaggaa     1920
```

```
agcagcacgt ccgatggcgg cgccggcacc gacgaggccg atccaggact gttcacattc    1980
gactcggcgc ccgttttcat cccggtgacg gcgctctcag tgttgaacat tgtggccctc    2040
gccgtcgggg catggcgcgc cgtcatcggg actgcggcgg tcgttcatgg tggcccgggc    2100
atcggagagt tcgtgtgctg tggctggatg gtgttgtgct tctggccgtt cgtgagaggg    2160
cttgtcagca ggggaaagca tggaatcccg tggagcgtca aggtgaaggc tggtttgatt    2220
gtggctgcgt tcgtgcacct ctgcacaagg aactaa                              2256

<210> SEQ ID NO 2
<211> LENGTH: 751
<212> TYPE: PRT
<213> ORGANISM: Hordeum vulgare

<400> SEQUENCE: 2

Met Ala Gly Gly Lys Lys Leu Gln Glu Arg Val Ala Leu Ala Arg Thr
1               5                   10                  15

Ala Trp Met Leu Ala Asp Phe Ala Ile Leu Phe Leu Leu Ala Ile
            20                  25                  30

Val Ala Arg Arg Ala Ala Ser Leu Arg Glu Arg Gly Gly Thr Trp Leu
    35                  40                  45

Ala Ala Leu Val Cys Glu Ala Trp Phe Ala Phe Val Trp Ile Leu Asn
50                  55                  60

Met Asn Gly Lys Trp Ser Pro Val Arg Phe Asp Thr Tyr Pro Asp Asn
65                  70                  75                  80

Leu Ala Asn Arg Met Glu Glu Leu Pro Ala Val Asp Met Phe Val Thr
                85                  90                  95

Thr Ala Asp Pro Ala Leu Glu Pro Pro Leu Ile Thr Val Asn Thr Val
            100                 105                 110

Leu Ser Leu Leu Ala Leu Asp Tyr Pro Asp Val Gly Lys Leu Ala Cys
        115                 120                 125

Tyr Val Ser Asp Asp Gly Cys Ser Pro Val Thr Cys Tyr Ala Leu Arg
    130                 135                 140

Glu Ala Ala Lys Phe Ala Gly Leu Trp Val Pro Phe Cys Lys Arg His
145                 150                 155                 160

Asp Val Ala Val Arg Ala Pro Phe Met Tyr Phe Ser Ser Thr Pro Glu
                165                 170                 175

Val Gly Thr Gly Thr Ala Asp His Glu Phe Leu Glu Ser Trp Ala Leu
            180                 185                 190

Met Lys Ser Glu Tyr Glu Arg Leu Ala Ser Arg Ile Glu Asn Ala Asp
        195                 200                 205

Glu Gly Ser Ile Met Arg Asp Ser Gly Asp Glu Phe Ala Glu Phe Ile
    210                 215                 220

Asp Ala Glu Arg Gly Asn His Pro Thr Ile Val Lys Val Leu Trp Asp
225                 230                 235                 240

Asn Ser Lys Ser Lys Val Gly Glu Gly Phe Pro His Leu Val Tyr Leu
                245                 250                 255

Ser Arg Glu Lys Ser Pro Arg His Arg His Asn Phe Gln Ala Gly Ala
            260                 265                 270

Met Asn Val Leu Thr Arg Val Ser Ala Val Met Thr Asn Ala Pro Ile
        275                 280                 285

Met Leu Asn Val Asp Cys Asp Met Phe Ala Asn Asn Pro Gln Val Ala
    290                 295                 300

Leu His Ala Met Cys Leu Leu Leu Gly Phe Asp Asp Glu Ile His Ser
305                 310                 315                 320
```

```
Gly Phe Val Gln Val Pro Gln Lys Phe Tyr Gly Gly Leu Lys Asp Asp
                325                 330                 335

Pro Phe Gly Asn Gln Met Gln Val Ile Thr Lys Lys Ile Gly Gly Gly
                340                 345                 350

Ile Ala Gly Ile Gln Gly Met Phe Tyr Gly Thr Gly Cys Phe His
                355                 360                 365

Arg Arg Lys Val Ile Tyr Gly Met Pro Pro Asp Thr Val Lys His
370                 375                 380

Glu Thr Arg Gly Ser Pro Ser Tyr Lys Glu Leu Gln Val Arg Phe Gly
385                 390                 395                 400

Ser Ser Lys Val Leu Ile Glu Ser Ser Arg Asn Ile Ile Ser Gly Asp
                405                 410                 415

Leu Leu Ala Arg Pro Thr Val Asp Val Ser Ser Arg Ile Glu Met Ala
                420                 425                 430

Lys Gln Val Gly Asp Cys Asn Tyr Glu Ala Gly Thr Cys Trp Gly Lys
                435                 440                 445

Glu Ile Gly Trp Val Tyr Gly Ser Met Thr Glu Asp Ile Leu Thr Gly
                450                 455                 460

Gln Arg Ile His Ala Ala Gly Trp Lys Ser Ala Leu Leu Asp Thr Asn
465                 470                 475                 480

Pro Pro Ala Phe Leu Gly Cys Ala Pro Thr Gly Gly Pro Ala Ser Leu
                485                 490                 495

Thr Gln Phe Lys Arg Trp Ala Thr Gly Val Leu Glu Ile Leu Ile Ser
                500                 505                 510

Arg Asn Ser Pro Ile Leu Gly Thr Ile Phe Gln Arg Leu Gln Leu Arg
                515                 520                 525

Gln Cys Leu Gly Tyr Leu Ile Val Glu Ala Trp Pro Val Arg Ala Pro
                530                 535                 540

Phe Glu Leu Cys Tyr Ala Leu Leu Gly Pro Phe Cys Leu Leu Thr Asn
545                 550                 555                 560

Gln Ser Phe Leu Pro Thr Ala Ser Asp Glu Gly Phe Arg Ile Pro Val
                565                 570                 575

Ala Leu Phe Leu Ser Tyr His Ile Tyr His Leu Met Glu Tyr Lys Glu
                580                 585                 590

Cys Gly Leu Ser Ala Arg Ala Trp Trp Asn Asn His Arg Met Gln Arg
                595                 600                 605

Ile Thr Ser Ala Ser Ala Trp Leu Leu Ala Phe Leu Thr Val Ile Leu
                610                 615                 620

Lys Thr Leu Gly Leu Ser Glu Thr Val Phe Glu Val Thr Arg Lys Glu
625                 630                 635                 640

Ser Ser Thr Ser Asp Gly Gly Ala Gly Thr Asp Glu Ala Asp Pro Gly
                645                 650                 655

Leu Phe Thr Phe Asp Ser Ala Pro Val Phe Ile Pro Thr Ala Leu
                660                 665                 670

Ser Val Leu Asn Ile Val Ala Leu Ala Val Gly Ala Trp Arg Ala Val
                675                 680                 685

Ile Gly Thr Ala Ala Val Val His Gly Gly Pro Gly Ile Gly Glu Phe
                690                 695                 700

Val Cys Cys Gly Trp Met Val Leu Cys Phe Trp Pro Phe Val Arg Gly
705                 710                 715                 720

Leu Val Ser Arg Gly Lys His Gly Ile Pro Trp Ser Val Lys Val Lys
                725                 730                 735

Ala Gly Leu Ile Val Ala Ala Phe Val His Leu Cys Thr Arg Asn
```

<210> SEQ ID NO 3
<211> LENGTH: 2253
<212> TYPE: DNA
<213> ORGANISM: Oryza sativa

<400> SEQUENCE: 3

| | | | | | |
|---|---|---|---|---|---|
| atggaggcgg | cggctagagg | caacaagaag | ctgcaggaga | gggtgcccat | ccggcgcacc | 60 |
| gcgtggaggc | tcgccgacct | cgccatcctc | ttcctcctcc | tcgccctcct | cctccaccgc | 120 |
| gtcctccacg | acagcggcgc | gccatggcgg | cgcgccgcgc | tcgcctgcga | ggcgtggttc | 180 |
| accttcatgt | ggctgctcaa | cgtgaacgcc | aagtggagcc | ccgtccgttt | cgacacgttc | 240 |
| ccggagaacc | tcgccgaaag | gatcgacgag | ctcccggcgg | tggacatgtt | cgtgacgacg | 300 |
| gcggacccgg | tgctggagcc | gccgctggtg | accgtgaaca | cggtgctgtc | gctgctcgcc | 360 |
| ctcgactacc | cggccgccgg | cgagaagctg | gcgtgctacg | tctccgacga | cgggtgctcg | 420 |
| ccgctgacgt | gctacgcgct | gcgggaggcc | gcccggttcg | ccaggacgtg | ggtgcccttc | 480 |
| tgccggcggc | acgcgtcgc | cgtcagggcg | cccttccggt | acttctcctc | cacgccggag | 540 |
| ttcggcccgg | cggatggcaa | gttcttggag | gactggacat | tcatgaagag | cgagtatgag | 600 |
| aagttggtcc | accggatcga | ggacgccgat | gagccttccc | ttctgcggca | cggcggtggt | 660 |
| gagttcgcag | agtttctgga | tgttgagagg | gggaaccacc | ctactatcat | aaaggttctg | 720 |
| tgggataaca | acaggagcag | gacaggagat | ggcttccctc | gtctgatata | cgtctcaagg | 780 |
| gagaagagcc | ccaacctaca | ccatcactac | aaggctggcg | ccatgaatgc | cctgacaagg | 840 |
| gtgtcagcac | tgatgaccaa | cgccccattc | atgctaaacc | tagactgcga | catgtttgta | 900 |
| aacaaccccc | gggtcgtcct | ccatgccatg | tgccttctgt | taggttttga | cgatgagatc | 960 |
| agctgcgcgt | ttgttcagac | gccgcagaaa | ttctacggtg | ccttgaagga | tgatcctttc | 1020 |
| gggaaccagc | tggaagttag | tttgatgaaa | gttggacgtg | ggattgcagg | gcttcagggc | 1080 |
| atattttatt | gtggaacagg | ctgctttcac | cgcagaaaag | tcatttacgg | catgaggaca | 1140 |
| gggcgagaag | gcaccacagg | ttattcatct | aacaaggagc | tccatagtaa | attcggaagt | 1200 |
| tcaaataatt | ttaaggaatc | agccagggat | gtcatttatg | ggaacttgtc | aacagagcca | 1260 |
| atagtagata | tatcaagttg | cgttgatgtt | gccaaagaag | tagctgcctg | caactacgag | 1320 |
| attggcacat | gttggggtca | ggaggttggt | tgggtctatg | atcactgac | agaagacgtg | 1380 |
| ttgaccggac | aacggatcca | tgcagcgggt | tggagatcca | cgctgatgga | aatcgaacca | 1440 |
| ccagcattca | tgggttgtgc | accaaatgga | gggcccgcct | gcctaaccca | gttgaagaga | 1500 |
| tgggcatcag | gttttttaga | aatactcatc | agtcggaata | acccaatcct | cacaaccaca | 1560 |
| tttaagagtc | tccaattccg | acaatgcctt | gcatacctgc | acagctatgt | gtggcctgtg | 1620 |
| agggcaccttt | tcgaattgtg | ctatgcattg | ttggggcctt | attgcttact | atcaaaccaa | 1680 |
| tccttcttgc | caaagacatc | agaagacggt | ttctacatcg | cattagctct | attcattgcc | 1740 |
| tataacacat | acatgttcat | ggagttcata | gagtgtgggc | agtctgcacg | tgcatgttgg | 1800 |
| aacaaccaca | ggatgcaacg | gatcacctca | gcttctgctt | ggctactggc | atttcttacc | 1860 |
| gtcatcctca | agaccttagg | cttctccgag | actgtgttcg | aggtcacccg | caaagacaag | 1920 |
| agcacatcag | atggtgattc | caacaccgat | gagcctgagc | cagggaggtt | cacccttcgac | 1980 |
| gaatcgacgg | tgttcattcc | cgtgacagca | cttgcaatgt | taagtgtcat | tgcaatcgct | 2040 |
| gtaggagcat | ggagggtggt | tttggtgaca | acggaaggct | tgcccggtgg | ccctggtatc | 2100 |

```
agtgaattca tctcctgtgg gtggctggtg ctgtgcttca tgccattgct gagaggtcta    2160
gtgggaagtg gtcgatatgg cattccttgg agtatcaaga tgaaggcctg cttgcttgtt    2220
gctatattct tgctcttctg caaaagaaat taa                                 2253
```

<210> SEQ ID NO 4
<211> LENGTH: 750
<212> TYPE: PRT
<213> ORGANISM: Oryza sativa

<400> SEQUENCE: 4

| Met | Glu | Ala | Ala | Ala | Arg | Gly | Asn | Lys | Lys | Leu | Gln | Glu | Arg | Val | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ile Arg Arg Thr Ala Trp Arg Leu Ala Asp Leu Ala Ile Leu Phe Leu
                20                  25                  30

Leu Leu Ala Leu Leu Leu His Arg Val Leu His Asp Ser Gly Ala Pro
        35                  40                  45

Trp Arg Arg Ala Ala Leu Ala Cys Glu Ala Trp Phe Thr Phe Met Trp
    50                  55                  60

Leu Leu Asn Val Asn Ala Lys Trp Ser Pro Val Arg Phe Asp Thr Phe
65                  70                  75                  80

Pro Glu Asn Leu Ala Glu Arg Ile Asp Glu Leu Pro Ala Val Asp Met
                85                  90                  95

Phe Val Thr Thr Ala Asp Pro Val Leu Glu Pro Pro Leu Val Thr Val
            100                 105                 110

Asn Thr Val Leu Ser Leu Leu Ala Leu Asp Tyr Pro Ala Ala Gly Glu
        115                 120                 125

Lys Leu Ala Cys Tyr Val Ser Asp Asp Gly Cys Ser Pro Leu Thr Cys
    130                 135                 140

Tyr Ala Leu Arg Glu Ala Ala Arg Phe Ala Arg Thr Trp Val Pro Phe
145                 150                 155                 160

Cys Arg Arg His Gly Val Ala Val Arg Ala Pro Phe Arg Tyr Phe Ser
                165                 170                 175

Ser Thr Pro Glu Phe Gly Pro Ala Asp Gly Lys Phe Leu Glu Asp Trp
            180                 185                 190

Thr Phe Met Lys Ser Glu Tyr Glu Lys Leu Val His Arg Ile Glu Asp
        195                 200                 205

Ala Asp Glu Pro Ser Leu Leu Arg His Gly Gly Glu Phe Ala Glu
    210                 215                 220

Phe Leu Asp Val Glu Arg Gly Asn His Pro Thr Ile Ile Lys Val Leu
225                 230                 235                 240

Trp Asp Asn Asn Arg Ser Arg Thr Gly Asp Gly Phe Pro Arg Leu Ile
                245                 250                 255

Tyr Val Ser Arg Glu Lys Ser Pro Asn Leu His His Tyr Lys Ala
            260                 265                 270

Gly Ala Met Asn Ala Leu Thr Arg Val Ser Ala Leu Met Thr Asn Ala
        275                 280                 285

Pro Phe Met Leu Asn Leu Asp Cys Asp Met Phe Val Asn Asn Pro Arg
    290                 295                 300

Val Val Leu His Ala Met Cys Leu Leu Leu Gly Phe Asp Asp Glu Ile
305                 310                 315                 320

Ser Cys Ala Phe Val Gln Thr Pro Gln Lys Phe Tyr Gly Ala Leu Lys
                325                 330                 335

Asp Asp Pro Phe Gly Asn Gln Leu Glu Val Ser Leu Met Lys Val Gly
            340                 345                 350

```
Arg Gly Ile Ala Gly Leu Gln Gly Ile Phe Tyr Cys Gly Thr Gly Cys
        355                 360                 365

Phe His Arg Arg Lys Val Ile Tyr Gly Met Arg Thr Gly Arg Glu Gly
    370                 375                 380

Thr Thr Gly Tyr Ser Ser Asn Lys Glu Leu His Ser Lys Phe Gly Ser
385                 390                 395                 400

Ser Asn Asn Phe Lys Glu Ser Ala Arg Asp Val Ile Tyr Gly Asn Leu
                405                 410                 415

Ser Thr Glu Pro Ile Val Asp Ile Ser Ser Cys Val Asp Val Ala Lys
            420                 425                 430

Glu Val Ala Ala Cys Asn Tyr Glu Ile Gly Thr Cys Trp Gly Gln Glu
        435                 440                 445

Val Gly Trp Val Tyr Gly Ser Leu Thr Glu Asp Val Leu Thr Gly Gln
    450                 455                 460

Arg Ile His Ala Ala Gly Trp Arg Ser Thr Leu Met Glu Ile Glu Pro
465                 470                 475                 480

Pro Ala Phe Met Gly Cys Ala Pro Asn Gly Pro Ala Cys Leu Thr
                485                 490                 495

Gln Leu Lys Arg Trp Ala Ser Gly Phe Leu Glu Ile Leu Ile Ser Arg
            500                 505                 510

Asn Asn Pro Ile Leu Thr Thr Thr Phe Lys Ser Leu Gln Phe Arg Gln
        515                 520                 525

Cys Leu Ala Tyr Leu His Ser Tyr Val Trp Pro Val Arg Ala Pro Phe
    530                 535                 540

Glu Leu Cys Tyr Ala Leu Leu Gly Pro Tyr Cys Leu Leu Ser Asn Gln
545                 550                 555                 560

Ser Phe Leu Pro Lys Thr Ser Glu Asp Gly Phe Tyr Ile Ala Leu Ala
                565                 570                 575

Leu Phe Ile Ala Tyr Asn Thr Tyr Met Phe Met Glu Phe Ile Glu Cys
            580                 585                 590

Gly Gln Ser Ala Arg Ala Cys Trp Asn Asn His Arg Met Gln Arg Ile
        595                 600                 605

Thr Ser Ala Ser Ala Trp Leu Leu Ala Phe Leu Thr Val Ile Leu Lys
    610                 615                 620

Thr Leu Gly Phe Ser Glu Thr Val Phe Glu Val Thr Arg Lys Asp Lys
625                 630                 635                 640

Ser Thr Ser Asp Gly Asp Ser Asn Thr Asp Glu Pro Glu Pro Gly Arg
                645                 650                 655

Phe Thr Phe Asp Glu Ser Thr Val Phe Ile Pro Val Thr Ala Leu Ala
            660                 665                 670

Met Leu Ser Val Ile Ala Ile Ala Val Gly Ala Trp Arg Val Val Leu
        675                 680                 685

Val Thr Thr Glu Gly Leu Pro Gly Pro Gly Ile Ser Glu Phe Ile
    690                 695                 700

Ser Cys Gly Trp Leu Val Leu Cys Phe Met Pro Leu Leu Arg Gly Leu
705                 710                 715                 720

Val Gly Ser Gly Arg Tyr Gly Ile Pro Trp Ser Ile Lys Met Lys Ala
                725                 730                 735

Cys Leu Leu Val Ala Ile Phe Leu Leu Phe Cys Lys Arg Asn
            740                 745                 750

<210> SEQ ID NO 5
<211> LENGTH: 2289
<212> TYPE: DNA
<213> ORGANISM: Oryza sativa
```

<400> SEQUENCE: 5

```
atggcggtgg tggcggcggc ggcggccacc ggttccacca ccagatcagg cggcggcggc      60
ggcgagggga cgaggtccgg gaggaagaag ccgccgccgc cgccgctgca ggagagggtg     120
cccctcgggc ggcgcgcggc gtgggcgtgg cggctggccg gcctcgccgt cctcctcctc     180
ctcctcgccc tcctcgccct ccggctgctt cgccaccacg gcggcgccgg gggcgacggc     240
ggcgtgtggc gcgtggcgct cgtgtgcgag gcgtggttcg cggcgctgtg cgcgctcaac     300
gtgagcgcca agtggagccc cgtccggttc gtcacgcggc cggagaacct cgtggcggag     360
ggcaggacgc cgtcgacgac ggcggcggag tacggcgagc tgccggcggt ggacatgctg     420
gtgacgacgg cggacccggc gctggagccg ccgctggtga cggtgaacac ggtgctctcg     480
ctgctcgccc tcgactaccc cgcgcgccgg cgagcggctgg cctgctacgt ctccgacgac     540
gggtgctcgc cgctgacgtg ccacgcgctg cgggaggccg ccgggttcgc cgccgcgtgg     600
gtgcccttct gccgccggta cggcgtcgcc gtcagggccc cgttccggta cttctcctcc     660
tcctcctcgc cggagtccgg cggcccggcc gatcgcaagt tcttggacga ctggacattc     720
atgaaggatg agtatgacaa gttagtgcgg cgcatcaaga caccgacga cgctccctc     780
ctccggcacg gcggcggcga gttcttcgcc gagttcttga acgtcgagag gaggaatcac     840
cccaccatcg tcaagacgag ggtgtcagct gtgatgacca cgcaccgat catgctgaac     900
atggactgcg acatgtttgt gaacaatccc caggccgtcc tccatgcgat gtgcctgctg     960
ctggggttcg acgacgaggc cagcagcggg ttcgtccagg cgccgcagag attctacgac    1020
gccctcaagg acgatccatt tgggaaccag atggagtgtt ttttcaagag atttatcagt    1080
ggggttcaag gagttcaggg tgccttttat gctggaaccg gctgcttca ccgtaggaaa     1140
gcagtttatg gcgtgccacc gaacttcaat ggagccgaga gagaagatac cataggttca    1200
tcgtcttata aggagcttca taccaggttt ggaaactcag aggaattgaa cgaatcagca    1260
agaaacatca tttgggatct gtcctctaag ccaatggttg atatatcaag tcgcattgaa    1320
gtggcaaaag cagtttcagc ttgcaactat gatattggca catgttgggg acaggaggtt    1380
ggttgggtct atggatcact aacagaagac atattgaccg gacagcggat acacgcgatg    1440
ggttggagat ccgtattgat ggtaaccgaa ccacccgcat tcatgggctc cgcgccgatt    1500
ggaggaccag cctgcctaac tcagttcaag agatgggcaa ctggccaatc tgagataatc    1560
atcagccgga caacccaat tctcgcaacc atgttcaagc gcctcaaatt ccggcaatgt    1620
cttgcctacc tgatcgtcct tgggtggcct ctgagagcgc ttttgagct atgctatgga    1680
ttgtgggac ttattgcat actcacaaac caatccttct tgccaaaggc atcagaagat    1740
ggtttcagcg tccccgttagc cctattcata tcctataaca catacaactt catggagtac    1800
atggcgtgcg ggctctccgc ccgtgcatgg tggaacaatc ataggatgca acggatcatc    1860
tcggtctctg cctggacact agcatttctt accgtgctcc tcaagtcctt aggcctctcc    1920
gaaactgttt ttgaggtcac cggcaaggac aaaagcatgt ctgatgacga tgacaacacc    1980
gatggtgctg accctgggag gttcaccttc gactcattgc cggtgttcat ccccgtgacg    2040
gcacttgcga tgttaaacat cgttgcggtc actgtcggag catgtagggt agctttcggg    2100
acagcggaag gtgtgccctg tgccccgggt atcggcgaat tcatgtgttg tgggtggctg    2160
gtgctgtgct tcttcccgtt tgtaagaggg atagtgtggg gcaagggaag ctatgggatc    2220
ccttggagtg tcaagctgaa ggctagctta cttgtggcta tgtttgttac cttctgcaaa    2280
agaaactaa                                                            2289
```

```
<210> SEQ ID NO 6
<211> LENGTH: 762
<212> TYPE: PRT
<213> ORGANISM: Oryza sativa

<400> SEQUENCE: 6

Met Ala Val Val Ala Ala Ala Ala Thr Gly Ser Thr Thr Arg Ser
1               5                   10                  15

Gly Gly Gly Gly Gly Glu Gly Thr Arg Ser Gly Arg Lys Lys Pro Pro
            20                  25                  30

Pro Pro Pro Leu Gln Glu Arg Val Pro Leu Gly Arg Arg Ala Ala Trp
        35                  40                  45

Ala Trp Arg Leu Ala Gly Leu Ala Val Leu Leu Leu Leu Ala Leu
    50                  55                  60

Leu Ala Leu Arg Leu Leu Arg His His Gly Gly Ala Gly Gly Asp Ala
65                  70                  75                  80

Gly Val Trp Arg Val Ala Leu Val Cys Glu Ala Trp Phe Ala Ala Leu
                85                  90                  95

Cys Ala Leu Asn Val Ser Ala Lys Trp Ser Pro Val Arg Phe Val Thr
            100                 105                 110

Arg Pro Glu Asn Leu Val Ala Glu Gly Arg Thr Pro Ser Thr Thr Ala
        115                 120                 125

Ala Glu Tyr Gly Glu Leu Pro Ala Val Asp Met Leu Val Thr Thr Ala
    130                 135                 140

Asp Pro Ala Leu Glu Pro Pro Leu Val Thr Val Asn Thr Val Leu Ser
145                 150                 155                 160

Leu Leu Ala Leu Asp Tyr Pro Arg Ala Gly Glu Arg Leu Ala Cys Tyr
                165                 170                 175

Val Ser Asp Asp Gly Cys Ser Pro Leu Thr Cys His Ala Leu Arg Glu
            180                 185                 190

Ala Ala Gly Phe Ala Ala Ala Trp Val Pro Phe Cys Arg Arg Tyr Gly
        195                 200                 205

Val Ala Val Arg Ala Pro Phe Arg Tyr Phe Ser Ser Ser Ser Ser Pro
    210                 215                 220

Glu Ser Gly Gly Pro Ala Asp Arg Lys Phe Leu Asp Asp Trp Thr Phe
225                 230                 235                 240

Met Lys Asp Glu Tyr Asp Lys Leu Val Arg Arg Ile Lys Asn Thr Asp
                245                 250                 255

Glu Arg Ser Leu Leu Arg His Gly Gly Gly Phe Phe Ala Glu Phe
        260                 265                 270

Leu Asn Val Glu Arg Arg Asn His Pro Thr Ile Val Lys Thr Arg Val
    275                 280                 285

Ser Ala Val Met Thr Asn Ala Pro Ile Met Leu Asn Met Asp Cys Asp
290                 295                 300

Met Phe Val Asn Asn Pro Gln Ala Val Leu His Ala Met Cys Leu Leu
305                 310                 315                 320

Leu Gly Phe Asp Asp Glu Ala Ser Ser Gly Phe Val Gln Ala Pro Gln
                325                 330                 335

Arg Phe Tyr Asp Ala Leu Lys Asp Asp Pro Phe Gly Asn Gln Met Glu
            340                 345                 350

Cys Phe Phe Lys Arg Phe Ile Ser Gly Val Gln Gly Val Gln Gly Ala
        355                 360                 365

Phe Tyr Ala Gly Thr Gly Cys Phe His Arg Arg Lys Ala Val Tyr Gly
    370                 375                 380
```

Val Pro Pro Asn Phe Asn Gly Ala Glu Arg Glu Asp Thr Ile Gly Ser
385                 390                 395                 400

Ser Ser Tyr Lys Glu Leu His Thr Arg Phe Gly Asn Ser Glu Glu Leu
            405                 410                 415

Asn Glu Ser Ala Arg Asn Ile Ile Trp Asp Leu Ser Ser Lys Pro Met
        420                 425                 430

Val Asp Ile Ser Ser Arg Ile Glu Val Ala Lys Ala Val Ser Ala Cys
            435                 440                 445

Asn Tyr Asp Ile Gly Thr Cys Trp Gly Gln Glu Val Gly Trp Val Tyr
450                 455                 460

Gly Ser Leu Thr Glu Asp Ile Leu Thr Gly Gln Arg Ile His Ala Met
465                 470                 475                 480

Gly Trp Arg Ser Val Leu Met Val Thr Glu Pro Pro Ala Phe Met Gly
                485                 490                 495

Ser Ala Pro Ile Gly Gly Pro Ala Cys Leu Thr Gln Phe Lys Arg Trp
            500                 505                 510

Ala Thr Gly Gln Ser Glu Ile Ile Ser Arg Asn Asn Pro Ile Leu
            515                 520                 525

Ala Thr Met Phe Lys Arg Leu Lys Phe Arg Gln Cys Leu Ala Tyr Leu
        530                 535                 540

Ile Val Leu Gly Trp Pro Leu Arg Ala Pro Phe Glu Leu Cys Tyr Gly
545                 550                 555                 560

Leu Leu Gly Pro Tyr Cys Ile Leu Thr Asn Gln Ser Phe Leu Pro Lys
                565                 570                 575

Ala Ser Glu Asp Gly Phe Ser Val Pro Leu Ala Leu Phe Ile Ser Tyr
            580                 585                 590

Asn Thr Tyr Asn Phe Met Glu Tyr Met Ala Cys Gly Leu Ser Ala Arg
        595                 600                 605

Ala Trp Trp Asn Asn His Arg Met Gln Arg Ile Ile Ser Val Ser Ala
610                 615                 620

Trp Thr Leu Ala Phe Leu Thr Val Leu Leu Lys Ser Leu Gly Leu Ser
625                 630                 635                 640

Glu Thr Val Phe Glu Val Thr Gly Lys Asp Lys Ser Met Ser Asp Asp
                645                 650                 655

Asp Asp Asn Thr Asp Gly Ala Asp Pro Gly Arg Phe Thr Phe Asp Ser
            660                 665                 670

Leu Pro Val Phe Ile Pro Val Thr Ala Leu Ala Met Leu Asn Ile Val
            675                 680                 685

Ala Val Thr Val Gly Ala Cys Arg Val Ala Phe Gly Thr Ala Glu Gly
        690                 695                 700

Val Pro Cys Ala Pro Gly Ile Gly Glu Phe Met Cys Cys Gly Trp Leu
705                 710                 715                 720

Val Leu Cys Phe Phe Pro Phe Val Arg Gly Ile Val Trp Gly Lys Gly
                725                 730                 735

Ser Tyr Gly Ile Pro Trp Ser Val Lys Leu Lys Ala Ser Leu Leu Val
            740                 745                 750

Ala Met Phe Val Thr Phe Cys Lys Arg Asn
            755                 760

<210> SEQ ID NO 7
<211> LENGTH: 2379
<212> TYPE: DNA
<213> ORGANISM: Oryza sativa

<400> SEQUENCE: 7

```
atggcggcgg cgagcggcga aaggaggag gaggagaaga agctgcagga gagggcgccg      60
atccggcgca cggcgtggat gctggccaat ttcgtcgtac tcttcctcct cctcgccctc    120
ctcgtccgcc gcgccaccgc cgccgacgcc gaggagcgcg gcgtcggcgg cgcggcgtgg    180
cgcgtggcgt tcgcctgcga ggcgtggttc gcgttcgtgt ggctgctcaa catgaacgcc    240
aagtggagcc ccgccggtt cgacacctac ccggagaacc tcgccggaag gtgtggcgcc    300
gcccatcgtc ctagaaagtc gtcgtgcatc tccggccatc tcgatctcat gcggagacag    360
tgtgctttga tgcaggatcg acgagctgcc ggcggtcgac atgttcgtga cgacggcgga    420
cccggcgctc gagccgccgg tggtgacggt gaacaaggtg ctctcgctgc tcgccgtcga    480
ctactacccg ggcggcggcg cgcgcggcgg cggcgaaggc tggcctgcta cgtctctgac    540
gacgggtgct cgccggtgac gtactacgcg ctgcgggagg ccgccgggtt cgcgaggacg    600
tgggtgccct tctgccggcg gcacggcgtc gccgtcaggg cccccttccg gtacttcgcc    660
tccgcgccgg agttcggccc ggccgaccgg aagttcttag acgattggac attcatgaag    720
agtgagtacg acaagctagt ccgtcggatc gaggacgccg acgagaccac ccttctgcgg    780
caaggcggcg cgagttcgc cgagttcatg acgccaaga ggacgaacca ccgcgccatt     840
gtcaaggtta tatgggataa taacagcaag aacaggatag gcgaagaagg agggttcccg    900
catctcatat acgtctcaag ggagaagagc cccggacacc accatcacta caaggccggc    960
gccatgaacg ccctgacgag ggtgtcagcc gtgatgacca acgcaccgat catgctgaac   1020
gtggactgcg acatgttcgc gaacgatccc caggtcgtcc tccacgcgat gtgcctgctg   1080
ctggggttcg acgacgagat ctccagcggg ttcgttcagg tgccgcagag tttctacggc   1140
gacctcaagg acgatccttt cgggaacaag ctggaggtta tttacaaggg cttattttat   1200
ggtggaacgg gttgcttcca ctgtagaaaa gccatttacg gcatcgaacc agactccatt   1260
gtggtaggaa gagagggcgc cgcaggttcg ccatcttaca aggagcttca gttcaagttt   1320
gaaagttcag aggagttgaa ggaatcagct cggtacatca tttctgggga tatgtccggt   1380
gagccaatag tagatatatc aagtcacatt gaggttgcaa aagaagtttc ttcctgcaac   1440
tatgagagtg gcacacattg gggtctggag gttggttggg cctatggatc aatgaccgaa   1500
gacattttga ctgggcagcg gatccatgca gcaggttgga gatctgcaaa gttggaaacc   1560
gaaccaccag cattcttggg ctgcgcacca acgggtggac cagcttgcct aacccagttc   1620
aagagatggg caacgggttt gtttgagata ctcataagcc agaataaccc actccttctg   1680
agcatattca agcatctcca attccgacaa tgccttgcgt acctgactct ttatgtgtgg   1740
gctgtgaggg gatttgttga gctatgctat gaattgttgg ttccttattg cctactcaca   1800
aatcaatcct tcttgtcaaa ggcatcagaa aattgtttca acatcacatt agcactattc   1860
ttgacctata atacatacaa cttcgtggag tacatggaat gtgggctctc tgtacgtgcc   1920
tggtggaaca accacagaat gcaacggatc atttcagcct ctgcatggct actagcattt   1980
tttactgtgc tcctcaagac cataggcctc tccgagactg tgttcgaggt cacccgtaag   2040
gagaagagca catcggatgg caatggccaa aacgatgagg ttgaccccgga gagattcacc   2100
tttgacgcat caccagtgtt catccccgtt acggcgctga caatgttgaa cattgttgca   2160
atcacaattg gtacatggag ggcagttttt ggacaacag aagacgtgcc tggtggtccg    2220
ggtataagtg aattcatgtc ttgtggatgg ctgctactgt gcttattgcc atttgtgaga   2280
gggctagtgg gcaagggaag ctatggtatc ccatggagtg tcaagctgaa ggctagtttg   2340
ctggtggcct tgttcctgtt ctgctccaat agaaattag                           2379
```

<210> SEQ ID NO 8
<211> LENGTH: 792
<212> TYPE: PRT
<213> ORGANISM: Oryza sativa

<400> SEQUENCE: 8

Met Ala Ala Ala Ser Gly Glu Lys Glu Glu Glu Lys Lys Leu Gln
1               5                   10                  15

Glu Arg Ala Pro Ile Arg Arg Thr Ala Trp Met Leu Ala Asn Phe Val
            20                  25                  30

Val Leu Phe Leu Leu Leu Ala Leu Leu Val Arg Arg Ala Thr Ala Ala
            35                  40                  45

Asp Ala Glu Glu Arg Gly Val Gly Gly Ala Ala Trp Arg Val Ala Phe
50                  55                  60

Ala Cys Glu Ala Trp Phe Ala Phe Val Trp Leu Leu Asn Met Asn Ala
65                  70                  75                  80

Lys Trp Ser Pro Ala Arg Phe Asp Thr Tyr Pro Glu Asn Leu Ala Gly
                85                  90                  95

Arg Cys Gly Ala Ala His Arg Pro Arg Lys Ser Ser Cys Ile Ser Gly
            100                 105                 110

His Leu Asp Leu Met Arg Arg Gln Cys Ala Leu Met Gln Asp Arg Arg
        115                 120                 125

Ala Ala Gly Gly Arg His Val Arg Asp Asp Gly Pro Gly Ala Arg
    130                 135                 140

Ala Ala Gly Gly Asp Gly Glu Gln Gly Ala Leu Ala Ala Arg Arg Arg
145                 150                 155                 160

Leu Leu Pro Gly Arg Arg Arg Arg Arg Arg Arg Leu Ala Cys
                165                 170                 175

Tyr Val Ser Asp Asp Gly Cys Ser Pro Val Thr Tyr Tyr Ala Leu Arg
            180                 185                 190

Glu Ala Ala Gly Phe Ala Arg Thr Trp Val Pro Phe Cys Arg Arg His
        195                 200                 205

Gly Val Ala Val Arg Ala Pro Phe Arg Tyr Phe Ala Ser Ala Pro Glu
    210                 215                 220

Phe Gly Pro Ala Asp Arg Lys Phe Leu Asp Asp Trp Thr Phe Met Lys
225                 230                 235                 240

Ser Glu Tyr Asp Lys Leu Val Arg Arg Ile Glu Asp Ala Asp Glu Thr
                245                 250                 255

Thr Leu Leu Arg Gln Gly Gly Gly Glu Phe Ala Glu Phe Met Asp Ala
            260                 265                 270

Lys Arg Thr Asn His Arg Ala Ile Val Lys Val Ile Trp Asp Asn Asn
        275                 280                 285

Ser Lys Asn Arg Ile Gly Glu Glu Gly Gly Phe Pro His Leu Ile Tyr
    290                 295                 300

Val Ser Arg Glu Lys Ser Pro Gly His His His Tyr Lys Ala Gly
305                 310                 315                 320

Ala Met Asn Ala Leu Thr Arg Val Ser Ala Val Met Thr Asn Ala Pro
                325                 330                 335

Ile Met Leu Asn Val Asp Cys Asp Met Phe Ala Asn Asp Pro Gln Val
            340                 345                 350

Val Leu His Ala Met Cys Leu Leu Leu Gly Phe Asp Asp Glu Ile Ser
        355                 360                 365

Ser Gly Phe Val Gln Val Pro Gln Ser Phe Tyr Gly Asp Leu Lys Asp
    370                 375                 380

```
Asp Pro Phe Gly Asn Lys Leu Glu Val Ile Tyr Lys Gly Leu Phe Tyr
385                 390                 395                 400

Gly Gly Thr Gly Cys Phe His Cys Arg Lys Ala Ile Tyr Gly Ile Glu
                405                 410                 415

Pro Asp Ser Ile Val Val Gly Arg Gly Ala Ala Gly Ser Pro Ser
            420                 425                 430

Tyr Lys Glu Leu Gln Phe Lys Phe Glu Ser Glu Glu Leu Lys Glu
        435                 440                 445

Ser Ala Arg Tyr Ile Ile Ser Gly Asp Met Ser Gly Glu Pro Ile Val
    450                 455                 460

Asp Ile Ser Ser His Ile Glu Val Ala Lys Glu Val Ser Ser Cys Asn
465                 470                 475                 480

Tyr Glu Ser Gly Thr His Trp Gly Leu Glu Val Gly Trp Ala Tyr Gly
                485                 490                 495

Ser Met Thr Glu Asp Ile Leu Thr Gly Gln Arg Ile His Ala Ala Gly
                500                 505                 510

Trp Arg Ser Ala Lys Leu Glu Thr Glu Pro Ala Phe Leu Gly Cys
        515                 520                 525

Ala Pro Thr Gly Gly Pro Ala Cys Leu Thr Gln Phe Lys Arg Trp Ala
    530                 535                 540

Thr Gly Leu Phe Glu Ile Leu Ile Ser Gln Asn Asn Pro Leu Leu Leu
545                 550                 555                 560

Ser Ile Phe Lys His Leu Gln Phe Arg Gln Cys Leu Ala Tyr Leu Thr
                565                 570                 575

Leu Tyr Val Trp Ala Val Arg Gly Phe Val Glu Leu Cys Tyr Glu Leu
                580                 585                 590

Leu Val Pro Tyr Cys Leu Leu Thr Asn Gln Ser Phe Leu Ser Lys Ala
            595                 600                 605

Ser Glu Asn Cys Phe Asn Ile Thr Leu Ala Leu Phe Leu Thr Tyr Asn
    610                 615                 620

Thr Tyr Asn Phe Val Glu Tyr Met Glu Cys Gly Leu Ser Val Arg Ala
625                 630                 635                 640

Trp Trp Asn Asn His Arg Met Gln Arg Ile Ile Ser Ala Ser Ala Trp
                645                 650                 655

Leu Leu Ala Phe Phe Thr Val Leu Leu Lys Thr Ile Gly Leu Ser Glu
                660                 665                 670

Thr Val Phe Glu Val Thr Arg Lys Glu Lys Ser Thr Ser Asp Gly Asn
            675                 680                 685

Gly Gln Asn Asp Glu Val Asp Pro Glu Arg Phe Thr Phe Asp Ala Ser
    690                 695                 700

Pro Val Phe Ile Pro Val Thr Ala Leu Thr Met Leu Asn Ile Val Ala
705                 710                 715                 720

Ile Thr Ile Gly Thr Trp Arg Ala Val Phe Gly Thr Thr Glu Asp Val
                725                 730                 735

Pro Gly Gly Pro Gly Ile Ser Glu Phe Met Ser Cys Gly Trp Leu Leu
            740                 745                 750

Leu Cys Leu Leu Pro Phe Val Arg Gly Leu Val Gly Lys Gly Ser Tyr
        755                 760                 765

Gly Ile Pro Trp Ser Val Lys Leu Lys Ala Ser Leu Leu Val Ala Leu
    770                 775                 780

Phe Leu Phe Cys Ser Asn Arg Asn
785                 790
```

<210> SEQ ID NO 9
<211> LENGTH: 3927
<212> TYPE: DNA
<213> ORGANISM: Hordeum vulgare

<400> SEQUENCE: 9

| | | | | | |
|---|---|---|---|---|---|
| ggtcaattcc | tgtctaaaga | gtagcagacc | tagcaggtta | tcccagtcag | gattgtagta | 60 |
| ttgccagaat | tcgggtgggc | caaacgggtc | tagggttcaa | aatagaccgg | gattacaaat | 120 |
| tcagagtgcc | aatttcaggg | attcaaagtt | caggatttga | tttagctttc | gtctataact | 180 |
| ttagggtttg | ttttgaactt | ttttcgtgca | gtggacggct | cgcataacgt | tgtgccgagc | 240 |
| gtttgtgtaa | caaaaacagt | cgctggcgac | ttggcgagct | cgttaggcgt | gacgtgcatg | 300 |
| ggtccaataa | tttaccgtgc | gtacgtgagt | gatatcgtca | aggataacgg | atccaaactg | 360 |
| gagtcctatt | ctccacacgc | catggttttg | catggatccg | gctgggtggc | acgctggacc | 420 |
| aagtgagcag | cgagcacaca | cttccgtagc | aaagagacaa | gagcaccatc | cctgtcccaa | 480 |
| agattatcat | acggtggcag | tggtacatgg | cagaaccaag | taaagataac | tttctcctgt | 540 |
| cctcccaccc | tccgagaccc | catcacaagt | catagtctag | ttttgttttt | gtcctgatcg | 600 |
| gaaatgcgcc | gaggagagga | gaggatagtt | ttatctggtc | catataaatg | cactcgagcg | 660 |
| gttgttgctt | gtggagctgt | gttcgtggag | cttagctagt | ctgctactgc | tactgctggc | 720 |
| tagtggctac | ctgctctcgg | ccacggccat | ggcgggcggc | aagaagctgc | aggagagggt | 780 |
| cgccctggcg | agaaccgcgt | ggatgctggc | cgacttcgcg | atcctcttcc | tcctcctcgc | 840 |
| catcgtggcc | cgccgcgccg | cctcgctccg | ggagcgcggc | gggacgtggt | tggcggcgct | 900 |
| cgtctgcgag | gcgtggttcg | ccttcgtgtg | gatcctcaac | atgaacggca | gtggagccc | 960 |
| cgtccggttc | gacacctacc | ccgacaacct | cgccaacagg | tactctacgt | acgtacccac | 1020 |
| ggcgacaaga | cccaccatgc | tgaccctac | aacttcctca | aattttgatc | tagctagtgt | 1080 |
| ctgtgataat | tttgctagga | tggaggagct | cccggcggtg | gacatgttcg | tcacgaccgc | 1140 |
| ggacccggcg | ctggagcctc | cgttgatcac | ggtgaacacg | gtgctctcgc | tgctcgccct | 1200 |
| ggactacccg | gacgtcggca | agctggcgt | ctacgtctct | gacgacggct | gctccccggt | 1260 |
| gacgtgctac | gcgctgcgtg | aggccgccaa | gttcgccggc | ctctgggtcc | ctttctgcaa | 1320 |
| gaggcacgac | gttgctgtga | gggccccatt | catgtacttc | tcttccacgc | cggaggttgg | 1380 |
| cacaggcaca | gccgaccacg | agttcctgga | aagctgggcg | ctcatgaagg | ttaggcgcca | 1440 |
| atggtgacca | tgtcagttta | caaaataatg | tttggtcgtc | catcatcgcc | atggccattc | 1500 |
| atcttcctcg | tgtacgtgtg | actttcagag | cgaatatgag | agactagcca | gccgaatcga | 1560 |
| gaacgccgat | gagggctcca | ttatgcgtga | cagcggcgac | gagttcgccg | agttcatcga | 1620 |
| cgccgagcgc | gggaaccatc | ctaccatcgt | taaggtcgcc | gcactgacca | tgtccatgca | 1680 |
| tgtgtccatg | aacatcgtgt | catgacaaac | gcatagcaaa | tccgtgtctc | gtgctaatat | 1740 |
| cgtcacggtt | aatttgggcc | gagttcaggt | tctgtgggat | aacagcaaga | gcaaagtggg | 1800 |
| ggaaggattc | ccacatctgg | tgtacctctc | tcgagagaaa | agcccagac | atcgccacaa | 1860 |
| cttccaggct | ggtgccatga | atgttctggt | gagcactctc | tttcgctcaa | cacagtgttg | 1920 |
| cactgctaat | cagtgtcaca | caagcagcac | accacatttt | atactaatta | agctgatcat | 1980 |
| ttcgtggtgc | agacaagggt | gtcagccgtg | atgaccaacg | ctcccatcat | gctgaatgtg | 2040 |
| gactgcgaca | tgttcgccaa | caatccgcag | gtcgccctac | acgcgatgtg | cctcctattg | 2100 |
| gggttcgacg | acgagatcca | cagcgggttc | gtccaagtgc | cacagaagtt | ctacggtggc | 2160 |
| ctcaaggacg | atcccttttgg | caaccagatg | caggttataa | ccaaggtact | acatatgcat | 2220 |

```
gtgcacaagt gctcttgtcg tcgtgctgtg caccactagg tagtgttaca gttgtactgg   2280 ttttgtggc atgttcagaa aattggaggt ggaatcgccg ggatccaagg catgttctac    2340
ggcggcacgg gctgttttca ccgcaggaaa gtcatttacg gcatgccgcc acctgacacc   2400
ctcaaacacg agacaagagg tgaaactggg cacacaacag atgtgatcat caggcgtaaa   2460
ttggagtatg catttcagtt cgactagggc atttcaaatg gctaagtgtt cttaatttgc   2520
caggttcacc atcttacaag gagctgcaag tcaggtttgg gagctcaaag gtgttgatcg   2580
aatcatctag gaacatcatc tcaggagacc tgctcgctag accaaccgtt gatgtatcga   2640
gtcgcatcga aatggcaaaa caagtcggcg attgcaacta tgaggctggc acgtgttggg   2700
gcaaggagat tggttgggtc tatggatcaa tgacagagga cattttgacc ggacaacgga   2760
tccatgcggc gggttggaaa tcggccttgt tggacaccaa cccaccggca ttcttgggat   2820
gtgctccgac cgggggaccg gccagcttga cccagttcaa gagatgggca acaggggttc   2880
tggagatact catcagccgg aacagcccta tcctcggcac catcttccaa cgcctccaac   2940
tccggcaatg ccttggctat ctcatcgtcg aggcgtggcc cgtgagggcg cctttcgagc   3000
tgtgctatgc actattggga cctttctgcc ttctcacaaa ccagtccttc ttgccaacgg   3060
tacatacact ttcgcggttc gccaagatac attatgcagc taaacaaaaa tgctgtgtga   3120
tttgtttgat aatgaagcag gacctagttg gctaatatgt atgtaaattc agatattttt   3180
tttatgattg gtacatttgt tgttttgcag gcatcggatg aaggttttcg catcccagta   3240
gctctattct tgagttacca catataccac ttgatggagt acaaggagtg cgggctctct   3300
gcccgcgcct ggtggaacaa ccacaggatg caacgcatca cctcggcctc cgcctggctc   3360
ctcgccttcc tcaccgtgat cctcaagaca ctagggctct ctgagaccgt gttcgaggtc   3420
acccgcaagg aaagcagcac gtccgatggc ggcgccggca ccgacgaggc cgatccagga   3480
ctgttcacat tcgactcggc gcccgttttc atcccggtga cggcgctctc agtgttgaac   3540
attgtggccc tcgccgtcgg ggcatggcgc gccgtcatcg ggactgcggc ggtcgttcat   3600
ggtgccccgg gcatcggaga gttcgtgtgc tgtggctgga tggtgttgtg cttctggccg   3660
ttcgtgagag ggcttgtcag caggggaaag catggaatcc cgtggagcgt caaagtgaag   3720
gctggtttga ttgtggctgc gttcgtgcac ctctgcacaa ggaactaacc ggccgggctg   3780
gccatcgaaa tattggaagc gtaattttag ttctaccatt ggaacatgta acgaagactc   3840
aagcaggaat taaagcgtgt tattaaagga agtttgaccc aatgtatcta tctatctctc   3900
ccaatctctc tcaataataa agcaaat                                       3927

<210> SEQ ID NO 10
<211> LENGTH: 8900
<212> TYPE: DNA
<213> ORGANISM: Oryza sativa

<400> SEQUENCE: 10
atgacttagt gacgatatga tcggtcgatc tggtgttatg cgttagtggg gaagagagtg    60
gaaggaagaa aacatgaaga aggttaacat catagcatca gaattctttg tgtaatctgg   120
tctatctaaa agtgacttaa atgtgtgaat aattttacat tcgctcccct tgtcgtagaa   180
aaaaaaatca tatcccaata aaaagacagg gagaaggaca taagactaaa atatccctca   240
ttactactac tttggtccct aaaacaaata atcttttact ggtaggtact aagcggcatt   300
aaatagatta aatttctttg atttgtacaa caaaaacagc tataggaggg taggaattaa   360
tatatttttt tagataaagt ttttatcttt ggaagttata atttattttg ggatggggag   420
```

```
ggagacaact acagtgtttc gtttggatcg ttctgtctgt tatgcccgtg atcttttcag    480
ttcagaactt cagagagcga taaaactgtg ggggcaagtg ctctggcgcc ggcaataatg    540
gaggcggcgg ctagaggcaa caagaagctg caggagaggg tgcccatccg gcgcaccgcg    600
tggaggctcg ccgacctcgc catcctcttc ctcctcctcg ccctcctcct ccaccgcgtc    660
ctccacgaca gcggcgcgcc atggcggcgc gccgcgctcg cctgcgaggc gtggttcacc    720
ttcatgtggc tgctcaacgt gaacgccaag tggagccccg tccgtttcga cacgttcccg    780
gagaacctcg ccgaaaggta aggtgcccaa gaattaatca ggaatgattc aagccaacat    840
ccagaaaaaa gaagatgatt ctgacgagct ggttggtttt gcatctcttt cttgttgtta    900
ggatcgacga gctcccggcg gtggacatgt tcgtgacgac ggcggacccg gtgctggagc    960
cgccgctggt gaccgtgaac acggtgctgt cgctgctcgc cctcgactac ccggccgccg   1020
gcgagaagct ggcgtgctac gtctccgacg acgggtgctc gccgctgacg tgctacgcgc   1080
tgcgggaggc cgcccggttc gccaggacgt gggtgccctt ctgccggcgg cacggcgtcg   1140
ccgtcagggc gcccttccgg tacttctcct ccacgccgga gttcggcccg gcggatggca   1200
agttcttgga ggactggaca ttcatgaagg ttagctatgg caaccgcaac acctctcagt   1260
ttctttctct ctctttttttt tttccatttt ggaagtacta acgaatttaa aaatataagg   1320
aaacatgata accacaacac gtctcagttt cttctctctt ttttaatcca ttttggaagt   1380
actaacaaat ttaaaaatat aaggaaaaca tgataaccac agcacgtctc agtttctttc   1440
ctttttttt tccaatttgg aagtactaac aaatttaaaa atataaggaa acatgatttg   1500
actcgtgctc taaattaaaa tcgattagat gaaatccggg ataccgatat ttaagtcagt   1560
cttataaaag aagcgtcgaa tgggtaggat accgtcaagt gattaatcct aatatggatt   1620
attagtcaga attatacgga atttcaacgt tcataaaaca aataaatata tttgcttggc   1680
cgtccacctt gggtgatatt taagcacatt agtaccctta agtactttaa aatatttaat   1740
ttaaagtttc taaaacaaca tgtacagatt tattttacaa agtgtaaaaa tgtatttatt   1800
tattatatat tataataaaa ataattaaat atatatttttt gagatcgttc gtaacttcaa   1860
taattatgta accgggaggg agtacgtaaa ccggtcatat tgccagagtt aaatcgtcga   1920
ttgatctaga attgaatgcc attgccatat atgctcagtg taacgagctt tagttcggct   1980
gctgctggag tcaattagta gatcggacga ttagtcgcga atcagcctga ttaattgggc   2040
cagcccggcc attttggcgt ccacgtcgcc acaactcgtc acgaatggca gagtcgtatc   2100
ggtttgtctt ccgtgtacca ctgtaccagt acagttggcc ttataatcga ttggaacggc   2160
cgtcattttc cacacttttt cgtaagcaga aatgcagcgt ttcgatatgt cttctttagc   2220
tattctgtga gcttccttgt ttagccaaac cagtgttaac cacccttgcc tctgaggagg   2280
agtttagtat cttttagctg ctgctcctta aatacacata tctcgttgct agtagggatt   2340
aatttattaa tgttccactg caaaatttcc aaaatttccg aaattccagg tctactggtc   2400
cctgatagaa tattatgttg gcaaaagaaa tagttttta attacacata tcttatttaa   2460
gtttaatcaa aatttgttca aatttcaact tatttcggtc tgaaattttg acaatttcct   2520
gaaatttgtt tctatcggtt ccccggtaga aatatatgca aaccggtatg tagaaccgtg   2580
gttacaggat gcacgctttt atcttggagt ccaaaacagc acaagcgaaa ggaagggcct   2640
attcagattg atggcatttt caactatacc gttatttggt aaaatgtata attatgtggc   2700
tacgtttagt ttgtaaccaa atattggcaa tgtgtataga attttggcaa tactattaag   2760
ccaatcctac caaaatttgg gcaacgttgc caatttatca aaatttagc attgccaaat   2820
```

```
tttgataagg tttatttttgg catcaatctg aatggacccg aagttatcat tgagtagtca    2880
tggttcctga tcttaattcg ttcatggcca tcttgtttat gtgcaaacat ttcagagcga    2940
gtatgagaag ttggtccacc ggatcgagga cgccgatgag ccttcccttc tgcggcacgg    3000
cggtggtgag ttcgcagagt ttctggatgt tgagaggggg aaccacccta ctatcataaa    3060
ggtatcgatc cccacctgac tatataaaaa ctttcaaata tggattctgg tccctccaac    3120
tccaaagtgt gtcccttgca cagagtttct caactcattt ctcaccatga ccctgaactt    3180
ctgtgcttaa cttggtttgg ttctctgctg gatgatttag gttctgtggg ataacaacag    3240
gagcaggaca ggagatggct tccctcgtct gatatacgtc tcaagggaga agagccccaa    3300
cctacaccat cactacaagg ctggcgccat gaatgccctg gtcagtgcta catagctctt    3360
tttgttacta gagaaatttt acggttattg agagagtata tgtagatacc gaaattttgc    3420
aacacaaatt ttaatacatc gaggtactaa gttttacacc agaaaatatg gtacctctcg    3480
gtacactatt tgttactaaa caacatggaa agttcagaca atgtttgtta ctcaccaaca    3540
cggcaagttc agacactgtt tgtgttactc atgattgggg aagttcagat atttgattgt    3600
tcttaccatg atttttttgtc agacaagggt gtcagcactg atgaccaacg ccccattcat    3660
gctaaaccta gactgcgaca tgtttgtaaa caacccccgg gtcgtcctcc atgccatgtg    3720
ccttctgtta ggttttgacg atgagatcag ctgcgcgttt gttcagacgc cgcagaaatt    3780
ctacggtgcc ttgaaggatg atcctttcgg gaaccagctg gaagttagtt tgatggtaca    3840
caactagctc ttgcttgtac gataatttat ttaatttagt tgatgatcca actaaactag    3900
gttgatgatc ttgtgtgatt ttcagaaagt tggacgtggg attgcagggc ttcagggcat    3960
attttattgt ggaacaggct gctttcaccg cagaaaagtc atttacggca tgaggacagg    4020
gcgagaaggc accacaggtg aaattgggca aacactgatg tgattgtcat acattagggc    4080
tccatttggt attgcggtag atcataataa tcacgtttgc tgcaaatgtt ttttgacgtt    4140
tggcagttgg ccaaccgctt ttcttttttaa ttatctacgt tagaaatgat aataattata    4200
attatctaat cataatttgg tatgtaaaca caaacaacaa caattattag tattagttttt    4260 catgtcagcc taaactagta agagaattca aatttaattc ttcaggttat tcatctaaca    4320
aggagctcca tagtaaattc ggaagttcaa ataattttaa ggaatcagcc agggatgtca    4380
tttatgggaa cttgtcaaca gagccaatag tagatatatc aagttgcgtt gatgttgcca    4440
aagaagtagc tgcctgcaac tacgagattg cacatgttg gggtcaggag gtacagccat    4500
tgccacatgt ctataggatg ttactatgca gtttaattta ctattctata tgtttcataa    4560
atgtcattcc atatattcac aggttggttg ggtctatgga tcactgacag aagacgtgtt    4620
gaccggacaa cggatccatg cagcgggttg gagatccacg ctgatggaaa tcgaaccacc    4680
agcattcatg ggttgtgcac caaatggagg gcccgcctgc ctaacccagt tgaagagatg    4740
ggcatcaggt ttttagaaa tactcatcag tcggaataac ccaatcctca caaccacatt    4800
taagagtctc caattccgac aatgccttgc atacctgcac agctatgtgt ggcctgtgag    4860
ggcacctttc gaattgtgct atgcattgtt ggggccttat tgcttactat caaaccaatc    4920
cttcttgcca aggtactac tgcatcacta accaatgcat cggttataat cttctgtact    4980
ctccttgcct tcttaacaca gtgttgcacc tcatttgcat attcaaagat aaaaaaatct    5040
ttccaattga atggctagag agtgaggtat atatgaacta ttaactctac tattgcagac    5100
atcagaagac ggtttctaca tcgcattagc tctattcatt gcctataaca catacatgtt    5160
catggagttc atagagtgtg ggcagtctgc acgtgcatgt tggaacaacc acaggatgca    5220
```

```
acggatcacc tcagcttctg cttggctact ggcatttctt accgtcatcc tcaagacctt    5280
aggcttctcc gagactgtgt tcgaggtcac ccgcaaagac aagagcacat cagatggtga    5340
ttccaacacc gatgagcctg agccagggag gttcaccttc gacgaatcga cggtgttcat    5400
tcccgtgaca gcacttgcaa tgttaagtgt cattgcaatc gctgtaggag catggagggt    5460
ggttttggtg acaacggaag gcttgcccgg tggccctggt atcagtgaat tcatctcctg    5520
tgggtggctg gtgctgtgct tcatgccatt gctgagaggt ctagtgggaa gtggtcgata    5580
tggcattcct tggagtatca agatgaaggc ctgcttgctt gttgctatat tcttgctctt    5640
ctgcaaaaga aattaattgc agctggtgtg cagcaacaat tagtccatac tattatttga    5700
gcatgcaaac actaggtttc atcttcatat tattatgtcc gcaaacgttg actaagctct    5760
agaaaaggga acaattcaat cactaattcg aagcaaaaac tggttgttta ctgtaagaga    5820
gaatctactc gtccatggca agttgtccca ccggtgcaaa cttgatctta gtggcatata    5880
tatagtagat ttcctcttat tgtacggcct gtatgcatgc atgaatcctt caaagtagaa    5940
gcattggagc ggtcccgtgc aaatttattt tcttggatgg atctactatt ataaaaattg    6000
aagatgtttt tgctgatact ttgatacgtc atccgtgttt gaatcggttg taattttatg    6060
ttttattttt aatctctatc tctacctaaa aagaacaaga aatttccata atcggtaaaa    6120
aggaaaaaaa gtccgactaa aaaggtaaaa aaagggaaaa aaaagtccga ctcaaaaacc    6180
gataaaaaaa acttctgtcg tgaaaaaaat tgtccgactc aggtaaaaaa aggtctcgcc    6240
agtaaaaaaa gacaagaaaa agtccctttt tttttcatcg gtgacttttt tcacgcgaaa    6300
tagttttacc gtacgcacgc gctattggtt tttcgtctg gttttttaaa tccgatctgt     6360
tcaccacgca tctccctggt gcttttggtt ttttcatcaa tttttttatc accgggtttt    6420
tatcccatgc gttttttggtt tttcttgtac gattttttaa tccgatttat tcgtggcacg    6480
tctaccgagt tgaaccttgg cgtcacgctg gcgccatatt aatcgtgcgt ttttacttca    6540
atttgattgc aaaaagaaat cgattcccac tcatccctcg tcattttctc catgattttc    6600
tgggctttat ttcgccggat ttaatctaat ggttgccgat gatgacagcg atcttcccca    6660
attgttttta tcctgagttt tacgctctga ttttgggtaa acaaccaat tttgggtgat      6720 taagaaagat tcgaccggat ttgatgggtc gaacgaaaca tgccaaatga gggaggtagc    6780
ggaccagcct agggctgaaa actgcttcac tcgtggctgg gtggaaacaa gaaggccaaa    6840
cggagggagg tagcgaactg gcataggatt gaaatgtaag gaaggctttt ggcccaaaac    6900
tcaagaaaga ttttgggaag gaatcgggcg gcgccgggca aaggagggag ggaaggggag    6960
cttcacgggg tggcggtgga ttgggaaggc cggcgcggcg gtgtggagaa gaggaggccg    7020
gcggcggtgg ggatagagag gatggccagc gaaggtgggg atggagagga tggaccggcg    7080
tggtggggaa gggcgacacg aggagaggct gccgcgggcg acgccggcgc agccgtgctc    7140
ggctgagcgt cggccgactc cgcgtggcgg taggaatgga gaggagggga aaggttcgac    7200
acggtgggga gctcaatccg gggacgccgg catgctgcga tggacaggag tcggtggaga    7260
ggggatagag actcgctcgc ctgccggctg ccacttgccc cgctccatcg gtcgggagag    7320
gagaggggat agagagaaga ggggagaaag agaggaggaa gaagaggagg gtgagatgga    7380
tgacatatgg ggcccacgtg ggtcccacca ttttttttatt attttctgtg tgagactaac    7440
ttgtggggcc catgtgggtc ccaccacttt tttattattt tttgtgtgag attgatatgt    7500
gggtcccgca gattttatta ttttttccagc tcgaattacc acgtaagtgc cacgtcaatg    7560
ccacgttaga tgaagaccga gtcaaattag ccacgttggc gccacgtcag tcaaaaccgc    7620
```

| | |
|---|---|
| cctcaaaacc gtcgagggac ctaatctgca ccggttttga tagttgaggg acccgttgtg | 7680 |
| tctggttttc cggttgaggg atgaaatcgg atttgttgac aagttaaggg acctcagatg | 7740 |
| aacttattcc tctgggtagc gacgcagggg acttgggaga ggcccacgag ccagccacat | 7800 |
| cggaacaagc aggggacacc gtagcacctg agcccagcga agaggtctcc acctctgtcg | 7860 |
| gctgggagag aaataagttc actttaggtc ccttaattta tcgtcgagtt tgaaattcat | 7920 |
| ccctaaacca aaatacgata taactcatcc cccaatttat aataacgtat caactttgat | 7980 |
| cctggcggta tagcgccgc ttttggctga tatggtgagt gggacctacc tgggctccac | 8040 |
| atgtcagcgg acggagttag gggcggtgct tgtcttcctc ttctctagcg cggtggacgg | 8100 |
| cggggcaggg acggcgctcg gccttcctct tctctagcag cgaacggcgg gggtaggtg | 8160 |
| gactgtggcg gatgttgcac gatcttctct atatcaccag cccatcccgc gactccgcct | 8220 |
| tcgaggcttc aacttgtccg acaacaacgt agttaaattc atcctcacca cgtggttccc | 8280 |
| cttcggcgcc agcagcaatg cgtcgcagcc ggtgacgcag tccgtggtgt ggttcgcgaa | 8340 |
| gcagtcgttg tccggcgaga caaccgttgg cactatgcat tccgtgctca cgtcacggt | 8400 |
| agacggccag ctcgcgctca ccgaagtaga tggccgcatg ctatggcggg caccggtctc | 8460 |
| ccggctgatg cgcggctcca tcctcgtgct ccgtgactct gatagcctcc ggccggttcg | 8520 |
| tcggtgacgc cagctgaagg atcgaacaac aagaactaag ccaaccaaat gggggtgaat | 8580 |
| ggttgtagta tacatacata ttatacatac atcctagtta tattattact taactaatac | 8640 |
| cctctttccg atgccctcct ggtgcttcga gaagccaccc ttgattgccg agttccttac | 8700 |
| aacaatccgt catgaccatc caactgtggc taaatacgga ggagtacccg ccccaggaaa | 8760 |
| ttaacttagt actatataca cgcgcggagg aatacccgta ctgagccatc accatcagcg | 8820 |
| gcccacctcg cttctgcagc atataacctc aaataatgat atgtagtaat ctaaacacca | 8880 |
| tgcttaaatt accaaatgct | 8900 |

<210> SEQ ID NO 11
<211> LENGTH: 4620
<212> TYPE: DNA
<213> ORGANISM: Oryza sativa

<400> SEQUENCE: 11

| | |
|---|---|
| ggcttccgtc attcataggc atccgatgga ttgggctaac tgagccaccg aggaactttc | 60 |
| ggaattttt tagaattttg acggaaatta ccatacaaat acggttaccg acaaaacatt | 120 |
| cggaaaaacc tccatcccat ttccggaaga tattaccgtt tctatttcca ccaccgtcga | 180 |
| ttatcgttac tgactaaaac ggtcggtgca aaccggaaac agtagctgga aatctcaaca | 240 |
| aacaaagtta aggaccgacg acacactta ctggtgatag aataaacaca tgcatgttgg | 300 |
| aaaatagaag tgttgaagaa aacgatactc tcgtcgtgcc cccgcgatgc gtgcgtggag | 360 |
| tgaggagaag acaatgattt ttttttcgttt ttaatactat agtagataat aatgggagaa | 420 |
| accaagaaac gtactcgctc gctagctacg cctacgcgcg cgccgcggcg tgggcgcgcg | 480 |
| tgtgcggttg ccgcgtgcgt tgctcgctcg acgcatggct cgatcgcttc gtcgctcgat | 540 |
| cgatccgtca atggcggtgg tggcggcggc ggcggccacc ggttccacca ccagatcagg | 600 |
| cggcggcggc ggcgaggga cgaggtccgg gaggaagaag ccgccgccgc cgccgctgca | 660 |
| ggagagggtg ccctcggggc ggcgcggcg gtgggcgtgg cggctggccg ggcctcgcgt | 720 |
| cctcctcctc ctcctcgccc tcctcgccct ccggctgctt cgccaccacg gcggcgccgg | 780 |
| gggcgacggc ggcgtgtggc gcgtggcgct cgtgtgcgag gcgtggttcg cggcgctgtg | 840 |

```
cgcgctcaac gtgagcgcca agtggagccc cgtccggttc gtcacgcggc cggagaacct    900
cgtggcggag ggcaggacgc cgtcgacgac ggcggcggag tacggcgagc tgccggcggt    960
ggacatgctg gtgacgacgg cggacccggc gctggagccg ccgctggtga cggtgaacac   1020
ggtgctctcg ctgctcgccc tcgactaccc gcgcgccggc gagcggctgg cctgctacgt   1080
ctccgacgac gggtgctcgc cgctgacgtg ccacgcgctg cgggaggccg ccgggttcgc   1140
cgccgcgtgg gtgcccttct gccgccggta cggcgtcgcc gtcagggccc cgttccggta   1200
cttctcctcc tcctcctcgc cggagtccgg cggcccggcc gatcgcaagt tcttggacga   1260
ctggacattc atgaaggtca atcaactata cttggaaaag tcaatattct cgagtttctt   1320
acatgtcatc taaataatcc ggaacacagc gtcatgttcc gatgatctta tgtttatggc   1380
cattttcttg tttgatcaat tcatatata ggatgagtat gacaagttag tgcggcgcat    1440
caagaacacc gacgagcgct ccctcctccg gcacggcggc ggcgagttct cgccgagtt    1500 cttgaacgtc gagaggagga atcaccccac catcgtcaag gtcgatggca atagctagct   1560
cttcggcatt ttttacctc atcgtgatac atgaacttct ctgctcacta agccccgttc    1620
gaaattattg aagatgaaga ttaagtatga acatgcgaaa tgagaaagtt attactacat   1680
tgttaattga gttttaaata ttttaaactt aaaaaataga tttatctgat attttaaagc   1740
aatttcgata tagaaagttt tccagtttta aaaacatgct atatgggcat gtaaaacgag   1800
aaactcatta ctacattatt aattgagttt taattatttt aaacttaaaa aatggactta   1860
cctgatattt tagagcaatt ctgatataga aagttttcgc atgaaacaca ccgtttagcc   1920
gttttaaaaa atatgctaat gaaaaccgaa gtagaatctg cagtgacaaa gcattttttt   1980
ctctctctct ctgtgcagac gagggtgtca gctgtgatga ccaacgcacc gatcatgctg   2040
aacatggact gcgacatgtt tgtgaacaat ccccaggccg tcctccatgc gatgtgcctg   2100
ctgctggggt tcgacgacga ggccagcagc gggttcgtcc aggcgccgca gagattctac   2160
gacgccctca aggacgatcc atttgggaac cagatggagt gttttttcaa ggtacatagc   2220
tagtgtactg atgatcaatg ctagtagcta gtatttctgc cttcatctgt atgttggagt   2280
attaatctat cgatggttaa tgttctgatt gtttgaaatc aaccttttaa aataaacgtc   2340
aagaattata gaaccggagg gagtagctgt cgtgcttggc tgtacatttg cttatatatg   2400
gaaaatgagt tgtctgatca aatctgaatt tactatgcac aaaatgtttc ttcattaatc   2460
cgtatcccgt tctatgctgc ttattaaccc cactaatatt ccaaataagt taaactgatc   2520
ttgtgtcatg tttagagatt tatcagtggg gttcaaggag ttcagggtgc cttttatgct   2580
ggaaccggct gctttcaccg taggaaagca gtttatggcg tgccaccgaa cttcaatgga   2640
gccgagagag aagataccat aggtgaaatt gggcatacac tgatgtgatt gttaggagta   2700
catcaatcat gccatctcac acccttaaat tgagagacct ggcataattc ttcaggttca   2760
tcgtcttata aggagcttca taccaggttt ggaaactcag aggaattgaa cgaatcagca   2820
agaaacatca tttgggatct gtcctctaag ccaatggttg atatatcaag tcgcattgaa   2880
gtggcaaaag cagtttcagc ttgcaactat gatattggca catgttgggg acaggaggta   2940
aagacaactt ccattgccat attttttgtag gttatgctac agtgcagtac acttttctgc   3000
aagtctcata caattcatcc ctcatattct aatcaggttg gttgggtcta tggatcacta   3060
acagaagaca tattgaccgg acagcggata cacgcgatgg gttggagatc cgtattgatg   3120
gtaaccgaac cacccgcatt catgggctcc gcgccgattg gaggaccagc ctgcctaact   3180
cagttcaaga gatgggcaac tggccaatct gagataatca tcagccggaa caacccaatt   3240
```

```
ctcgcaacca tgttcaagcg cctcaaattc cggcaatgtc ttgcctacct gatcgtcctt    3300
gggtggcctc tgagagcgcc ttttgagcta tgctatggat tgttgggacc ttattgcata    3360
ctcacaaacc aatccttctt gccaaaggta atcatttgca tgccactcat taatacattc    3420
cttatatttt tcaagtactt ttcaattggt tggctagaga gtgatatgga tgaactatta    3480
tactcttggt atcctgtagg catcagaaga tggtttcagc gtcccgttag ccctattcat    3540
atcctataac acatacaact tcatggagta catggcgtgc gggctctccg cccgtgcatg    3600
gtggaacaat cataggatgc aacggatcat ctcggtctct gcctggacac tagcatttct    3660
taccgtgctc ctcaagtcct taggcctctc cgaaactgtt tttgaggtca ccggcaagga    3720
caaaagcatg tctgatgacg atgacaacac cgatggtgct gaccctggga ggttcacctt    3780
cgactcattg ccggtgttca tccccgtgac ggcacttgcg atgttaaaca tcgttgcggt    3840
cactgtcgga gcatgtaggg tagctttcgg gacagcggaa ggtgtgccct gtgcccgggg    3900
tatcggcgaa ttcatgtgtt gtgggtggct ggtgctgtgc ttcttcccgt ttgtaagagg    3960
gatagtgtgg ggcaagggaa gctatgggat cccttggagt gtcaagctga aggctagctt    4020
acttgtggct atgtttgtta ccttctgcaa aagaaactaa tttcaacatc taaccataga    4080
caagtaaatt ttaccccag ctcaatggta tgataggagc atgtatcata tgtatcaaga    4140
aacacctcat cattttccat cgctcccatc cgcgtcgctc ccgtcccagg ggcggcacgg    4200
acggcgcctc atcctcctcc gccgcctcct cccttctcct cccctttgcc tcgccaccgc    4260
ccgagcggcg cgtcggcaaa gccgaccggc cacaaggacg cgcgtggcgg ggccctctcc    4320
cctcctcgag gaagccagcg gcggggacac cggggctgct cgggagcggc ggtccgcggc    4380 gcggaggcg cgcgccgggg gttggcgtgg cggatccggc cacgccggag gcggatccgt    4440 ctccccggc agcggatctg gcccctccgt gtccagggcc gagcaacagc gagcggcggt    4500
cagcggcgcg ggaggcggcg ccgaggggtc gtcgcgcga atccggccac gccggaggtg    4560
gatccgcctc ccctggcggc ggatccggcc tccccgcatc caggggccaa gcgacggcga    4620
```

<210> SEQ ID NO 12
<211> LENGTH: 6540
<212> TYPE: DNA
<213> ORGANISM: Oryza sativa

<400> SEQUENCE: 12

```
tcttttttatt gttattaggt gataaaccat gaatattatt tatgtgtgac ttgttttttct      60 aaatctttta ataaattttt taaataagac gaacaattat acaatggaca tagaaagtcg     120
tcagaacata acttaaaata tgacggagga agggagtaag agataagggg atgtcgcagc     180
taatccatct ccctcagtaa ttactgctcg ttttctggtc atcggatcgc tacgttttag     240
agctaggcca gacgatgtga cgccatgcat gcaggccgtg cagatcgccc aagagaaat     300 taattattac tcgacatcga tgattgatct cggccggccg gccgttctct ctcgacgcga     360
cgtcgtcacg cggcggttca tcgacggcgc ccgtgggagac gcgacaaacg ccagcgatcg     420
agcaagagca accagagaaa cccatggctg ccattgatat ttgattgaag gtgctagcta     480
cgccggtata aatatggaga ggagagacgt gcagctctgc ttctagctcg acttctcgag     540
tggtgacgaa gctagttagc agtaacaatg gcggcggcga gcggcgagaa ggaggaggag     600
gagaagaagc tgcaggagag ggcgccgatc cggcgcacgg cgtggatgct ggccaatttc     660
gtcgtactct tcctcctcct cgccctcctc gtccgccgcg ccaccgccgc cgacgccgag     720
gagcgcggcg tcggcggcgc ggcgtggcgc gtggcgttcg cctgcgaggc gtggttcgcg     780
```

| | |
|---|---|
| ttcgtgtggc tgctcaacat gaacgccaag tggagcccg cccggttcga cacctacccg | 840 |
| gagaacctcg ccggaaggtg tggcgccgcc catcgtccta gaaagtcgtc gtgcatctcc | 900 |
| ggccatctcg atctcatgcg gagacagtgt gctttgatgc aggatcgacg agctgccggc | 960 |
| ggtcgacatg ttcgtgacga cggcggaccc ggcgctcgag ccgccggtgg tgacggtgaa | 1020 |
| caaggtgctc tcgctgctcg ccgtcgacta ctacccgggc ggcggcggcg ccggcggcgg | 1080 |
| cgaaggctgg cctgctacgt ctctgacgac gggtgctcgc cggtgacgta ctacgcgctg | 1140 |
| cgggaggccg ccgggttcgc gaggacgtgg gtgcccttct gccggcggca cggcgtcgcc | 1200 |
| gtcagggccc ccttccggta cttcgcctcc gcgccggagt tcggcccggc cgaccggaag | 1260 |
| ttcttagacg attggacatt catgaaggta aggctttatg ctatccctgg ataagtaaat | 1320 |
| actccccaaa gttttaggt tacaagacgt tttaacttta gttaaaatta aattgcttta | 1380 |
| agtttgacca gtttgttga aaaaaaaat agtaagagca agtataataa tgagctataa | 1440 |
| gtctactata agcttacgtg gaggagagag gtaacaaaaa aaaaatcaag agtattgatt | 1500 |
| ctaatacaag agctagctta acacaagttt caagataaat acattaaata tataagtgag | 1560 |
| agatagatag aggagaagaa aattataact aatcttatag ctaatctatt atatatatta | 1620 |
| gctttaagat ggactaatag tagaaagtga gctatactat tatccttgct ctaacatttt | 1680 |
| caacccaaaa caaatttatt aagaaaatat attcaattat tgatttgatt aaactaattt | 1740 |
| agtattataa atattgttat atttgtctat aaacttagtt aagcttgaaa tactttgact | 1800 |
| ttgaccaaag tcaagacgta ttataacctg aaatagaggg aaataaattt cacagaatcg | 1860 |
| aaggttatgg ggcatcctta atgcaaaacc cgggttttac aatttgtttc atgaaacctc | 1920 |
| aagttttagg ggcaaagtgt ttcatgaaac tcagctacaa gcttatatcg tctatccgac | 1980 |
| taatatattt atctatatta attgtataaa aatgtttgag atctttttta aaatacatat | 2040 |
| atatacacgt tatctgcttt atcatttatt attatcggtt atgattatgg tgagttttgt | 2100 |
| atgcggtgaa aagttgaaaa aacaattaaa ctagataaga gaaatgtgta ttttgagcca | 2160 |
| acaatgtgaa tttattaaaa aaacaataat gtaataatga aatatgagta tttacataaa | 2220 |
| tataggtttt tttttgaaat atcttactct aaaatatgag atttcttaaa acaaatcaca | 2280 |
| ataactgaag ttaatagata ccccaataac gtggggttct gtgaaattta ttctaaataa | 2340 |
| atttaggggc ggatcaggtt taattgagct agcccataac attatgggtc aagaatagag | 2400 |
| ctacgcgagg ccccaaggtc cagattcgtc cctgttggta tgctaggtgc acaactgtgc | 2460 |
| taactatttt tttagcgtat cacaacgtga tgtgctaaac aacgacatag tcactgggac | 2520 |
| actagtttga ctattaatta tcagttacta ttactaagta taaaacttat aaaagataca | 2580 |
| tacaagttaa tataacattt tgaaacttt attcaggaca aatctaatta accatacaac | 2640 |
| attcaaaagt agaaccgaaa cgttcaaata gaatttgacg gtcaaagttt aaacatatat | 2700 |
| tactacacga attcgaaaac aacacatatt atgaccagag tgagaacatg ctaacatcca | 2760 |
| aaatgacaaa ggagaaaaag aaataaccac agcttacaca gagaaatttt ataatttaac | 2820 |
| acttctttcg tttcccaatt atttttaattg atacttgtga gaataacatg tggggccatc | 2880 |
| tgagtaaatg aaaatgtcca aaatgttaaa taatcaaaac acattttaaa acgtgttaaa | 2940 |
| ttatcgaatc tctttagcac tttaatcttt aacggcatat tgattgtgta taattctaga | 3000 |
| gtgagtacga caagctagtc cgtcggatcg aggacgccga cgagaccacc cttctgcggc | 3060 |
| aaggcggcg cgagttcgcc gagttcatgg acgccaagag gacgaaccac cgcgccattg | 3120 |
| tcaaggtcga ttccccacat ggctagcttt caaactgatc atgtcagaac tacatcaaat | 3180 |

```
ctttcttgtc tctcatgaca tgaacttctc atatcgggga gatcatcatc aggttatatg   3240
ggataataac agcaagaaca ggataggcga agaaggaggg ttcccgcatc tcatatacgt   3300
ctcaagggag aagagccccg gacaccacca tcactacaag gccggcgcca tgaacgccct   3360
ggtactagct cgatcagtgc actgatatct actgttagct cgatcgacat gtaatgggag   3420
tcagattcag atcgagccca gagatgtgcg ttagtactga aaacatgtgt acatttctct   3480
ctcttgtgtg tgcagacgag ggtgtcagcc gtgatgacca acgcaccgat catgctgaac   3540
gtggactgcg acatgttcgc gaacgatccc caggtcgtcc tccacgcgat gtgcctgctg   3600
ctggggttcg acgacgagat ctccagcggg ttcgttcagg tgccgcagag tttctacggc   3660
gacctcaagg acgatccttt cgggaacaag ctggaggtta tttacaaggt acgtgcgtac   3720
acaagtggtt gtccgttata atacatctac cagtgtattc ctccctccgt ttcatattat   3780
aaactgcttt gattttttt cctcatcaat cttctttagt tttgaccaaa tttatagcta   3840 gaaaaaaat taacaatatc tataacatca aattacacta aattcatttc attatatata   3900
acattgaata tattttacaa atatgtttgt ttgccttaaa aagtattact atattttttc   3960
tataaatttg attaaactta aaaatatttt actaaaaaag tcaaagcgac ttgtcatatg   4020
aaacatatga agtacttcct ccgtttcaca atgtaagtca ttttagcatt ttccacattc   4080
atattgatgt ttaatgaatc tagatagata tatatgtcta gattcattaa cataaatatg   4140
aatgtggaaa atgctagaat gacttacatt gtgaataaac ggagggagta ctaattaatg   4200
ataacactta tccattctta tagtgaaagt ttgaaagtac atctttgtgt aacccaattg   4260
aaagtaacaa ttaaaactac actatatatc cacttctgaa tatagatgct agatttctat   4320
ctatagaaaa aaaactagac taattttgca gtacgtgtgt tcagaaactt ctaggcgggg   4380
ttgcagggat ttagggctta ttttatggtg aacgggttg cttccactgt agaaaagcca   4440
tttacggcat cgaaccagac tccattgtgg taggaagaga gggcgccgca ggtgaagttg   4500
gagcatacac agtgatgtga tggttatcac ttatcaggag aacattagtc ttatcattct   4560
agtagaacta aatcgcgaga cttttcaatt tgcttctcta ggttcgccat cttacaagga   4620
gcttcagttc aagtttgaaa gttcagagga gttgaaggaa tcagctcggt acatcatttc   4680
tggggatatg tccggtgagc caatagtaga tatatcaagt cacattgagg ttgcaaaaga   4740
agtttcttcc tgcaactatg agagtggcac acattggggt ctggaggtat agacaacttt   4800
catttgtcat attttttgtag gttatgctac aatgcactac acttttaaac aagcttcata   4860
gcaagtcatt ccatatatct acaggttggt tgggcctatg gatcaatgac cgaagacatt   4920
ttgactgggc agcggatcca tgcagcaggt tggagatctg caaagttgga aaccgaacca   4980
ccagcattct tgggctgcgc accaacgggt ggaccagctt gcctaaccca gttcaagaga   5040
tgggcaacgg gtttgtttga gatactcata agccagaata acccactcct tctgagcata   5100
ttcaagcatc tccaattccg acaatgcctt gcgtacctga ctctttatgt gtgggctgtg   5160
aggggatttg ttgagctatg ctatgaattg ttggttcctt attgcctact cacaaatcaa   5220
tccttcttgt caaaggtact ctctccatac ttatctttac attgcttata taattgtaag   5280
tattaattag tttttgtagt acaaatattt gtagaacttt tacatattca tgaacaattc   5340
ttttagtact tccaattggt tgggagcaga gaagtgatgc agtaatatct tgttcctata   5400
ggcatcagaa aattgtttca acatcacatt agcactattc ttgacctata atacatacaa   5460
cttcgtggag tacatggaat gtgggctctc tgtacgtgcc tggtgaaca accacagaat   5520 gcaacggatc atttcagcct ctgcatggct actagcattt tttactgtgc tcctcaagac   5580
```

-continued

```
cataggcctc tccgagactg tgttcgaggt cacccgtaag gagaagagca catcggatgg    5640
caatggccaa aacgatgagg ttgacccgga gagattcacc tttgacgcat caccagtgtt    5700
catccccgtt acggcgctga caatgttgaa cattgttgca atcacaattg gtacatggag    5760
ggcagttttt gggacaacag aagacgtgcc tggtggtccg ggtataagtg aattcatgtc    5820
ttgtggatgg ctgctactgt gcttattgcc atttgtgaga gggctagtgg gcaagggaag    5880
ctatggtatc ccatggagtg tcaagctgaa ggctagtttg ctggtggcct tgttcctgtt    5940
ctgctccaat agaaattagt ttcagcatgt aagcatagtc agcttaacat gtttcatgta    6000
tgtattattt gagcaatatg tttgtaattc catttagcaa atgacgacaa ctataaacat    6060
atggagtatt tcactttcag ctggtggtgt tgttggtaaa cataactgag ttctataaga    6120
tagcagttca accactaaga gcgtcatcgg ttggttaaga gctgattata tactaaaaca    6180
acttattaga gattaaaata taatttatag gtaaaagctt tcatatgtgt catttgcgac    6240
ttaaaagcca atgctgaaaa caactatatt gaaaataccc taaaatgaac cccacaatta    6300
attttcaaaa tttaaatttt ggtaacaact aattctttct agggcaaacg atgagaccct    6360
aagttccaaa caaagagtaa ttctttattc cgaataccta caagtacatt attataaaaa    6420
tacgagtgct tttccattct taagaacgta ccaccaggta tcaggtatca atctaaataa    6480
cttttggtta catatgggta cgattgggct aaccaattgc tagatagaat acatcaatcc    6540
```

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
ttgaccggac aacggatcc                                                    19

<210> SEQ ID NO 14
<211> LENGTH: 18
<212> TYPE: DNA
<213> ORGANISM: Artificial
<220> FEATURE:
<223> OTHER INFORMATION: primer

<400> SEQUENCE: 14
ctggagatac tcatcagc                                                     18

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tcgagcggtt gttgcttgtg                                                   20

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
caccatggcg ggcggcaaga agctg                                             25

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
cgtcaccggg atgaaaac                                              18

<210> SEQ ID NO 18
<211> LENGTH: 18
<212> TYPE: DNA
<213> ORGANISM: Artificial
<220> FEATURE:
<223> OTHER INFORMATION: primer

<400> SEQUENCE: 18
tgacgctcca cggcattc                                              18

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ggctggccat cgaaatattg                                            20

<210> SEQ ID NO 20
<211> LENGTH: 18
<212> TYPE: DNA
<213> ORGANISM: Artificial
<220> FEATURE:
<223> OTHER INFORMATION: primer

<400> SEQUENCE: 20
gagcgttggt catcacgg                                              18

<210> SEQ ID NO 21
<211> LENGTH: 17
<212> TYPE: DNA
<213> ORGANISM: Artificial
<220> FEATURE:
<223> OTHER INFORMATION: primer

<400> SEQUENCE: 21
cacatcgcgt gtagggc                                               17

<210> SEQ ID NO 22
<211> LENGTH: 26
<212> TYPE: DNA
<213> ORGANISM: Artificial
<220> FEATURE:
<223> OTHER INFORMATION: primer

<400> SEQUENCE: 22
cctgcttgag tcttcgttac atgttc                                     26

<210> SEQ ID NO 23
<211> LENGTH: 26
<212> TYPE: DNA
<213> ORGANISM: Artificial
<220> FEATURE:
<223> OTHER INFORMATION: primer

```
<400> SEQUENCE: 23
cctgcttgag tcttcgttac atgttc                                           26

<210> SEQ ID NO 24
<211> LENGTH: 19
<212> TYPE: DNA
<213> ORGANISM: Artificial
<220> FEATURE:
<223> OTHER INFORMATION: primer

<400> SEQUENCE: 24
cgcttccaat atttcgatg                                                   19

<210> SEQ ID NO 25
<211> LENGTH: 44
<212> TYPE: DNA
<213> ORGANISM: Artificial
<220> FEATURE:
<223> OTHER INFORMATION: primer

<400> SEQUENCE: 25
ctaatacgac tcactatagg gctcgagcgg ccgcccgggc aggt                       44

<210> SEQ ID NO 26
<211> LENGTH: 8
<212> TYPE: DNA
<213> ORGANISM: Artificial
<220> FEATURE:
<223> OTHER INFORMATION: primer

<400> SEQUENCE: 26 acctgccc                                                                8

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
ggatcctaat acgactcact atagggc                                          27

<210> SEQ ID NO 28
<211> LENGTH: 17
<212> TYPE: DNA
<213> ORGANISM: Artificial
<220> FEATURE:
<223> OTHER INFORMATION: primer

<400> SEQUENCE: 28
aatagggctc gagcggc                                                     17

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
gtttcagcct tgcgaccata ct                                               22

<210> SEQ ID NO 30
<211> LENGTH: 18
```

```
<212> TYPE: DNA
<213> ORGANISM: Artificial
<220> FEATURE:
<223> OTHER INFORMATION: primer

<400> SEQUENCE: 30
ggtaattcca gctccaat                                                      18

<210> SEQ ID NO 31
<211> LENGTH: 18
<212> TYPE: DNA
<213> ORGANISM: Artificial
<220> FEATURE:
<223> OTHER INFORMATION: primer

<400> SEQUENCE: 31
gtttatggtt gagactag                                                      18

<210> SEQ ID NO 32
<211> LENGTH: 19
<212> TYPE: DNA
<213> ORGANISM: Artificial
<220> FEATURE:
<223> OTHER INFORMATION: primer

<400> SEQUENCE: 32
gtgaggctgg tgctgatta                                                     19

<210> SEQ ID NO 33
<211> LENGTH: 24
<212> TYPE: DNA
<213> ORGANISM: Artificial
<220> FEATURE:
<223> OTHER INFORMATION: primer

<400> SEQUENCE: 33
cgtggtgcag ctagcatttg agac                                               24

<210> SEQ ID NO 34
<211> LENGTH: 22
<212> TYPE: DNA
<213> ORGANISM: Artificial
<220> FEATURE:
<223> OTHER INFORMATION: primer

<400> SEQUENCE: 34
cctgtcgtgt cgtcggtcta aa                                                 22

<210> SEQ ID NO 35
<211> LENGTH: 22
<212> TYPE: DNA
<213> ORGANISM: Artificial
<220> FEATURE:
<223> OTHER INFORMATION: primer

<400> SEQUENCE: 35
acgcagatcc agcagcctaa ag                                                 22

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
agtgtcctgt ccacccactc                                                    20
```

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
agcatgaagt ggatccttgg                                          20

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
cgaccagggc aaccgcacca c                                        21

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39
acggtgttga tggggttcat g                                        21

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
ggtacctccc aggctgactg t                                        21

<210> SEQ ID NO 41
<211> LENGTH: 21
<212> TYPE: DNA
<213> ORGANISM: Artificial
<220> FEATURE:
<223> OTHER INFORMATION: primer

<400> SEQUENCE: 41
gtggtggcgt ccatcttgtt a                                        21

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
tgctgtggct ggatggtgtt                                          20

<210> SEQ ID NO 43
<211> LENGTH: 27
<212> TYPE: DNA
<213> ORGANISM: Artificial
<220> FEATURE:
<223> OTHER INFORMATION: primer

```
<400> SEQUENCE: 43
gctttattat tgagagagat tgggaga                                      27

<210> SEQ ID NO 44
<211> LENGTH: 18
<212> TYPE: DNA
<213> ORGANISM: Artificial
<220> FEATURE:
<223> OTHER INFORMATION: primer

<400> SEQUENCE: 44
aggcgtggtt cgcgttcg                                                18

<210> SEQ ID NO 45
<211> LENGTH: 18
<212> TYPE: DNA
<213> ORGANISM: Artificial
<220> FEATURE:
<223> OTHER INFORMATION: primer

<400> SEQUENCE: 45
cagcgcgtag tacgtcac                                                18

<210> SEQ ID NO 46
<211> LENGTH: 18
<212> TYPE: DNA
<213> ORGANISM: Artificial
<220> FEATURE:
<223> OTHER INFORMATION: primer

<400> SEQUENCE: 46
cagccgtgat gaccaacg                                                18

<210> SEQ ID NO 47
<211> LENGTH: 18
<212> TYPE: DNA
<213> ORGANISM: Artificial
<220> FEATURE:
<223> OTHER INFORMATION: primer

<400> SEQUENCE: 47
gttgccaaag ggatcgtc                                                18

<210> SEQ ID NO 48
<211> LENGTH: 23
<212> TYPE: DNA
<213> ORGANISM: Artificial
<220> FEATURE:
<223> OTHER INFORMATION: primer

<400> SEQUENCE: 48
gcggtcgtga cgaacatgtc cac                                          23

<210> SEQ ID NO 49
<211> LENGTH: 17
<212> TYPE: DNA
<213> ORGANISM: Artificial
<220> FEATURE:
<223> OTHER INFORMATION: primer

<400> SEQUENCE: 49
gacgctccac gggattc                                                 17

<210> SEQ ID NO 50
<211> LENGTH: 22
```

```
<212> TYPE: DNA
<213> ORGANISM: Artificial
<220> FEATURE:
<223> OTHER INFORMATION: primer

<400> SEQUENCE: 50
ggttagttcc ttgtgcagag gt                                            22

<210> SEQ ID NO 51
<211> LENGTH: 22
<212> TYPE: DNA
<213> ORGANISM: Artificial
<220> FEATURE:
<223> OTHER INFORMATION: primer

<400> SEQUENCE: 51
gagctgtgtt cgtggagctt ag                                            22

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
ctgctctcgg ccacggccat                                               20

<210> SEQ ID NO 53
<211> LENGTH: 24
<212> TYPE: DNA
<213> ORGANISM: Artificial
<220> FEATURE:
<223> OTHER INFORMATION: primer

<400> SEQUENCE: 53
ccgccggtta gttccttgtg caga                                          24

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
ggagagttcg tgtgctgtgg                                               20

<210> SEQ ID NO 55
<211> LENGTH: 26
<212> TYPE: DNA
<213> ORGANISM: Artificial
<220> FEATURE:
<223> OTHER INFORMATION: primer

<400> SEQUENCE: 55
caccatgagc cccgtccggt tcgaca                                        26

<210> SEQ ID NO 56
<211> LENGTH: 21
<212> TYPE: DNA
<213> ORGANISM: Artificial
<220> FEATURE:
<223> OTHER INFORMATION: primer

<400> SEQUENCE: 56
caaacctcag ggaagcagtc a                                             21
```

```
<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
agtgtcctgt ccacccactc                                              20

<210> SEQ ID NO 58
<211> LENGTH: 19
<212> TYPE: DNA
<213> ORGANISM: Artificial
<220> FEATURE:
<223> OTHER INFORMATION: primer

<400> SEQUENCE: 58
gcatcgtact ggtgctgct                                               19

<210> SEQ ID NO 59
<211> LENGTH: 23
<212> TYPE: DNA
<213> ORGANISM: Artificial
<220> FEATURE:
<223> OTHER INFORMATION: primer

<400> SEQUENCE: 59
gcgcttctca cgggacacgt aca                                          23

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
gatgcgtaca actcgagcaa                                              20

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
cgttgctgaa gtcaagtgga                                              20

<210> SEQ ID NO 62
<211> LENGTH: 21
<212> TYPE: DNA
<213> ORGANISM: Artificial
<220> FEATURE:
<223> OTHER INFORMATION: primer

<400> SEQUENCE: 62
cgctgcaaac gagaaagaag g                                            21

<210> SEQ ID NO 63
<211> LENGTH: 18
<212> TYPE: DNA
<213> ORGANISM: Artificial
<220> FEATURE:
<223> OTHER INFORMATION: primer
```

```
<400> SEQUENCE: 63
ggcgctgaaa tccagagg                                                   18

<210> SEQ ID NO 64
<211> LENGTH: 19
<212> TYPE: DNA
<213> ORGANISM: Artificial
<220> FEATURE:
<223> OTHER INFORMATION: primer

<400> SEQUENCE: 64
cggaaatcca taggaaagg                                                  19

<210> SEQ ID NO 65
<211> LENGTH: 16
<212> TYPE: DNA
<213> ORGANISM: Artificial
<220> FEATURE:
<223> OTHER INFORMATION: primer

<400> SEQUENCE: 65
cggcggaaca tgcaac                                                     16

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
ggattgaccc agctgaaaac                                                 20

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
gagttgttga cgtagtggtc                                                 20

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
cgagcacccc aatctacaga                                                 20

<210> SEQ ID NO 69
<211> LENGTH: 2333
<212> TYPE: DNA
<213> ORGANISM: Hordeum vulgare cv. Himalaya

<400> SEQUENCE: 69
gagctgtgtt cgtggagctt agctagtctg ctactgctac tgctggctag tggctacctg      60
ctctcggcca cggccatggc gggcggcaag aagctgcagg agagggtcgc cctggcgaga     120
accgcgtgga tgctggccga cttcgcgatc ctcttcctcc tcctcgccat cgtgcccgc      180 cgcgccgcct cgctccggga gcgcggcggg acgtggttgg cggcgctcgt ctgcgaggcg     240
```

| | |
|---|---|
| tggttcgcct tcgtgtggat cctcaacatg aacggcaagt ggagcccgt ccggttcgac | 300 |
| acctacccg acaacctcgc caacaggatg gaggagctcc cggcggtgga catgttcgtc | 360 |
| acgaccgcgg acccggcgct ggagcctccg ttgatcacgg tgaacacggt gctctcgctg | 420 |
| ctcgccctgg actacccgga cgtcggcaag ctggcgtgct acgtctctga cgacggctgc | 480 |
| tccccggtga cgtgctacgc gctgcgtgag gccgccaagt tcgccggcct ctgggtccct | 540 |
| ttctgcaaga ggcacgacgt tgctgtgagg gccccattca tgtacttctc ttccacgccg | 600 |
| gaggttggca caggcacagc cgaccacgag ttcctggaaa gctgggcgct catgaagagc | 660 |
| gaatatgaga gactagccag ccgaatcgag aacgccgatg agggctccat tatgcgtgac | 720 |
| agcggcgacg agttcgccga gttcatcgac gccgagcgcg ggaaccatcc taccatcgtt | 780 |
| aaggttctgt gggataacag caagagcaaa gtggggaag gattcccaca tctggtgtac | 840 |
| ctctctcgag agaaaagccc cagacatcgc cacaacttca aggctggtgc catgaatgtt | 900 |
| ctgacaaggg tgtcagccgt gatgaccaac gctcccatca tgctgaatgt ggactgcgac | 960 |
| atgttcgcca caatccgca ggtcgcccta cacgcgatgt gcctcctatt ggggttcgac | 1020 |
| gacgagatcc acagcgggtt cgtccaagtg ccacagaagt tctacggtgg cctcaaggac | 1080 |
| gatccctttg caaccagat gcaggttata accagaaaa ttggaggtgg aatcgccggg | 1140 |
| atccaaggca tgttctacgg cggcacgggc tgttttcacc gcaggaaagt catttacggc | 1200 |
| atgccgccac ctgacaccgt caaacacgag acaagaggtt caccatctta caaggagctg | 1260 |
| caagtcaggt ttgggagctc aaaggtgttg atcgaatcat ctaggaacat catctcagga | 1320 |
| gacctgctcg ctagaccaac cgttgatgta tcgagtcgca tcgaaatggc aaaacaagtc | 1380 |
| ggcgattgca actatgaggc tggcacgtgt tggggcaagg agattggttg ggtctatgga | 1440 |
| tcaatgacag aagacatttt gaccggacaa cggatccatg cggcgggttg gaaatcggcc | 1500 |
| ttgttggaca ccaaccccacc ggcattcttg ggatgtgctc cgaccggggg accgccagc | 1560 |
| ttgacccagt tcaagagatg ggcaacaggg gttctggaga tactcatcag ccggaacagc | 1620 |
| cctatcctcg gcaccatctt ccaacgcctc caactccggc aatgccttgg ctatctcatc | 1680 |
| gtcgaggcgt ggcccgtgag ggcgcctttc gagctgtgct atgcactatt gggacctttc | 1740 |
| tgccttctca caaaccagtc cttcttgcca acggcatcgg atgaaggttt tcgcatccca | 1800 |
| gtagctctat tcttgagtta ccacatatac cacttgatgg agtacaagga gtgcgggctc | 1860 |
| tctgcccgcg cctggtggaa caaccacagg atgcaacgca tcacctcggc ctccgcctgg | 1920 |
| ctcctcgcct tcctcaccgt gatcctcaag acactagggc tctctgagac cgtgttcgag | 1980 |
| gtcacccgca aggaaagcag cacgtccgat ggcggcgccg gcaccgacga ggccgatcca | 2040 |
| ggactgttca cattcgactc ggcgcccgtt ttcatcccgg tgacggcgct ctcagtgttg | 2100 |
| aacattgtgg ccctcgccgt cggggcatgg gcgccgtca tcgggactgc ggcggtcgtt | 2160 |
| catggtggcc cgggcatcgg agagttcgtg tgctgtggct ggatggtgtt gtgcttctgg | 2220 |
| ccgttcgtga gagggcttgt cagcagggga aagcatggaa tcccgtggag cgtcaaggtg | 2280 |
| aaggctggtt tgattgtggc tgcgttcgtg cacctctgca caaggaacta acc | 2333 |

<210> SEQ ID NO 70
<211> LENGTH: 751
<212> TYPE: PRT
<213> ORGANISM: Hordeum vulgare cv. Himalaya

<400> SEQUENCE: 70

Met Ala Gly Gly Lys Lys Leu Gln Glu Arg Val Ala Leu Ala Arg Thr

```
            1               5                   10                  15
Ala Trp Met Leu Ala Asp Phe Ala Ile Leu Phe Leu Leu Ala Ile
                    20                  25                  30

Val Ala Arg Arg Ala Ala Ser Leu Arg Glu Arg Gly Gly Thr Trp Leu
            35                  40                  45

Ala Ala Leu Val Cys Glu Ala Trp Phe Ala Phe Val Trp Ile Leu Asn
            50                  55                  60

Met Asn Gly Lys Trp Ser Pro Val Arg Phe Asp Thr Tyr Pro Asp Asn
65                      70                  75                  80

Leu Ala Asn Arg Met Glu Glu Leu Pro Ala Val Asp Met Phe Val Thr
                    85                  90                  95

Thr Ala Asp Pro Ala Leu Glu Pro Pro Leu Ile Thr Val Asn Thr Val
                100                 105                 110

Leu Ser Leu Leu Ala Leu Asp Tyr Pro Asp Val Gly Lys Leu Ala Cys
            115                 120                 125

Tyr Val Ser Asp Asp Gly Cys Ser Pro Val Thr Cys Tyr Ala Leu Arg
            130                 135                 140

Glu Ala Ala Lys Phe Ala Gly Leu Trp Val Pro Phe Cys Lys Arg His
145                 150                 155                 160

Asp Val Ala Val Arg Ala Pro Phe Met Tyr Phe Ser Ser Thr Pro Glu
                165                 170                 175

Val Gly Thr Gly Thr Ala Asp His Glu Phe Leu Glu Ser Trp Ala Leu
            180                 185                 190

Met Lys Ser Glu Tyr Glu Arg Leu Ala Ser Arg Ile Glu Asn Ala Asp
            195                 200                 205

Glu Gly Ser Ile Met Arg Asp Ser Gly Asp Glu Phe Ala Glu Phe Ile
            210                 215                 220

Asp Ala Glu Arg Gly Asn His Pro Thr Ile Val Lys Val Leu Trp Asp
225                 230                 235                 240

Asn Ser Lys Ser Lys Val Gly Glu Gly Phe Pro His Leu Val Tyr Leu
                245                 250                 255

Ser Arg Glu Lys Ser Pro Arg His Arg His Asn Phe Lys Ala Gly Ala
            260                 265                 270

Met Asn Val Leu Thr Arg Val Ser Ala Val Met Thr Asn Ala Pro Ile
            275                 280                 285

Met Leu Asn Val Asp Cys Asp Met Phe Ala Asn Asn Pro Gln Val Ala
            290                 295                 300

Leu His Ala Met Cys Leu Leu Leu Gly Phe Asp Asp Glu Ile His Ser
305                 310                 315                 320

Gly Phe Val Gln Val Pro Gln Lys Phe Tyr Gly Gly Leu Lys Asp Asp
                325                 330                 335

Pro Phe Gly Asn Gln Met Gln Val Ile Thr Lys Lys Ile Gly Gly Gly
                340                 345                 350

Ile Ala Gly Ile Gln Gly Met Phe Tyr Gly Gly Thr Gly Cys Phe His
            355                 360                 365

Arg Arg Lys Val Ile Tyr Gly Met Pro Pro Asp Thr Val Lys His
            370                 375                 380

Glu Thr Arg Gly Ser Pro Ser Tyr Lys Glu Leu Gln Val Arg Phe Gly
385                 390                 395                 400

Ser Ser Lys Val Leu Ile Glu Ser Arg Asn Ile Ile Ser Gly Asp
                405                 410                 415

Leu Leu Ala Arg Pro Thr Val Asp Val Ser Ser Arg Ile Glu Met Ala
                420                 425                 430
```

```
Lys Gln Val Gly Asp Cys Asn Tyr Glu Ala Gly Thr Cys Trp Gly Lys
            435                 440                 445

Glu Ile Gly Trp Val Tyr Gly Ser Met Thr Glu Asp Ile Leu Thr Gly
    450                 455                 460

Gln Arg Ile His Ala Ala Gly Trp Lys Ser Ala Leu Leu Asp Thr Asn
465                 470                 475                 480

Pro Pro Ala Phe Leu Gly Cys Ala Pro Thr Gly Gly Pro Ala Ser Leu
                485                 490                 495

Thr Gln Phe Lys Arg Trp Ala Thr Gly Val Leu Glu Ile Leu Ile Ser
            500                 505                 510

Arg Asn Ser Pro Ile Leu Gly Thr Ile Phe Gln Arg Leu Gln Leu Arg
            515                 520                 525

Gln Cys Leu Gly Tyr Leu Ile Val Glu Ala Trp Pro Val Arg Ala Pro
            530                 535                 540

Phe Glu Leu Cys Tyr Ala Leu Leu Gly Pro Phe Cys Leu Leu Thr Asn
545                 550                 555                 560

Gln Ser Phe Leu Pro Thr Ala Ser Asp Glu Gly Phe Arg Ile Pro Val
                565                 570                 575

Ala Leu Phe Leu Ser Tyr His Ile Tyr His Leu Met Glu Tyr Lys Glu
            580                 585                 590

Cys Gly Leu Ser Ala Arg Ala Trp Trp Asn Asn His Arg Met Gln Arg
            595                 600                 605

Ile Thr Ser Ala Ser Ala Trp Leu Leu Ala Phe Leu Thr Val Ile Leu
            610                 615                 620

Lys Thr Leu Gly Leu Ser Glu Thr Val Phe Glu Val Thr Arg Lys Glu
625                 630                 635                 640

Ser Ser Thr Ser Asp Gly Gly Ala Gly Thr Asp Glu Ala Asp Pro Gly
                645                 650                 655

Leu Phe Thr Phe Asp Ser Ala Pro Val Phe Ile Pro Val Thr Ala Leu
                660                 665                 670

Ser Val Leu Asn Ile Val Ala Leu Ala Val Gly Ala Trp Arg Ala Val
            675                 680                 685

Ile Gly Thr Ala Ala Val Val His Gly Gly Pro Gly Ile Gly Glu Phe
            690                 695                 700

Val Cys Cys Gly Trp Met Val Leu Cys Phe Trp Pro Phe Val Arg Gly
705                 710                 715                 720

Leu Val Ser Arg Gly Lys His Gly Ile Pro Trp Ser Val Lys Val Lys
                725                 730                 735

Ala Gly Leu Ile Val Ala Ala Phe Val His Leu Cys Thr Arg Asn
            740                 745                 750

<210> SEQ ID NO 71
<211> LENGTH: 3203
<212> TYPE: DNA
<213> ORGANISM: Hordeum vulgare cv. Himalaya

<400> SEQUENCE: 71
gagctgtgtt cgtggagctt agctagtctg ctactgctac tgctggctag tggctacctg      60
ctctcggcca cggccatggc gggcggcaag aagctgcagg agagggtcgc cctggcgaga     120
accgcgtgga tgctggccga cttcgcgatc tccttcctcc tcctcgccat cgtgcccgc      180 cgcgccgcct cgctccggga gcgcggcggg acgtggttgg cggcgctcgt ctgcgaggcg     240
tggttcgcct tcgtgtggat cctcaacatg aacggcaagt ggagccccgt ccggttcgac     300
acctaccccg acaacctcgc caacaggtac tctacgtacg tacccacggc gacaagaccc     360
```

```
accatgctga cccctacaac ttcctcaaat tttgatctag ctagtgtctg tgataatttt     420
gctaggatgg aggagctccc ggcggtggac atgttcgtca cgaccgcgga cccggcgctg     480
gagcctccgt tgatcacggt gaacacggtg ctctcgctgc tcgccctgga ctacccggac     540
gtcggcaagc tggcgtgcta cgtctctgac gacggctgct ccccggtgac gtgctacgcg     600
ctgcgtgagg ccgccaagtt cgccggcctc tgggtccctt tctgcaagag gcacgacgtt     660
gctgtgaggc ccccattcat gtacttctct tccacgccgg aggttggcac aggcacagcc     720
gaccacgagt tcctggaaag ctgggcgctc atgaaggtta ggcgccaatg gtgaccatgt     780
cagtttacaa aataatgttt ggtcgtccat catcgccatg ccattcatc ttcctcgtgt     840
acgtgtgact ttcagagcga atatgagaga ctagccagcc gaatcgagaa cgccgatgag     900
ggctccatta tgcgtgacag cggcgacgag ttcgccgagt tcatcgacgc cgagcgcggg     960
aaccatccta ccatcgttaa ggtcgccgca ctgaccatgt ccatgcatgt gtccatgaac    1020
atcgtgtcat gacaaacgca tagcaaatcc gtgtctcgtg ctaatatcgt cacggttaat    1080
ttgggccgag ttcaggttct gtgggataac agcaagagca aagtggggga aggattccca    1140
catctggtgt acctctctcg agagaaaagc cccagacatc gccacaactt caaggctggt    1200
gccatgaatg ttctggtgag cactctcttt cgctcaacac agtgttgcac tgctaatcag    1260
tgtcacacaa gcagcacacc acattttata ctaattaagc tgatcatttc gtggtgcaga    1320
caagggtgtc agccgtgatg accaacgctc ccatcatgct gaatgtggac tgcgacatgt    1380
tcgccaacaa tccgcaggtc gccctacacg cgatgtgcct cctattgggg ttcgacgacg    1440
agatccacag cggggttcgtc caagtgccac agaagttcta cggtggcctc aaggacgatc    1500
cctttggcaa ccagatgcag gttataacca aggtactaca tatgcatgtg cacaagtgct    1560
cttgtcgtcg tgctgtgcac cactaggtag tgttacagtt gtactggttt ttgtgcatg     1620
ttcagaaaat tggaggtgga atcgccggga tccaaggcat gttctacggc ggcacgggct    1680
gttttcaccg caggaaagtc atttacggca tgccgccacc tgacaccgtc aaacacgaga    1740
caagaggtga aactgggcac acaacagatg tgatcatcag gcgtaaattg gagtatgcat    1800
ttcagttcga ctagggcatt tcaaatggct aagtgttctt aatttgccag gttcaccatc    1860
ttacaaggag ctgcaagtca ggtttgggag ctcaaaggtg ttgatcgaat catctaggaa    1920
catcatctca ggagacctgc tcgctagacc aaccgttgat gtatcgagtc gcatcgaaat    1980
ggcaaaacaa gtcggcgatt gcaactatga ggctggcacg tgttggggca aggaggtatg    2040
cttagctacc tgttgccgta ttttttgcagg tttcgctaca gtacatctac aatcttttgc    2100
agttttctc tagttacagt ttcttccatg tattttttgca gattggttgg gtctatggat    2160
caatgacaga agacatttg accggacaac ggatccatgc ggcgggttgg aaatcggcct    2220
tgttggacac caacccaccg gcattcttgg gatgtgctcc gaccggggga ccggccagct    2280
tgacccagtt caagagatgg gcaacagggg ttctggagat actcatcagc cggaacagcc    2340
ctatcctcgg caccatcttc caacgcctcc aactccggca atgccttggc tatctcatcg    2400
tcgaggcgtg gcccgtgagg gcgccttttcg agctgtgcta tgcactattg gaccctttct    2460
gccttctcac aaaccagtcc ttcttgccaa cggtacatac actttcgcgg ttcgccaaga    2520
tacattatgc agctaaacaa aaatgctgtg tgatttgttt gataatgaag caggacctag    2580
ttggctaata tgtatgtaaa ttcagatatt tttttatga ttggtacatt tgttgttttg    2640
caggcatcgg atgaaggttt tcgcatccca gtagctctat tcttgagtta ccacatatac    2700
cacttgatgg agtacaagga gtgcgggctc tctgcccgcg cctggtggaa caaccacagg    2760
```

-continued

```
atgcaacgca tcacctcggc ctccgcctgg ctcctcgcct tcctcaccgt gatcctcaag    2820
acactagggc tctctgagac cgtgttcgag gtcacccgca aggaaagcag cacgtccgat    2880
ggcggcgccg gcaccgacga ggccgatcca ggactgttca cattcgactc ggcgcccgtt    2940
ttcatcccgg tgacggcgct ctcagtgttg aacattgtgg ccctcgccgt cggggcatgg    3000
cgcgccgtca tcgggactgc ggcggtcgtt catggtggcc cgggcatcgg agagttcgtg    3060
tgctgtggct ggatggtgtt gtgcttctgg ccgttcgtga gagggcttgt cagcagggga    3120
aagcatggaa tcccgtggag cgtcaaggtg aaggctggtt tgattgtggc tgcgttcgtg    3180
cacctctgca aaggaactaa acc                                            3203
```

<210> SEQ ID NO 72
<211> LENGTH: 2284
<212> TYPE: DNA
<213> ORGANISM: Triticum aestivum

<400> SEQUENCE: 72

```
ctgctctcgg ccgcggccat ggcgggcggc aagaagctgc acgagagggt cgccctgggg      60
agaactgcgt ggatgctggc cgacttcgtg atcctcctcc tcctcctcgc cctcgtggcc     120
cgccgcgccg cgtcgctcgg ggagcgcggc gggacgtggc tggcggcgct cgtctgcgag     180
gcgtggttcg ccttcgtctg gatcctcaac atgaacggca gtggagccc cgtccggttc     240 gacacctacc ccgagaacct ctcccacagg ctggaggagc tcccggcggt ggacatgttc     300
gtcacgacgg cggacccggc gctggagccg ccgttgatca cggtgaacac ggtgctctcg     360
ctgctcgccc tggactaccc ggacgtcggc aagctggcgt gctacgtctc cgacgacggc     420
tgctccccgg tgacgtgcta cgcgctgcgc gaggccgcca gttcgccag cctctggatt     480 cccttctgca agaggtatga cgttggtgtg agggcccctt tcatgtactt ctcttccgcg     540
ccggaggttg gcaccggtac agccgaccac gagttcctgg aaagctgggc actcatgaag     600
accgaatatg agaagctggc cagccggatc gagaacgccg acgaggtctc cattctgcgt     660
gacggcggcg aagagttcgc cgagttcatc gacgccgagc gcgggaacca tcctaccatc     720
gttaaggttc tctgggataa cagcaagagc aaagcagggg aaggattccc acatctggtg     780
tacctctctc gagagaaaag ccccagacat cgccacaact tcaaggccgg tgccatgaat     840
gttctgacaa gggtgtcggc cgtgatgacc aacgctccaa tcatgctgaa tgtggactgc     900
gacatgttcg ccaacaaccc gcaggtcgcc ctgcacgcga tgtgcctcct gttggggttc     960
gacgacgaga tccacagcgg gttcgtccag gcgccacaga agttctacgg tggcctcaag    1020
gatgacccct ttggcaacca gatgcaggtt ataaccaaga aaattggagg tgggctcgcc    1080
gggatccaag gcaccttcta cggcggcacg ggctgttttc accgcaggaa ggtcatctac    1140
ggcatgccgc ctccggacac cgtcaagcac gagacaagag gttcaccatc ttacaaggag    1200
ctgcaagcca gtttgggag ctcaaaggag ttgatcgaat catctaggaa catcatctca    1260
ggggacctgc tcgctagacc aaccgtagat atatcgagtc gtgtcgaaat ggcaaaacaa    1320
gtaggcgact gcaactatga ggctggcaca tgttggggcc aagagattgg gtgggtctat    1380
ggatcaatga cagaggacat tttgaccggt caacggatcc aggcggcggg ttgggaatcg    1440
gccttgttgg acaccgaccc accggcattc ctggatgtg ctccgaccgg tggaccagcc     1500
agcttgaccc agttcaagag atgggcaaca gggcttctgg agatactcat cagccggaac    1560
agccccatcc tcggcaccat cttcaagggc ctccaactcc ggcaatgcct tggctatctc    1620
atcgtagacg cgtggcccgt gagggcgcct ttcgagctgt gctatgcgct cttgggacct    1680
```

-continued

| | | | | |
|---|---|---|---|---|
| ttctgccttc | tcacaaacca | atccttctta | ccaacggcat | cagatgaagg | ttttcacatc | 1740 |
| ccagcggctc | tattttgac | ttacaacata | taccacctga | tggagtacaa | ggagtgcggg | 1800 |
| ctctcggtcc | gcgcctggtg | aacaaccat | aggatgcaac | gcatcacctc | ggcctccgcc | 1860 |
| tggctcctcg | ccttcctcac | cgtcatcctc | aagacgctag | gctctccga | daccgtgttc | 1920 |
| gaggtcaccc | gcaaggagag | cagcacgtca | tccgatggcg | gcgcgggcac | cgacgatgcc | 1980 |
| gatcctgggt | tgttcacctt | tgactcggcg | cccgttttca | tcccagtgac | ggcgctctca | 2040 |
| gtgttgaaca | ttgtcgccct | caccgtcgcg | gcatggcgcg | ccgtcgtcgg | gacggtggcg | 2100 |
| ggcgttcatg | gtggcccggg | cgtcggagag | ttcgtgtgct | gtggctggat | ggtgttgtgc | 2160 |
| ttctggccat | tcgtgagagg | gcttgtcagt | agtggaaagt | atgggatccc | gtggagtgtc | 2220 |
| agggtgaagg | ctgggttgat | tgtggctgcg | ttcgtgcacc | tctgcacaag | gaactaaccg | 2280 |
| gccg | | | | | 2284 |

<210> SEQ ID NO 73
<211> LENGTH: 2284
<212> TYPE: DNA
<213> ORGANISM: Triticum aestivum

<400> SEQUENCE: 73

| | | | | |
|---|---|---|---|---|
| ctgctctcgg | ccacggccat | ggcgggcggc | aagaagctgc | aggagagggt | cgccctgggc | 60 |
| aggagtgcgt | ggatgctggc | cgacttcgtg | atcctcttcc | tcctcctcgc | cctcgtggcc | 120 |
| cgccgcgccg | cgtcgctcgg | ggagcgcggc | gggacgtggc | tggcagcgct | cgtctgcgag | 180 |
| gcgtggttcg | ccttcgtgtg | gatcctcaac | atgaacggca | agtggagccc | cgtccggttc | 240 |
| gacacctacc | ccgacaacct | ctcccacagg | atggaggagc | tcccagcggt | ggacatgttc | 300 |
| gtcacgacgg | cggacccggc | gctggagccg | ccgttgatca | cggtgaacac | ggtgctctcg | 360 |
| ctgctcgccc | tggactaccc | gcacgtcggc | aagctggcgt | gctacgtctc | cgacgacggc | 420 |
| tgctccccct | tgacgtgcta | cggtctgcac | gaggccgcca | agttcgccag | cctctgggtt | 480 |
| cccttctgca | agaggcacga | cgttggtgtg | agggccccct | tcatgtactt | ctcttccgcg | 540 |
| ccggaggttg | acaccggtac | agtcgaccac | gagttcctgg | aaagctgggc | actcatgaag | 600 |
| agcgaatatg | agaagctggc | cagccggatc | gagaacgccg | acgaggtctc | cattctgcgt | 660 |
| gacggcggcg | acgagttcgc | cgagttcatc | gacgccgagc | gcgggaacca | tcctaccatc | 720 |
| gttaaggttc | tctgggataa | cagcaagaac | aaaacaggtg | aaggattccc | acatctggtg | 780 |
| tacctctcga | gagagaaaag | ccccagacat | cgtcacaact | ttaaggccgg | tgccatgaat | 840 |
| gttctgacaa | gggtgtcggc | cgtgatgacc | aacgctccga | tcatgctgaa | tgtggactgc | 900 |
| gacatgtttg | ccaacaaccc | gcaggtcgcc | ctacacgcga | tgtgcctcct | gttgggttc | 960 |
| gacgacgaga | tccacagcgg | gttcgtccag | gcgccacaga | agttctacgg | tggcctcaag | 1020 |
| gatgacccct | ttggcaacca | gatgcaggtt | ataaccaaga | aaattggagg | tgggctcgcc | 1080 |
| gggatccaag | gcacgttcta | cggcggcacg | gctgttttc | accgcaggaa | ggtcatttac | 1140 |
| ggcatgccgc | ctccggacac | cgtcaagcac | gagacaagag | gttcaccatc | ttacaaggag | 1200 |
| ctgcaagcca | gtttgggag | ctcaaaggag | ttgatcgaat | catctaggaa | catcatctca | 1260 |
| ggagacctgc | tcgctagacc | aaccgtagat | atatcaagtc | gggtcgaaat | ggcaaaacaa | 1320 |
| gtaggcgact | gcaactatga | ggctggcaca | tatgggggcc | aagagattgg | gtgggtctat | 1380 |
| ggatcaatga | cagaggacat | tttgaccggg | caacggatcc | aagcggcggg | ttggaaatcg | 1440 |
| gccttgttgg | acaccgaccc | accggcattc | ttgggatgtg | ctccgacagg | ggggccggct | 1500 |

```
agcttgaccc agttcaagag atgggcaaca gggcttctgg agatactcat cagccggaac   1560
agccccatcc tcggcaccat cttcaggcgc ctccaactcc ggcaatgcct tgcctatctc   1620
atcgtcaacg cgtggcccat gagggcacct ttcgagatgt gttacgcgct attgggacct   1680
ttctgccttc tcacaaacca gtccttcttg ccaacgacat ctaatgaagg ttttcgcatc   1740
ccagcggctc tattcttgag ttaccacgta taccacctga tggagtacaa ggagtgcggg   1800
ctctcggtcc gcgcctggtg gaacaaccac aggatgcaac gcatcacctc ggcctccgcc   1860
tggctcctcg ccttcctcac cgtcatcctc aagacgctag gctctccga ccgtgttc    1920 gaggtcaccc gcaaggagag cagcacgtcc tccgatggtg gcgcgggcac cgacgaggcc   1980
gatactgggc tgttcacctt cgactcggcg cccgttttca tcccggtgac ggcgctctca   2040
atgctgaaca ttgtcgccct cgccgtcgcg gcatggcgcg ccgttgtcgg gacggcggcg   2100
ggcgttcatg gtggcccggg agtcggagag ttcgtgtgct gtggctggat ggtgctgtgc   2160
ttctggccgt tcatgagagg gcttgtcagc agtggaaagt atgggatccc gtggagtgtc   2220
agggtgaagg ctgggttgat tgtggctgcg ttcgtgcacc tctgcacaag gaactaaccg   2280
gcgg                                                                2284

<210> SEQ ID NO 74
<211> LENGTH: 2363
<212> TYPE: DNA
<213> ORGANISM: Triticum aestivum

<400> SEQUENCE: 74
ggaaatgcac cgagcagagg ttagtttatc cggtctttat aaatgcactc tgtggtgttg     60
tgctagctag ctagtctgct acctctcggc cgcggccatg gcgggcggca agaagctgca    120
ggagagggtc gccctgggga gaactgcgtg gatgctggcc gacttcgtga tcctcctcct    180
cctcctcgcc ctcgtggccc gccgcgccgc gtcgctcggg gagcgcggcg ggacgtggct    240
ggcggcgctc gtctgcgagg cgtggttcgc cttcgtctgg atcctcaaca tgaacggcaa    300
gtggagcccc gtccggttcg acacctaccc cgacaacctc tcccacagga tggaggagct    360
cccggcggtg gacatgttcg tcacgacggc agacccggcg ctggagccgc cgttgatcac    420
ggtgaacacg tgctctcgc tgctcgcccct ggactacccg gacgtcggca ggctggcgtg    480
ctacgtctcc gacgacggct gctccccgt gacgtgctac gcgctgcgcg aggccgccaa    540
gttcgccggc ctctgggttc cctttttgcaa gaggcacgac gttggtgtga gggccccttt    600
catgtacttc tcttccgcgc cggaggttgg caacggaaca gtcgaccacg agttcctgga    660
aagctgggca ctcatgaaga gccaatatga aagctggcc cgccggatcg agaacgccga    720
cgagggcaca attatgcgtg acggcggcga cgagttcgcc gagttcatcg acgccgagcg    780
cgggaaccat cctaccatcg ttaaggttct ctgggacaac agcaagagca agcagggga    840 agaattccca catctggtgt acctctctcg agagaaaagc cccagacatc gtcacaactt    900
caaggccggt gccatgaatg ttctgacaag ggtgtcggcc gtgatgacca acgctccgat    960
catgctgaat gtggactgcg acatgttcgc caacaacccg caggtcgccc tacacgcgat   1020
gtgcctcctg ttggggttcg acgacgagat ccacagcggg ttcgtccagg cgccacagaa   1080
gttctacggc ggcctcaagg atgaccccct tggcaaccag atgcaggtta taaccaagaa   1140
aatcggaggt gggctcgccg ggatccaagg catgttctac ggcgggacag gctgtttca   1200 caggaggaaa gtcattttacg gcgtgccgcc accagacacc gtcaaacacg agatgaaagg   1260
ttcaccatct tacaaggagc tgcaggccaa gtttgggagc tcaaaggagt tgatcgaatc   1320
```

```
atctaggaac atcatctcag gagacctgct cgctagacca accgtagatt tatcgagtcg    1380
cgtcgaaatg gcaaaacaag taggcgactg caactatgag gctggcacat gttggggcca    1440
ggagattggc tgggtctatg gatcaatgac agaggacatc ttgaccgggc tgcggatcca    1500
tgcggcgggt tgggaatcgg ccttattgga caccgagcca ccggcattcc tgggatgtgc    1560
tccgaccggt ggaccggcca gcttgaccca gttcaagaga tgggcaacag ggcttctgga    1620
gatactcatc agccagaaca gcccgatcct cggcaccatc ttccgacgcc tccaactccg    1680
gcaatgcctt gcctatctca tcgtagaagc gtggcccgtg cgggcgcctt cgagctgtg     1740
ctatgcgcta ctgggacctt tctgccttct cacaaaccag tccttcttgc aacggcatc     1800
ggatgaaggt ttccgcatcc cagcggctct attcttgacc tgccacatat accacctgat    1860
ggagtacaag gagtgcgggc tctcggtccg cgcctggtgg aacaaccaca ggatgcaacg    1920
catcacctcg gcctccgcct ggctcctcgc cttcctcacc gtcattctca agacgctagg    1980
gctctccgag accgtgttcg aggtcacccg caaggaaagc agcacgtcct ccgatgcgg     2040
cgcgggcacc gacgaggccg atcctgggct cttcaccttc gactcggcgc cgttttcat     2100
cccggtgacg gtgctctcaa tgctgaacat tgtcgccctc gccgtcgcgg catggcgtgc    2160
tgttgtcggg gcggcggcgg gcgttcatgg tggcccgggc atcggggagt tcgtgtgctg    2220
tggctggatc gtgctgtgct tctggccgtt cgtgagaggg cttgtcagca ggggaaagta    2280
tggaatcccg tggagtgtca gggtgaaggc tggtttgatt gtggctgcgt tcgtgcacat    2340
ctgcacaagg aactaaccgg cgg                                             2363

<210> SEQ ID NO 75
<211> LENGTH: 752
<212> TYPE: PRT
<213> ORGANISM: Triticum aestivum

<400> SEQUENCE: 75

Met Ala Gly Gly Lys Lys Leu His Glu Arg Val Ala Leu Gly Arg Thr
1               5                   10                  15

Ala Trp Met Leu Ala Asp Phe Val Ile Leu Leu Leu Leu Ala Leu
            20                  25                  30

Val Ala Arg Arg Ala Ala Ser Leu Gly Glu Arg Gly Gly Thr Trp Leu
        35                  40                  45

Ala Ala Leu Val Cys Glu Ala Trp Phe Ala Phe Val Trp Ile Leu Asn
    50                  55                  60

Met Asn Gly Lys Trp Ser Pro Val Arg Phe Asp Thr Tyr Pro Glu Asn
65                  70                  75                  80

Leu Ser His Arg Leu Glu Glu Leu Pro Ala Val Asp Met Phe Val Thr
                85                  90                  95

Thr Ala Asp Pro Ala Leu Glu Pro Pro Leu Ile Thr Val Asn Thr Val
            100                 105                 110

Leu Ser Leu Leu Ala Leu Asp Tyr Pro Asp Val Gly Lys Leu Ala Cys
        115                 120                 125

Tyr Val Ser Asp Asp Gly Cys Ser Pro Val Thr Cys Tyr Ala Leu Arg
    130                 135                 140

Glu Ala Ala Lys Phe Ala Ser Leu Trp Ile Pro Phe Cys Lys Arg Tyr
145                 150                 155                 160

Asp Val Gly Val Arg Ala Pro Phe Met Tyr Phe Ser Ser Ala Pro Glu
                165                 170                 175

Val Gly Thr Gly Thr Ala Asp His Glu Phe Leu Glu Ser Trp Ala Leu
            180                 185                 190
```

```
Met Lys Thr Glu Tyr Glu Lys Leu Ala Ser Arg Ile Glu Asn Ala Asp
    195                 200                 205

Glu Val Ser Ile Leu Arg Asp Gly Gly Glu Phe Ala Glu Phe Ile
    210                 215                 220

Asp Ala Glu Arg Gly Asn His Pro Thr Ile Val Lys Val Leu Trp Asp
225                 230                 235                 240

Asn Ser Lys Ser Lys Ala Gly Glu Gly Phe Pro His Leu Val Tyr Leu
                245                 250                 255

Ser Arg Glu Lys Ser Pro Arg His Arg His Asn Phe Lys Ala Gly Ala
                260                 265                 270

Met Asn Val Leu Thr Arg Val Ser Ala Val Met Thr Asn Ala Pro Ile
    275                 280                 285

Met Leu Asn Val Asp Cys Asp Met Phe Ala Asn Asn Pro Gln Val Ala
    290                 295                 300

Leu His Ala Met Cys Leu Leu Leu Gly Phe Asp Asp Glu Ile His Ser
305                 310                 315                 320

Gly Phe Val Gln Ala Pro Gln Lys Phe Tyr Gly Gly Leu Lys Asp Asp
                325                 330                 335

Pro Phe Gly Asn Gln Met Gln Val Ile Thr Lys Lys Ile Gly Gly Gly
                340                 345                 350

Leu Ala Gly Ile Gln Gly Thr Phe Tyr Gly Gly Thr Gly Cys Phe His
                355                 360                 365

Arg Arg Lys Val Ile Tyr Gly Met Pro Pro Asp Thr Val Lys His
370                 375                 380

Glu Thr Arg Gly Ser Pro Ser Tyr Lys Glu Leu Gln Ala Lys Phe Gly
385                 390                 395                 400

Ser Ser Lys Glu Leu Ile Glu Ser Ser Arg Asn Ile Ile Ser Gly Asp
                405                 410                 415

Leu Leu Ala Arg Pro Thr Val Asp Ile Ser Ser Arg Val Glu Met Ala
                420                 425                 430

Lys Gln Val Gly Asp Cys Asn Tyr Glu Ala Gly Thr Cys Trp Gly Gln
                435                 440                 445

Glu Ile Gly Trp Val Tyr Gly Ser Met Thr Glu Asp Ile Leu Thr Gly
    450                 455                 460

Gln Arg Ile Gln Ala Ala Gly Trp Glu Ser Ala Leu Leu Asp Thr Asp
465                 470                 475                 480

Pro Pro Ala Phe Leu Gly Cys Ala Pro Thr Gly Gly Pro Ala Ser Leu
                485                 490                 495

Thr Gln Phe Lys Arg Trp Ala Thr Gly Leu Leu Glu Ile Leu Ile Ser
                500                 505                 510

Arg Asn Ser Pro Ile Leu Gly Thr Ile Phe Lys Gly Leu Gln Leu Arg
                515                 520                 525

Gln Cys Leu Gly Tyr Leu Ile Val Asp Ala Trp Pro Val Arg Ala Pro
    530                 535                 540

Phe Glu Leu Cys Tyr Ala Leu Leu Gly Pro Phe Cys Leu Leu Thr Asn
545                 550                 555                 560

Gln Ser Phe Leu Pro Thr Ala Ser Asp Glu Gly Phe His Ile Pro Ala
                565                 570                 575

Ala Leu Phe Leu Thr Tyr Asn Ile Tyr His Leu Met Glu Tyr Lys Glu
                580                 585                 590

Cys Gly Leu Ser Val Arg Ala Trp Trp Asn Asn His Arg Met Gln Arg
                595                 600                 605

Ile Thr Ser Ala Ser Ala Trp Leu Leu Ala Phe Leu Thr Val Ile Leu
    610                 615                 620
```

```
Lys Thr Leu Gly Leu Ser Glu Thr Val Phe Glu Val Thr Arg Lys Glu
625                 630                 635                 640

Ser Ser Thr Ser Ser Asp Gly Ala Gly Thr Asp Ala Asp Pro
            645                 650                 655

Gly Leu Phe Thr Phe Asp Ser Ala Pro Val Phe Ile Pro Val Thr Ala
            660                 665                 670

Leu Ser Val Leu Asn Ile Val Ala Leu Thr Val Ala Ala Trp Arg Ala
            675                 680                 685

Val Val Gly Thr Val Ala Gly Val His Gly Gly Pro Gly Val Gly Glu
            690                 695                 700

Phe Val Cys Cys Gly Trp Met Val Leu Cys Phe Trp Pro Phe Val Arg
705                 710                 715                 720

Gly Leu Val Ser Ser Gly Lys Tyr Gly Ile Pro Trp Ser Val Arg Val
            725                 730                 735

Lys Ala Gly Leu Ile Val Ala Ala Phe Val His Leu Cys Thr Arg Asn
            740                 745                 750

<210> SEQ ID NO 76
<211> LENGTH: 752
<212> TYPE: PRT
<213> ORGANISM: Triticum aestivum

<400> SEQUENCE: 76

Met Ala Gly Gly Lys Lys Leu Gln Glu Arg Val Ala Leu Gly Arg Ser
1               5                   10                  15

Ala Trp Met Leu Ala Asp Phe Val Ile Leu Phe Leu Leu Leu Ala Leu
            20                  25                  30

Val Ala Arg Arg Ala Ala Ser Leu Gly Glu Arg Gly Gly Thr Trp Leu
            35                  40                  45

Ala Ala Leu Val Cys Glu Ala Trp Phe Ala Phe Val Trp Ile Leu Asn
            50                  55                  60

Met Asn Gly Lys Trp Ser Pro Val Arg Phe Asp Thr Tyr Pro Asp Asn
65                  70                  75                  80

Leu Ser His Arg Met Glu Glu Leu Pro Ala Val Asp Met Phe Val Thr
            85                  90                  95

Thr Ala Asp Pro Ala Leu Glu Pro Pro Leu Ile Thr Val Asn Thr Val
            100                 105                 110

Leu Ser Leu Leu Ala Leu Asp Tyr Pro His Val Gly Lys Leu Ala Cys
            115                 120                 125

Tyr Val Ser Asp Asp Gly Cys Ser Pro Leu Thr Cys Tyr Gly Leu His
            130                 135                 140

Glu Ala Ala Lys Phe Ala Ser Leu Trp Val Pro Phe Cys Lys Arg His
145                 150                 155                 160

Asp Val Gly Val Arg Ala Pro Phe Met Tyr Phe Ser Ser Ala Pro Glu
            165                 170                 175

Val Asp Thr Gly Thr Val Asp His Glu Phe Leu Glu Ser Trp Ala Leu
            180                 185                 190

Met Lys Ser Glu Tyr Glu Lys Leu Ala Ser Arg Ile Glu Asn Ala Asp
            195                 200                 205

Glu Val Ser Ile Leu Arg Asp Gly Gly Asp Glu Phe Ala Glu Phe Ile
            210                 215                 220

Asp Ala Glu Arg Gly Asn His Pro Thr Ile Val Lys Val Leu Trp Asp
225                 230                 235                 240

Asn Ser Lys Asn Lys Thr Gly Glu Gly Phe Pro His Leu Val Tyr Leu
            245                 250                 255
```

```
Ser Arg Glu Lys Ser Pro Arg His Arg His Asn Phe Lys Ala Gly Ala
            260                 265                 270

Met Asn Val Leu Thr Arg Val Ser Ala Val Met Thr Asn Ala Pro Ile
            275                 280                 285

Met Leu Asn Val Asp Cys Asp Met Phe Ala Asn Pro Gln Val Ala
            290                 295                 300

Leu His Ala Met Cys Leu Leu Gly Phe Asp Asp Glu Ile His Ser
305                 310                 315                 320

Gly Phe Val Gln Ala Pro Gln Lys Phe Tyr Gly Gly Leu Lys Asp Asp
                325                 330                 335

Pro Phe Gly Asn Gln Met Gln Val Ile Thr Lys Lys Ile Gly Gly Gly
                340                 345                 350

Leu Ala Gly Ile Gln Gly Thr Phe Tyr Gly Thr Gly Cys Phe His
            355                 360                 365

Arg Arg Lys Val Ile Tyr Gly Met Pro Pro Asp Thr Val Lys His
            370                 375                 380

Glu Thr Arg Gly Ser Pro Ser Tyr Lys Glu Leu Gln Ala Lys Phe Gly
385                 390                 395                 400

Ser Ser Lys Glu Leu Ile Glu Ser Arg Asn Ile Ile Ser Gly Asp
            405                 410                 415

Leu Leu Ala Arg Pro Thr Val Asp Ile Ser Ser Arg Val Glu Met Ala
            420                 425                 430

Lys Gln Val Gly Asp Cys Asn Tyr Glu Ala Gly Thr Tyr Trp Gly Gln
            435                 440                 445

Glu Ile Gly Trp Val Tyr Gly Ser Met Thr Glu Asp Ile Leu Thr Gly
            450                 455                 460

Gln Arg Ile Gln Ala Ala Gly Trp Lys Ser Ala Leu Leu Asp Thr Asp
465                 470                 475                 480

Pro Pro Ala Phe Leu Gly Cys Ala Pro Thr Gly Gly Pro Ala Ser Leu
                485                 490                 495

Thr Gln Phe Lys Arg Trp Ala Thr Gly Leu Leu Glu Ile Leu Ile Ser
            500                 505                 510

Arg Asn Ser Pro Ile Leu Gly Thr Ile Phe Arg Arg Leu Gln Leu Arg
            515                 520                 525

Gln Cys Leu Ala Tyr Leu Ile Val Asn Ala Trp Pro Met Arg Ala Pro
            530                 535                 540

Phe Glu Met Cys Tyr Ala Leu Leu Gly Pro Phe Cys Leu Leu Thr Asn
545                 550                 555                 560

Gln Ser Phe Leu Pro Thr Thr Ser Asn Glu Gly Phe Arg Ile Pro Ala
                565                 570                 575

Ala Leu Phe Leu Ser Tyr His Val Tyr His Leu Met Glu Tyr Lys Glu
                580                 585                 590

Cys Gly Leu Ser Val Arg Ala Trp Trp Asn Asn His Arg Met Gln Arg
                595                 600                 605

Ile Thr Ser Ala Ser Ala Trp Leu Leu Ala Phe Leu Thr Val Ile Leu
            610                 615                 620

Lys Thr Leu Gly Leu Ser Glu Thr Val Phe Glu Val Thr Arg Lys Glu
625                 630                 635                 640

Ser Ser Thr Ser Ser Asp Gly Gly Ala Gly Thr Asp Glu Ala Asp Thr
                645                 650                 655

Gly Leu Phe Thr Phe Asp Ser Ala Pro Val Phe Ile Pro Val Thr Ala
                660                 665                 670

Leu Ser Met Leu Asn Ile Val Ala Leu Ala Val Ala Ala Trp Arg Ala
```

```
                675                 680                 685
Val Val Gly Thr Ala Ala Gly Val His Gly Pro Gly Val Gly Glu
        690                 695                 700

Phe Val Cys Cys Gly Trp Met Val Leu Cys Phe Trp Pro Phe Met Arg
705                 710                 715                 720

Gly Leu Val Ser Ser Gly Lys Tyr Gly Ile Pro Trp Ser Val Arg Val
                725                 730                 735

Lys Ala Gly Leu Ile Val Ala Ala Phe Val His Leu Cys Thr Arg Asn
                740                 745                 750

<210> SEQ ID NO 77
<211> LENGTH: 752
<212> TYPE: PRT
<213> ORGANISM: Triticum aestivum

<400> SEQUENCE: 77

Met Ala Gly Gly Lys Lys Leu Gln Glu Arg Val Ala Leu Gly Arg Thr
1               5                   10                  15

Ala Trp Met Leu Ala Asp Phe Val Ile Leu Leu Leu Leu Ala Leu
            20                  25                  30

Val Ala Arg Arg Ala Ala Ser Leu Gly Glu Arg Gly Gly Thr Trp Leu
        35                  40                  45

Ala Ala Leu Val Cys Glu Ala Trp Phe Ala Phe Val Trp Ile Leu Asn
    50                  55                  60

Met Asn Gly Lys Trp Ser Pro Val Arg Phe Asp Thr Tyr Pro Asp Asn
65              70                  75                  80

Leu Ser His Arg Met Glu Glu Leu Pro Ala Val Asp Met Phe Val Thr
                85                  90                  95

Thr Ala Asp Pro Ala Leu Glu Pro Pro Leu Ile Thr Val Asn Thr Val
            100                 105                 110

Leu Ser Leu Leu Ala Leu Asp Tyr Pro Asp Val Gly Arg Leu Ala Cys
        115                 120                 125

Tyr Val Ser Asp Asp Gly Cys Ser Pro Val Thr Cys Tyr Ala Leu Arg
    130                 135                 140

Glu Ala Ala Lys Phe Ala Gly Leu Trp Val Pro Phe Cys Lys Arg His
145                 150                 155                 160

Asp Val Gly Val Arg Ala Pro Phe Met Tyr Phe Ser Ser Ala Pro Glu
                165                 170                 175

Val Gly Asn Gly Thr Val Asp His Glu Phe Leu Glu Ser Trp Ala Leu
            180                 185                 190

Met Lys Ser Gln Tyr Glu Lys Leu Ala Arg Arg Ile Glu Asn Ala Asp
        195                 200                 205

Glu Gly Thr Ile Met Arg Asp Gly Gly Asp Glu Phe Ala Glu Phe Ile
    210                 215                 220

Asp Ala Glu Arg Gly Asn His Pro Thr Ile Val Lys Val Leu Trp Asp
225                 230                 235                 240

Asn Ser Lys Ser Lys Ala Gly Glu Glu Phe Pro His Leu Val Tyr Leu
                245                 250                 255

Ser Arg Glu Lys Ser Pro Arg His Arg His Asn Phe Lys Ala Gly Ala
            260                 265                 270

Met Asn Val Leu Thr Arg Val Ser Ala Val Met Thr Asn Ala Pro Ile
        275                 280                 285

Met Leu Asn Val Asp Cys Asp Met Phe Ala Asn Asn Pro Gln Val Ala
    290                 295                 300

Leu His Ala Met Cys Leu Leu Leu Gly Phe Asp Asp Glu Ile His Ser
```

```
            305                 310                 315                 320
Gly Phe Val Gln Ala Pro Gln Lys Phe Tyr Gly Gly Leu Lys Asp Asp
                    325                 330                 335

Pro Phe Gly Asn Gln Met Gln Val Ile Thr Lys Lys Ile Gly Gly Gly
                    340                 345                 350

Leu Ala Gly Ile Gln Gly Met Phe Tyr Gly Gly Thr Gly Cys Phe His
                    355                 360                 365

Arg Arg Lys Val Ile Tyr Gly Val Pro Pro Asp Thr Val Lys His
                    370                 375             380

Glu Met Lys Gly Ser Pro Ser Tyr Lys Glu Leu Gln Ala Lys Phe Gly
385                 390                 395                 400

Ser Ser Lys Glu Leu Ile Glu Ser Ser Arg Asn Ile Ile Ser Gly Asp
                    405                 410                 415

Leu Leu Ala Arg Pro Thr Val Asp Leu Ser Ser Arg Val Glu Met Ala
                    420                 425                 430

Lys Gln Val Gly Asp Cys Asn Tyr Glu Ala Gly Thr Cys Trp Gly Gln
                    435                 440                 445

Glu Ile Gly Trp Val Tyr Gly Ser Met Thr Glu Asp Ile Leu Thr Gly
                    450                 455                 460

Leu Arg Ile His Ala Ala Gly Trp Glu Ser Ala Leu Leu Asp Thr Glu
465                 470                 475                 480

Pro Pro Ala Phe Leu Gly Cys Ala Pro Thr Gly Pro Ala Ser Leu
                    485                 490                 495

Thr Gln Phe Lys Arg Trp Ala Thr Gly Leu Leu Glu Ile Leu Ile Ser
                    500                 505                 510

Gln Asn Ser Pro Ile Leu Gly Thr Ile Phe Arg Arg Leu Gln Leu Arg
                    515                 520                 525

Gln Cys Leu Ala Tyr Leu Ile Val Glu Ala Trp Pro Val Arg Ala Pro
                    530                 535                 540

Phe Glu Leu Cys Tyr Ala Leu Leu Gly Pro Phe Cys Leu Leu Thr Asn
545                 550                 555                 560

Gln Ser Phe Leu Pro Thr Ala Ser Asp Glu Gly Phe Arg Ile Pro Ala
                    565                 570                 575

Ala Leu Phe Leu Thr Cys His Ile Tyr His Leu Met Glu Tyr Lys Glu
                    580                 585                 590

Cys Gly Leu Ser Val Arg Ala Trp Trp Asn Asn His Arg Met Gln Arg
                    595                 600                 605

Ile Thr Ser Ala Ser Ala Trp Leu Leu Ala Phe Leu Thr Val Ile Leu
                    610                 615                 620

Lys Thr Leu Gly Leu Ser Glu Thr Val Phe Glu Val Thr Arg Lys Glu
625                 630                 635                 640

Ser Ser Thr Ser Ser Asp Gly Ala Gly Thr Asp Glu Ala Asp Pro
                    645                 650                 655

Gly Leu Phe Thr Phe Asp Ser Pro Val Phe Ile Pro Val Thr Val
                    660                 665                 670

Leu Ser Met Leu Asn Ile Val Ala Leu Ala Val Ala Ala Trp Arg Ala
                    675                 680                 685

Val Val Gly Ala Ala Ala Gly Val His Gly Gly Pro Gly Ile Gly Glu
                    690                 695                 700

Phe Val Cys Cys Gly Trp Ile Val Leu Cys Phe Trp Pro Phe Val Arg
705                 710                 715                 720

Gly Leu Val Ser Arg Gly Lys Tyr Gly Ile Pro Trp Ser Val Arg Val
                    725                 730                 735
```

Lys Ala Gly Leu Ile Val Ala Ala Phe Val His Ile Cys Thr Arg Asn
            740                 745                 750

<210> SEQ ID NO 78
<211> LENGTH: 3114
<212> TYPE: DNA
<213> ORGANISM: Triticum aestivum

<400> SEQUENCE: 78

| | | | | | |
|---|---|---|---|---|---|
| ctgctctcgg | ccgcggccat | ggcgggcggc | aagaagctgc | acgagagggt | cgccctgggg | 60 |
| agaactgcgt | ggatgctggc | cgacttcgtg | atcctcctcc | tcctcctcgc | cctcgtggcc | 120 |
| cgccgcgccg | cgtcgctcgg | ggagcgcggc | gggacgtggc | tggcggcgct | cgtctgcgag | 180 |
| gcgtggttcg | ccttcgtctg | gatcctcaac | atgaacggca | agtggagccc | cgtccggttc | 240 |
| gacacctacc | ccgagaacct | ctcccacagg | tacgtacgtt | cttgtgcaca | ctaactgcaa | 300 |
| aataatgttg | acctacagct | tcgtgcagct | tcttccttaa | actgtgtcgt | gtctgtgatg | 360 |
| attttgctag | gctggaggag | ctcccggcgg | tggacatgtt | cgtcacgacg | gcggacccgg | 420 |
| cgctggagcc | gccgttgatc | acggtgaaca | cggtgctctc | gctgctcgcc | ctggactacc | 480 |
| cggacgtcgg | caagctggcg | tgctacgtct | ccgacgacgg | ctgctccccg | gtgacgtgct | 540 |
| acgcgctgcg | cgaggccgcc | aagttcgcca | gcctctggat | tcccttctgc | aagaggtatg | 600 |
| acgttggtgt | gagggcccct | ttcatgtact | tctcttccgc | gccggaggtt | ggcaccggta | 660 |
| cagccgacca | cgagttcctg | aaagctgggc | cactcatgaa | ggttaggcgc | catggtgacc | 720 |
| atttcagttt | ccataatgtt | tggtcgtcca | tcgtcgccat | gaccatgcat | cttcctcgtg | 780 |
| tacgtgtgac | tttcagaccg | aatatgagaa | gctggccagc | cggatcgaga | acgccgacga | 840 |
| ggtctccatt | ctgcgtgacg | gcggcgaaga | gttcgccgag | ttcatcgacg | ccgagcgcgg | 900 |
| gaaccatcct | accatcgtta | aggtcgccgc | actgaccatg | tccatgtaca | tcgtgtcatg | 960 |
| ccaaacgcgt | agcaaatccg | tctcgtgcta | atatcgtcac | ggttaacctg | tgtgagttca | 1020 |
| ggttctctgg | gataacagca | agagcaaagc | aggggaagga | ttcccacatc | tggtgtacct | 1080 |
| ctctcgagag | aaaagcccca | gacatcgcca | caacttcaag | gccggtgcca | tgaatgttct | 1140 |
| ggtgagcact | ctcttgtaca | aacagtgtt | tcactggtaa | tcagtgtgtc | acacaaacag | 1200 |
| cacaataagt | ggcagttgaa | agttcagaca | tgtgtacaat | gcgcttgata | atttgcaagc | 1260 |
| aaataattaa | gctgagcgtt | tcgtggtgca | gacaagggtg | tcggccgtga | tgaccaacgc | 1320 |
| tccaatcatg | ctgaatgtgg | actgcgacat | gttcgccaac | aacccgcagg | tcgccctgca | 1380 |
| cgcgatgtgc | ctcctgttgg | ggttcgacga | cgagatccac | agcgggttcg | tccaggcgcc | 1440 |
| acagaagttc | tacggtggcc | tcaaggatga | ccccctttggc | aaccagatgc | aggttataac | 1500 |
| caaggtacta | catatgcatg | tgcacaagtg | ctgttgtggt | agtgcaccac | tagggtagtg | 1560 |
| ttacagttgc | actggttttt | ctggcatgtt | cagaaaattg | gaggtgggct | cgccgggatc | 1620 |
| caaggcacct | tctacggcgg | cacgggctgt | tttcaccgca | ggaaggtcat | ctacggcatg | 1680 |
| ccgcctccgg | acaccgtcaa | gcacgagaca | agaggtaata | aaactgggca | cgcacaagat | 1740 |
| gagatcatcc | gacgtaaatt | gaagtatttg | gtcagtgcat | ttcagttcga | ctagggcata | 1800 |
| tcaaatggct | gttctgaatt | tgccaggttc | accatcttac | aaggagctgc | aagccaagtt | 1860 |
| tgggagctca | aaggagttga | tcgaatcatc | taggaacatc | atctcagggg | acctgctcgc | 1920 |
| tagaccaacc | gtagatatat | cgagtcgtgt | cgaaatggca | aaacaagtag | gcgactgcaa | 1980 |
| ctatgaggct | ggcacatgtt | ggggccaaga | ggtgtgctta | gcttcgttgc | cgtatttttg | 2040 |
| caggttttgc | tacagtacgg | ccacatctac | acaccttctg | cagtttctct | ctattacagt | 2100 |

```
ttcttccatg tattttttgca gattgggtgg gtctatggat caatgacaga ggacattttg    2160
accggtcaac ggatccaggc ggcgggttgg gaatcggcct tgttggacac cgacccaccg    2220
gcattcctgg gatgtgctcc gaccggtgga ccagccagct tgacccagtt caagagatgg    2280
gcaacagggc ttctggagat actcatcagc cggaacagcc ccatcctcgg caccatcttc    2340
aagggcctcc aactccggca atgccttggc tatctcatcg tagacgcgtg gcccgtgagg    2400
gcgcctttcg agctgtgcta tgcgctcttg gacctttct gccttctcac aaaccaatcc     2460
ttcttaccaa cggtacacac atttttgcca tgacccatta ctacattgct catagctgaa    2520
attttagtgc atttgccgtt ttgcaggcat cagatgaagg ttttcacatc ccagcggctc    2580 tattttttgac ttacaacata taccacctga tggagtacaa ggagtgcggg ctctcggtcc   2640
gcgcctggtg gaacaaccat aggatgcaac gcatcacctc ggcctccgcc tggctcctcg    2700
ccttcctcac cgtcatcctc aagacgctag ggctctccga ccgtgttc gaggtcaccc      2760 gcaaggagag cagcacgtca tccgatggcg gcgcgggcac cgacgatgcc gatcctgggt    2820
tgttcacctt tgactcggcg cccgttttca tcccagtgac ggcgctctca gtgttgaaca    2880
ttgtcgccct caccgtcgcg gcatggcgcg ccgtcgtcgg gacggtggcg ggcgttcatg    2940
gtggcccggg cgtcggagag ttcgtgtgct gtggctggat ggtgttgtgc ttctggccat    3000
tcgtgagagg gcttgtcagt agtggaaagt atgggatccc gtggagtgtc agggtgaagg    3060
ctgggttgat tgtggctgcg ttcgtgcacc tctgcacaag gaactaaccg gccg          3114

<210> SEQ ID NO 79
<211> LENGTH: 3178
<212> TYPE: DNA
<213> ORGANISM: Triticum aestivum

<400> SEQUENCE: 79
ctgctctcgg ccacggccat ggcgggcggc aagaagctgc aggagagggt cgccctgggc      60
aggagcgcgt ggatgctggc cgacttcgtg atcctcttcc tcgtcctcgc cctcgtggcc    120
cgccgcgccg cgtcgctcgg ggagcgcggc gggacgtggc tggcagcgct cgtctgcgag    180
gcgtggttcg ccttcgtgtg gatcctcaac atgaacggca agtggagccc cgtccggttc    240
gacacctacc ccgagaacct ctcccacagg tacgtacgtt cttgtgcaca ctaactgcaa    300
aataatgttg acctacagct tcgtgcaact tcttccttaa gctgtgtcgt gtctgtgatg    360
attttgctag gatggaagag ctcccggcgg tggacatgtt cgtcacgacg gcggacccgg    420
cgctggagcc gccgttgatc acggtgaaca cggtgctctc gctgctcgcc ctggactacc    480
cgcacgtcgg caagctggcg tgctacgtct ccgacgacgg ctgctccccc ttgacgtgct    540
actctctgcg cgaggccgcc aagttcgcca gcctctgggt tcccttctgc aagaggcacg    600
acgttggtgt gagggcccct ttcatgtact tctcttccgc gccggaggtt gacaccggta    660
cagtcgacca cgagttcctg gaaagctggg cactcatgaa ggtcagccga tgatgatgat    720 gtcagttttcc ataatgtttg gtcgtccatc atcgccatga ccatgcatct tccttgtgta    780
cgtgtgactt tcagagcgaa tatgagaagc tggccagccg gatcgagacg cgacgaggtc    840
tcattctgcg tgacgcggc gacgagttcc ccgagttcat cgacgccgag cgcgggaacc      900
atcctaccat cgttaaggtc gctgcactga ccatatccac gtgtccatgt acatcgtgtc    960
gtgccaaacg catagcgaat ccgtctcgtg ctaatatcgt cacggttaac ctgtctgagt   1020
tcaggttctc tgggataaca gcaagaacaa aacaggtgaa ggattccac atctggtgta    1080 cctctcgaga gagaaaagcc ccagacatcg tcacaacttt aaggccggtg ccatgaatgt    1140
```

```
tctggtgagc actctcttct actcaataca gtgttgcact actaatcagt gtgtcacaca    1200
aacagcaaaa agtggcagat aaaagctcag acggttgcac gacacatttg atactaatta    1260
agctgagcat ttcgtggtgc agacaagggt gtcggccgtg atgaccaacg ctccgatcat    1320
gctgaatgtg gactgcgaca tgtttgccaa caacccgcag gtcgccctac acgcgatgtg    1380
cctcctgttg gggttcgacg acgagatcca cagcgggttc gtccaggcgc acagaagtt     1440 ctacggtggc ctcaaggatg accccttggg caaccagatg caggttataa ccaaggtact    1500
acatatgcat gtgcacaagt gctgttgtgg tagtgcacca ctagggtagt gttacagttg    1560
cactggtttt tctggcatgt tcagaaaatt ggaggtgggc tcgccgggat ccaaggcacg    1620
ttctacggcg gcacgggctg ttttcaccgc aggaaggtca tttacggcat gccgcctccg    1680
gacaccgtca agcacgagac aagaggtaat aaaactgggc acacaaaaga tgaggcatcc    1740
ggcgtaaatt ggagtatttg gccagtgcat ttcagttcga ctagggcata tcaaatggct    1800
ttctgaattt gccaggttca ccatcttaca aggagctgca agccaagttt gggagctcaa    1860
aggagttgat cgaatcatct aggaacatca tctcaggaga cctgctcgct agaccaaccg    1920
tagatatatc aagtcgggtc gaaatggcaa acaagtagg cgactgcaac tatgaggctg     1980
gcacatgttg gggccaagag gtgtgcttag cttcgttgcc gtattttgc aggttttgct     2040 acagtacggc cacatctaca aaccttctgc agtttctctc tattacagtt tcttccatct    2100
atttttgcag attgggtggg tctatggatc aatgacagag gacatttga ccgggcaacg     2160 gatccaagcg gcgggttgga aatcggcctt gttggacacc gacccaccgg cattcttggg    2220
atgtgctccg acaggggggc cggctagctt gacccagttc aagagatggg caacagggct    2280
tctggagata ctcatcagcc ggaacagccc catcctcggc accatcttca ggcgcctcca    2340
actccggcaa tgccttgcct atctcatcgt caacgcgtgg cccatgaggg cacctttcga   2400
gatgtgttac gcgctattgg gacctttctg ccttctcaca aaccagtcct tcttgccaac    2460
ggtacacaca tttttgccat gaccctttac tacattgctc atagctgaaa tttcagtaca    2520
cgtggtgatg tggaaacaca agtctatgca actaaacaaa aatgtttgtg taatttgttt    2580
gataagattt gtgcatttgc tgttttgcag acatctaatg aaggttttcg catcccagcg    2640
gctctattct tgagttacca cgtataccac ctgatggagt acaaggagtg cgggctctcg    2700
gtccgcgcct ggtggaacaa ccacaggatg caacgcatca cctcggcctc cgcctggctc    2760
ctcgccttcc tcaccgtcat cctcaagacg ctagggctct ccgagaccgt gttcgaggtc    2820
acccgcaagg agagcagcac gtcctccgat ggtggcgcgg gcaccgacga ggccgatact    2880
gggctgttca ccttcgactc ggcgccgtt ttcatcccgg tgacggcgct ctcaatgctg      2940
aacattgtcg ccctcgccgt cgcggcatgg cgcgccgttg tcgggacggc ggcgggcgtt    3000
catggtggcc cggagtcgg agagttcgtg tgctgtggct ggatggtgct gtgcttctgg     3060
ccgttcatga gagggcttgt cagcagtgga aagtatggga tcccgtggag tgtcagggtg    3120
aaggctgggt tgattgtggc tgcgttcgtg cacctctgca caaggaacta accggcgg      3178
```

<210> SEQ ID NO 80
<211> LENGTH: 3261
<212> TYPE: DNA
<213> ORGANISM: Triticum aestivum

<400> SEQUENCE: 80

```
ggaaatgcac cgagcagagg ttagtttatc cggtctttat aaatgcactc tgtggtgttg      60
tgctagctag ctagtctgct acctctcggc cgcggccatg gcgggcggca agaagctgca    120
```

```
ggagagggtc gccctgggga gaactgcgtg gatgctggcc gacttcgtga tcctcctcct    180
cctcctcgcc ctcgtggccc gccgcgccgc gtcgctcggg gagcgcggcg ggacgtggct    240
ggcggcgctc gtctgcgagg cgtggttcgc cttcgtctgg atcctcaaca tgaacggcaa    300
gtggagcccc gtccggttcg acacctaccc cgacaacctc tcccacaggt acgtacgttc    360
ttgtgcacac taactgcaaa ataatgttga cctacagcta cgtgcagctt cttccttaaa    420
ctgtgtcgtg tctgtgatga ttttgctagg atggaggagc tcccggcggt ggacatgttc    480
gtcacgacgg cagacccggc gctggagccg ccgttgatca cggtgaacac ggtgctctcg    540
ctgctcgccc tggactaccc ggacgtcggc aggctggcgt gctacgtctc cgacgacggc    600
tgctcccccg tgacgtgcta cgcgctgcgc gaggccgcca gttcgccgg cctctgggtt    660 cccttttgca agaggcacga cgttggtgtg agggcccctt tcatgtactt ctcttccgcg    720
ccggaggttg gcaacggaac agtcgaccac gagttcctgg aaagctgggc actcatgaag    780
gttagtcgcc atggtgatca tgccggttta tgtttggtcg tccatcatcg ccatgaccat    840
gcatcttcct cgtgtacgtg tgacttcaga gccaatatga aagctggcc cgccggatcg    900 agaacgccga cgagggcaca attatgcgtg acggcggcga cgagttcgcc gagttcatcg    960
acgccgagcg cgggaaccat cctaccatcg ttaaggtcgg tgcactgacc atgttcattt   1020
gtccatgtac atcgtgtcgt gccaaacgca tagcaaatcc gtctcgtgct aatatcgtca   1080
cggttaatct gtctgagttc aggttctctg gacaacagc aagagcaaag caggggaaga    1140
attcccacat ctggtgtacc tctctcgaga gaaaagcccc agacatcgtc acaacttcaa   1200
ggccggtgcc atgaatgttc tggtgagcac tctcttctac tcaatacaat gttgcactac   1260
taatcagtgt gtcacacaaa cagcaaaaag tggaagataa aagttcagac ggcatgacac   1320
ttttgatact aattaagctg agcatttcgt ggtgcagaca agggtgtcgg ccgtgatgac   1380
caacgctccg atcatgctga atgtggactg cgacatgttc gccaacaacc cgcaggtcgc   1440
cctacacgcg atgtgcctcc tgttggggtt cgacgacgag atccacagcg ggttcgtcca   1500
ggcgccacag aagttctacg gcggcctcaa ggatgacccc tttggcaacc agatgcaggt   1560
tataaccaag gtacacaagt gctgctgtgg ttgtactgtt acagttttt tttttgagcga   1620 tgggtagtgt tacagttgta ctggttttc tggcatgttc agaaaatcgg aggtgggctc   1680
gccgggatcc aaggcatgtt ctacggcggg acaggctgtt ttcacaggag gaaagtcatt   1740
tacggcgtgc cgccaccaga caccgtcaaa cacgagatga aagtaataa aactgggcac    1800 acaaaagatg agatcatccg gcgtaaattg gagtatttgg tcagtgcatt tcggttcgac   1860
tagggcaaca tcaaatggct gttccgaatt tgccaggttc accatcttac aaggagctgc   1920
aggccaagtt tgggagctca aaggagttga tcgaatcatc taggaacatc atctcaggag   1980
acctgctcgc tagaccaacc gtagatttat cgagtcgcgt cgaaatggca aaacaagtag   2040
gcgactgcaa ctatgaggct ggcacatgtt ggggccagga ggtatgctta gcttccgttg   2100
ccgtattttt gcaggttttg ctacagtaca tctacaacta caaaccttct gcagtttctc   2160
tctagttaca gtttcttcca tatatatt tttgcagatt ggctgggtct atggatcaat    2220
gacagaggac atcttgaccg ggctgcggat ccatgcggcg ggttgggaat cggccttatt   2280
ggacaccgag ccaccggcat tcctgggatg tgctccgacc ggtggaccgg ccagcttgac   2340
ccagttcaag agatgggcaa cagggcttct ggagatactc atcagccaga acagcccgat   2400
cctcggcacc atcttccgac gcctccaact ccggcaatgc cttgcctatc tcatcgtaga   2460
agcgtggccc gtgcgggcgc ctttcgagct gtgctatgcg ctactgggac ctttctgcct   2520
```

```
tctcacaaac cagtccttct tgccaacggt acatacactt ttgccatgac ccattactac    2580
attatatgca actaaacaaa aatgttgtgt gatttgtttg ataatgaagc gcgacctagt    2640
tggttaatgt gtaaatatat attttcatga tttttacatt tgctgttttg caggcatcgg    2700
atgaaggttt ccgcatccca gcggctctat tcttgacctg ccacatatac cacctgatgg    2760
agtacaagga gtgcgggctc tcggtccgcg cctggtggaa caaccacagg atgcaacgca    2820
tcacctcggc ctccgcctgg ctcctcgcct tcctcaccgt cattctcaag acgctagggc    2880
tctccgagac cgtgttcgag gtcacccgca aggaaagcag cacgtcctcc gatggcggcg    2940
cgggcaccga cgaggccgat cctgggctct tcaccttcga ctcggcgccc gtttcatcc     3000 cggtgacggt gctctcaatg ctgaacattg tcgccctcgc cgtcgcggca tggcgtgctg    3060 ttgtcgggc ggcggcgggc gttcatggtg gcccgggcat cggggagttc gtgtgctgtg     3120
gctggatcgt gctgtgcttc tggccgttcg tgagagggct tgtcagcagg ggaaagtatg    3180
gaatcccgtg gagtgtcagg gtgaaggctg gtttgattgt ggctgcgttc gtgcacatct    3240
gcacaaggaa ctaaccggcg g                                              3261
```

POLYSACCHARIDE SYNTHASES (H)

CROSS REFERENCE TO RELATED APPLICATIONS

This application is a U.S. National Phase filing under 35 U.S.C. §371 of International Application PCT/AU2008/001906, filed Dec. 24, 2008, and published as WO 2009/079714 on Jul. 2, 2009. PCT/AU2008/001906 claimed benefit of priority from Australian Patent Application No. AU2007907071, filed Dec. 24, 2007. The entire contents of each of the prior applications are incorporated herein by reference.

PRIORITY CLAIM

The present invention claims priority to Australian provisional patent application 2007907071 the content of which is hereby incorporated by reference.

FIELD OF THE INVENTION

The present invention relates generally to polysaccharide synthases. More particularly, the present invention relates to (1,3;1,4)-β-D-glucan synthases.

BACKGROUND OF THE INVENTION

The various tissues of cereal grains have diverse functions during grain development, dormancy and after germination.

For example, the pericarp and seed coat tissues are concerned with the protection of the seed during development and during dormancy. However, by grain maturity, these outer grain tissues have died and the tissue residues consist almost entirely of cell wall residues. The nucellar tissue between the seed coat and the aleurone surface is involved in transfer of nutrients to the developing grain, however, at maturity this tissue has also collapsed to leave cell wall remnants. The thin walled cells of the starchy endosperm of mature grain are dead, but are packed with starch and storage protein. In contrast, the thick-walled, nucleated, aleurone cells are alive at grain maturity, and are packed with protein bodies and lipid droplets. At the interface of the starchy endosperm lies the scutellum, which functions in delivering nutrients to the developing endosperm and, during germination, transfers digestion products of the endosperm reserves to the developing embryo.

The different structure and function of each tissue type in the grain is determined, at least in part, by the cell wall composition of each of these cell types.

Non-cellulosic polysaccharides are key components in the cell walls of cereal grain tissues and include, for example, (1,3;1,4)-β-D-glucans, heteroxylans (mainly arabinoxylans), glucomannans, xyloglucans, pectic polysaccharides and cellose. These non-cellulosic polysaccharides usually constitute less than 10% of the overall weight of the grain, but nevertheless are key determinants of grain quality.

Although the precise physical relationships between individual non-cellulosic polysaccharides and other wall components have not been described, it is generally considered that in the wall, microfibrils of cellulose are embedded in a matrix phase of non-cellulosic polysaccharides and protein. Wall integrity is maintained predominantly through extensive non-covalent interactions, especially hydrogen bonding, between the matrix phase and microfibrillar constituents. In the walls of some grain tissues covalent associations between heteroxylans, lignin and proteins are present. The extent of covalent associations between components also varies with the wall type and genotype.

Non-cellulosic polysaccharides, especially heteroxylans and (1,3;1,4)-β-D-glucans, constitute a relatively high proportion of the walls of the aleurone and starchy endosperm, and probably also of the scutellum. In these tissues, cellulose contents are correspondingly lower. The generally low cellulose content of these walls, together with the fact that they contain no lignin, are thought to be related to a limited requirement for structural rigidity of walls in central regions of the grain, and to a requirement to rapidly depolymerize wall components following germination of the grain.

In contrast, in the cell walls of the pericarp-seed coat, which provides a protective coat for the embryo and endosperm and which is not mobilized during germination, cellulose and lignin contents are much higher and the concentrations of non-cellulosic polysaccharides are correspondingly lower.

(1,3;1,4)-β-D-glucans, also referred to as mixed-linkage or cereal β-glucans, are non-cellulosic polysaccharides which naturally occur in plants of the monocotyledon family Poaceae, to which the cereals and grasses belong, and in related families of the order Poales.

These non-cellulosic polysaccharides are important constituents of the walls of the starchy endosperm and aleurone cells of most cereal grains, where they can account for up to 70%-90% by weight of the cell walls.

Barley, oat and rye grains are rich sources of (1,3;1,4)-β-D-glucan, whereas wheat, rice and maize have lower concentrations of this polysaccharide. The (1,3;1,4)-β-D-glucans are also relatively minor components of walls in vegetative tissues of cereals and grasses. Although present as a relatively minor component in vegetative tissues (1,3;1,4)-β-D-glucan) is still important in terms of, for example, the digestibility of vegetative tissue by animals and in the use of crop residues for bioethanol production.

(1,3;1,4)-β-D-glucans are important in large-scale food processing activities that include brewing and stockfeed manufacture. Moreover, the non-starchy polysaccharides of cereals, such as (1,3;1,4)-β-D-glucans, have attracted renewed interest in recent years because of their potentially beneficial effects in human nutrition.

However, despite this interest, major gaps remain in our knowledge of the genes and enzymes that control non-cellulosic polysaccharide biosynthesis, including (1,3;1,4)-β-D-glucan biosynthesis, in cereal grain.

(1,3;1,4)-β-D-glucan concentrations in grain are thought to be influenced by both genotype and environment. For example, the concentration of (1,3;1,4)-β-D-glucan in cereal grains depends on the genotype, the position of the grain on the spike and environmental factors such as planting location, climatic conditions during development and soil nitrogen.

Identification of the genes encoding (1,3;1,4)-β-D-glucan synthases would be desirable, as this would facilitate modulation of the level of (1,3;1,4)-β-D-glucan produced by a cell, and therefore, allow the qualities of grain or vegetative tissue to be altered. Therefore, in order to enable the modulation of the level of (1,3;1,4)-β-D-glucan in a cell and associated changes in grain or vegetative tissue quality, there is a clear need to identify genes that encode (1,3;1,4)-β-D-glucan synthases.

Reference to any prior art in this specification is not, and should not be taken as, an acknowledgment or any form of

SUMMARY OF THE INVENTION

In accordance with the present invention, nucleotide sequences and corresponding amino acid sequences that encode a family of (1,3;1,4)-β-D-glucan synthases are provided. In accordance with the present invention, it has been revealed that (1,3;1,4)-β-D-glucan synthases are encoded by members of the CslH gene family.

As a result of the identification of nucleotide sequences and corresponding amino acid sequences that encode (1,3;1,4)-β-D-glucan synthases, the present invention provides, inter alia, methods and compositions for modulating the level and/or activity of (1,3;1,4)-β-D-glucan synthase in a cell and/or modulating the level of (1,3;1,4)-β-D-glucan produced by the cell.

Therefore, in a first aspect, the present invention provides a method for modulating the level of (1,3;1,4)-β-D-glucan produced by a cell, the method comprising modulating the level and/or activity of a CslH-encoded (1,3;1,4)-β-D-glucan synthase in the cell.

In some embodiments, the level and/or activity of a (1,3;1,4)-β-D-glucan synthase is modulated by modulating the expression of a CslH nucleic acid in the cell. Therefore, in a second aspect, the present invention provides a method for modulating the level and/or activity of a (1,3;1,4)-β-D-glucan synthase in a cell, the method comprising modulating the expression of a CslH nucleic acid in the cell.

In some embodiments, the present invention contemplates increasing the level of (1,3;1,4)-β-D-glucan produced by a cell, by expressing, overexpressing or introducing a CslH nucleic acid into the cell. Alternatively, in further embodiments the present invention also provides methods for down-regulating expression of a CslH-encoded (1,3;1,4)-β-D-glucan synthase in a cell by knockout or knockdown of a CslH nucleic acid in a cell.

The present invention also facilitates the production of (1,3;1,4)-β-D-glucan in a recombinant expression system. For example, (1,3;1,4)-β-D-glucan may be recombinantly produced by introducing a CslH nucleic acid under the control of a promoter, into a cell, wherein the cell subsequently expresses a CslH-encoded (1,3;1,4)-β-D-glucan synthase and produces (1,3;1,4)-β-D-glucan. Therefore, in a third aspect, the present invention provides a method for producing (1,3;1,4)-β-D-glucan, the method comprising transforming a cell with an isolated CslH nucleic acid and allowing the cell to express the isolated CslH nucleic acid.

In a fourth aspect, the present invention also provides (1,3;1,4)-β-D-glucan produced according to the method of the third aspect of the invention.

In a fifth aspect, the present invention also provides a cell comprising:

a modulated level and/or activity of CslH-encoded (1,3;1,4)-β-D-glucan synthase relative to a wild type cell of the same taxon; and/or modulated expression of a CslH nucleic acid relative to a wild type cell of the same taxon.

In some embodiments, the cell further comprises a modulated level of (1,3;1,4)-β-D-glucan relative to a wild type cell of the same taxon.

Furthermore, in a sixth aspect, the present invention provides a multicellular structure comprising one or more cells according to the fifth aspect of the invention.

The present invention also provides cereal grain comprising one or more cells according to the fifth aspect of the invention. Therefore, in a seventh aspect, the present invention provides a cereal grain comprising a modulated level of (1,3;1,4)-β-D-glucan, wherein the grain comprises one or more cells comprising a modulated level and/or activity of a CslH-encoded (1,3;1,4)-β-D-glucan synthase and/or modulated expression of a CslH nucleic acid.

In an eighth aspect, the present invention also provides flour comprising:

flour produced by the milling of the grain of the seventh aspect of the invention; and optionally, flour produced by the milling of one or more other grains.

As set out above, the present invention is predicated, in part, on the identification and isolation of CslH nucleotide sequences and CslH amino acid sequences that encode (1,3;1,4)-β-D-glucan synthases.

Therefore, in a ninth aspect, the present invention provides an isolated CslH nucleic acid or a complement, reverse complement or fragment thereof.

In a tenth aspect, the present invention provides a genetic construct or vector comprising an isolated nucleic acid molecule of the ninth aspect of the invention.

In an eleventh aspect, the present invention provides a cell comprising the isolated nucleic acid molecule of the ninth aspect of the invention or genetic construct of the tenth aspect of the invention.

In a twelfth aspect, the present invention provides a multicellular structure comprising one or more of the cells of the eleventh aspect of the invention.

As set out above, the present invention also provides amino acid sequences for CslH-encoded (1,3;1,4)-β-D-glucan synthases.

Accordingly, in a thirteenth aspect, the present invention provides an isolated polypeptide comprising an amino acid sequence defining a CslH-encoded (1,3;1,4)-β-D-glucan synthase polypeptide or a fragment thereof.

In a fourteenth aspect, the present invention provides an antibody or an epitope binding fragment thereof, raised against an isolated CslH-encoded (1,3;1,4)-β-D-glucan synthase polypeptide as hereinbefore defined or an epitope thereof.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). The SEQ ID NOs: correspond numerically to the sequence identifiers <400> 1 (SEQ ID NO: 1), <400> 2 (SEQ ID NO: 2), etc. A summary of the sequence identifiers is provided in Table 1. A sequence listing is provided at the end of the specification.

TABLE 1

Summary of Sequence Identifiers

| Sequence Identifier | Sequence |
| --- | --- |
| SEQ ID NO: 1 | HvCslH1 coding region nucleotide sequence |
| SEQ ID NO: 2 | HvCslH1 amino acid sequence |
| SEQ ID NO: 3 | OsCslH1 coding region nucleotide sequence |
| SEQ ID NO: 4 | OsCslH1 amino acid sequence |
| SEQ ID NO: 5 | OsCslH2 coding region nucleotide sequence |
| SEQ ID NO: 6 | OsCslH2 amino acid sequence |
| SEQ ID NO: 7 | OsCslH3 coding region nucleotide sequence |
| SEQ ID NO: 8 | OsCslH3 amino acid sequence |

TABLE 1-continued

Summary of Sequence Identifiers

| Sequence Identifier | Sequence |
|---|---|
| SEQ ID NO: 9 | HvCslH1 genomic nucleotide sequence |
| SEQ ID NO: 10 | OsCslH1 genomic nucleotide sequence |
| SEQ ID NO: 11 | OsCslH2 genomic nucleotide sequence |
| SEQ ID NO: 12 | OsCslH3 genomic nucleotide sequence |
| SEQ ID NO: 13 | H1F1 primer nucleotide sequence |
| SEQ ID NO: 14 | H1F2 primer nucleotide sequence |
| SEQ ID NO: 15 | HvCslH1cF1 primer nucleotide sequence |
| SEQ ID NO: 16 | HvH1TOPOf primer nucleotide sequence |
| SEQ ID NO: 17 | H1R1 primer nucleotide sequence |
| SEQ ID NO: 18 | H1R2 primer nucleotide sequence |
| SEQ ID NO: 19 | H1R5 primer nucleotide sequence |
| SEQ ID NO: 20 | H1R6 primer nucleotide sequence |
| SEQ ID NO: 21 | H1R7 primer nucleotide sequence |
| SEQ ID NO: 22 | H1R10 primer nucleotide sequence |
| SEQ ID NO: 23 | HvCslH1cR1 primer nucleotide sequence |
| SEQ ID NO: 24 | HvH1TOPOr primer nucleotide sequence |
| SEQ ID NO: 25 | Adaptor 1 primer nucleotide sequence |
| SEQ ID NO: 26 | Adaptor 2 primer nucleotide sequence |
| SEQ ID NO: 27 | AP1 primer nucleotide sequence |
| SEQ ID NO: 28 | AP2 primer nucleotide sequence |
| SEQ ID NO: 29 | Hv18SRTr primer nucleotide sequence |
| SEQ ID NO: 30 | Hv18Sf primer nucleotide sequence |
| SEQ ID NO: 31 | Hv18Sr primer nucleotide sequence |
| SEQ ID NO: 32 | Hv GAPDH Q-PCR forward primer nucleotide sequence |
| SEQ ID NO: 33 | Hv GAPDH Q-PCR reverse primer nucleotide sequence |
| SEQ ID NO: 34 | Hv Cyclophilin Q-PCR forward primer nucleotide sequence |
| SEQ ID NO: 35 | Hv Cyclophilin Q-PCR reverse primer nucleotide sequence |
| SEQ ID NO: 36 | Hv α-Tubulin Q-PCR forward primer nucleotide sequence |
| SEQ ID NO: 37 | Hv α-Tubulin Q-PCR reverse primer nucleotide sequence |
| SEQ ID NO: 38 | Hv HSP70 Q-PCR forward primer nucleotide sequence |
| SEQ ID NO: 39 | Hv HSP70 Q-PCR reverse primer nucleotide sequence |
| SEQ ID NO: 40 | Hv EL1a Q-PCR forward primer nucleotide sequence |
| SEQ ID NO: 41 | Hv EL1a Q-PCR reverse primer nucleotide sequence |
| SEQ ID NO: 42 | HvCslH1 Q-PCR forward primer nucleotide sequence |
| SEQ ID NO: 43 | HvCslH1 Q-PCR reverse primer nucleotide sequence |
| SEQ ID NO: 44 | SJ27 primer nucleotide sequence |
| SEQ ID NO: 45 | SJ28 primer nucleotide sequence |
| SEQ ID NO: 46 | SJ72 primer nucleotide sequence |
| SEQ ID NO: 47 | SJ73 primer nucleotide sequence |
| SEQ ID NO: 48 | SJ79 primer nucleotide sequence |
| SEQ ID NO: 49 | SJ75 primer nucleotide sequence |
| SEQ ID NO: 50 | SJ85 primer nucleotide sequence |
| SEQ ID NO: 51 | SJ91 primer nucleotide sequence |
| SEQ ID NO: 52 | SJ163 primer nucleotide sequence |
| SEQ ID NO: 53 | SJ164 primer nucleotide sequence |
| SEQ ID NO: 54 | SJ183 primer nucleotide sequence |
| SEQ ID NO: 55 | SJ204 primer nucleotide sequence |
| SEQ ID NO: 56 | TUB primer nucleotide sequence |
| SEQ ID NO: 57 | TUB2F primer nucleotide sequence |
| SEQ ID NO: 58 | SJ107 primer nucleotide sequence |
| SEQ ID NO: 59 | SJ82 primer nucleotide sequence |
| SEQ ID NO: 60 | SJ94 primer nucleotide sequence |
| SEQ ID NO: 61 | SJ95 primer nucleotide sequence |
| SEQ ID NO: 62 | SJ97 primer nucleotide sequence |
| SEQ ID NO: 63 | SJ93 primer nucleotide sequence |
| SEQ ID NO: 64 | SJ44 primer nucleotide sequence |
| SEQ ID NO: 65 | SJ38 primer nucleotide sequence |
| SEQ ID NO: 66 | SJ96 primer nucleotide sequence |
| SEQ ID NO: 67 | SJ37 primer nucleotide sequence |
| SEQ ID NO: 68 | SJ244 primer nucleotide sequence |
| SEQ ID NO: 69 | HvCslH1 (cv. Himalaya) coding region nucleotide sequence |
| SEQ ID NO: 70 | HvCslH1 (cv. Himalaya) amino acid sequence |
| SEQ ID NO: 71 | HvCslH1 (cv. Himalaya) genomic nucleotide sequence |
| SEQ ID NO: 72 | TaCslH1-1 coding region nucleotide sequence |
| SEQ ID NO: 73 | TaCslH1-2 coding region nucleotide sequence |
| SEQ ID NO: 74 | TaCslH1-3 coding region nucleotide sequence |
| SEQ ID NO: 75 | TaCslH1-1 amino acid sequence |
| SEQ ID NO: 76 | TaCslH1-2 amino acid sequence |
| SEQ ID NO: 77 | TaCslH1-3 amino acid sequence |
| SEQ ID NO: 78 | TaCslH1-1 genomic nucleotide sequence |
| SEQ ID NO: 79 | TaCslH1-2 genomic nucleotide sequence |
| SEQ ID NO: 80 | TaCslH1-3 genomic nucleotide sequence |

DESCRIPTION OF EXEMPLARY EMBODIMENTS

It is to be understood that following description is for the purpose of describing particular embodiments only and is not intended to be limiting with respect to the above description.

The present invention is predicated, in part, on the identification of genes which encode biosynthetic enzymes for (1,3;1,4)-β-D-glucans.

"(1,3;1,4)-β-D-glucans" should be understood to include linear, unbranched polysaccharides in which β-D-glucopyranosyl monomers are polymerized through both (1→4)- and (1→3)-linkages.

The ratio of (1→4)- to (1→3)-linkages in naturally occurring (1,3;1,4)-β-D-glucans is generally in the range 2.2-2.6:1, although the ratio may also be outside of this range. For example, in (1,3;1,4)-β-D-glucan from sorghum endosperm the ratio is 1.15:1. The two types of linkages are not arranged in regular, repeating sequences. Single (1→3)-linkages are separated by two or more (1→4)-linkages. Regions of two or three adjacent (1→0.4)-linkages predominate, but again there is no regularity in the arrangement of these units. The linkage sequence does not depend on preceding linkages further away than two glucose units and follows a second order Markov chain distribution. Moreover, up to 10% of the chain may consist of longer stretches of 5 to 20 adjacent (1→0.4)-linkages. Thus, cereal (1,3;1,4)-β-D-glucans may be considered as (1→3)-β-linked copolymers of cellotriosyl (G4G4G$_{Red}$), cellotetraosyl (G4G4G4G$_{Red}$) units and longer (1→4)-β-D-oligoglucosyl units.

The ratio of tri- to tetra-saccharide units in endogenous (1,3;1,4)-β-D-glucans varies between cereal species. For example, in wheat the ratio is 3.0-4.5:1, in barley 2.9-3.4:1, in rye 2.7:1 and in oats 1.8-2.3:1. Furthermore, the observed ratios may also vary according to the temperature and conditions of (1,3;1,4)-β-D-glucan extraction.

The average molecular masses reported for cereal (1,3;1,4)-β-D-glucans range from 48,000 (DP ~300) to 3,000,000 (DP ~1850), depending on the cereal species, cell wall type, extraction procedure and the method used for molecular mass determination. They are invariably polydisperse with respect to molecular mass and this is illustrated by a weight average to number average molecular mass ratio ($M_w/M_n$) of 1.18 for barley (1,3;1,4)-β-D-glucan. Certain barley (1,3;1,4)-β-D-glucans are also covalently-associated with small amounts of protein and have estimated molecular masses of up to 40,000,000.

The extractability of (1,3;1,4)-β-D-glucans from walls of cereal grains is a function of their degree of self-association and their association with other wall polysaccharides and proteins. In particular, extractability depends on the molecular mass and linkage distribution in the (1,3;1,4)-β-D-glucan chains. Extensive association with other polymers and very high molecular masses render the (1,3;1,4)-β-D-glucans more difficult to extract from grain.

For example, a portion of the (1,3;1,4)-β-D-glucan from barley, oat and rye flours may be extracted by water at pH 7.0 and 40° C. Further fractions can be solubilised at higher temperatures. The proportion of total (1,3;1,4)-β-D-glucan that is water-soluble at 40° C. varies within and between species. For example, waxy (high amylose) barleys have a higher proportion of water-soluble (1,3;1,4)-β-D-glucan than normal barleys. (1,3;1,4)-β-D-glucans extracted from barley at 40° C. have a slightly lower tri-/tetrasaccharide ratio (1.7:1) than those extracted at 65° C. (2.0:1). Complete extraction of cereal (1,3;1,4)-β-D-glucans from grain requires the use of alkaline extractants such as 4 M NaOH or aqueous Ba(OH)$_2$, containing NaBH$_4$ to prevent alkali-induced degradation from the reducing terminus. Alkali-extracted barley (1,3;1,4)-β-D-glucan fractions have higher molecular masses, higher ratios of (1→4):(1→3) linkages, more contiguously linked (1→0.4)-linked segments and higher tri-: tetra-saccharide ratios than their water-extractable counterparts. Other extractants, such as dimethylsulphoxide, hot perchloric acid, trichloroacetic acid, N-methylmorpholino-N-oxide and dimethylacetamide-LiCl, may also be used to solubilise (1,3;1,4)-β-D-glucans, but these extractants may cause some depolymerisation or degradation of the polymer. Once extracted with hot water or alkali, the (1,3;1,4)-β-D-glucans are often soluble at neutral pH and room temperature. However, upon cooling, (1,3;1,4)-β-D-glucans can aggregate and precipitate.

As mentioned above, the present invention is predicated, in part, on the identification of biosynthetic enzymes, and their encoding genes, that catalyse the synthesis of (1,3;1,4)-β-D-glucan. Such enzymes are referred to herein as "(1,3;1,4)-β-D-glucan synthases".

The present invention arises, in part, from an analysis of expressed sequence tag libraries and other sequence databases including cellulose synthase (CesA) genes. More particularly, it was noted in these analyses that the CesA genes were in fact members of a much larger super-family of genes, which included both the CesA genes and the cellulose synthase-like (Csl) gene family.

The Csl gene families in most vascular plants are very large and have been divided into several groups, designated CslA to CslH. In *Arabidopsis thaliana* there are 29 known Csl genes and in rice about 37. Overall, the *Arabidopsis* genome is believed to contain more than 700 genes involved in cell wall metabolism. However, in general, the specific functions of these genes are poorly understood.

Furthermore, in contrast to the CesA genes, it has proved difficult to define the functions of the Csl genes. In fact, of the multiple Csl genes in higher plants, only the CslA and CslF groups have been assigned a function.

In accordance with the present invention, it has been revealed that members of the CslH gene family encode (1,3;1,4)-β-D-glucan synthases.

As a result of the identification of CslH nucleotide sequences, and corresponding amino acid sequences that encode (1,3;1,4)-β-D-glucan synthases, the present invention provides, inter alia, methods and compositions for modulating the level and/or activity of (1,3;1,4)-β-D-glucan synthase in a cell and/or modulating the level of (1,3;1,4)-β-D-glucan produced by the cell.

Therefore, in a first aspect, the present invention provides a method for modulating the level of (1,3;1,4)-β-D-glucan produced by a cell, the method comprising modulating the level and/or activity of a CslH-encoded (1,3;1,4)-β-D-glucan synthase in the cell.

The "cell" may be any suitable eukaryotic or prokaryotic cell. As such, a "cell" as referred to herein may be a eukaryotic cell including a fungal cell such as a yeast cell or mycelial fungus cell; an animal cell such as a mammalian cell or an insect cell; or a plant cell. Alternatively, the cell may also be a prokaryotic cell such as a bacterial cell including an *E. coli* cell, or an archaea cell.

In some embodiments, the cell is a plant cell, a vascular plant cell, including a monocotyledonous or dicotyledonous angiosperm plant cell, or a gymnosperm plant cell. In some embodiments the plant is a monocotyledonous plant cell. In some embodiments, the plant is a member of the order Poales. In some embodiments, the monocotyledonous plant cell is a cereal crop plant cell.

As used herein, the term "cereal crop plant" includes members of the Poales (grass family) that produce edible grain for human or animal food. Examples of Poales cereal crop plants which in no way limit the present invention include wheat, rice, maize, millet, sorghum, rye, triticale, oats, barley, teff, wild rice, spelt and the like. However, the term cereal crop plant should also be understood to include a number of non-Poales species that also produce edible grain and are known as the pseudocereals, such as amaranth, buckwheat and quinoa.

In other embodiments, the present invention also contemplates the use of other monocotyledonous plants, such as other non-cereal plants of the Poales, specifically including pasture grasses such as *Lolium* spp.

As set out above, the present invention is predicated, in part, on modulating the level and/or activity of a CslH-encoded (1,3;1,4)-β-D-glucan synthase in a cell.

A "CslH-encoded (1,3;1,4)-β-D-glucan synthase" should be regarded as any CslH-encoded protein which catalyses the synthesis of (1,3;1,4)-β-D-glucan and, optionally, catalyses the polymerisation of glucopyranosyl monomers.

In some embodiments, the CslH-encoded (1,3;1,4)-β-D-glucan synthase comprises the amino acid sequence set forth in SEQ ID NO: 2 or an amino acid sequence which is at least 50% identical thereto.

In some embodiments the CslH-encoded (1,3;1,4)-β-D-glucan synthase comprises at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99% at least 99.5% or 100% amino acid sequence identity to SEQ ID NO: 2.

When comparing amino acid sequences, the compared sequences should be compared over a comparison window of at least 100 amino acid residues, at least 200 amino acid residues, at least 400 amino acid residues, at least 800 amino acid residues or over the full length of SEQ ID NO: 2. The comparison window may comprise additions or deletions (i.e.

gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19. 3 of Ausubel et al. (*Current Protocols in Molecular Biology*, John Wiley & Sons Inc, 1994-1998, Chapter 15, 1998).

Examples of additional CslH-encoded (1,3;1,4)-β-D-glucan synthases contemplated by the present invention include CslH-encoded (1,3;1,4)-β-D-glucan synthase orthologs of SEQ ID NO: 2.

For example, barley (*Hordeum vulgare*) orthologs or allelic variants of SEQ ID NO: 2 include, for example, polypeptides comprising the amino acid sequence set forth in SEQ ID NO: 70. Rice (*Oryza sativa*) orthologs of SEQ ID NO: 2 include, for example, polypeptides comprising the amino acid sequences set forth in any of SEQ ID NO: 4, SEQ ID NO: 6 and SEQ ID NO: 8. Wheat (*Triticum aestivum*) orthologs of SEQ ID NO: 2 include, for example, polypeptides comprising the amino acid sequences set forth in SEQ ID NO: 75, SEQ ID NO: 76 and SEQ ID NO: 77.

As referred to herein, modulation of the "level" of the CslH-encoded (1,3;1,4)-β-D-glucan synthase should be understood to include modulation of the level of CslH transcripts and/or CslH-encoded (1,3;1,4)-β-D-glucan synthase polypeptides in the cell. Modulation of the "activity" of the CslH-encoded (1,3;1,4)-β-D-glucan synthase should be understood to include modulation of the total activity, specific activity, half-life and/or stability of the CslH-encoded (1,3;1,4)-β-D-glucan synthase in the cell.

By "modulating" with regard to the level and/or activity of the CslH-encoded (1,3;1,4)-β-D-glucan synthase is intended decreasing or increasing the level and/or activity of CslH-encoded (1,3;1,4)-β-D-glucan synthase in the cell. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the level or activity of CslH-encoded (1,3;1,4)-β-D-glucan synthase in the cell. By "increasing" is intended, for example, a 1%, 5%, 10%, 20%, 30%, 40%, 50%, 60%, 70%, 80%, 90%, 100%, 2-fold, 5-fold, 10-fold, 20 fold, 50-fold, 100-fold increase in the level of activity of CslH-encoded (1,3;1,4)-β-D-glucan synthase in the cell. "Modulating" also includes introducing a CslH-encoded (1,3;1,4)-β-D-glucan synthase into a cell which does not normally express the introduced enzyme, or the substantially complete inhibition of CslH-encoded (1,3;1,4)-β-D-glucan synthase activity in a cell that normally has such activity.

In some embodiments, the level of (1,3;1,4)-β-D-glucan produced by a cell is increased by increasing the level and/or activity of CslH-encoded (1,3;1,4)-β-D-glucan synthase in the cell. In another embodiment, the level of (1,3;1,4)-β-D-glucan produced by a cell is decreased by decreasing the level and/or activity of CslH-encoded (1,3;1,4)-β-D-glucan synthase in the cell.

The methods of the present invention contemplate any means known in the art by which the level and/or activity of a CslH-encoded (1,3;1,4)-β-D-glucan synthase in a cell may be modulated. This includes methods such as the application of agents which modulate CslH-encoded (1,3;1,4)-β-D-glucan synthase activity in a cell, such as the application of a CslH-encoded (1,3;1,4)-β-D-glucan synthase agonist or antagonist; the application of agents which mimic CslH-encoded (1,3;1, 4)-β-D-glucan synthase activity in a cell; modulating the expression of a CslH nucleic acid which encodes CslH-encoded (1,3;1,4)-β-D-glucan synthase in the cell; or effecting the expression of an altered or mutated CslH nucleic acid in a cell such that a (1,3;1,4)-β-D-glucan synthase with increased or decreased specific activity, half-life and/or stability is expressed by the cell.

In some embodiments, the level and/or activity of a (1,3;1,4)-β-D-glucan synthase is modulated by modulating the expression of a CslH nucleic acid in the cell.

Therefore, in a second aspect, the present invention provides a method for modulating the level and/or activity of a (1,3;1,4)-β-D-glucan synthase in a cell, the method comprising modulating the expression of a CslH nucleic acid in the cell.

As used herein, the term "CslH nucleic acid" should be understood to include to a nucleic acid molecule which:
  encodes a CslH-encoded (1,3;1,4)-β-D-glucan synthase as defined herein; and/or
  comprises at least 50% nucleotide sequence identity to the nucleotide sequence set forth in SEQ ID NO: 1; and/or
  hybridises to a nucleic acid molecule comprising one or more of the nucleotide sequence set forth in SEQ ID NO: 1 under stringent conditions.

In some embodiments the CslH nucleic acid comprises at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99% at least 99.5% or 100% sequence identity to SEQ ID NO: 1.

When comparing nucleic acid sequences to SEQ ID NO: 1 to calculate a percentage identity, the compared nucleotide sequences should be compared over a comparison window of at least 300 nucleotide residues, at least 600 nucleotide residues, at least 1200 nucleotide residues, at least 2400 nucleotide residues or over the full length of SEQ ID NO: 1. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19. 3 of Ausubel et al. ("Current Protocols in Molecular Biology" John Wiley & Sons Inc, 1994-1998, Chapter 15, 1998).

As set out above, the CslH nucleic acid may also comprise a nucleic acid that hybridises to a nucleic acid molecule comprising the nucleotide sequence set forth in SEQ ID NO: 1 under stringent conditions. As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilizing agents such as formamide. Stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary medium stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity of hybridisation is also a function of post-hybridization washes, and is influenced by the ionic strength and temperature of the final wash solution. For DNA-DNA hybrids, the $T_m$ can be approximated from the equation of Meinkoth and Wahl (*Anal. Biochem.* 138: 267-284, 1984), ie. $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of different degrees of complementarity. For example, sequences with ≥90% identity can be hybridised by decreasing the $T_m$ by about 10° C. Generally, stringent conditions are selected to be lower than the thermal melting point ($T_m$) for the specific sequence and its complement at a defined ionic strength and pH. For example, high stringency conditions can utilize a hybridization and/or wash at, for example, 1, 2, 3, 4 or 5° C. lower than the thermal melting point ($T_m$); medium stringency conditions can utilize a hybridization and/or wash at, for example, 6, 7, 8, 9, or 10° C. lower than the thermal melting point ($T_m$); low stringency conditions can utilize a hybridization and/or wash at, for example, 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used. An extensive guide to the hybridization of nucleic acids is found in Tijssen (*Laboratory Techniques in Biochemistry and Molecular Biology-Hybridization with Nucleic Acid Probes*, Pt I, Chapter 2, Elsevier, New York, 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, 2$^{nd}$ ed., Cold Spring Harbor Laboratory Press, Plainview, N.Y., 1989).

Examples of additional CslH nucleic acids contemplated by the present invention include nucleic acids having coding regions which are orthologs of SEQ ID NO: 1.

For example, barley (*Hordeum vulgare*) coding region orthologs or allelic variants of SEQ ID NO: 1 include, for example, nucleic acids comprising the nucleotide sequence set forth in SEQ ID NO: 69. Rice (*Oryza sativa*) coding region orthologs of SEQ ID NO: 1 include, for example, nucleic acids comprising the nucleotide sequence set forth in any of SEQ ID NO: 3, SEQ ID NO: 5 and SEQ ID NO: 7. Wheat (*Triticum aestivum*) coding region orthologs of SEQ ID NO: 1 include, for example, nucleic acids comprising the nucleotide sequence set forth in SEQ ID NO: 72, SEQ ID NO: 73 and SEQ ID NO: 74.

The CslH nucleic acids contemplated by the present invention may also comprise one or more non-translated regions such as 3' and 5' untranslated regions and/or introns. For example, the CslH nucleic acids contemplated by the present invention may comprise, for example, mRNA sequences, cDNA sequences or genomic nucleotide sequences In some specific embodiments, the CslH nucleic acid may comprise a genomic nucleotide sequence from an organism which may include one or more non-protein-coding regions and/or one or more introns. Genomic nucleotide sequences which comprise a CslH nucleic acid include, for example:

barley (*Hordeum vulgare*) CslH genomic nucleotide sequences, for example, as set forth in SEQ ID NO: 9 and/or SEQ ID NO: 71;

rice (*Oryza sativa*) CslH genomic nucleotide sequences, for example, as set forth in any one or more of SEQ ID NO: 10, SEQ ID NO: 11 and/or SEQ ID NO: 12; and/or wheat (*Triticum aestivum*) CslH genomic nucleotide sequences, for example, as set forth in any one or more of SEQ ID NO: 78, SEQ ID NO: 79 and/or SEQ ID NO: 80.

As mentioned above, the present invention provides methods for modulating the expression of a CslH nucleic acid in a cell. The present invention contemplates any method by which the expression of a CslH nucleic acid in a cell may be modulated.

The term "modulating" with regard to the expression of the CslH nucleic acid is generally intended to refer to decreasing or increasing the transcription and/or translation of a CslH nucleic acid. By "decreasing" is intended, for example, a 1%, 5%, 10%, 20%, 30%, 40%, 50%, 60%, 70%, 80%, 90%, 91%, 92%, 93%, 94%, 95%, 96%, 97%, 98%, 99%, 100% reduction in the transcription and/or translation of a CslH nucleic acid. By "increasing" is intended, for example a 1%, 5%, 10%, 20%, 30%, 40%, 50%, 60%, 70%, 80%, 90%, 100%, 2-fold, 5-fold, 10-fold, 20-fold, 50-fold, 100-fold or greater increase in the transcription and/or translation of a CslH nucleic acid. Modulating also comprises introducing expression of a CslH nucleic acid not normally found in a particular cell; or the substantially complete inhibition (eg. knockout) of expression of a CslH nucleic acid in a cell that normally has such activity.

Methods for modulating the expression of a particular nucleic acid molecule in a cell are known in the art and the present invention contemplates any such method. Exemplary methods for modulating the expression of a CslH nucleic acid include: genetic modification of the cell to upregulate or downregulate endogenous CslH nucleic acid expression; genetic modification by transformation with a CslH nucleic acid; administration of a nucleic acid molecule to the cell which modulates expression of an endogenous CslH nucleic acid in the cell; and the like.

In some embodiments, the expression of a CslH nucleic acid is modulated by genetic modification of the cell. The term "genetically modified", as used herein, should be understood to include any genetic modification that effects an alteration in the expression of a CslH nucleic acid in the genetically modified cell relative to a non-genetically modified form of the cell. Exemplary types of genetic modification contemplated herein include: random mutagenesis such as transposon, chemical, UV or phage mutagenesis together with selection of mutants which overexpress or underexpress an endogenous CslH nucleic acid; transient or stable introduction of one or more nucleic acid molecules into a cell which direct the expression and/or overexpression of CslH nucleic acid in the cell; site-directed mutagenesis of an endogenous CslH nucleic acid; introduction of one or more nucleic acid molecules which inhibit the expression of an endogenous CslH nucleic acid in the cell, eg. a cosuppression construct or an RNAi construct; and the like.

In one particular embodiment, the genetic modification comprises the introduction of a nucleic acid into a cell of interest.

The nucleic acid may be introduced using any method known in the art which is suitable for the cell type being used, for example, those described in Sambrook and Russell (*Molecular Cloning—A Laboratory Manual*, 3$^{rd}$ Ed., Cold Spring Harbor Laboratory Press, 2000).

In some embodiments of the invention wherein the cell is a plant cell, suitable methods for introduction of a nucleic acid molecule may include: *Agrobacterium*-mediated transformation, microprojectile bombardment based transformation methods and direct DNA uptake based methods. Roa-Rodriguez et al. (*Agrobacterium-mediated transformation of plants*, 3$^{rd}$ Ed. CAMBIA Intellectual Property Resource, Canberra, Australia, 2003) review a wide array of suitable *Agrobacterium*-mediated plant transformation methods for a wide range of plant species. Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology Vol.* 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art.

The introduced nucleic acid may be single stranded or double stranded. The nucleic acid may be transcribed into mRNA and translated into a CslH-encoded (1,3;1,4)-β-D-glucan synthase or another protein; may encode for a non-translated RNA such as an RNAi construct, cosuppression construct, antisense RNA, tRNA, miRNA, siRNA, ntRNA and the like; or may act directly in the cell. The introduced nucleic acid may be an unmodified DNA or RNA or a modified DNA or RNA which may include modifications to the nucleotide bases, sugar or phosphate backbones but which retain functional equivalency to a nucleic acid. The introduced nucleic acid may optionally be replicated in the cell; integrated into a chromosome or any extrachromosomal elements of the cell; and/or transcribed by the cell. Also, the introduced nucleic acid may be either homologous or heterologous with respect to the host cell. That is, the introduced nucleic acid may be derived from a cell of the same species as the genetically modified cell (ie. homologous) or the introduced nucleic may be derived from a different species (ie. heterologous). The transgene may also be a synthetic transgene.

In one particular embodiment, the present invention contemplates increasing the level of (1,3;1,4)-β-D-glucan produced by a cell, by expressing, overexpressing or introducing a CslH nucleic acid into the cell.

By identifying CslH nucleotide sequences which encode (1,3;1,4)-β-D-glucan synthases, in further embodiments, the present invention also provides methods for down-regulating expression of a CslH-encoded (1,3;1,4)-β-D-glucan synthase in a cell.

For example, the identification of CslH genes as encoding (1,3;1,4)-β-D-glucan synthases facilitates methods such as knockout or knockdown of a CslH-encoded (1,3;1,4)-β-D-glucan synthase in a cell using methods such as:

insertional mutagenesis of a CslH nucleic acid in a cell, including knockout or knockdown of a CslH nucleic acid in a cell, by homologous recombination with a knockout construct (for an example of targeted gene disruption in plants see Terada et al., *Nat. Biotechnol.* 20: 1030-1034, 2002);

post-transcriptional gene silencing (PTGS) or RNAi of a CslH nucleic acid in a cell (for review of PTGS and RNAi see Sharp, *Genes Dev.* 15(5): 485-490, 2001; and Hannon, *Nature* 418: 244-51, 2002);

transformation of a cell with an antisense construct directed against a CslH nucleic acid (for examples of antisense suppression in plants see van der Krol et al., *Nature* 333: 866-869; van der Krol et al., *BioTechniques* 6: 958-967; and van der Krol et al., *Gen. Genet.* 220: 204-212);

transformation of a cell with a co-suppression construct directed against a CslH nucleic acid (for an example of co-suppression in plants see van der Krol et al., *Plant Cell* 2(4): 291-299);

transformation of a cell with a construct encoding a double stranded RNA directed against a CslH nucleic acid (for an example of dsRNA mediated gene silencing see Waterhouse et al., *Proc. Natl. Acad. Sci. USA* 95: 13959-13964, 1998);

transformation of a cell with a construct encoding an siRNA or hairpin RNA directed against a CslH nucleic acid (for an example of siRNA or hairpin RNA mediated gene silencing in plants see Lu et al., *Nucl. Acids Res.* 32(21): e171; doi:10.1093/nar/gnh170, 2004); and/or insertion of a miRNA target sequence such that it is in operable connection with CslH nucleic acid (for an example of miRNA mediated gene silencing see Brown et al., *Blood* 110(13): 4144-4152, 2007).

The present invention also facilitates the downregulation of a CslH nucleic acid in a cell via the use of synthetic oligonucleotides such as siRNAs or microRNAs directed against a CslH nucleic acid which are administered to a cell (for examples of synthetic siRNA mediated silencing see Caplen et al., *Proc. Natl. Acad. Sci. USA* 98: 9742-9747, 2001; Elbashir et al., *Genes Dev.* 15: 188-200, 2001; Elbashir et al., *Nature* 411: 494-498, 2001; Elbashir et al., *EMBO J.* 20: 6877-6888, 2001; and Elbashir et al., *Methods* 26: 199-213, 2002).

In addition to the examples above, the introduced nucleic acid may also comprise a nucleotide sequence which is not directly related to a CslH nucleic acid but, nonetheless, may directly or indirectly modulate the expression of CslH nucleic acid in a cell. Examples include nucleic acid molecules that encode transcription factors or other proteins which promote or suppress the expression of an endogenous CslH nucleic acid molecule in a cell; and other non-translated RNAs which directly or indirectly promote or suppress endogenous CslH-encoded (1,3;1,4)-β-D-glucan synthase expression and the like.

In order to effect expression of an introduced nucleic acid in a genetically modified cell, where appropriate, the introduced nucleic acid may be operably connected to one or more control sequences. The term "control sequences" should be understood to include any nucleotide sequences which are necessary or advantageous for the transcription, translation and or post-translational modification of the operably connected nucleic acid or the transcript or protein encoded thereby. Each control sequence may be native or foreign to the operably connected nucleic acid. The control sequences may include, but are not limited to, a leader, polyadenylation sequence, propeptide encoding sequence, promoter, enhancer or upstream activating sequence, signal peptide encoding sequence, and transcription terminator. Typically, a control sequence at least includes a promoter.

The term "promoter" as used herein, describes any nucleic acid which confers, activates or enhances expression of a nucleic acid molecule in a cell. Promoters are generally positioned 5' (upstream) to the genes that they control. In the construction of heterologous promoter/gene combinations, it may be desirable to position the promoter at a distance from the gene transcription start site that is approximately the same as the distance between that promoter and the gene it controls in its natural setting, ie. the gene from which the promoter is derived. As is known in the art, some variation in this distance can be accommodated without loss of promoter function.

A promoter may regulate the expression of an operably connected nucleotide sequence constitutively, or differentially with respect to the cell, tissue, organ or developmental stage at which expression occurs, in response to external stimuli such as physiological stresses, pathogens, or metal ions, amongst others, or in response to one or more transcriptional activators. As such, the promoter used in accordance with the methods of the present invention may include a constitutive promoter, an inducible promoter, a tissue-specific promoter or an activatable promoter.

The present invention contemplates the use of any promoter which is active in a cell of interest. As such, a wide array of promoters which are active in any of bacteria, fungi, animal cells or plant cells would be readily ascertained by one of ordinary skill in the art. However, in some embodiments, plant cells are used. In these embodiments, plant-active constitutive, inducible, tissue-specific or activatable promoters are typically used.

Plant constitutive promoters typically direct expression in nearly all tissues of a plant and are largely independent of environmental and developmental factors. Examples of constitutive promoters that may be used in accordance with the present invention include plant viral derived promoters such as the Cauliflower Mosaic Virus 35S and 19S (CaMV 35S and CaMV 19S) promoters; bacterial plant pathogen derived promoters such as opine promoters derived from *Agrobacterium* spp., eg. the *Agrobacterium*-derived nopaline synthase (nos) promoter; and plant-derived promoters such as the rubisco small subunit gene (rbcS) promoter, the plant ubiquitin promoter (Pubi), the rice actin promoter (Pact) and the oat globulin promoter.

"Inducible" promoters include, but are not limited to, chemically inducible promoters and physically inducible promoters. Chemically inducible promoters include promoters which have activity that is regulated by chemical compounds such as alcohols, antibiotics, steroids, metal ions or other compounds. Examples of chemically inducible promoters include: alcohol regulated promoters (eg. see European Patent 637 339); tetracycline regulated promoters (eg. see U.S. Pat. No. 5,851,796 and U.S. Pat. No. 5,464,758); steroid responsive promoters such as glucocorticoid receptor promoters (eg. see U.S. Pat. No. 5,512,483), estrogen receptor promoters (eg. see European Patent Application 1 232 273), ecdysone receptor promoters (eg. see U.S. Pat. No. 6,379,945) and the like; metal-responsive promoters such as metallothionein promoters (eg. see U.S. Pat. No. 4,940,661, U.S. Pat. No. 4,579,821 and U.S. Pat. No. 4,601,978); and pathogenesis related promoters such as chitinase or lysozyme promoters (eg. see U.S. Pat. No. 5,654,414) or PR protein promoters (eg. see U.S. Pat. No. 5,689,044, U.S. Pat. No. 5,789,214, Australian Patent 708850, U.S. Pat. No. 6,429,362).

The inducible promoter may also be a physically regulated promoter which is regulated by non-chemical environmental factors such as temperature (both heat and cold), light and the like. Examples of physically regulated promoters include heat shock promoters (eg. see U.S. Pat. No. 5,447,858, Australian Patent 732872, Canadian Patent Application 1324097); cold inducible promoters (eg. see U.S. Pat. No. 6,479,260, U.S. Pat. No. 6,084,08, U.S. Pat. No. 6,184,443 and U.S. Pat. No. 5,847,102); light inducible promoters (eg. see U.S. Pat. No. 5,750,385 and Canadian Patent 132 1563); light repressible promoters (eg. see New Zealand Patent 508103 and U.S. Pat. No. 5,639,952).

"Tissue specific promoters" include promoters which are preferentially or specifically expressed in one or more specific cells, tissues or organs in an organism and/or one or more developmental stages of the organism. It should be understood that a tissue specific promoter may, in some cases, also be inducible.

Examples of plant tissue specific promoters include: root specific promoters such as those described in US Patent Application 2001047525; fruit specific promoters including ovary specific and receptacle tissue specific promoters such as those described in European Patent 316 441, U.S. Pat. No. 5,753,475 and European Patent Application 973 922; and seed specific promoters such as those described in Australian Patent 612326 and European Patent application 0 781 849 and Australian Patent 746032.

In some embodiments, the tissue specific promoter is a seed and/or grain specific promoter. Exemplary seed or grain specific promoters include puroindoline-b gene promoters (for example see Digeon et al., *Plant Mol. Biol.* 39: 1101-1112, 1999); Pbf gene promoters (for example see Mena et al., *Plant J.* 16: 53-62, 1998); $GS_{1-2}$ gene promoters (for example see Muhitch et al., *Plant Sci.* 163: 865-872, 2002); glutelin or Gt1 gene promoters (for example see Okita et al., *J. Biol. Chem.* 264: 12573-12581, 1989; Zheng et al., *Plant J.* 4: 357-366, 1993; Sindhu et al., *Plant Sci.* 130: 189-196, 1997; Nandi et al., *Plant Sci.* 163: 713-722, 2002); Hor2-4 gene promoters (for example see Knudsen and Müller, *Planta* 195: 330-336, 1991; Patel et al., *Mol. Breeding.* 6: 113-123, 2000; Wong et al., *Proc. Natl. Acad. Sci. USA* 99: 16325-16330, 2002); lipoxygenase 1 gene promoters (for example see Rouster et al., *Plant J.* 15: 435-440, 1998); Chi26 gene promoters (for example see Leah et al., *Plant J.* 6: 579-589, 1994); Glu-D1-1 gene promoters (for example see Lamacchia et al., *J. Exp. Bot.* 52: 243-250, 2001; Zhang et al., *Theor. Appl. Genet.* 106: 1139-1146, 2003); Hor3-1 gene promoters (for example see Sörensen et al., *Mol. Gen. Genet.* 250: 750-760, 1996; Horvath et al., *Proc. Natl. Acad. Sci. USA* 97: 1914-1919, 2000) and Waxy (Wx) gene promoters (for example see Yao et al., *Acta Phytophysiol. Sin.* 22: 431-436, 1996; Terada et al., *Plant Cell Physiol.* 41: 881-888, 2000; Liu et al., *Transgenic Res.* 12: 71-82, 2003). In one specific embodiment, the seed specific promoter is an endosperm specific promoter.

The promoter may also be a promoter that is activatable by one or more defined transcriptional activators, referred to herein as an "activatable promoter". For example, the activatable promoter may comprise a minimal promoter operably connected to an Upstream Activating Sequence (UAS), which comprises, inter alia, a DNA binding site for one or more transcriptional activators.

As referred to herein the term "minimal promoter" should be understood to include any promoter that incorporates at least an RNA polymerase binding site and, preferably a TATA box and transcription initiation site and/or one or more CAAT boxes. When the cell is a plant cell, the minimal promoter may be derived from, for example, the Cauliflower Mosaic Virus 35S (CaMV 35S) promoter. The CaMV 35S derived minimal promoter may comprise, for example, a sequence that corresponds to positions −90 to +1 (the transcription initiation site) of the CaMV 35S promoter (also referred to as a −90 CaMV 35S minimal promoter), −60 to +1 of the CaMV 35S promoter (also referred to as a −60 CaMV 35S minimal promoter) or −45 to +1 of the CaMV 35S promoter (also referred to as a −45 CaMV 35S minimal promoter).

As set out above, the activatable promoter may comprise a minimal promoter fused to an Upstream Activating Sequence (UAS). The UAS may be any sequence that can bind a transcriptional activator to activate the minimal promoter. Exemplary transcriptional activators include, for example: yeast derived transcription activators such as Gal4, Pdr1, Gcn4 and Ace1; the viral derived transcription activator, VP16; Hap1 (Hach et al., *J Biol Chem* 278: 248-254, 2000); Gaf1 (Hoe et al., *Gene* 215(2): 319-328, 1998); E2F (Albani et al., *J Biol Chem* 275: 19258-19267, 2000); HAND2 (Dai and Cserjesi, *J Biol Chem* 277: 12604-12612, 2002); NRF-1 and EWG (Herzig et al., *J Cell Sci* 113: 4263-4273, 2000); P/CAF (Itoh et al., *Nucl Acids Res* 28: 4291-4298, 2000); MafA (Kataoka et al., *J Biol Chem* 277: 49903-49910, 2002); human activating transcription factor 4 (Liang and Hai, *J Biol Chem* 272: 24088-24095, 1997); Bcl10 (Liu et al., *Biochem Biophys Res Comm* 320(1): 1-6, 2004); CREB-H (Omori et al., *Nucl Acids Res* 29: 2154-2162, 2001); ARR1 and ARR2 (Sakai et al., *Plant J* 24(6): 703-711, 2000); Fos (Szuts and Bienz, *Proc Natl Acad Sci USA* 97: 5351-5356, 2000); HSF4 (Tanabe et al., *J Biol Chem* 274: 27845-27856, 1999); MAML1 (Wu et al., *Nat Genet.* 26: 484-489, 2000).

In some embodiments, the UAS comprises a nucleotide sequence that is able to bind to at least the DNA-binding domain of the GAL4 transcriptional activator. UAS sequences, which can bind transcriptional activators that comprise at least the GAL4 DNA binding domain, are referred to herein as $UAS_G$. In a particular embodiment, the $UAS_G$ comprises the sequence 5'-CGGAGTACTGTCCTC-CGAG-3' or a functional homolog thereof.

As referred to herein, a "functional homolog" of the $UAS_G$ sequence should be understood to refer to any nucleotide sequence which can bind at least the GAL4 DNA binding domain and which may comprise a nucleotide sequence having at least 50% identity, at least 65% identity, at least 80% identity or at least 90% identity with the $UAS_G$ nucleotide sequence.

The UAS sequence in the activatable promoter may comprise a plurality of tandem repeats of a DNA binding domain target sequence. For example, in its native state, $UAS_G$ comprises four tandem repeats of the DNA binding domain target sequence. As such, the term "plurality" as used herein with regard to the number of tandem repeats of a DNA binding domain target sequence should be understood to include at least 2, at least 3 or at least 4 tandem repeats.

As mentioned above, the control sequences may also include a terminator. The term "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

Modulating the level of (1,3;1,4)-β-D-glucan in a cell, by modulating the level and/or activity of a CslH-encoded (1,3;1,4)-β-D-glucan synthase in the cell, has several industrial applications.

For example, (1,3;1,4)-β-D-glucans are known to form viscous solutions. The viscosity-generating properties of soluble cereal (1,3;1,4)-β-D-glucans are critical determinants in many aspects of cereal processing. For example, incompletely degraded (1,3;1,4)-β-D-glucans from malted barley and cereal adjuncts can contribute to wort and beer viscosity and are associated with problems in wort separation and beer filtration (eg. see Bamforth, *Brew. Dig.* 69 (5): 12-16, 1994) Therefore, for example, in some embodiments, the present invention may be applied to reduce the level of (1,3;1,4)-β-D-glucan in barley grain, by reducing the level and/or activity of a CslH-encoded (1,3;1,4)-β-D-glucan synthase in one or more cells of the barley grain, to increase its suitability for beer production.

Soluble cereal (1,3;1,4)-β-D-glucans are also considered to have antinutritive effects in monogastric animals such as pigs and poultry. The "antinutritive" effects have been attributed to the increased viscosity of gut contents, which slows both the diffusion of digestive enzymes and the absorption of degradative products of enzyme action. This, in turn, leads to slower growth rates. Moreover, in dietary formulations for poultry, high (1,3;1,4)-β-D-glucan concentrations are associated with 'sticky' faeces, which are indicative of the poor digestibility of the (1,3;1,4)-β-D-glucans and which may present major handling and hygiene problems for producers. Therefore, in another embodiment, the present invention may be applied to reducing the level of (1,3;1,4)-β-D-glucan in one or more cells of a plant used for animal feed, to improve the suitability of the plant as animal feed.

However, cereal (1,3;1,4)-β-D-glucans are important components of dietary fibre in human and animal diets. As used herein, the term "dietary fibre" should be understood to include the edible parts of plants or analogous carbohydrates that are resistant to digestion and absorption in the human small intestine with complete or partial fermentation in the large intestine. "Dietary fibre" includes polysaccharides (specifically including (1,3;1,4)-β-D-glucans), oligosaccharides, lignin and associated plant substances. In at least human diets, dietary fibres promote beneficial physiological effects including general bowel health, laxation, blood cholesterol attenuation, and/or blood glucose attenuation.

Humans and monogastric animals produce no enzymes that degrade (1,3;1,4)-β-D-glucans, although there are indications that some depolymerization occurs in the stomach and small intestine, presumably due to the activity of commensal microorganisms. By comparison, the soluble (1,3;1,4)-β-D-glucans and other non-starchy polysaccharides are readily fermented by colonic micro-organisms and make a small contribution to digestible energy. In contrast to their antinutritive effects in monogastric animals, oat and barley (1,3;1,4)-β-D-glucans at high concentrations in humans have beneficial effects, especially for non-insulin-dependent diabetics, by flattening glucose and insulin responses that follow a meal. High concentrations of (1,3;1,4)-β-D-glucans (eg. 20% w/v) in food have also been implicated in the reduction of serum cholesterol concentrations, by lowering the uptake of dietary cholesterol or resorption of bile acids from the intestine.

Therefore, in another embodiment, the present invention may be applied to increasing the dietary fibre content of an edible plant or edible plant part, by increasing the level of (1,3;1,4)-β-D-glucan in the plant, or part thereof. In some embodiments, the edible plant or edible part of a plant is a cereal crop plant or part thereof.

(1,3;1,4)-β-D-glucans, in common with a number of other polysaccharides, in particular (1→3)-β-D-glucans, are also thought to modify immunological responses in humans by a process that is mediated through binding to receptors on cells of the reticuloendothelial system (leucocytes and macrophages). In addition, they may have the capacity to activate the proteins of the human complement pathway, a system that is invoked as a first line of defence before circulating antibodies are produced.

The present invention also facilitates the production of (1,3;1,4)-β-D-glucan in a recombinant expression system. For example, a (1,3;1,4)-β-D-glucan may be recombinantly produced by introducing a CslH nucleic acid under the control of a promoter, into a cell, wherein the cell subsequently expresses a CslH-encoded (1,3;1,4)-β-D-glucan synthase and produces (1,3;1,4)-β-D-glucan.

A vast array of recombinant expression systems that may be used to express a CslH nucleic acid are known in the art. Exemplary recombinant expression systems include: bacterial expression systems such as *E. coli* expression systems (reviewed in Baneyx, *Curr. Opin. Biotechnol.* 10: 411-421, 1999; eg. see also *Gene expression in recombinant microorganisms*, Smith (Ed.), Marcel Dekker, Inc. New York, 1994; and *Protein Expression Technologies: Current Status and Future Trends*, Baneyx (Ed.), Chapters 2 and 3, Horizon Bioscience, Norwich, UK, 2004), *Bacillus* spp. expression systems (eg. see *Protein Expression Technologies Current Status and Future Trends*, supra, chapter 4) and *Streptomyces* spp. expression systems (eg. see Practical *Streptomyces* Genetics, Kieser et al., (Eds.), Chapter 17, John Imes Foundation, Norwich, UK, 2000); fungal expression systems including yeast expression systems such as *Saccharomyces* spp., *Schizosaccharomyces pombe, Hansenula polymorpha* and *Pichia* spp. expression systems and filamentous fungi expression systems (eg. see *Protein Expression Technologies: Current Status and Future Trends*, supra, chapters 5, 6 and 7; Buckholz and Gleeson, *Bio/Technology* 9(11): 1067-1072, 1991; Cregg et al., *Mol. Biotechnol.* 16(1): 23-52, 2000; Cereghino and Cregg, *FEMS Microbiology Reviews* 24: 45-66, 2000; Cregg et al., *Bio/Technology* 11: 905-910, 1993); mammalian cell expression systems including Chinese Hamster Ovary (CHO) cell based expression systems (eg. see *Protein Expression Technologies: Current Status and Future Trends*, supra, chapter 9); insect cell cultures including baculovirus expression systems (eg. see *Protein Expression Technologies: Current Status and Future Trends*, supra, chapter 8; Kost and Condreay, *Curr. Opin. Biotechnol.* 10: 428-433, 1999; *Baculovirus Expression Vectors: A Laboratory Manual* W H Freeman & Co., New York, 1992; and *The Baculovirus Expression System: A Laboratory Manual*, Chapman & Hall, London, 1992); Plant cell expression systems such as tobacco, soybean, rice and tomato cell expression systems (eg. see review of Hellwig et al., *Nat Biotechnol* 22: 1415-1422, 2004); and the like.

Therefore, in a third aspect, the present invention provides a method for producing (1,3;1,4)-β-D-glucan, the method comprising transforming a cell with an isolated CslH nucleic acid and allowing the cell to express the isolated CslH nucleic acid.

In some embodiments, the cell is a cell from a recombinant expression system as hereinbefore defined.

In a fourth aspect, the present invention also provides (1,3;1,4)-β-D-glucan produced according to the method of the third aspect of the invention.

In a fifth aspect, the present invention also provides a cell comprising:
 a modulated level and/or activity of CslH-encoded (1,3;1,4)-β-D-glucan synthase relative to a wild type cell of the same taxon; and/or
 modulated expression of a CslH nucleic acid relative to a wild type cell of the same taxon.

In some embodiments, the cell further comprises a modulated level of (1,3;1,4)-β-D-glucan relative to a wild type cell of the same taxon.

In some embodiments, the cell of the fifth aspect of the invention is produced according to the methods of the first or second aspects of the present invention as described herein. In further embodiments, the cell is a plant cell, a monocot plant cell, a Poales plant cell and/or a cereal crop plant cell.

Furthermore, in a sixth aspect, the present invention provides a multicellular structure comprising one or more cells according to the fifth aspect of the invention.

As referred to herein, a "multicellular structure" includes any aggregation of one or more cells. As such, the term "multicellular structure" specifically encompasses tissues, organs, whole organisms and parts thereof. Furthermore, a multicellular structure should also be understood to encompass multicellular aggregations of cultured cells such as colonies, plant calli, suspension cultures and the like.

As mentioned above, in some embodiments of the invention, the cell is a plant cell and as such, the present invention includes a whole plant, plant tissue, plant organ, plant part, plant reproductive material or cultured plant tissue, comprising one or more plant cells according to the sixth aspect of the invention.

In another embodiment, the present invention provides a cereal crop plant comprising one or more cells according to the fifth aspect of the invention.

In a particular embodiment, the present invention provides cereal grain comprising one or more cells according to the fifth aspect of the invention.

Therefore, in a seventh aspect, the present invention provides a cereal grain comprising a modulated level of (1,3;1,4)-β-D-glucan, wherein the grain comprises one or more cells comprising a modulated level and/or activity of a CslH-encoded (1,3;1,4)-β-D-glucan synthase and/or modulated expression of a CslH nucleic acid.

In some embodiments, the grain may have an increased level of (1,3;1,4)-β-D-glucan compared to wild type grain from the same species. In alternate embodiments, the grain may have a decreased level of (1,3;1,4)-β-D-glucan compared to wild type grain from the same species.

In some embodiments wherein the grain is a wheat grain, the wheat grain comprises level of (1,3;1,4)-β-D-glucan of at least 1%, at least 1.1%, at least 1.2%, at least 1.3%, at least 1.4%, at least 1.5%, at least 1.6%, at least 1.7%, at least 1.8% or 1.9% on a fresh weight basis of air dried whole grain.

In an eighth aspect, the present invention also provides flour comprising:
 flour produced by the milling of the grain of the seventh aspect of the invention; and
 optionally, flour produced by the milling of one or more other grains.

As such, the flour produced by the milling of the grain of the seventh aspect of the invention may comprise, for example approximately 10%, 20%, 30%, 40%, 50%, 60%, 70%, 80%, 90% or 100% by weight of the flour of the ninth aspect of the invention.

As referred to herein "milling" contemplates any method known in the art for milling grain, such as those described by Brennan et al. (Manual of Flour and Husk Milling, Brennan et al. (Eds.), AgriMedia, ISBN: 3-86037-277-7).

In some embodiments, the flour produced by the milling of the grain of the seventh aspect of the invention used in the flour comprises an increased level of (1,3;1,4)-β-D-glucan compared to wild type flour.

The "flour produced by the milling of one or more other grains" may be flour produced by milling grain derived from any cereal plant, as hereinbefore defined. This component of the flour of the eighth aspect of the invention may, for example, comprise 0%, 10%, 20%, 30%, 40%, 50%, 60%, 70%, 80% or 90% by weight.

In some embodiments, the flour produced by the milling of one or more other grains is wheat flour and, therefore, the flour of the eighth aspect of the invention may be particularly suitable for producing bread, cakes, biscuits and the like.

As set out above, the present invention is predicated, in part, on the identification and isolation of CslH nucleotide sequences and CslH amino acid sequences that encode (1,3;1,4)-β-D-glucan synthases.

Therefore, in a ninth aspect, the present invention provides an isolated CslH nucleic acid as hereinbefore defined, or a complement, reverse complement or fragment thereof.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be isolated because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (eg. polymerase chain reaction and the like).

The isolated nucleic acid molecules of the present invention may comprise any polyribonucleotide or polydeoxyribonucleotide, which may be unmodified RNA or DNA or modified RNA or DNA. For example, the isolated nucleic acid molecules of the invention may comprise single- and double-stranded DNA, DNA that is a mixture of single- and double-stranded regions, single- and double-stranded RNA, and RNA that is mixture of single- and/or double-stranded regions, hybrid molecules comprising DNA and RNA that may be single-stranded or, more typically, double-stranded or a mixture of single- and double-stranded regions. In addition, the isolated nucleic acid molecules may comprise of triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As set out above, the present invention also provides fragments of a nucleotide sequence. "Fragments" of a nucleotide sequence should be at least 15, 20, 30, 40, 50, 100, 150, 200, 250, 300, 325, 350, 375, 400, 450, 500, 550, or 600 nucleotides (nt) in length. These fragments have numerous uses that include, but are not limited to, diagnostic probes and primers. Of course, larger fragments, such as those of 601-3000 nt in length are also useful according to the present invention as are fragments corresponding to most, if not all, of a CslH nucleic acid.

In some embodiments, the fragment may comprise a functional fragment of a CslH nucleic acid. That is, the polynucleotide fragments of the invention may encode a polypeptide having (1,3;1,4)-β-D-glucan synthase functional activity as defined herein.

In a tenth aspect, the present invention provides a genetic construct or vector comprising an isolated nucleic acid molecule of the ninth aspect of the invention.

The vector or construct may further comprise one or more of: an origin of replication for one or more hosts; a selectable marker gene which is active in one or more hosts; or one or more control sequences which enable transcription of the isolated nucleic acid molecule in a cell.

"Selectable marker genes" include any nucleotide sequences which, when expressed by a cell, confer a phenotype on the cell that facilitates the identification and/or selection of these transformed cells. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (eg. nptI and nptII) and hygromycin phosphotransferase genes (eg. hpt); herbicide resistance genes including glufosinate, phosphinothricin or bialaphos resistance genes such as phosphinothricin acetyl transferase encoding genes (eg. bar), glyphosate resistance genes including 3-enoyl pyruvyl shikimate 5-phosphate synthase encoding genes (eg. aroA), bromyxnil resistance genes including bromyxnil nitrilase encoding genes, sulfonamide resistance genes including dihydropterate synthase encoding genes (eg. sul) and sulfonylurea resistance genes including acetolactate synthase encoding genes; enzyme-encoding reporter genes such as GUS and chloramphenicolacetyltransferase (CAT) encoding genes; fluorescent reporter genes such as the green fluorescent protein-encoding gene; and luminescence-based reporter genes such as the luciferase gene, amongst others.

Furthermore, it should be noted that the selectable marker gene may be a distinct open reading frame in the construct or may be expressed as a fusion protein with the CslH-encoded (1,3;1,4)-β-D-glucan synthase polypeptide.

The tenth aspect of the invention extends to all genetic constructs essentially as described herein, which include further nucleotide sequences intended for the maintenance and/or replication of the genetic construct in prokaryotes or eukaryotes and/or the integration of the genetic construct or a part thereof into the genome of a eukaryotic or prokaryotic cell.

In some embodiments, the vector or construct is adapted to be at least partially transferred into a plant cell via *Agrobacterium*-mediated transformation. Accordingly, the vector or construct may comprise left and/or right T-DNA border sequences.

Suitable T-DNA border sequences would be readily ascertained by one of skill in the art. However, the term "T-DNA border sequences" may include substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA*, 82(15): 5112-5116, 1985) and the review of Gelvin (*Microbiology and Molecular Biology Reviews*, 67(1): 16-37, 2003).

Although in some embodiments, the vector or construct is adapted to be transferred into a plant via *Agrobacterium*-mediated transformation, the present invention also contemplates any suitable modifications to the genetic construct which facilitate bacterial mediated insertion into a plant cell via bacteria other than *Agrobacterium* sp., for example, as described in Broothaerts et al. (*Nature* 433: 629-633, 2005).

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell. Exemplary methods for cloning nucleic acid molecules are described in Sambrook et al. (2000, supra)

In an eleventh aspect, the present invention provides a cell comprising the isolated nucleic acid molecule of the ninth aspect of the invention or genetic construct of the tenth aspect of the invention.

The isolated nucleic acid molecule of the tenth or eleventh aspects of the invention or genetic construct of the twelfth aspect of the invention may be introduced into a cell via any means known in the art.

The isolated nucleic acid molecule or construct referred to above may be maintained in the cell as a DNA molecule, as part of an episome (eg. a plasmid, cosmid, artificial chromosome or the like) or it may be integrated into the genomic DNA of the cell.

As used herein, the term "genomic DNA" should be understood in its broadest context to include any and all DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like.

The isolated nucleic acid molecule may be operably connected to, inter alia, a control sequence and/or a promoter such that the cell may express the isolated nucleic acid molecule.

The cell may be any prokaryotic or eukaryotic cell. As such, the cell may be a prokaryotic cell such as a bacterial cell including an *E. coli* cell or an *Agrobacterium* spp. cell, or an archaea cell. The cell may also be a eukaryotic cell including a fungal cell such as a yeast cell or mycelial fungus cell; an animal cell such as a mammalian cell or an insect cell; or a plant cell. In a particular embodiment, the cell is a plant cell. In some embodiments, the plant cell is a monocot plant cell, a Poales plant cell, or a cereal crop plant cell.

In a twelfth aspect, the present invention provides a multicellular structure, as hereinbefore defined, comprising one or more of the cells of the eleventh aspect of the invention.

As mentioned above, in some embodiments, the cell is a plant cell and as such, the present invention should be understood to specifically include a whole plant, plant tissue, plant organ, plant part, plant reproductive material, or cultured plant tissue, comprising one or more cells of the eleventh aspect of the invention.

In a further embodiment, the present invention provides a monocot plant, a Poales plant or a cereal crop plant or part thereof, comprising one or more cells of the eleventh aspect of the invention.

In some embodiments, the present invention provides cereal grain comprising one or more cells of the eleventh aspect of the invention.

As set out above, the present invention also provides amino acid sequences for CslH-encoded (1,3;1,4)-β-D-glucan synthases. Accordingly, in a thirteenth aspect, the present invention provides an isolated CslH-encoded (1,3;1,4)-β-D-glucan synthase as hereinbefore defined, or a fragment thereof.

The isolated polypeptides may comprise of amino acids joined to each other by peptide bonds or modified peptide bonds, ie., peptide isosteres, and may contain amino acids other than the 20 gene-encoded amino acids. The isolated polypeptides of the present invention may be modified by either natural processes, such as post-translational processing, or by chemical modification techniques which are well known in the art.

Modifications can occur anywhere in the isolated polypeptide, including the peptide backbone, the amino acid sidechains and/or the termini. It will be appreciated that the same type of modification may be present in the same or varying degrees at several sites in a given isolated polypeptide. Also, an isolated polypeptide of the present invention may contain many types of modifications.

The polypeptides may be branched, for example, as a result of ubiquitination, and/or they may be cyclic, with or without branching. Cyclic, branched, and branched cyclic polypeptides may result from post-translation natural processes or may be made by synthetic methods.

Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, PEGylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties* 2$^{nd}$ Ed., Creighton (ed.), W.H. Freeman and Company, New York, 1993); *Posttranslational Covalent Modification Of Proteins*, Johnson (Ed.), Academic Press, New York, 1983; Seifter et al., *Meth Enzymol* 182: 626-646, 1990); Rattan et al., *Ann NY Acad Sci* 663: 48-62, 1992.).

As set out above, the present invention also provides fragments of isolated polypeptides. Polypeptide fragments may be "free-standing" or comprised within a larger polypeptide of which the fragment forms a part or region.

The polypeptide fragments can be at least 3, 4, 5, 6, 8, 9, 10, 11, 12, 13, 15, 20, 25, 30, 35, 40, 45, 50, 60, 70, 80, 90, 100, 110, 120, 130, 140, or 150 amino acids in length.

In some embodiments, the fragment is a functional fragment and thus comprises (1,3;1,4)-β-D-glucan synthase functional activity. However, even if the fragment does not retain one or more biological functions of a CslH-encoded (1,3;1,4)-β-D-glucan synthase, other functional activities may still be retained. For example, the fragments may lack CslH-encoded (1,3;1,4)-β-D-glucan synthase functional activity but retain the ability to induce and/or bind to antibodies which recognize the complete or mature forms of an isolated CslH-encoded (1,3;1,4)-β-D-glucan synthase polypeptide. A peptide, polypeptide or protein fragment which has the ability to induce and/or bind to antibodies which recognize the complete or mature forms of the isolated CslH-encoded (1,3;1,4)-β-D-glucan synthase polypeptide is referred to herein as a "CslH-encoded (1,3;1,4)-β-D-glucan synthase epitope".

A CslH-encoded (1,3;1,4)-β-D-glucan synthase epitope may comprise as few as three or four amino acid residues. In some embodiments the epitope may comprise, for example, at least 5, at least 10, at least 20, at least 50, at least 100 or at least 200 amino acid residues. Whether a particular epitope of an isolated CslH-encoded (1,3;1,4)-β-D-glucan synthase polypeptide retains such immunologic activities can readily be determined by methods known in the art. As such, one CslH-encoded (1,3;1,4)-β-D-glucan synthase polypeptide fragment is a polypeptide comprising one or more CslH-encoded (1,3;1,4)-β-D-glucan synthase epitopes.

A polypeptide comprising one or more CslH-encoded (1,3;1,4)-β-D-glucan synthase epitopes may be produced by any conventional means for making polypeptides including synthetic and recombinant methods known in the art. In some embodiments, CslH-encoded (1,3;1,4)-β-D-glucan synthase epitope-bearing polypeptides may be synthesized using known methods of chemical synthesis. For instance, Houghten has described a simple method for the synthesis of large numbers of peptides (Houghten, *Proc. Natl. Acad. Sci. USA* 82: 5131-5135, 1985).

The isolated CslH-encoded (1,3;1,4)-β-D-glucan synthase polypeptides and CslH-encoded (1,3;1,4)-β-D-glucan synthase epitope-bearing polypeptides are useful, for example, in the generation of antibodies that bind to the isolated CslH-encoded (1,3;1,4)-β-D-glucan synthase polypeptides of the invention.

Such antibodies are useful, inter alia, in the detection and localization of (1,3;1,4)-β-D-glucan synthase polypeptides and in affinity purification of (1,3;1,4)-β-D-glucan synthase polypeptides. The antibodies may also routinely be used in a variety of qualitative or quantitative immunoassays using methods known in the art. For example see Harlow et al., *Antibodies: A Laboratory Manual*, (Cold Spring Harbor Laboratory Press 2$^{nd}$ Ed., 1988).

Accordingly, in a fourteenth aspect, the present invention provides an antibody or an epitope binding fragment thereof, raised against an isolated CslH-encoded (1,3;1,4)-β-D-glucan synthase polypeptide as hereinbefore defined or an epitope thereof.

The antibodies of the present invention include, but are not limited to, polyclonal, monoclonal, multispecific, chimeric antibodies, single chain antibodies, Fab fragments, F(ab') fragments, fragments produced by a Fab expression library and epitope-binding fragments of any of the above.

The term "antibody", as used herein, refers to immunoglobulin molecules and immunologically active portions of immunoglobulin molecules, i.e., molecules that contain an antigen-binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies of the present invention may be monospecific, bispecific, trispecific, or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. For example, see PCT publications WO 93/17715; WO 92/08802; WO 91/00360; WO 92/05793; Tutt et al., *J. Immunol.* 147: 60-69, 1991; U.S. Pat. Nos. 4,474,893; 4,714,681; 4,925,648; 5,573,920; 5,601,819; and Kostelny et al. *J. Immunol.* 148: 1547-1553, 1992).

In some embodiments, the antibodies of the present invention may act as agonists or antagonists of CslH-encoded (1,3;1,4)-β-D-glucan synthase. In further embodiments, the antibodies of the present invention may be used, for example, to purify, detect, and target the polypeptides of the present invention, including both in vitro and in vivo diagnostic and therapeutic methods. For example, the antibodies have use in immunoassays for qualitatively and quantitatively measuring levels of CslH-encoded (1,3;1,4)-β-D-glucan synthase in biological samples. See, e.g., Harlow et al., *Antibodies: A Laboratory Manual* (Cold Spring Harbor Laboratory Press, 2nd ed. 1988).

The term "antibody", as used herein, should be understood to encompass derivatives that are modified, eg. by the covalent attachment of any type of molecule to the antibody such that covalent attachment does not prevent the antibody from binding to a CslH-encoded (1,3;1,4)-β-D-glucan synthase or an epitope thereof. For example, the antibody derivatives include antibodies that have been modified, eg., by glycosylation, acetylation, pegylation, phosphorylation, amidation, derivatization by known protecting/blocking groups, proteolytic cleavage, linkage to a cellular ligand or other protein, etc. Furthermore, any of numerous chemical modifications may also be made using known techniques. These include specific chemical cleavage, acetylation, formylation, metabolic synthesis of tunicamycin, etc. Additionally, the derivative may contain one or more non-classical amino acids.

Antibodies may be generated using methods known in the art.

For example, if in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For example, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde.

Animals such as rabbits, rats and mice may be immunized with either free or carrier-coupled peptides, for instance, by intraperitoneal and/or intradermal injection of emulsions containing about 100 micrograms of peptide or carrier protein and Freund's adjuvant. Several booster injections may be needed, for example, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Polyclonal antibodies to a CslH-encoded (1,3;1,4)-β-D-glucan synthase polypeptide or a polypeptide comprising one or more CslH-encoded (1,3;1,4)-β-D-glucan synthase epitopes can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, for example, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

As another example, monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed., 1988) and Hammerling et al., in: *Monoclonal Antibodies and T-Cell Hybridomas* (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. For example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Antibody fragments which recognize one or more CslH-encoded (1,3;1,4)-β-D-glucan synthase epitopes may also be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labelled antigen or antigen bound or captured to a solid surface or bead. Phages used in these methods are typically filamentous phage including fd and M13 binding domains expressed from phage with Fab, Fv or disulfide stabilized Fv antibody domains recombinantly fused to either the phage gene III or gene VIII protein.

Examples of phage display methods include those disclosed in Brinkman et al. (*J. Immunol. Methods* 182: 41-50, 1995), Ames et al. (*J. Immunol. Methods* 184: 177-186, 1995), Kettleborough et al. (*Eur. J. Immunol.* 24: 952-958, 1994), Persic et al. (*Gene* 187: 9-18, 1997), Burton et al. (*Advances in Immunology* 57: 191-280, 1994); PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the antibody coding regions from the phage can be isolated and used to generate whole antibodies or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al. (*BioTechniques* 12(6): 864-869, 1992); and Sawai et al. (*AJRI* 34:26-34, 1995); and Better et al. (*Science* 240: 1041-1043, 1988).

Examples of techniques which can be used to produce single-chain Fvs and antibodies include those described in U.S. Pat. Nos. 4,946,778 and 5,258,498; Huston et al. (*Methods in Enzymology* 203: 46-88, 1991); Shu et al. (*Proc. Natl. Acad. Sci. USA* 90: 7995-7999, 1993); and Skerra et al. (*Science* 240: 1038-1040, 1988).

The present invention is further described by the following non-limiting examples:

BRIEF DESCRIPTION OF THE DRAWINGS

FIG. 10 shows the nucleotide sequence identity, protein sequence identity and protein sequence similarity between CslH sequences derived from Barley (*Hordeum vulgare*) and Rice (*Oryza sativa*).

FIG. 11 shows a ClustalW multiple sequence alignment of CslH amino acid sequences derived from Barley (*Hordeum vulgare*) and Rice (*Oryza sativa*). HvCslH1 (SEQ ID NO: 2); OsCSLH3 (SEQ ID NO: 8); OsCSLH1 (SEQ ID NO: 4); and OsCSLH2 (SEQ ID NO: 6).

FIG. 17 shows a comparison of the barley CslH1 gene cDNA and genomic sequences against the genomic sequences of the three wheat CslH1 gene homeologs (TaCslH1-1, 1-2 and 1-3). The DNA sequences of the barley cDNA (top, HvCslH1 from cv. Schooner (SEQ ID NO: 1) and HvCslH1Him from cv. Himalaya, (SEQ ID NO: 69) and genomic clones (HvCslH1g from cv. Morex (SEQ ID NO: 9) and HvCslH1gHim from cv. Himalaya (SEQ ID NO: 71) were aligned with the three wheat sequences (TaCslH1-1, 1-2 and 1-3, (SEQ ID NO: 78, 80 and 81, respectively) in BioEdit using the Muscle comparison programme. The alignment position is numbered above the sequences and dashes indicate gaps introduced to optimise the alignment. Nucleotides identical to the wheat genomic sequence (TaCslH1-1) are indicated by dots. The exon/intron boundaries are shown in bold in the wheat genomic sequence (TaCslH1-1). For reference, the ATG initiation codon of the CslH coding region starts at alignment position 98 and the stop codon TAA starts at position 3320, both are underlined.

FIG. 19 shows the results of semi quantitative RT-PCR and Q-PCR expression analysis of the barley cv. Himalaya CslH1 gene during coleoptile development. Panel A shows semi quantitative RT-PCR showing the expression pattern of the barley CslH1 gene during growth of the coleoptile and in young leaf(L), root (R) and mid stage endosperm(E). A constitutively expressed gene (alpha tubulin) is shown as a control. Panel B shows normalized expression levels (Q-PCR) for HvCslH1 in developing coleoptiles at various times (days) after the initiation of germination.

FIG. 27 shows a comparison of the DNA coding sequence and amino acid sequence identity/similarity for barley and wheat CslH sequences. HvCslH1=DNA coding sequence from barley cv. Schooner (SEQ ID NO: 1) and corresponding amino acid sequence (SEQ ID NO: 2); HvCslH1 (Him) DNA coding sequence from barley cv. Himalaya (SEQ ID NO: 69) and corresponding amino acid sequence (SEQ ID NO: 70); TaCslH1-1=DNA coding sequence from wheat cv. Chinese Spring (SEQ ID NO: 72) and corresponding amino acid sequence (SEQ ID NO: 75); TaCslH1-2=DNA coding sequence from wheat cv. Chinese Spring (SEQ ID NO: 73) and corresponding amino acid sequence (SEQ ID NO: 76); TaCslH1-3=DNA coding sequence from wheat cv. Chinese Spring (SEQ ID NO: 74) and corresponding amino acid sequence (SEQ ID NO: 77).

EXAMPLE 1

Barley has Only One CSLH Gene

Figure 6:
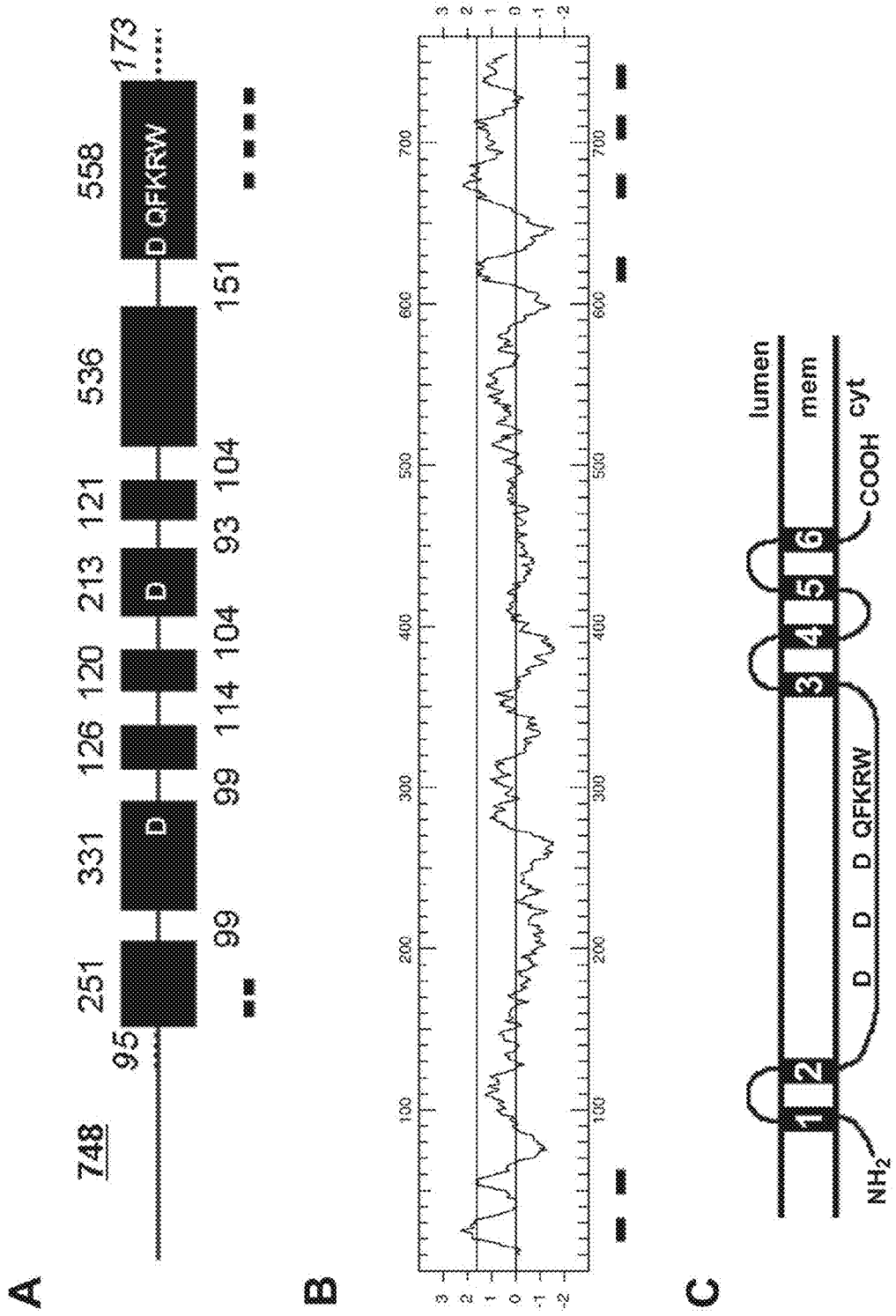
FIG. 6 shows structural features of HvCslH1. (A) Exon-intron structure of HvCslH1. Black bars indicate exons, the thin black line introns and 5' and 3' UTRs. Numbers above boxes show size of exons, numbers below the line show intron size. Italicised numbers refer to the size of 5' and 3' UTRs, bold-underline, the length of known sequence upstream of the start codon. Numbers are in base pairs. Thick black bars indicate the six consensus trans-membrane domains as predicted by ARAMEMNON (http://aramemnon.botanik.uni-koeln.de/). (B) Kyte-Doolittle hydrophobicity plot (Kyte and Doolittle, *J Mol Biol* 157: 105-132, 1982) of HvCslH1. A 19 amino acid window with a +1.6 cutoff was used. The six predicted transmembrane domains are indicated by black bars. Numbers refer to amino acids. (C) Predicted membrane topology of HvCslH1. NH$_2$, amino terminal; COOH, carboxy terminal; lumen, interior of ER, Golgi body or vesicle; cyt, cytoplasm, mem, membrane, D,D,D,QXXRW, signature motif of CAZy GT2 family. Sequence of the QXXRW motif in HvCslH1 is QFKRW.
Figure 7:
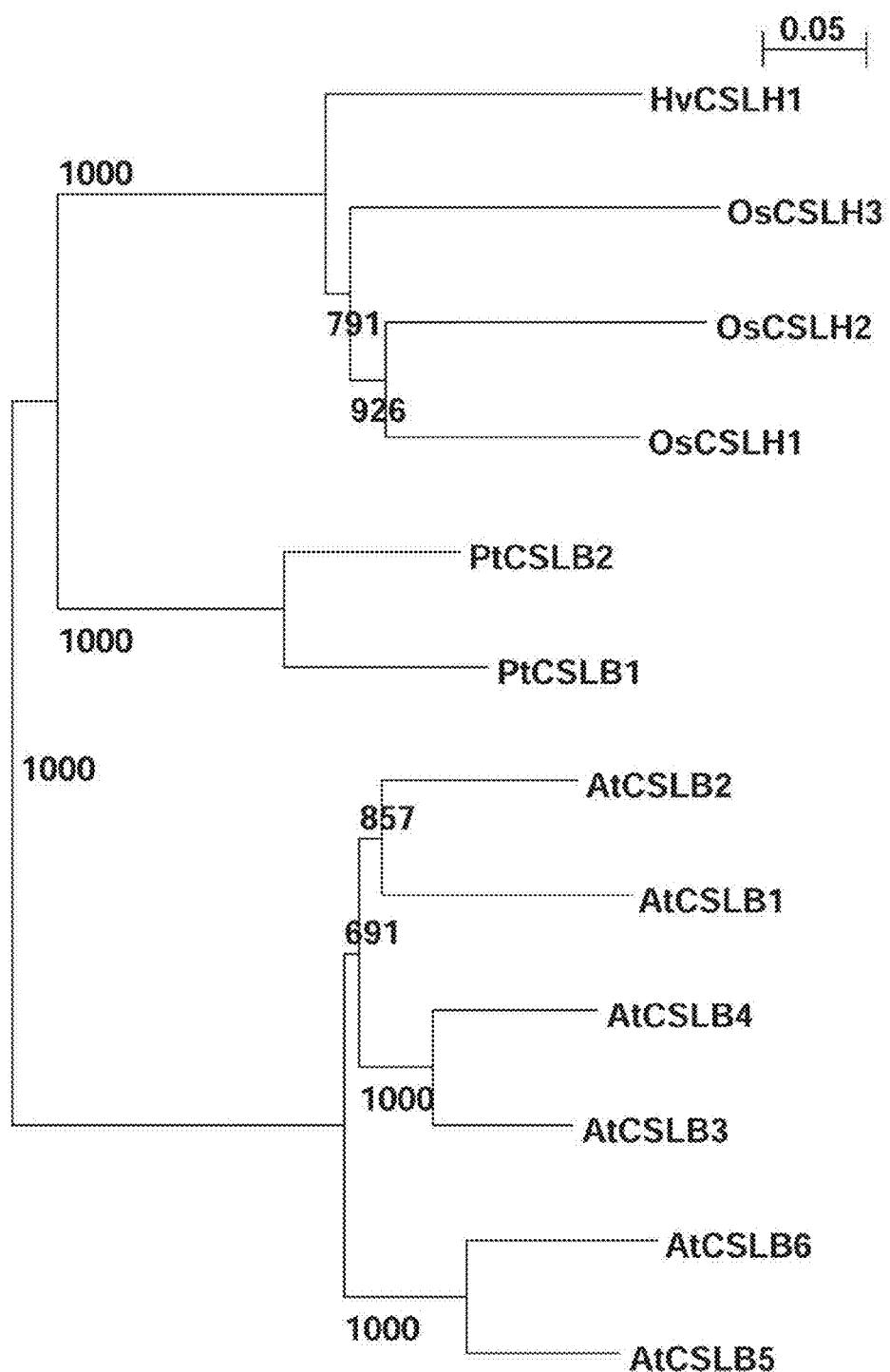
FIG. 7 shows a phylogenetic tree of full-length barley (*Hordeum vulgare*) and rice (*Oryza sativa*) CSLH sequences. *A. thaliana* and poplar (*Populus trichocarpa*) CSLB protein sequences are included because the CSLB family is the most closely related of the CSL families to the CSLH family. The alignment was generated using ClustalX and the in-built distance algorithm with neighbour joining used. The number of bootstrap replicates (from a total of 1,000) supporting each Glade is indicated below the internode for that Glade. Accession numbers are: HvCslH1 (FJ459581), OsCSLH1 (Os10g20090, AC119148), OsCSLH2 (Os04g35020, AL606632), OsCSLH3 (Os04g35030, AL606632), PtCSLB1 (http://genome.jgi-psf.org/Poptr1_1/Poptr1_1.home.html; ID no. 572982), PtCSLB2 (ID no. 684214), AtCSLB1 (At2G32610, NM_128820), AtCSLB2 (At2G32620, NM_128821), AtCSLB3 (At2G32530, NM_179859), AtCSLB4 (At2G32540, NM_128813), AtCSLB5 (At4G15290, NM_117617, AtCSLB6 (At4G15320, NM_117620).
Figure 8:
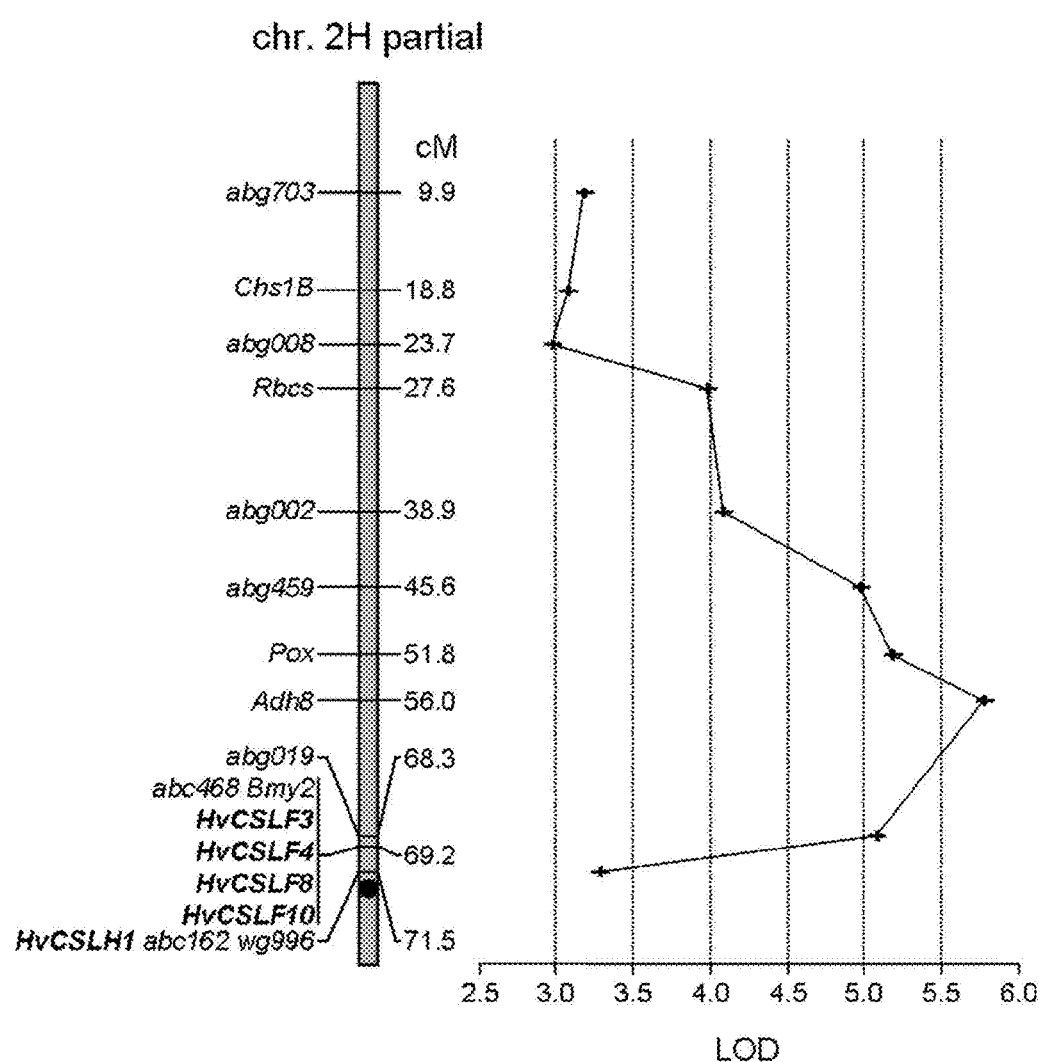
FIG. 8 shows a partial genomic map of the short arm of chromosome 2H where HvCslH1 is located. HvCslH1 and a cluster of four HvCSLF genes were mapped to an interval corresponding to 69.2-71.5 Mb on the Steptoe×Morex bin map close to the centromere (indicated by a black circle). HvCslH1 was placed in bin 8, co-segregating with the wg996 marker. On the Steptoe×Morex reference map, wg996 co-segregates with abc162 and is 2.3 cM south of abc468, the marker that co-segregates with the four HvCSLF genes (Burton et al., *Plant Physiol* 146: 1821-1833, 2008). Key markers are shown on the left, their distances from the top of the chromosome in centimorgans (cM) and the LOD (logarithm of the odds to the base 10) score in the malt β-glucan QTL analysis of Han et al. (*Theor Appl Genet.* 91: 921-927, 1995) are indicated on the right.

Candidate CSLH genes in barley were initially identified by querying online EST databases, such as the discontinued Stanford cell wall website, NCBI, HarvEST, GrainGenes, Barley Gene Index and BarleyBase, with rice CSLH sequences. All CSLH-related ESTs from barley could be aligned into a single contiguous sequence of ~1,500 bp that included the entire 3' untranslated region (UTR) and a region encoding the COOH-terminal 488 (of an expected ~750) amino acid residues of the protein (Table 2). This gene was designated HvCslH1. Screening of a barley BAC library with HvCslH1-derived probes identified several genomic clones all containing HvCslH1, from which the missing 5' end was obtained (data not shown). A 2,430 bp HvCslH1 cDNA fragment was PCR-amplified, contains a single 2,256 bp ORF, and encodes a protein with a predicted MW of 82.6 kDa and a pI of 7.0 (FIG. 6A). Analysis of the conceptual translation of this sequence with ARAMEMNON found between five and nine transmembrane domains (TMDs), with the consensus among the different programs being two $NH_2$-terminal and four COOH-terminal TMDs (FIG. 6B) and both termini of the mature protein predicted to be cytoplasmic. This topology also places the large, central domain containing the D,D,D, QFKRW motif within the cytoplasm (FIG. 6C). At the nucleotide level, HvCslH1 shares 68-74% identity (62-69% amino acid identity) (see Example 6) with the three rice CSLH genes (Hazen et al., *Plant Physiol* 128: 336-340, 2002). A phylogenetic reconstruction shows HvCslH1 to be the likely barley ortholog of OsCSLH1 (FIG. 7). Genetic mapping of HvCslH1 using a Sloop×Halcyon doubled haploid population (Read et al., *Aust J Agr Res* 54: 1145-1153, 2003) showed that HvCslH1 is on the short arm of chromosome 2H, approximately 1.5 cM from a cluster of four HvCSLF genes (HvCSLF3, 4, 8, 10) that Burton et al. (*Plant Physiol* 146: 1821-1833, 2008) reported was within a major QTL controlling β-glucan content in ungerminated barley grain (Han et al., *Theor Appl Genet* 91: 921-927, 1995; FIG. 8).

Supporting Information

A BAC library screening was employed to obtain a complete set of full-length HvCslH family members. BAC filters containing 6.5 equivalents of the barley genome (cv. Morex) were screened and three clearly positive clones identified (data not shown). When a blot of BAC DNA from these clones digested with Hind III was probed, the same three clones, 3-5-10, 3-7-3 and 3-7-8, were verified as being positive. The digestion pattern of BACs 3-5-10 and 3-7-8 appeared identical and many bands were common to BAC 3-7-3, indicating that all 3 BACs cover identical or very similar regions of the barley genome. When a genomic DNA blot was hybridised with the same probe, single bands were observed in lanes digested with Hind III, Eco RI or Eco RV, corroborating the BAC digestion results. As all HvCslH ESTs are also derived from a single gene (Table 2), these data strongly suggest that there is only one CSLH gene in the barley genome.

An adaptor primer PCR method (Siebert et al., *Nucl Acids Res* 23: 1087-1088, 1995) was used to identify the 5' end of HvCslH1. DNA was isolated from BACs 3-5-10 and 3-7-3, digested with a range of restriction enzymes producing blunt-ended DNA fragments to which adaptors were ligated. Nested PCR was then performed with adaptor- and HvCslH1-specific primers (Table 3) in order to amplify fragments containing the 5' end of the gene. Amplification of BAC 3-7-3 DNA digested with Nru I using primers AP2 and H1R6 successfully amplified a 1.3 kbp fragment that contained all but ~20 amino acids of the N-terminal sequence. Direct sequencing of BAC 3-7-3 DNA with the H1R10 primer, an antisense primer designed to anneal near the 5' end of the 1.3 kb fragment, enabled the remainder of the open reading frame plus 748 bp of upstream sequence to be identified. As predicted from earlier results, the sequence obtained from BAC 3-5-10 was identical to BAC 3-7-3, confirming that there is only one CSLH gene within the barley genome.

TABLE 2

List of ESTs derived from HvCslH1. ESTs are listed in order of alignment 5' to 3'.

| Accession no. (5' to 3') | Cultivar | Source tissue |
| --- | --- | --- |
| CA013594 | Barke | early endosperm, 0-16 hours after imbibition |
| BJ470984 | Haruna Nijo adult | top three leaves at heading stage |
| BJ471865 | Haruna Nijo adult | top three leaves at heading stage |
| BJ473288 | Haruna Nijo adult | top three leaves at heading stage |
| BJ452043 | Akashinriki | vegetative stage leaves |
| BJ471909 | Haruna Nijo adult | top three leaves at heading stage |
| AV932844 | Haruna Nijo adult | top three leaves at heading stage |
| BJ469514 | Haruna Nijo adult | top three leaves at heading stage |
| AV933503 | Haruna Nijo adult | top three leaves at heading stage |
| AV933012 | Haruna Nijo adult | top three leaves at heading stage |
| AV932649 | Haruna Nijo adult | top three leaves at heading stage |
| AV932549 | Haruna Nijo adult | top three leaves at heading stage |
| BJ475824 | Haruna Nijo adult | top three leaves at heading stage |
| BJ476822 | Haruna Nijo adult | top three leaves at heading stage |
| AV934650 | Haruna Nijo adult | top three leaves at heading stage |
| BJ477472 | Haruna Nijo adult | top three leaves at heading stage |
| AV935479 | Haruna Nijo adult | top three leaves at heading stage |
| AV935951 | Haruna Nijo adult | top three leaves at heading stage |
| AV832539 | Akashinriki | vegetative stage leaves |
| AV936586 | Haruna Nijo adult | top three leaves at heading stage |
| CB881459 | Barke | male inflorescences (approx. 2 mm in size), green anther stage |
| AV934667 | Haruna Nijo adult | top three leaves at heading stage |
| BJ475744 | Haruna Nijo adult | top three leaves at heading stage |
| BJ459600 | Akashinriki | vegetative stage leaves |
| AV832391 | Akashinriki | vegetative stage leaves |

TABLE 3

Primers used in cloning and amplifying HvCslH1 and in situ PCR analysis

| Gene | Primer name | Primer sequence (5' to 3') | Technique |
| --- | --- | --- | --- |
| HvCslH1 | H1F1 | TTGACCGGACAACGGATCC (SEQ ID NO: 13) | DNA blot analysis, BAC screening, gene mapping, in situ PCR |
| HvCslH1 | H1F2 | CTGGAGATACTCATCAGC (SEQ ID NO: 14) | Northern blotting, transgenic plant transgenic plant genomic DNA PCR screening |
| HvCslH1 | HvCslH1cF1 | TCGAGCGGTTGTTGCTTGTG (SEQ ID NO: 15) | HvCslH1 cDNA amplification |
| HvCslH1 | HvH1TOPOf | CACCATGGCGGGCGGCAAGAAGCTG (SEQ ID NO: 16) | Binary vector construction |
| HvCslH1 | H1R1 | CGTCACCGGGATGAAAAC (SEQ ID NO: 17) | DNA blot analysis, BAC screening, genome walking PCR, in situ PCR |
| HvCslH1 | H1R2 | TGACGCTCCACGGCATTC (SEQ ID NO: 18) | In situ PCR (priming cDNA synthesis) |
| HvCslH1 | H1R5 | GGCTGGCCATCGAAATATTG (SEQ ID NO: 19) | BAC screening, genome walking PCR, gene mapping, in situ PCR |

TABLE 3-continued

Primers used in cloning and amplifying
HvCslH1 and in situ PCR analysis

| Gene | Primer name | Primer sequence (5' to 3') | Technique |
|---|---|---|---|
| HvCslH1 | H1R6 | GAGCGTTGGTCATCACGG (SEQ ID NO: 20) | Genome walking PCR |
| HvCslH1 | H1R7 | CACATCGCGTGTAGGGC (SEQ ID NO: 21) | Genome walking PCR |
| HvCslH1 | H1R10 | CACTTGCCGTTCATGTTG (SEQ ID NO: 22) | Adaptor ligation PCR, BAC sequencing |
| HvCslH1 | HvCslH1cR1 | CCTGCTTGAGTCTTCGTTACATGTTC (SEQ ID NO: 23) | HvCslH1 cDNA amplification |
| HvCslH1 | HvH1TOPOr | CGCTTCCAATATTTCGATG (SEQ ID NO: 24) | Binary vector construction, Northern blotting, transgenic plant genomic DNA PCR screening |
| Generic Adaptor 1 | | CTAATACGACTCACTATAGGGCTC-GAG CGGCCGCCCGGGCAGGT (SEQ ID NO: 25) | Adaptor ligation PCR |
| Generic Adaptor 2 | | P-ACCTGCCC-NH2 (SEQ ID NO: 26) | Adaptor ligation PCR |
| Generic AP1 | | GGATCCTAATACGACTCACTAT-AGGGC (SEQ ID NO: 27) | Adaptor ligation PCR |
| Generic AP2 | | AATAGGGCTCGAGCGGC (SEQ ID NO: 28) | Adaptor ligation PCR |
| 18S rRNA | Hv18SRTr | GTTTCAGCCTTGCGACCATACT (SEQ ID NO: 29) | In situ PCR (priming cDNA synthesis) |
| 18S rRNA | Hv18Sf | GGTAATTCCAGCTCCAAT (SEQ ID NO: 30) | In situ PCR |
| 18S rRNA | Hv18Sr | GTTTATGGTTGAGACTAG (SEQ ID NO: 31) | In situ PCR |

EXAMPLE 2

Figure 1:
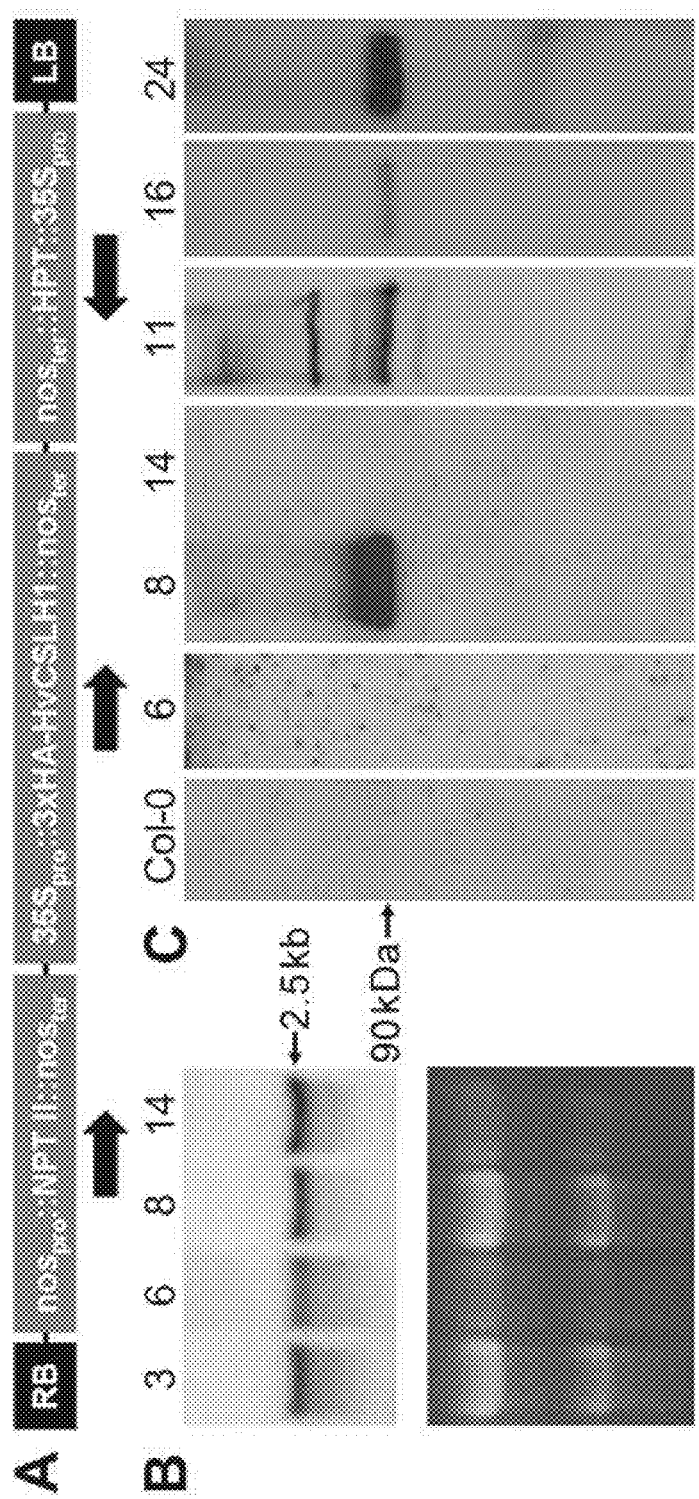
FIG. 1 shows (A) a schematic of the T-DNA of the HvCslH1::pGBW15 construct used in gain-of-function experiments in *Arabidopsis*. After Gateway cloning, the 3×HA tag was attached at the $NH_2$-terminal end of the full-length HvCslH1ORF. (B) Transcript levels in the leaves of mature HvCslH1 transgenic T1 plants as determined by Northern blot analysis. Upper panel, X-ray film exposure; lower panel, corresponding ethidium bromide-stained gel. The observed 2.5 kb transcript size corresponds to the expected size of the tagged HvCslH1 mRNA. (C) 3×HA-tagged HvCslH1 protein levels in 3-week-old pooled HvCslH1 transgenic $T_2$ lines as determined by Western blot analysis. Thirty micrograms of mixed microsomal membrane protein was loaded per lane and blots probed with the anti-HA antibody. B and C; Numbers refer to transgenic lines, Col-0, wild-type untransformed line. Col-0, lines 8 and 14 from the same blot, all other lines are from different blots.
Figure 15:
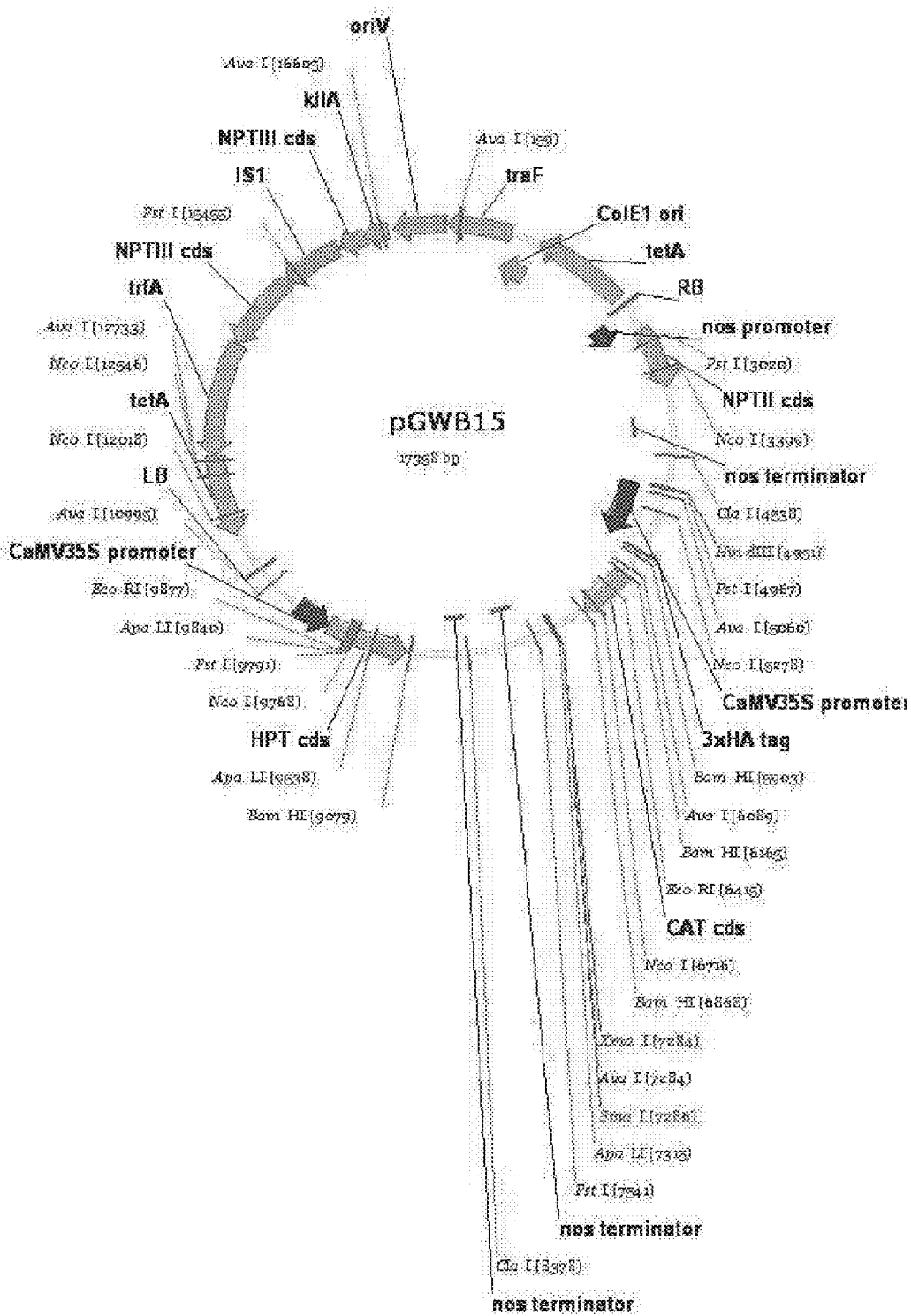
FIG. 15 shows a vector map of the pGWB15 vector used to express the CslH gene in *Arabidopsis*.

Expression of HvCslH1 in *Arabidopsis* Results in Deposition of (1,3;1,4)-β-D-Glucan For heterologous expression in *Arabidopsis*, the HvCslH1ORF was cloned into the Gateway-enabled binary vector pGWB15 (Nakagawa et al., *J Biosci Bioeng* 104: 34-41, 2007; FIG. 15), which placed HvCslH1 under the control of the CaMV 35S promoter and added a 3×HA epitope tag to the encoded protein's NH$_2$-terminal end (FIG. 1A). Initial selection of transformed *Arabidopsis* seeds identified a number of putative transgenic seedlings which PCR confirmed contained HvCslH1. RNA blot analysis of these T$_1$ plants showed that approximately 90% accumulated HvCslH1 transcripts in rosette leaves (FIG. 1B). Western blotting using an anti-HA tag antibody was used to detect HvCslH1 protein in these lines (FIG. 1C). A mixed microsomal membrane fraction (50,000-100,000×g pellet) was prepared from pooled three-week old kanamycin-resistant T$_2$ seedlings. Western blotting with the anti-HA antibody showed that only four of the 28 lines containing HvCslH1 transcripts accumulated a polypeptide of the expected size (~90 kDa) (FIG. 1C).

Occasionally proteins of higher and lower molecular mass were also detected (e.g. lane 11). The 90 kDa-protein was not observed in total protein extracts (data not shown) or in mixed-membrane fractions prepared from untransformed *Arabidopsis* plants (FIG. 1C, Col-0 lane). It is not known why HA-tagged HvCslH1 accumulated in only some of the plant lines that expressed HvCslH1 mRNA or why no correlation was apparent between HvCslH1 protein levels and either HvCslH1 transcript levels (compare FIGS. 1B and C) or with the number of HvCslH1 transgenes present in a plant (data not shown), although this has been previously observed (Burton et al., *Science* 311: 1940-1742, 2006) Lines 8, 11, 16 and 24, which expressed the HA-tagged HvCslH1, and line 6, which did not express detectable levels of the protein (control), were selected for subsequent experimental work.

Figure 2:
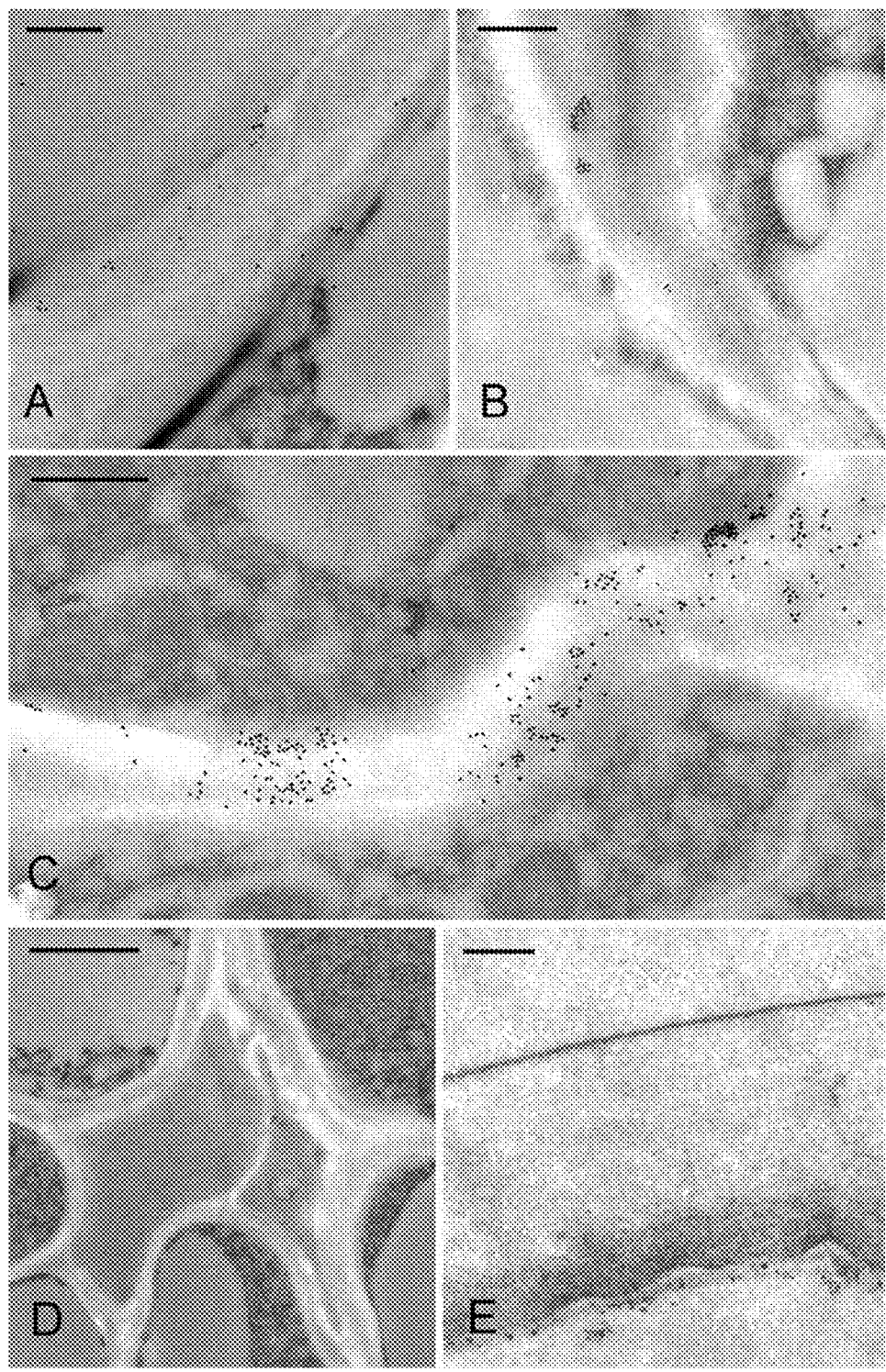
FIG. 2 shows transmission electron micrographs showing detection of β-glucan in walls of HvCslH1-expressing lines with a β-glucan-specific monoclonal antibody (Meikle et al., *Plant J* 5: 1-9, 1994). (A-C) line 8, 16, 11; (D) wild-type Col-0 control; (E) line 6. A and D show cells of the vascular bundle; B and C, mesophyll cells; E, epidermal cells. Scale bar=0.5 µm (A-C, E), 1 µm (D).

Immuno-EM was used to determine whether the walls of the transgenic *Arabidopsis* plants accumulated detectable levels of β-glucan. Thin sections of mature leaf pieces from self-pollinated progeny of lines 8, 11, 16, 24 and 6 (T$_2$ generation) were probed with a monoclonal antibody specific for β-glucan (Meikle et al., *Plant J* 5: 1-9, 1994), followed by detection using a secondary antibody conjugated to 18 nm gold particles. Gold particles were clearly evident in walls of the HA-tagged HvCslH1 positive lines 8, 11 and 16 (FIG. 2A, C, B, respectively) but not in the walls of either line 24, which also expressed HvCslH1 (data not shown), or line 6 (FIG. 2E) which had no detectable HvCslH1 protein. Each positive transgenic line showed a different pattern of tissue labeling. In line 8, patchy labeling was observed in the walls of epidermal cells and occasionally in xylem walls (FIG. 2A) whereas in line 11, epidermal and vascular tissue walls were only lightly labelled, but heavier (albeit more patchy) labeling was observed in mesophyll walls (FIG. 2C). Broadly distributed, light labeling was present in all walls of the mature leaf of line 16 (FIG. 2B). Irregular and inconsistent patterns of ectopic polysaccharide production by transgenic Arabidopsis lines expressing genes driven by the "constitutively"-expressed 35S promoter have been observed previously (Burton et al., 2006, supra). No labeling was seen in leaf sections of untransformed Arabidopsis (FIG. 2D). Reduced levels of labeling were seen in leaf sections of transgenic plants that had been pre-incubated with a Bacillus subtilis endo-hydrolase which specifically hydrolyses this β-glucan (Burton et al., 2006, supra; data not shown).

Figure 3:
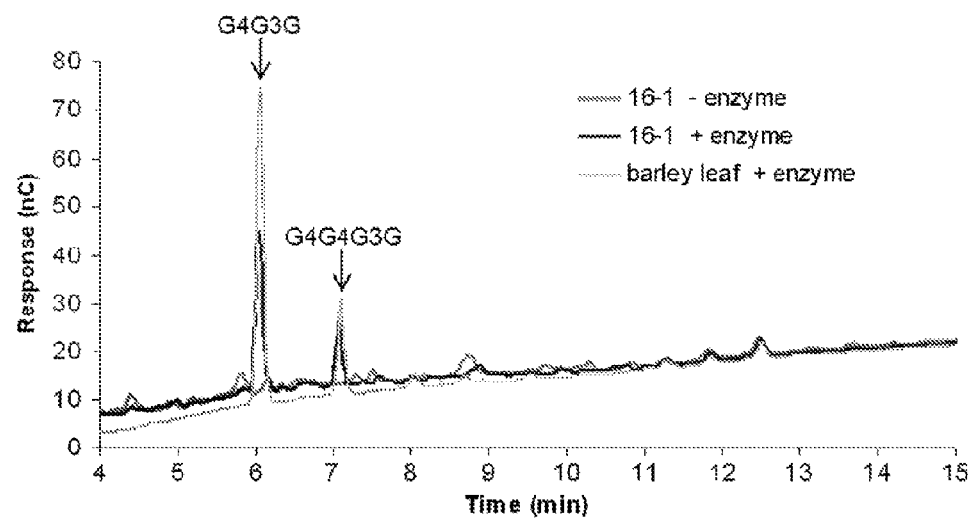
FIG. 3 shows HPAEC profiles of oligosaccharides released upon (1,3;1,4)-β-D-glucan endo-hydrolase digestion of alcohol insoluble residue (AIR) prepared from 145 day-old *Arabidopsis* line 16-1 rosette leaf tissue (■). 16-1 pre-enzyme treatment buffer wash (⸺). Barley mature leaf (entire sheath) AIR was used as the positive control sample (⸺). G4G3$G_R$ β-O-β-cellobiosyl D-glucose, DP3) and G4G4G3$G_R$ β-O-β-cellotriosyl D-glucose, DP4) peaks are indicated.
Figure 9:
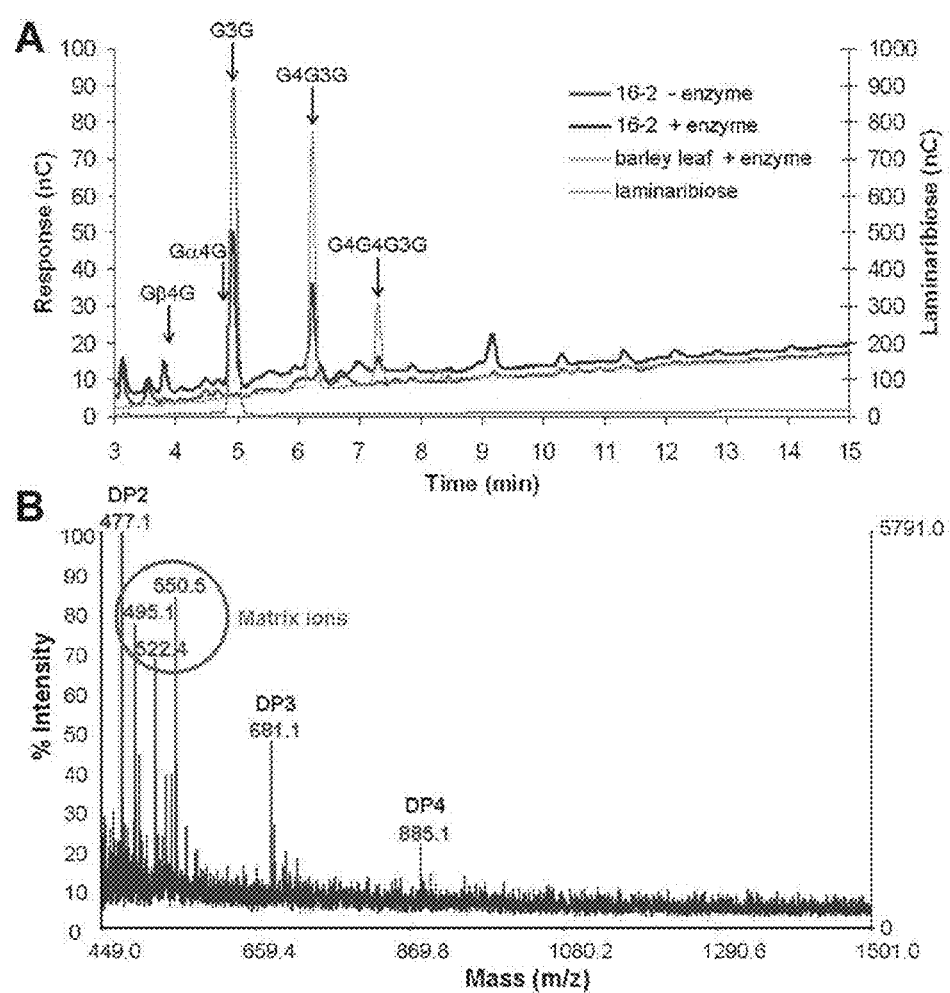
FIG. 9 shows (A) HPAEC profiles of oligosaccharides released upon (1,3;1,4)-β-D-glucan endo-hydrolase digestion of AIR prepared from 145 day-old combined leaf and stem material from *Arabidopsis* line 16-2 (■). pre-enzyme treatment buffer wash (∼). Barley mature leaf (entire sheath) AIR was used as the positive control sample (∼). Laminaribiose standard (∼). Retention times for maltose (Gα4G) and cellobiose (Gβ4G) are also marked by arrows. (B) MALDI-TOF MS chromatogram of enzyme-digested AIR of sample in A. DP2 (laminaribiose), DP3 β-O-β-cellobiosyl D-glucose) and DP4 β-O-β-cellotriosyl D-glucose) peaks are indicated.

To provide biochemical confirmation of the presence of β-glucan in transgenic Arabidopsis walls and to examine the fine structure of the nascent β-glucan, leaf and/or stem material was pooled from the self-pollinated $T_3$ and $T_4$ progeny of lines derived from plants 8, 11 and 16. These lines were homozygous for the HvCslH1 transgene. Because β-glucan was found to accumulate with plant age, samples were taken when plants were in senescence. Walls were prepared and digested with a (1,3:1,4)-β-glucan-specific endo-hydrolase and the released oligosaccharides profiled by HPAEC and MALDI-TOF MS. (1,3;1,4)-β-D-Glucan endo-hydrolase specifically hydrolyses (1,4)-β-glucosidic linkages when these linkages are on the reducing-end side of a (1,3)-β-D-glucosyl residue. The action of this enzyme yields a series of oligosaccharides with different degrees of polymerization (DP). The diagnostic oligosaccharides in this series are the trisaccharide $G4G3G_R$ and the tetrasaccharide $G4G4G3G_R$ (where G is β-D-glucopyranose, 3 and 4 indicate (1,3) and (1,4) linkages, respectively, and $G_R$ refers to the reducing terminal residue). Variable quantities of $G4G3G_R$ and $G4G4G3G_R$ were released when walls prepared from leaf or leaf and stem from lines 8 and 11 and two independent lines derived from plant 16 (lines 16-1 and 16-2) were treated with (1,3;1,4)-β-D-glucan endo-hydrolase (FIGS. 3, 9A). These oligosaccharides were not detected in the no-enzyme treatment control. The ratio of $G4G3G_R$ to $G4G4G3G_R$ (DP3:DP4) was estimated to be 3.5 in line 16-1, which is similar to the DP3:DP4 ratio of 3.6 obtained for β-glucan from the barley leaf sample. A peak that co-eluted with laminaribiose, a (1,3)-β-linked disaccharide of glucose ($G3G_R$), was also observed in lines 8, 11 and 16-2 at varying levels across samples (FIG. 9A, data not shown). This product was absent from the barley and no-enzyme treatment control samples (FIG. 9A), verifying its appearance is not due to a contaminating enzyme in the (1,3; 1,4)-β-D-glucan endo-hydrolase preparation or to endogenous disaccharide or enzyme activity within Arabidopsis. The identities of oligosaccharides in this profile were further confirmed by MALDI-TOF MS analysis, which showed the presence of $Hex_2$, $Hex_3$ and $Hex_4$ in ratios similar to those observed in the HPAEC profile (FIG. 9B). The amounts of β-glucan in lines 16-1 and 16-2, as estimated from the areas of the $G4G3G_R$ peaks, were 0.005% and 0.003% (w/w) of total wall, respectively.

EXAMPLE 3

HvCslH1 is Located in ER- and Golgi-Associated Vesicles but not the Plasma Membrane of Transgenic Arabidopsis Plants Expressing HvCslH1

Figure 4:
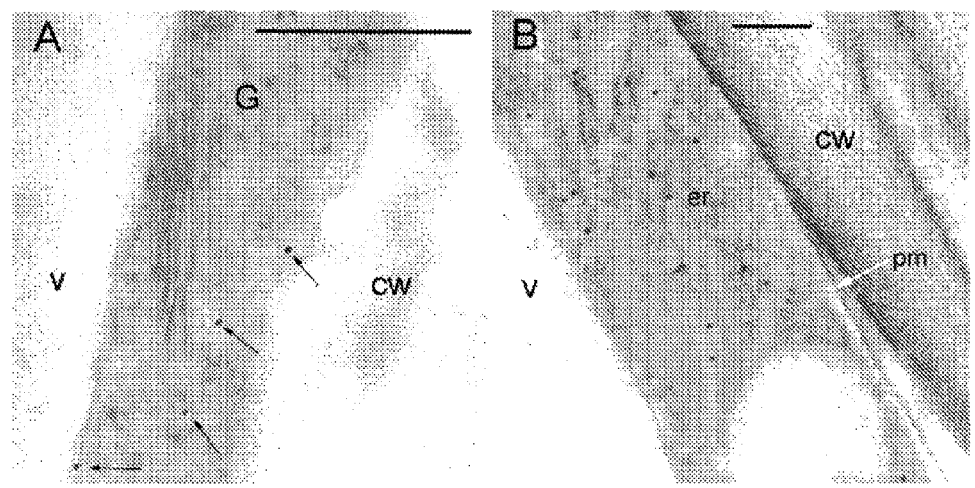
FIG. 4 shows transmission electron micrographs showing the detection of the 3×HA-tagged HvCslH1 protein by a gold-labelled anti-HA antibody in sections of high pressure-frozen leaves of *Arabidopsis* transgenic line 11. (A and B) mesophyll cells. G, Golgi body, cw, cell wall, v, vacuole, er, endoplasmic reticulum. Scale bar=0.5 µm (A), 0.2 µm (B). Arrows indicate Golgi-associated vesicle labeling.

Sections of high pressure-frozen leaves from line 11 were incubated with the gold-labelled anti-HA antibody to determine the sub-cellular location of HvCslH1. Labelling was seen in the endoplasmic reticulum and in Golgi-derived vesicles but not in the plasma membrane (FIG. 4A, B). Similar results were observed in labelled sections of roots and seedlings (data not shown).

EXAMPLE 4

HvCslH1 is Transcribed in Barley at Low Levels in Developing Grain, Floral Tissues and Cells of the Leaf Undergoing Secondary Cell Wall Thickening The levels of HvCslH1 transcripts in various barley tissues were determined using quantitative RT-PCR (QPCR). The gene-specific primers are presented in Table 4.

TABLE 4

List of primers used in Q-PCR analysis. PCR primers and PCR product sizes are given in base pairs, together with optimal acquisition temperatures for genesanalysed. Hv, Hordeum vulgare.

| Gene | Forward Primer (5' - 3')<br>Reverse Primer (5' - 3') | PCR product (bp) | Acquisition Temp. (° C.) |
|---|---|---|---|
| Hv GAPDH | GTGAGGCTGGTGCTGATTA<br>(SEQ ID NO: 32)<br>CGTGGTGCAGCTAGCATTTGAGAC<br>(SEQ ID NO: 33) | 198 | 80 |
| Hv Cyclophilin | CCTGTCGTGTCGTCGGTCTAAA<br>(SEQ ID NO: 34)<br>ACGCAGATCCAGCAGCCTAAAG<br>(SEQ ID NO: 35) | 122 | 79 |
| Hv α-Tubulin | AGTGTCCTGTCCACCCACTC<br>(SEQ ID NO: 36)<br>AGCATGAAGTGGATCCTTGG<br>(SEQ ID NO: 37) | 248 | 80 |
| Hv HSP70 | CGACCAGGGCAACCGCACCAC<br>(SEQ ID NO: 38)<br>ACGGTGTTGATGGGGTTCATG<br>(SEQ ID NO: 39) | 108 | 83 |

TABLE 4-continued

List of primers used in Q-PCR analysis. PCR primers and PCR product sizes are given in base pairs, together with optimal acquisition temperatures for genesanalysed. Hv, Hordeum vulgare.

| Gene | Forward Primer (5' - 3')<br>Reverse Primer (5' - 3') | PCR product (bp) | Acquisition Temp. (° C.) |
|---|---|---|---|
| Hv EL1a | GGTACCTCCCAGGCTGACTGT<br>(SEQ ID NO: 40)<br>GTGGTGGCGTCCATCTTGTTA<br>(SEQ ID NO: 41) | 164 | 80 |
| HvCslH1 | TGCTGTGGCTGGATGGTGTT<br>(SEQ ID NO: 42)<br>GCTTTATTATTGAGAGAGATTGGGAGA<br>(SEQ ID NO: 43) | 295 | 82 |

Figure 5:
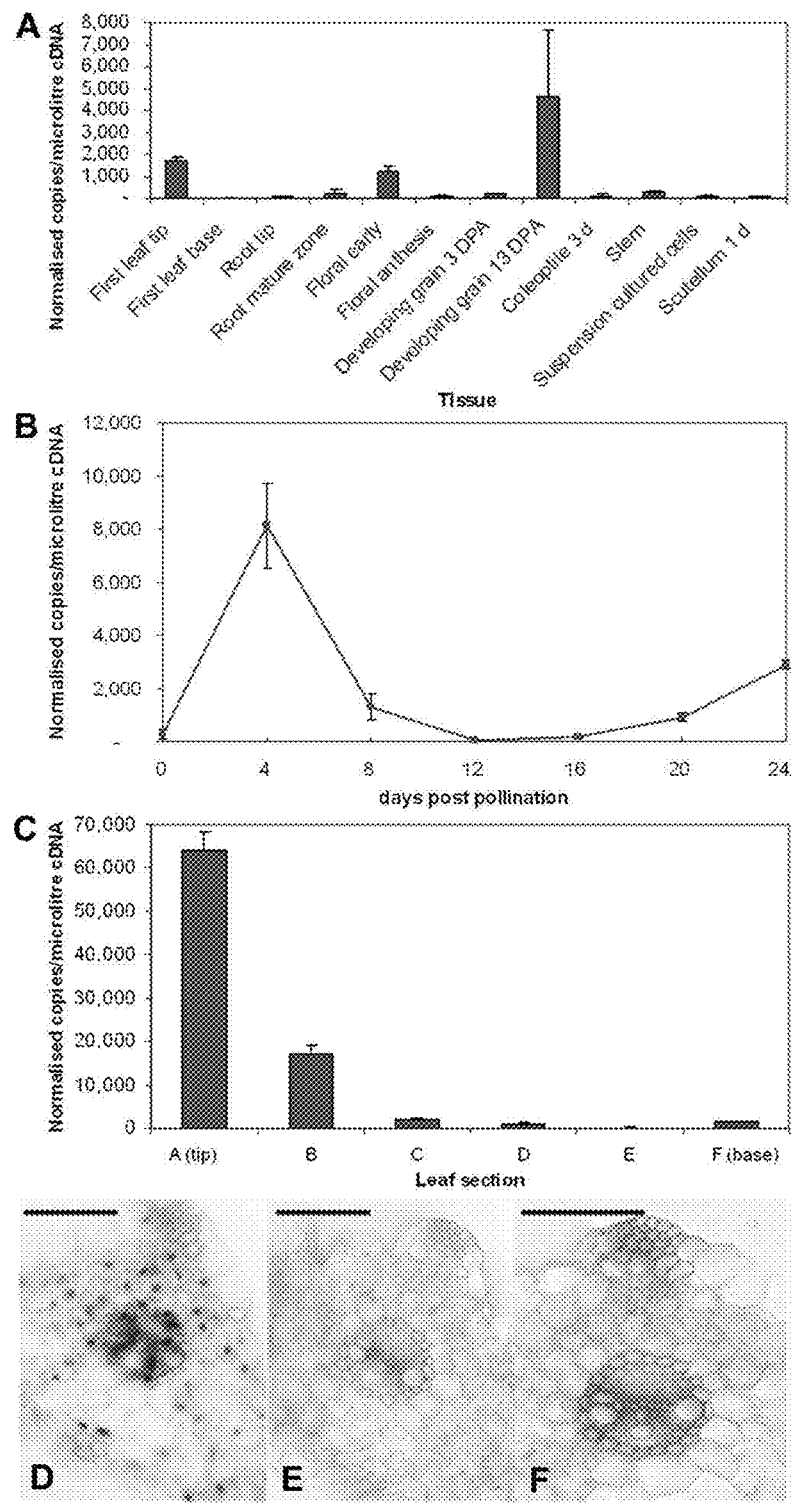
FIG. 5 shows HvCslH1 expression in barley as determined by QPCR and in situ PCR analyses. (A) Normalised levels of HvCslH1 transcript (copies/microlitre cDNA) in a range of barley tissues. Control genes for normalisation were GAPDH, cyclophilin and α-tubulin. (B) Normalised levels of HvCslH1 transcript in developing endosperm 0-24 days post-pollination. Control genes were GAPDH, α-tubulin and elongation factor-1a. (C) Normalised levels of HvCslH1 transcript in 10 day-old first leaf. Control genes were GAPDH, cyclophilin and HSP70. Error bars on QPCR plots indicate standard deviation. (D-F) In situ PCR images of the maturing zone of a 7 day-old first leaf using probes for 18S RNA (positive control, D), HvCslH1 (F) and a negative control (E). Scale bar=100 µm.

FIG. 5 (A-C) shows that across a set of barley vegetative and floral tissue cDNAs, HvCslH1 transcripts were accumulated to levels that were routinely less than 1,000s copies/μl cDNA. This value is lower than some of the other barley CESAs and CSLs we have studied where values are typically in the range of 10,000s and 100,000s copies/μl cDNA. Levels of HvCslH1 transcripts were relatively low in tissues comprising rapidly elongating cells, including coleoptile and leaf base, which are those that are actively synthesising β-glucan.

Figure 18:
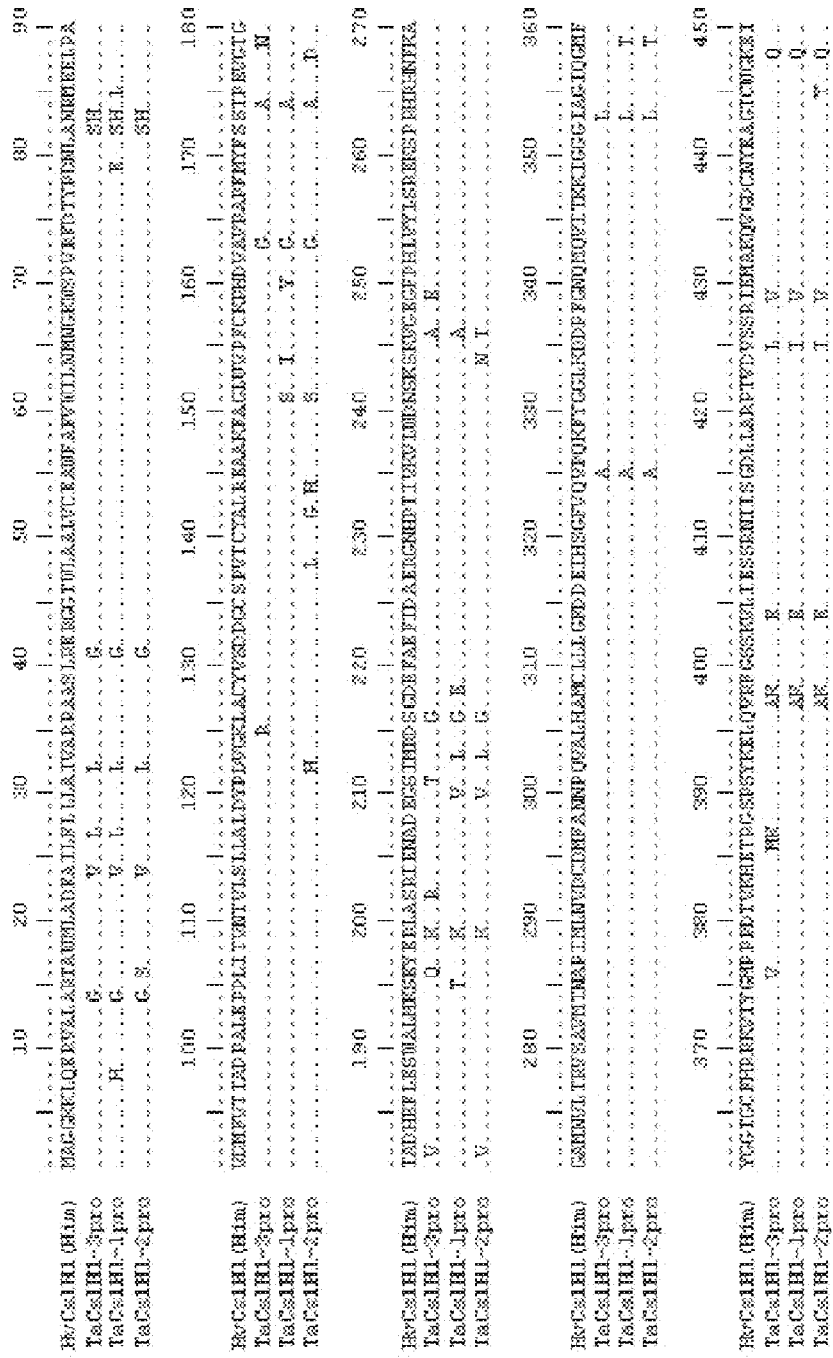
FIG. 18 shows a comparison of the amino acid sequences of the barley cv. Himalaya and wheat CslH1 proteins. The translated amino acid sequences of the barley gene (top, HvCslH1(Him)—SEQ ID NO: 70) were aligned with the three wheat sequences (indicated as TaCslH1-1pro—SEQ ID NO: 75, 1-2pro—SEQ ID NO: 76 and 1-3pro—SEQ ID NO: 77) in BioEdit using the Muscle comparison programme. The alignment position is numbered above the sequences and there is a single dash (indicating a gap) in the barley sequence introduced to optimise the alignment. Amino acids are shown in their single letter form and those identical to the barley sequence (HvCslH1(Him) are indicated by dots.
Figure 18:
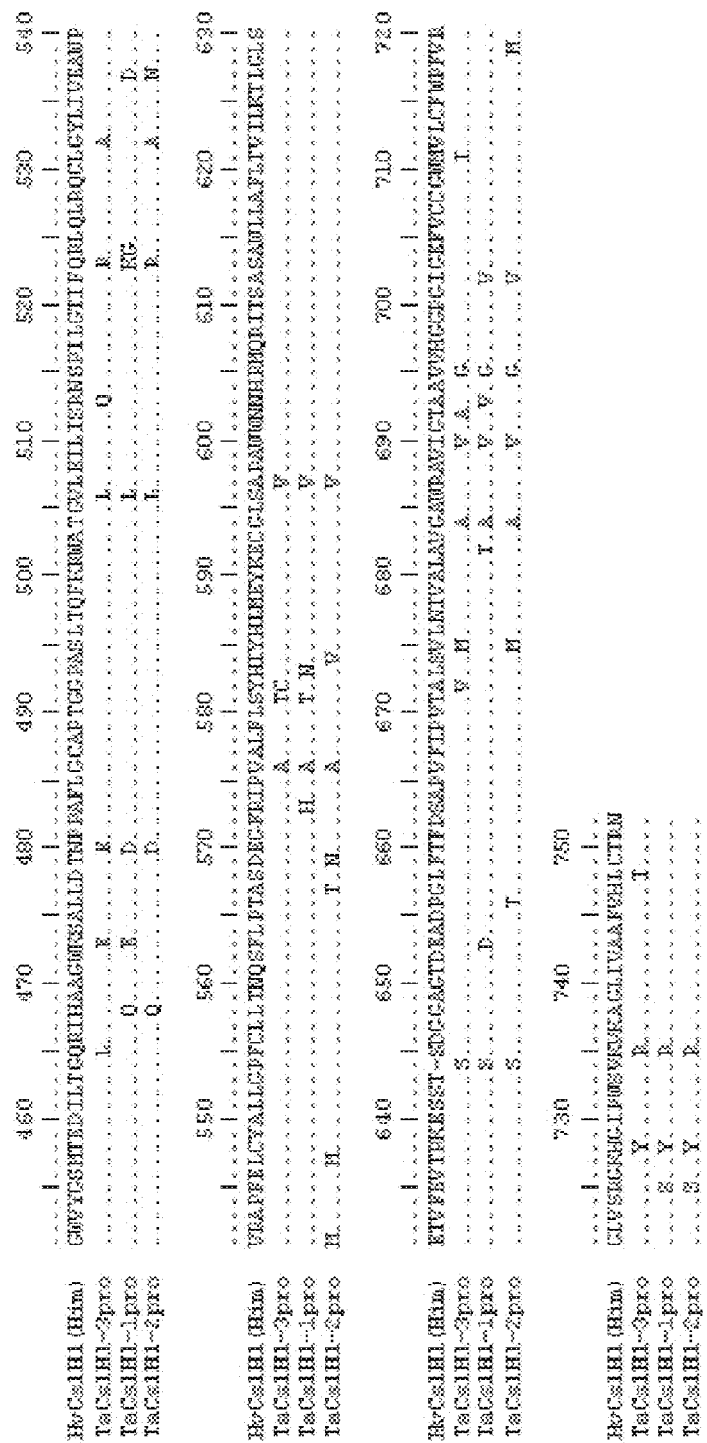

The highest levels of HvCslH1 transcripts were in leaf tip, where cells are no longer actively growing and less β-glucan accumulates (FIG. 5C; 2, 4). HvCslH1 transcription in leaf was characterised further using RNAs isolated from six zones within the ~13 cm-long leaves of 10 day-old seedlings, starting from the leaf tip. These zones comprises fully mature cells (zone A), to the leaf base comprising dividing cells (zone F). In situ PCR (see Example 5) was used to identify those cells in the leaf tip that contained the HvCslH1 mRNA. In this technique, cells in which gene transcripts are detected stain purple to dark brown (FIG. 5D, 18S RNA positive control). Cells where no transcription is detected stain light brown, as in the negative control (FIG. 5E). HvCslH1 was mostly transcribed in cells that are undergoing secondary wall thickening, such as interfascicular sclerenchymal fibre and xylem cells (FIG. 5F). Immuno-EM using sections taken from barley leaf and probed with the β-glucan antibody identified β-glucan in the walls of these cells.

HvCslH1 transcript levels were also investigated in more detail in a 24-day developing endosperm series (FIG. 5B). HvCslH1 expression was low throughout the starchy endosperm during development. Maximum transcript levels were reached at 4 DPA, approximately 1 day before β-glucan is first detected in endosperm walls. This transcription pattern is similar to that of several barley CSLF genes (HvCSLF3, 4, 7, 8 and 10) that are also expressed in developing grain, although HvCSLF9 and 6 show much higher transcript levels.

EXAMPLE 5

Discussion

The data presented here indicate that the product of HvCslH1, a member of the grass-specific CSLH gene family, mediates β-glucan biosynthesis in *Arabidopsis*. Barley appears to have only a single CSLH gene based on EST database analyses, genomic DNA blot analysis and BAC library screening. EST analyses of other grasses such as bread wheat, *Lolium multiflorum, Festuca arundinacae* and *Brachypodium distachon* (all subfamily Pooideae) have one identified CSLH gene, similar to barley, whereas maize, sorghum and sugar cane (all subfamily Panicoideae), like rice (subfamily Ehrhartoideae), appear to have multiple CSLH genes. When an epitope-tagged version of the HvCslH1 cDNA was heterologously expressed in *Arabidopsis*, three of four plant lines in which protein was detected accumulated a polysaccharide in their walls that was recognized by a β-glucan-specific monoclonal antibody. When isolated walls of the transgenic lines were digested with a specific (1,3;1,4)-β-D-glucan endo-hydrolase, the characteristic trisaccharide (G4G3G$_R$) and tetrasaccharide (G4G4G3G$_R$) were detected at ratios similar to those found in β-glucans from barley endosperm, demonstrating that the walls from the transgenic *Arabidopsis* lines contained β-glucan. Furthermore, epitope-tagged HvCslH1 was found in the endoplasmic reticulum and in Golgi-derived vesicles in cells of transgenic plants. The morphological phenotype of the transgenic *Arabidopsis* lines that expressed HvCslH1 appeared identical to wild-type plants.

Although the overall proportion of (1,3)- and (1,4)-β-glucosyl linkages and the ratios of the G4G3G$_R$ and G4G4G3G$_R$ products from (1,3;1,4)-β-D-glucan endo-hydrolase digestion of walls derived from plant line 16-1 was similar to those observed in β-glucans isolated from barley tissues, one unusual feature that was observed was that the major oligosaccharide released by (1,3;1,4)-β-D-glucan endo-hydrolase from the walls of line 16-2 was laminaribiose (G3G$_R$; FIG. 9A). The presence of G3G$_R$ in variable levels was also associated with increased levels of trisaccharide relative to the tetrasaccharide and, thus increased DP3:DP4 ratios. The presence of G3G$_R$ in wall digests of the majority of plant lines indicates a polysaccharide containing sections of alternating (1,3)-β- and (1,4)-β-linked glucosyl residues (-G3G4G3G4-). It is not known if these reside in a separate polysaccharide or constitute a portion of a β-glucan chain that also has the usual fine structural features. Alternating (1,3)-β-D-glucosyl and (1,4-β-D-glucosyl residues are not common in barley and other cereal β-glucans, but do represent a significant component of the β-glucan from the non-flowering plant Equisetum and are also detected in β-glucans from a number of fungi, including basidiomycetes and ascomycetes. It is possible that G3G$_R$ arises through misregulation of the β-glucan synthase in transgenic *Arabidopsis*, possibly because its membrane micro-environment is different or because an unknown factor that in barley suppresses (1,3)-β glucosidic linkage formation (or alternatively promotes (1,4)-β glucosidic linkage formation) is present at suboptimal levels in *Arabidopsis*. Minor variations in the level of this factor among the lines derived from plant 16 would account for the different structures that were obtained. Another possible explanation for the structural variability in the β-glucan may relate to subtle differences in post-assembly processing (see also Supporting Information below).

In barley, HvCslH1 was most highly transcribed in leaf tips, a tissue comprising fully mature cells. There is no evidence to indicate coordinate transcription of HvCslH1 and any of the barley CSLFs, suggesting that their encoded products are not components of a protein complex. HvCslH1 transcription, for example, was not high in elongating cells such as the coleoptile or developing endosperm, which in barley are the tissues where β-glucan is characteristically accumulated. Although usually found in primary cell walls of vegetative tissues where it is implicated in the control of cell expansion and possibly as a temporary store of glucose that can be mobilized as an energy source in the dark, β-glucan has also been found in the lignified cell walls of xylem tracheary elements and sclerenchyma fibres, where immuno-EM using the antibody to β-glucan shows labeling in both the middle lamella region (primary wall) and secondary wall of sclerenchyma cells. Because in situ PCR showing transcription of the HvCslH1 gene in the leaf was restricted to cells such as interfascicular sclerenchymal fibre and xylem cells, we suggest that a major role of this gene is in β-glucan synthesis during secondary wall development, although we cannot exclude a role in primary wall β-glucan synthesis elsewhere in the plant.

Regardless of how the fine structures of β-glucans are generated, it is clear that the CSLHs can mediate the synthesis of β-glucan in *Arabidopsis*, a finding that has implications for our understanding of how this polysaccharide is synthesised. Any mechanism(s) being considered for the assembly of β-glucan must account for the synthesis of the predominant cellotriosyl and cellotetraosyl units, the random linking of these (1,4)-β-units together by single (1,3)-β-linkages and the means by which the molar ratio of tri- to tetra-saccharide units is regulated. At least two glycosyltransferase activities might act in concert: one that processively adds (1,4)-β-linked glucose residues to assemble the tri- and tetra-saccharides and the other that adds single (1,3)-β-linkages. Based on our current knowledge of polysaccharide synthases several mechanisms are hypothetically possible. The simplest explanation is that the one polypeptide is responsible for the synthesis of both glucosidic linkage types. Our transgenic experiments indicate that CSLH proteins are independently able to make a β-glucan and could therefore conceivably make both types of p-linkages. The CSLH family is classified by the Carbohydrate Active Enzymes (CAZy) database as members of glycosyltransferase family 2 (GT2) (http://www.cazy.org; Coutinho et al., *J Mol Biol* 328: 307-317, 2003), a family that includes enzymes capable of independently catalyzing the synthesis of either (1,3)-β- or (1,4)-β-linkages but also examples of bifunctional enzymes, i.e. enzymes that can synthesize two types of glycosidic linkages. For example, hyaluronan synthases (HAS) synthesize a repeating disaccharide of (1,4)-β-glucuronic acid-(1,3)-β-N-acetylglucosamine units and both transferase activities reside in the one polypeptide. In mouse HAS1, the region that includes the D,D,D,QXXRW motif is responsible for both these activities. The active site of the CSLHs, also containing the D,D,D,QXXRW motif, might be similarly bifunctional. Another possibility is that the CSLHs synthesise only one type of glucosidic linkage with another glucosyltransferase, common to monocots and dicots, responsible for synthesis of a second linkage.

EXAMPLE 6

Materials and Methods

Binary Vector Construction and Plant Transformation

The HvCslH10RF was amplified from barley cv. Schooner mature leaf tip cDNA with Herculase® (Stratagene) using primers HvH1TOPOf and HvH1TOPOr (Table 3) and the PCR product cloned into pENTR/D-TOPO (Invitrogen). Using the manufacturer's protocol (Invitrogen), an LR reaction was used to clone the cDNA into the destination vector pGWB15 containing an $NH_2$-terminal 3×HA tag (Nakagawa et al., *J Biosci Bioeng* 104: 34-41, 2007) and the predicted sequence confirmed by DNA sequencing. The HvCslH1:: pGBW15 construct was transferred from *Escherichia coli* into *Agrobacterium tumefaciens* strain AGL1 via triparental mating using the helper plasmid pRK2013. *Arabidopsis thaliana* Col-0 plants were transformed using the floral dip method (Clough and Bent, *Plant J* 16: 735-743, 1998).

RNA Blot Analysis

Samples of ~10 µg total RNA extracted from mature rosette leaves of T1 plants using TRIzol® (Invitrogen) were prepared and separated on a 1% w/v agarose-formaldehyde gel (Farrell, *RNA methodologies: A laboratory guide for isolation and characterization*, Academic Press, Inc., San Diego, 1993). RNA was transferred to Hybond™ N' membranes, pre-hybridised and hybridised according to the method outlined in the Gene Images CDP-Star detection module (Amersham-Biosciences). A HvCslH1 fragment amplified with primers H1F2 and HvH1TOPOr (Table 3) was labeled using the Gene Images Random Prime labeling module (Amersham) following the manufacturer's protocol and used as the probe.

Quantitative PCR Analysis

RNA extractions, cDNA syntheses and QPCR were carried out as described in Burton et al. (*Science* 311, 1940-1942, 2006; *Plant Physiol* 134, 224-236, 2004) with the modifications listed in Burton et al. (*Plant Physiol* 146, 1821-1833, 2008). The primer sequences of the barley control genes are listed in Table 4.

In Situ PCR

In situ PCRs were conducted according to the method of Koltai & Bird (*Plant Physiol* 123: 1203-1212, 2000) with the following modifications. After tissue sectioning, genomic DNA was removed by treatment for 6 h at 37° C. in 1×DNase buffer and 4 U RNase-free DNase (Promega). cDNA synthesis was carried out using Thermoscript™ RT (Invitrogen) except that the RNase H step was omitted and a gene-specific primer (1 µg, Table 3) used for reverse transcription. PCRs were carried out in a final volume of 50 µL, containing 1×PCR buffer, 200 µm dNTPs (Promega), 0.2 nmol digoxigenin-11-dUTP (Roche), 2 mM $MgCl_2$, 200 ng of each primer and 2 U Taq DNA polymerase (Invitrogen). Cycling parameters were as follows: initial denaturation at 96° C. for 2 min, then 40 cycles of 94° C. for 30 sec, 59° C. for 30 sec, 72° C. for 1 min. Sections were then washed, incubated with 1.5 U alkaline phosphatase-conjugated anti-digoxigenin Fab fragments (Roche) and developed for 10-20 min as outlined by Koltai & Bird (2000, supra). For negative control sections, reverse transcriptase was omitted and all the Hv 18S rRNA primers included to check whether there was any amplification from genomic DNA.

Preparation of Mixed Microsomal Membranes

T1 seed of HvCslH1 transgenic plants was collected and ~100 seeds sown onto 1×MS agar media containing 50 mg/L kanamycin (Sigma). After 3 weeks, kanamycin-resistant seedlings were pooled, frozen in liquid N2 and ground at 4° C. in a mortar and pestle containing homogenising buffer (50 mM NaPO$_4$ buffer, pH 7.5, 0.5 M sucrose, 20 mM KCl, 10 mM DTT, 0.2 mM PMSF, 83 µL plant protease inhibitor cocktail (Sigma, P9599)). Homogenate was filtered through a 50 µM mesh and the S/N centrifuged at 6,000×g for 10 min at 4° C. The S/N was decanted and centrifuged at 50,000×g for 30 min at 4° C. in 4.5 ml ultracentrifuge tubes (Beckmann). The 50,000×g S/N was decanted and the pellet resuspended in 10 mM Tris-MES buffer, pH 7.5 using a glass-teflon homogenizer. The resuspended pellet was diluted to 4.5 mL with Tri-MES buffer and centrifuged at 100,000×g for 1 h at 4° C. The pellet was resuspended in 0.25 M sucrose, 10 mM Tris-MES buffer, pH 7.5, as outlined above. Protein concentration was measured using Bradford assay reagent (BioRad) using bovine serum albumin as the standard.

Western Blotting

Samples of membrane protein (30 µg) were incubated at 60° C. for 20-60 min in 200 mM dithiothreitol and sample buffer (37.5 mM Tris-HCl, pH 7.0, 10% glycerol, 3% sodium dodecylsulphate (SDS), 0.025% bromophenol blue) to give an SDS:protein ratio of 1.5 mg SDS to 30 µg protein before loading onto an 8% SDS-PAGE gel. After electrophoresis, gels were blotted onto nitrocellulose (OSMONIC™ Nitropure 22 µm) in Towbin buffer (25 mM Tris base, 192 mM glycine, 20% methanol) containing 0.05% SDS at 100 V for 90 min at 4° C. Membranes were then blocked overnight in Tris-buffered saline (TBS; 20 mM Tris base, 150 mM NaCl) containing 3% w/v milk powder before incubation for 1 h at RT in rat anti-HA polyclonal antibody (Roche) diluted 1:1000 in TBS containing 1% BSA. Membranes were washed 3%× in TBS containing 0.05% SDS (TBST), then incubated in anti-rat IgG HRP-conjugated antibody (Dako) diluted 1:1000 in TBS containing 3% w/v nonfat milk powder. Membranes were washed 3× in TBST before signal was detected with the SuperSignal® West Pico chemiluminescent substrate (Pierce).

Immuno-Electron Microscopy

*Arabidopsis* tissues were fixed and labeled with anti-(1,3; 1,4)-β-D-glucan specific antibody (Meikle et al., Plant J 5: 1-9, 1994) according to Burton et al. (Science 311, 1940-1942, 2006). For labeling with anti-HA antibody, plant tissue was placed between two copper planchets and rapidly frozen in a Leica EM high pressure freezer (set at 2.7×10$^5$ kPa and at an approximate rate of −10,000° C. s$^{-1}$). The planchets were transferred into 100% ethanol in a Leica automated freeze-substitution unit set at −50° C. for 72 h. Samples were brought to room temperature (RT) overnight, removed and infiltrated with LR White resin and embedded in gelatin capsules as detailed in Burton et al. (2006, supra). Thin sections of embedded leaf tissue were collected on formvar-coated gold grids and incubated in a 1:200 dilution of the rat anti-HA polyclonal antibody in phosphate buffered saline (PBS; 137 mM NaCl, 10 mM NaPO$_4$, 2.7 mM KCl, pH 7.4) containing 1% w/v BSA for 1 h at RT and then overnight at 4° C. Grids were washed several times in PBS, then incubated in a 1:20 dilution of anti-rat secondary antibody conjugated to 18 nm gold (Jackson ImmunoResearch) in PBS containing 1% w/v BSA for 1 h at RT. The grids were then washed, post stained and viewed under the TEM as described by Burton et al. (2006, supra)

Preparation of Cell Wall Material

Alcohol insoluble residue (AIR) was prepared by grinding plant material in liquid N2 using a mortar and pestle. Five volumes of 80% ethanol was added to the homogenate prior to mixing by rotation for 1 h at 4° C. After centrifugation at 3,400×g for 5 min, the supernatant was removed and the residue was refluxed twice at RT in 80% ethanol for 1 h, followed by refluxing in 50% ethanol twice for 1 h. The ethanol-soluble fraction was removed and the AIR was washed once in 100% ethanol prior to drying at 40° C. under vacuum.

(1,3;1,4)-β-3-D-Glucan Specific Endo-Hydrolase Digestion

AIR (100 mg, prepared as described above) was incubated in 5 mL 20 mM NaPO$_4$ buffer, pH 6.5 for 2 h at 50° C. with continuous mixing in an incubator with shaking at 200 rpm. After 2 h, the suspension was centrifuged (3,400×g, 5 min) and the supernatant (S/N) removed. Another 5 mL of buffer was added and the incubation and centrifugation repeated. The S/N from this second incubation was used as the no enzyme negative control. The pelleted AIR was resuspended in 5 mL NaPO$_4$ buffer to which 100 µl (1,3;1,4)-β-D-glucan endo-hydrolase (McCleary et al., *J Inst Brew* 91: 285-295, 1985) was added. The mixture was incubated for 2 h at 50° C. with continuous mixing after which the S/N was collected as the (1,3;1,4)-β-D-glucan endo-hydrolase-released oligosaccharides. The negative control and (1,3;1,4)-β-D-glucan endo-hydrolase-treated S/Ns were desalted on a graphitised carbon cartridge as described by Packer et al. (*Glycoconj J* 15: 737-747, 1998) and dried.

HPAEC Analysis

The dried (1,3;1,4)-β-D-glucan endo-hydrolase-released oligosaccharides were dissolved in 100 4 Milli H$_2$O and 20 µL injected onto a CarboPac PA1 column (Dionex) equilibrated with 50 mM NaOAc in 0.2 M NaOH using a Dionex BioLC ICS 300 system (Dionex) equipped with a pulsed amperometric detector (PAD) and autosampler. Oligosaccharides were eluted at 1 mL/min with a linear gradient of NaOAc from 50 mM in 0.2M NaOH to 350 mM in 0.2 M NaOH over 15 min. Laminaribiose (Seigaku), maltose and cellobiose (both from Sigma) were run as standards.

MALDI-TOF MS Analysis

Aliquots (30 µL) of the remaining (1,3;1,4)-β-D-glucan endo-hydrolase-released oligosaccharides were lyophilised, dissolved in DMSO and methylated using the NaOH method (Ciucanu and Kerek, *Carb Research* 131: 209-217, 1984). Methylated oligosaccharides were partitioned into dichloromethane (DCM) and the DCM phase washed 3× with MilliQ water. The DCM phase was dried under a N2 stream before re-dissolving in 10 µL 50% acetonitrile. A 1 µL aliquot was mixed with 1 µL 2,5-dihydroxy benzoic acid matrix (10 mg/mL dissolved in 50% acetonitrile) and 1 µL of the mix was spotted onto a MALDI plate for analysis in a MALDI TOF mass spectrometer (Voyager DSTR, Applied Biosystems).

EST Analyses, Contig Assembly and Bioinformatics

CSLH ESTs were obtained by querying public databases including the now discontinued Stanford Cell Wall website, NCBI (http://www.ncbi.nlm.nih.gov/), HarvEST (http://harvest.ucr.edu/), GrainGenes (http://wheat.pw.usda.gov/GG2/index.shtml), Barley Gene Index (http://compbio.dfci.harvard.edu/tgi/plant.html) and BarleyBase (www.barleybase.org) using the BLAST search tool (Altschul et al., *Nucl Acids Res* 25: 3389-3402, 1997). Sequences were assembled into contigs using either Sequencer™ 3.0 (GeneCodes) or ContigExpress, a module of Vector NTI® Advance 9.1.0 (Invitrogen). DNA or protein sequences were aligned using ClustalX (Thompson et al., *Nucl Acids Res* 24:

4876-4882, 1997). Phylogenetic analysis was carried out using the in-built neighbour joining algorithm and tree robustness assessed using 1000 bootstrapped replicates. Sequence similarities were calculated using MatGat 2.02 (http://bitincka.com/ledion/matgat/) (Campanella et al., *BMC Bioinformatics* 4: 29, 2003). Transmembrane domains were predicted using the suite of programs described in ARAMEMNON (http://aramemnon.botanik.uni-koeln.de) (Schwacke et al., *Plant Physiol* 131: 16-26, 2003). Motifs predicting post-translational modifications were identified using the programs listed in ExPasy under the Tools menu (http://www.expasy.org/tools/#pattern). Protein parameters were calculated using ProtParam at ExPasy (http://www.expasy.org/cgi-bin/protparam).

Barley BAC Screening

BAC filters containing 6.5 equivalents of the barley genome from the non-Yd2 cv. Morex (Clemson University Genomics Institute, CUGI) were blocked for 6 h at 65° C. in prehybidisation solution (0.53 M NaPO4 buffer pH 7.2, 7.5% w/v SDS, 1 mM EDTA, 11 µg/ml salmon sperm DNA). The radiolabeled cDNA and gDNA fragment amplified with primers H1F1 and H1R1 or H1R5 (Table 3) was added and incubated for 24 h at 65° C. Filters were washed 3× with 2×SSC, 0.1% SDS at RT. Final washes were done with 1×SSC, 0.1% SDS. Filters were exposed to X-ray film for 2 d. Positive BAC clones were identified and ordered as directed on the CUGI website (http://www.genome.clemson.edu). Clones were streaked onto LB agar containing 25 µg/ml chloramphenical and grown overnight at 37° C. Colonies for each clone were picked, placed on gridded nylon membranes resting on LB agar containing 25 µg/ml chloramphenicol and incubated overnight at 37° C. DNA was fixed to the membrane and denatured by placing on filter paper soaked in 0.4 M NaOH for 20 min, then neutralized by placing on filter paper soaked in neutralizing solution (1.5 M NaCl, 0.5 M Tris-HCl pH 7.2, 1 mM EDTA). Membranes were then washed 3× in 2×SSC, 0.1% SDS and hybridized using standard conditions (Sambrook et al., *Molecular cloning: a laboratory manual*, Cold Spring Harbour Laboratory Press, New York, 1989).

BAC DNA Isolation

Positive clones were cultured overnight in LB broth containing 25 µg/ml chloramphenicol at 37° C. Cells were pelleted by centrifugation (12,000×g, 3 min) and the pellet resuspended in 90 µL TES buffer (25 mM Tris-HCl pH 8.0, 10 mM EDTA, 15% w/v sucrose). An aliquot (180 µL) of lysis solution (0.2 M NaOH, 1% SDS) was added and mixed gently, followed by 135 µL 3 M NaOAc pH 4.6. The chromosomal DNA was pelleted by centrifugation (12,000×g, 15 min). The S/N was collected and 2 4 RNase A (10 mg/mL) added and incubated for 1 h at 37° C. A 400 µL aliquot of Tris-saturated phenol-chloroform (1:1 ratio) was added and the samples centrifuged again (12,000×g, 5 min). The S/N was collected and BAC DNA precipitated using 2-3 volumes chilled 95% ethanol for 10 min at RT. The BAC DNA was pelleted by centrifugation (15,000×g, 15 min), washed in 70% ethanol, resuspended in 20-50 µL TE and stored at 4° C.

Genome Walking

The adaptor ligation method of Siebert et al. (*Nucl Acids Res* 23: 1087-1088, 1995) was used to amplify fragments of genomic DNA upstream of known CSLH EST sequence. Restriction enzymes used to digest barley genomic DNA were Eco RV, Nru I, Pvu II, Sca I or Ssp I. Primary PCR reactions were conducted in 25 µL volumes containing 2 µL ligated DNA (1:10 dilution), 1×PCR buffer, 2 mM $MgCl_2$, 100 ng each of adaptor primer AP1 and antisense primer H1R7 (Table 3), 0.4 mM dNTPs and 1 unit Taq polymerase (Invitrogen). Cycle parameters were as follows: 96° C. for 2 min then 40 cycles of 94° C. for 30 sec, 59° C. for 30 sec, 72° C. for 1 min, and a final step at 72° C. for 7 min. A secondary PCR reaction was conducted with 1 µL of the primary PCR using 100 ng each of adaptor primer AP2 and the nested primer H1R6. Reaction composition and cycle parameters were the same as above except that an annealing temperature of 61° C. was used.

BAC Sequencing

For sequencing, between 0.5 and 1 µg of isolated BAC DNA was combined with 5 pmol primer and 1× Big Dye Terminator v 3.1 (BDT) mix (Applied Biosystems, USA) in a final volume of 20 µL. Cycle parameters were as follows: 96° C. for 15 min, then 65 cycles of 96° C. for 10 sec, 55° C. for 10 sec and 60° C. for 4 min. DNA was precipitated with 0.1 vol 3M NaOAc pH 5.2 and 2.5 vol 95% ethanol on ice for 10 min, then pelleted by spinning at 12,000×g for 30 min. The pellet was rinsed with 70% ethanol, dried and sent to AGRF (Brisbane, Australia) for sequencing.

Mapping of HvCslH1

Genetic mapping was done using a Sloop×Halcyon doubled haploid (DH) mapping population of 60 lines (Read et al., *Aust J Agric Res* 54: 1145-1153, 2003). Using standard methods of DNA blot hybridization (Sambrook et al., 1989, supra) a HvCslH1 probe PCR-amplified using primers H1F1 and H1R5 (Table 3) was hybridized to membranes containing parental line genomic DNA digested with one of six restriction enzymes (Bam HI, Dra I, Eco RI, Eco RV, Hind III, Xba I). The dihybrid population was then digested with enzymes that gave a clear polymorphism (Dra I). Polymorphisms were scored and HvCslH1 map location determined using the 'find best location' function of MapManager QT version 0.30 (Manly et al., *Mamm Genome* 12: 930-932, 2001). Map locations were correlated with QTL data using resources available at http://www.barleyworld.org/.

*Arabidopsis* Growth Conditions

*Arabidopsis* seeds were surface-sterilized in a sterilization solution (sodium hypochlorite (2% available chlorine), drop of Tween-20) for 15 min then rinsed 4× with sterile MilliQ water. Surface-sterilized seed was spread onto 85×25 mm Petri dishes containing 50 mL of sterile 1×MS medium (4.33 g/L Murashige and Skoog basal salts (Phytotechnology Laboratories), 2% w/v sucrose, 1% w/v bactoagar). For selection of transformants, 50 mg/L kanamycin (Sigma) was added to the medium. Plates were placed in a cold room for 3-5 days at 4° C. to synchronize germination. Cold-stratified plates were then transferred into controlled environment growth cabinets (Thermoline L+M model TPG 1260 TO-5× 400, Smithfield, NSW, Australia) with day and night temperatures of 23° C. and 17° C., respectively. The average light intensity at rosette leaf level was ~70 $\mu E\ m^{-2}\ sec^{-1}$ supplied by 3-foot fluorescent tubes (Sylvania Standard F30W/133-T8 Cool White) during a 16 h light cycle. After 3 weeks on MS plates, individual plantlets were transferred into hydrated 42 mm diameter Jiffy pellets. Nine rows of six pellets were arranged in trays with three trays being housed on each 2×3.5- foot wire rack shelf. Relative humidity was measured to be between 60 and 70%. Plants were watered with tap water supplemented with Peter's Professional™ General Purpose plant fertilizer (Scotts Australia) by sub-irrigation every 2-3 days.

Genomic DNA Extraction and PCR Analysis of *Arabidopsis* Transgenics

DNA was extracted from a single *Arabidopsis* leaf according to the method described in Edwards et al. (*Nucl Acids Res* 19: 1349, 1991). A 1 µL aliquot of genomic DNA was used as template in PCR screens of transgenic plants using primers H1F2 and HvCslH1TOPOr (Table 3) with the following cycling regime: 94° C. for 2 min followed by 35 cycles of 94° C. for 20 sec, 57° C. for 30 sec, 72° C. for 30 sec.

EXAMPLE 7

Alignment of CslH DNA and Amino Acid Sequences from Rice and Barley

An alignment of the DNA and amino acid sequences for the CslH sequences in both rice and barley was performed to calculate the percent identity and similarity between the sequences, the results of which are shown in FIG. 10. The DNA and protein sequences were aligned and compared using the default parameters in MatGAT version 2.02 downloaded from http://bitincka.com/ledion/matgat/.

Figure 12:
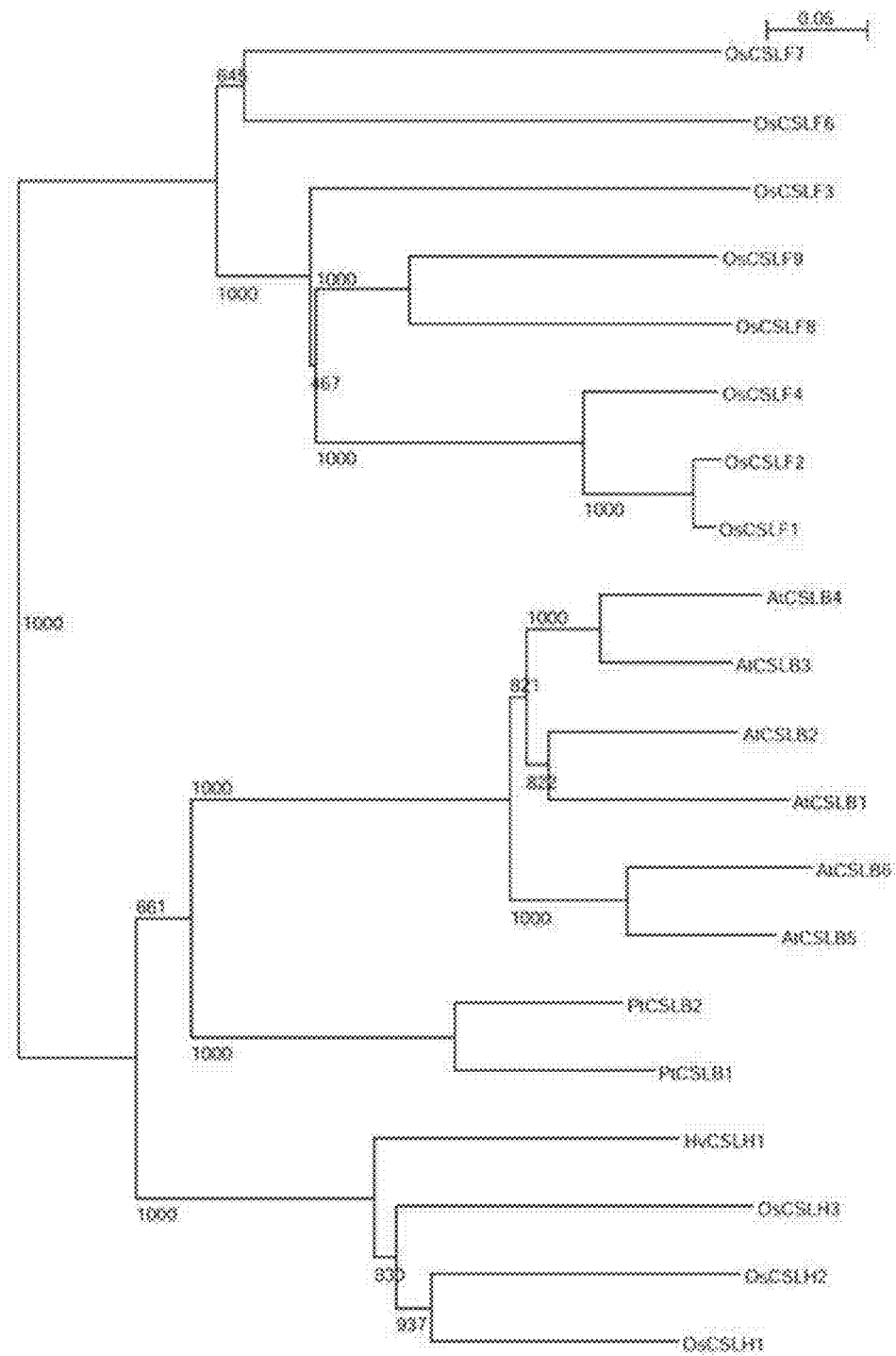
FIG. 12 is a phylogenetic tree showing the relationship of complete CslB, F and H amino acid sequences derived from Barley (*Hordeum vulgare*), Rice (*Oryza sativa*), *Arabidopsis thaliana* and poplar (*Populus trichocarpa*).

Multiple sequence alignments and phylogenetic tree generation was performed using the ClustalX program as described by Thompson et al. (*Nucl Acids Res* 25: 4876-4882, 1997). The protein alignment and resultant phylogenetic tree are shown in FIGS. 11 and 12, respectively.

EXAMPLE 8

Cross of HvCslH1 and OsCSLF2 Transgenic *Arabidopsis* Lines

Two transgenic *Arabidopsis* lines, 15-8 and 15-11, in which the tagged HvCslH1 protein was detected using an anti-HA antibody, were chosen to genetically cross with two other transgenic *Arabidopsis* lines containing OsCslF2, H37 and H17-4, as described by Burton et al. (*Science* 311: 1940-1942, 2006). It was thought that by expressing the HvCslH1 and OsCSLF2 proteins in the same cell types, higher levels of (1,3;1,4)-β-D-glucan above those observed in single gene (CSLH or CSLF only) transgenic *Arabidopsis* plants, could potentially be deposited into cell walls. In addition, this would aid in detecting (1,3;1,4)-β-D-glucan in immuno-electron microscopy studies as well as in chemical cell wall analyses.

Figure 13:
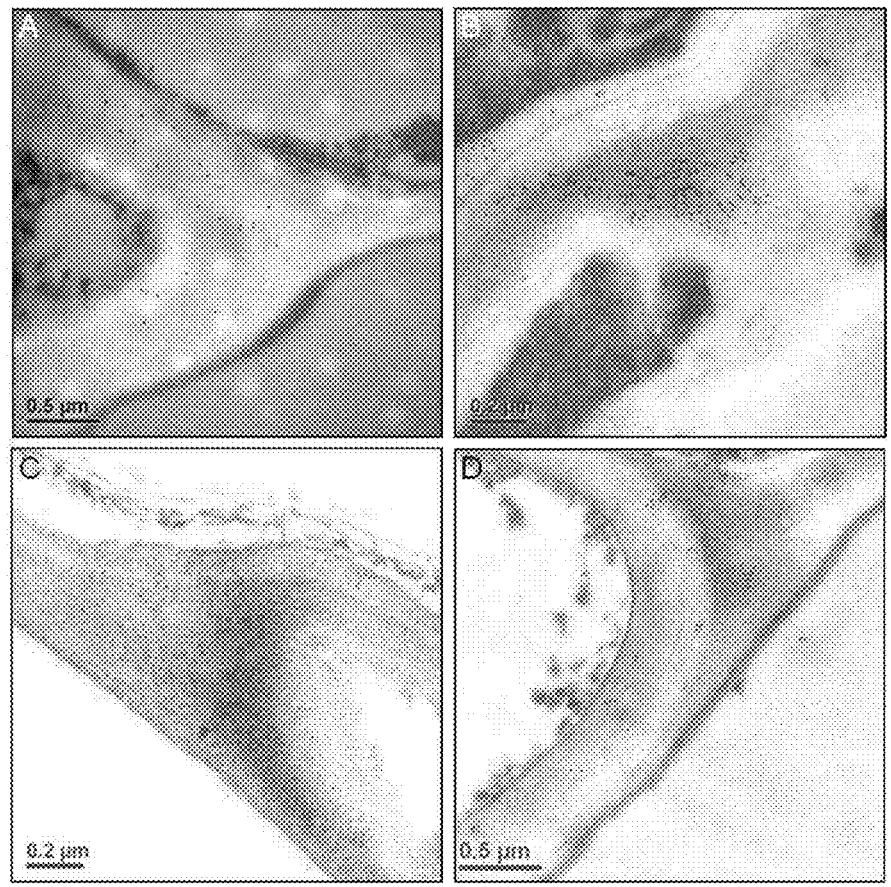
FIG. 13 shows transmission electron micrographs illustrating the detection of (1,3;1,4)-β-D-glucan with a (1,3;1,4)-β-D-glucan-specific monoclonal antibody in epidermal cell walls of four transgenic *Arabidopsis* plant lines used as parents in OsCSLF2×HvCslH1 transgenic plant crosses. HvCslH1 line individuals 15-8-3 and 15-11-7 are shown in panels A and B, respectively, and OsCSLF2 line individuals H37-5 and H17-4-4 in panels C and D, respectively.

All four of the parental lines were confirmed to contain (1,3;1,4)-β-D-glucan in their cell walls by immuno-electron microscopy (FIG. 13). Individuals from each of the four populations were used as male and female parents. Flowers of the female parent (e.g. individual H37-5) were emasculated prior to anther dehiscence and pollinated using dehisced anthers from the male parent (e.g. individual 15-8-3). Each crossed flower was labelled and the resulting seed pods collected upon dehydration.

Figure 14:
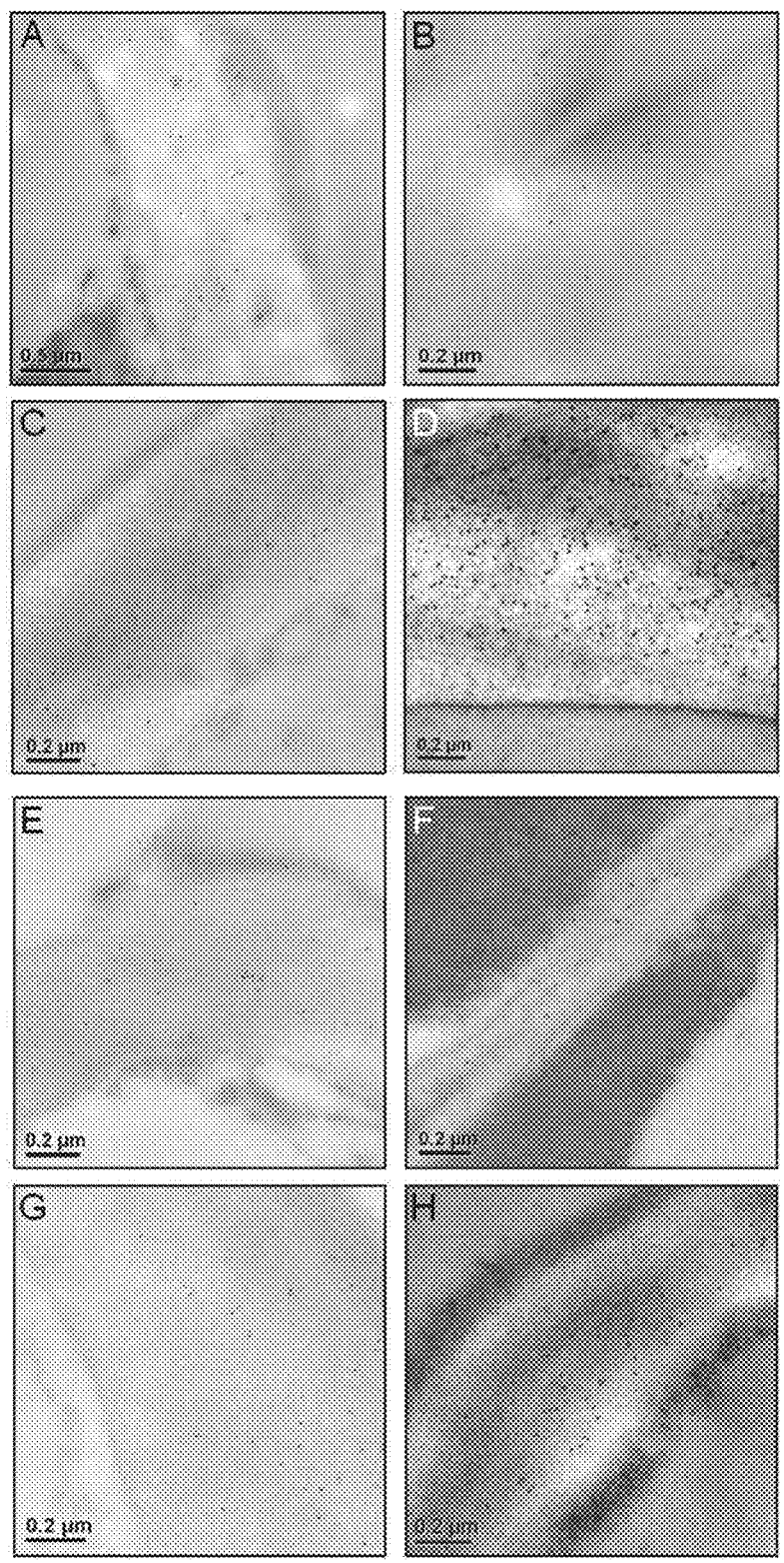
FIG. 14 shows transmission electron micrographs illustrating the detection of (1,3;1,4)-β-D-glucan with a (1,3;1,4)-β-D-glucan-specific monoclonal antibody in cell walls of progeny resulting from OsCSLF2×HvCslH1 transgenic plant crosses. An individual from a cross of 15-8-3×H37-5 is shown in (A), a sib of 15-8-3×H37-5 (B), 15-8-3×H37-7 (C), a sib of 15-8-3×H37-7 (D), 15-8-15×H37-16 (E and F), 15-11-13×H37-11 (G) and 15-11-7×H17-4 (H). Panels A-E, G-H show epidermal cells, panel F, mesophyll cells.

The progeny of each cross were sown in soil and their genotypes determined by PCR using leaf genomic DNA as template and HvCslH1-specific primers and, in a separate reaction, OsCslF2-specific primers. Mature leaves were fixed, embedded, sectioned and labeled with (1,3;1,4)-β-D-glucan monoclonal antibody. A number of the progeny were found to have greater levels of labelling than the parental lines, as observed in FIG. 14. For example, the labelling in the epidermal cells of the individual shown in Panel D is much heavier than compared to its 15-8-3×H37-7 parents (FIG. 13). A sib with the same genotype (FIG. 14, panel C) showed consistent yet lower levels of epidermal cell wall labeling.

EXAMPLE 9

Cloning of CslH cDNA and Genomic Sequences from Barley Cultivar Himalaya and Wheat A full length cDNA sequence of the CslH1 gene was isolated from barley cultivar Himalaya using a combination of barley EST sequences, PCR from cDNA using primers based on the rice CslH1 gene sequence (LOC_Os10g20090) and 5'RACE.

Figure 16:
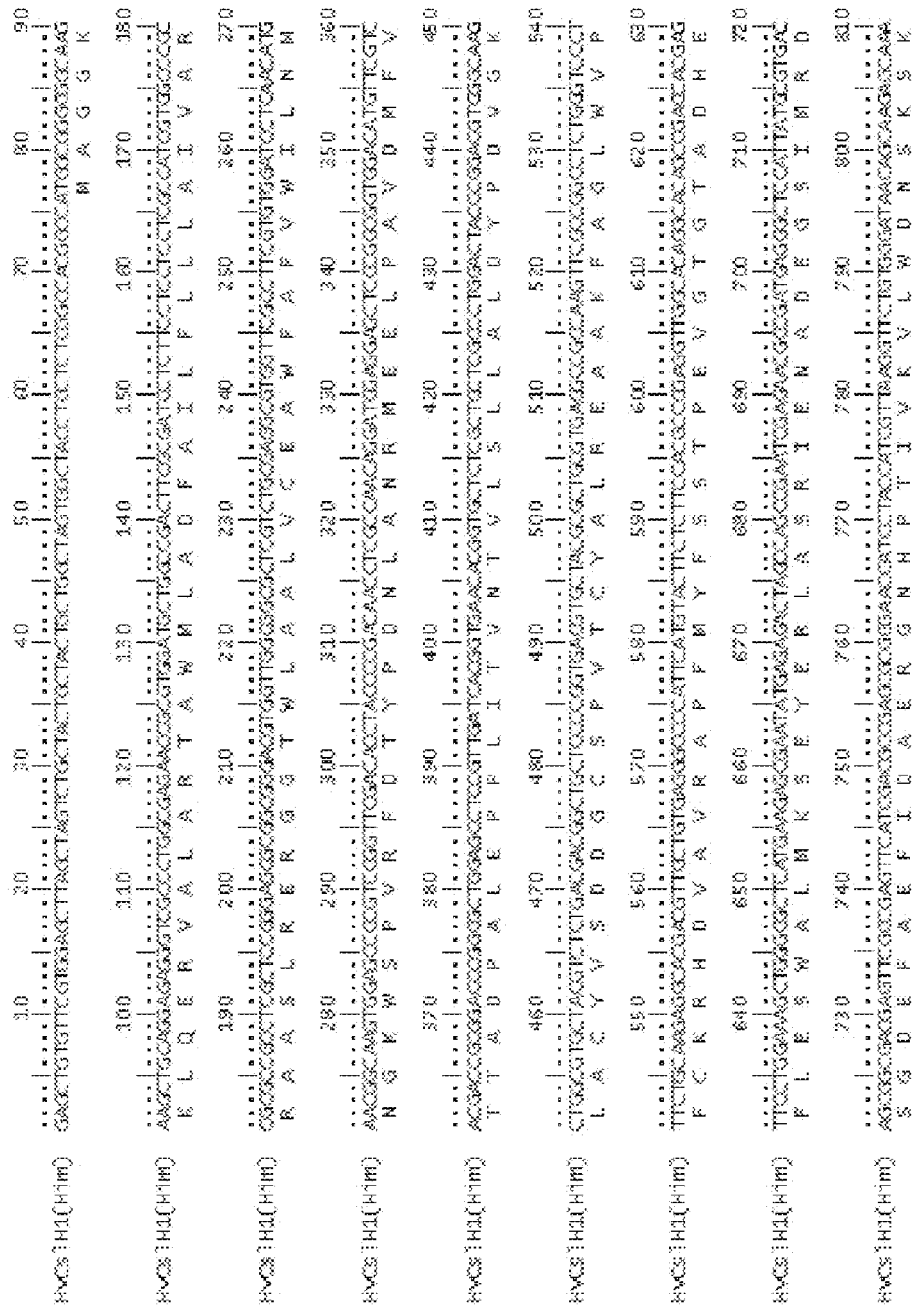
FIG. 16 shows the DNA sequence and translated amino acid sequence of the CslH1 gene cDNA from barley cv. Himalaya. The DNA sequence (SEQ ID NO: 69) is shown numbered every ten bases and the translated amino acid sequence (SEQ ID NO: 70) of the single large open reading frame is shown beneath in single letter form.
Figure 16:
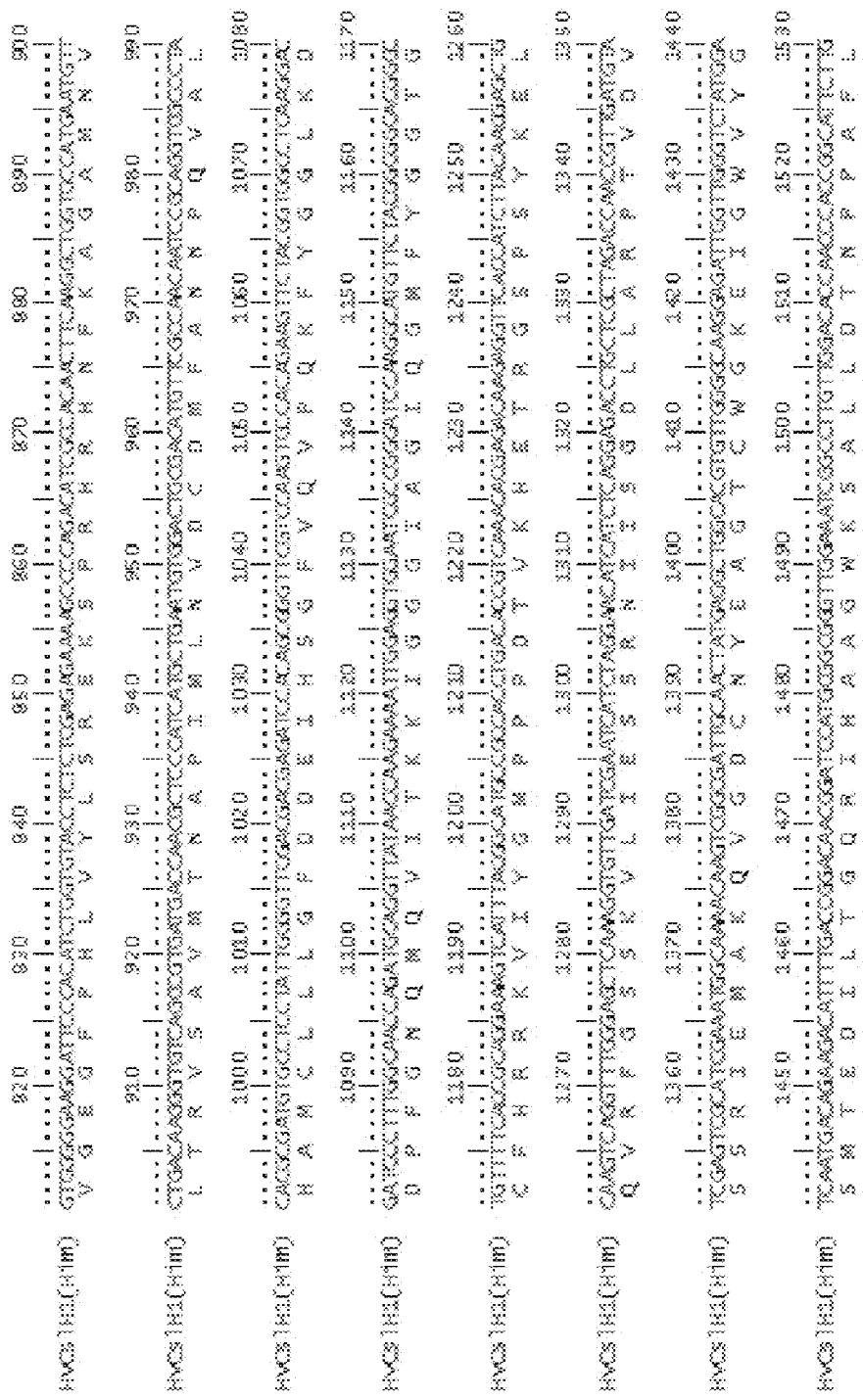
Figure 16:
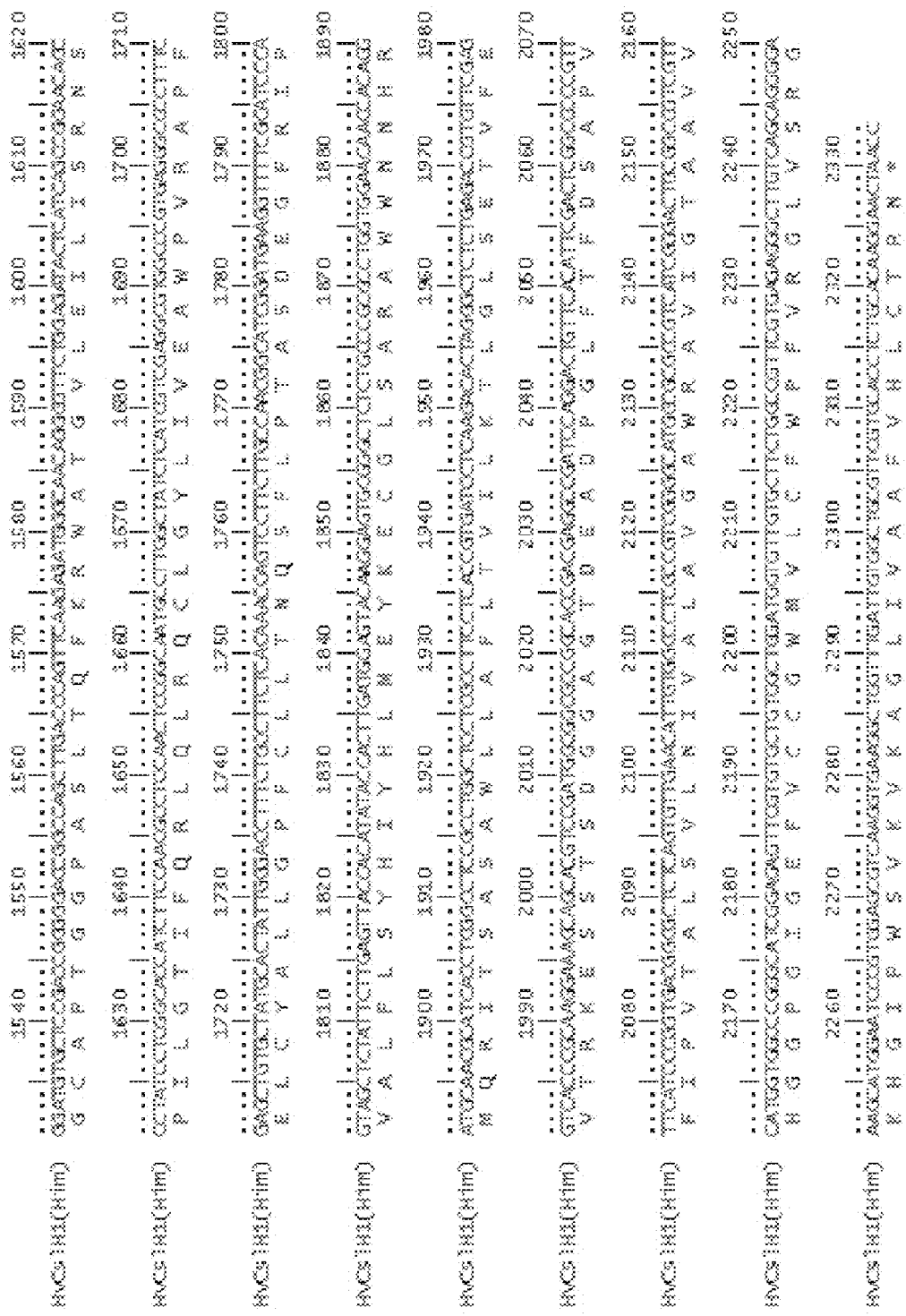

The 2333 bp consensus sequence designated HvCslH1 (Him) (SEQ ID NO: 69) is shown in FIG. 16. There is a single long open reading frame of 751 amino acids (SEQ ID NO: 70).

Figure 17:
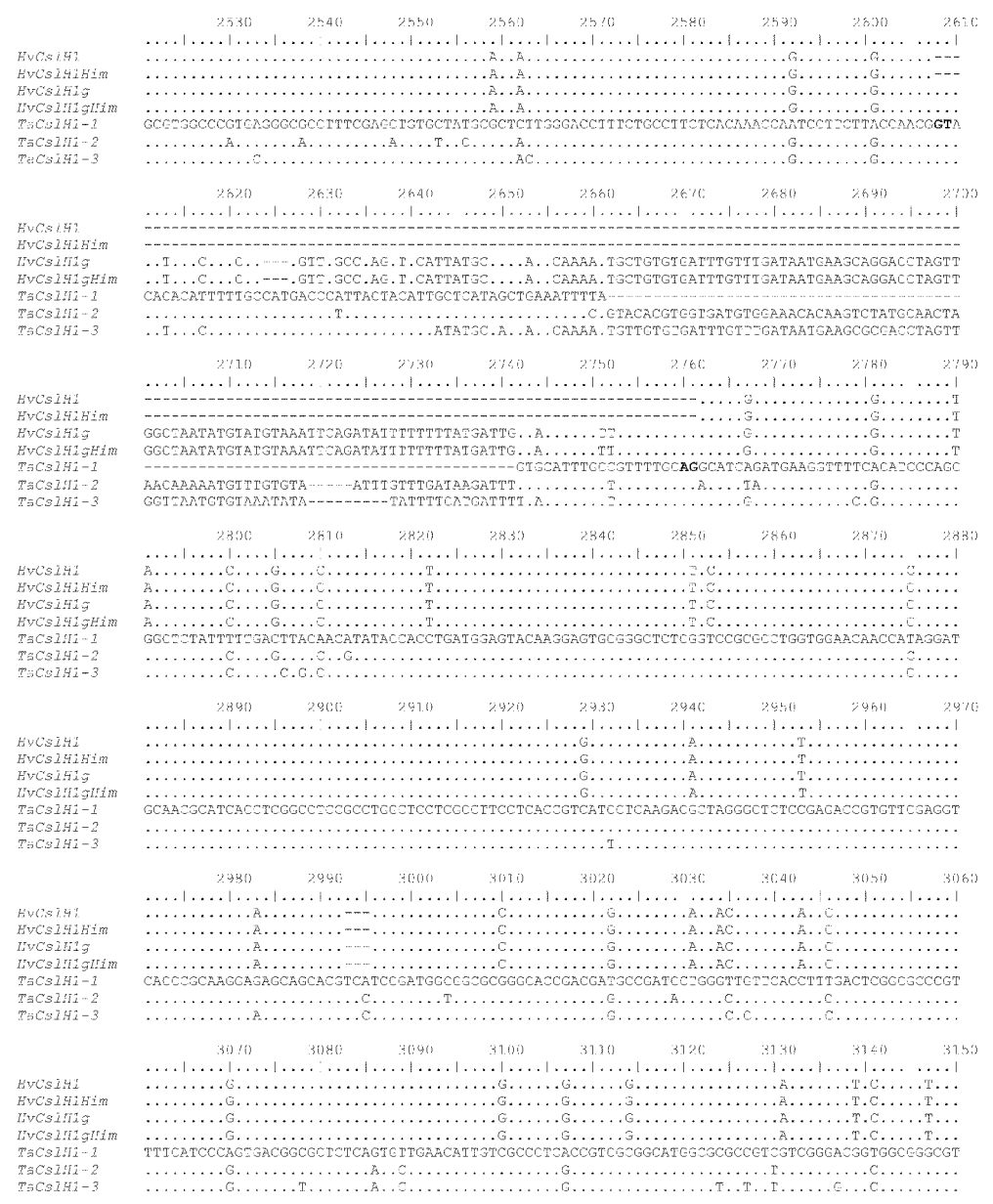

Oligonucleotide primers SJ91 and SJ85 were designed from the 5' and 3' ends of the consensus sequence and used to amplify a 3203 bp DNA fragment from genomic DNA designated HvCslH1gHim (SEQ ID NO: 71) in FIG. 17.

Alignment of the barley cDNA sequence and genomic sequences indicated that the CslH gene has eight small (approximately 100 bp) introns each flanked by the consensus GT.AG splice donor/acceptor sites (FIG. 17).

A wheat homolog of CslH1 was identified in the TIGR database as TC255929. Three classes of sequences made up this tentative consensus as exemplified by ESTs CJ614392, CJ609729 and CJ721204. PCR primers were designed from the barley sequence surrounding the ATG initiation codon (SJ163) and from the consensus sequence of all three EST types at the 3' end (SJ164) and used to amplify a full length genomic fragment from wheat cultivar Chinese Spring. Two sequence types were identified and designated TaCslH1-1 (SEQ ID NO: 78) and TaCslH1-2 (SEQ ID NO: 79). The third homeolog designated TaCslH1-3 (SEQ ID NO: 80) was isolated using primers SJ204 and SJ164 as described in more detail in materials and methods.

Comparison with the barley sequences indicated that the intron-exon junctions were conserved in all three genes (FIG. 17). The three wheat genes are 94.8-96.1% identical.

The predicted coding region sequences of the three wheat CslH1 genes (SEQ ID NO: 72, SEQ ID NO: 73 and SEQ ID NO: 74) each encode a polypeptide of 752 amino acids (SEQ ID NO: 75, SEQ ID NO: 76 and SEQ ID NO: 77).

The DNA coding sequences and amino acids sequences of the barley and wheat CSLH1 genes were aligned using the muscle alignment program and the percentage identity and similarity was calculated using a PAM250 matrix. A table showing the percentage identity and similarity is show in FIG. 27.

As shown in FIG. 27, the wheat proteins are about 94-95.0% identical to each other and about 92.6-93.1% identical to the barley proteins.

EXAMPLE 10

CslH Gene Expression in Barley and Wheat

Expression of the CslH1 gene was examined by semi quantitative (RT-PCR and gel electrophoresis) and quantitative (real time PCR) methods.

The coleoptile is a good tissue to examine expression of genes related to beta glucan biosynthesis since the levels of beta glucan increase as the coleoptile grows and then decline after growth has stopped. The CslH1 gene shows maximum expression only after growth has ceased and is high in the oldest tissues (6-8 days old, as shown in FIGS. 19A/B).

Figure 20:
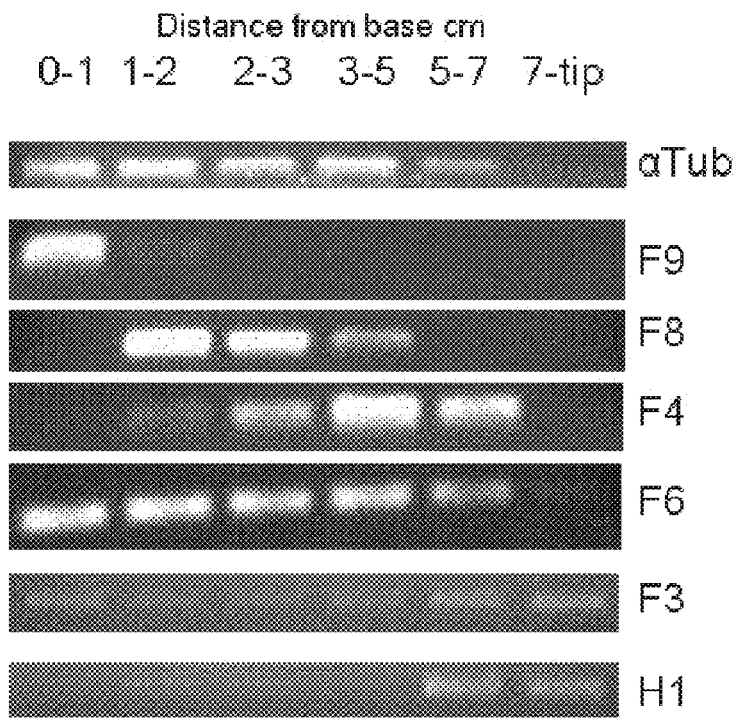
FIG. 20 shows the results of semi quantitative RT-PCR expression analysis of the barley CslF and CslH1 genes during leaf development. Semi quantitative RT-PCR showing the expression pattern of the barley CslH1 gene compared to other barley CslF genes. A constitutively expressed gene (alpha tubulin) is shown as a control.

Other tissues were also examined. In developing leaf, the CslH1 gene shows differential and maximum expression in the oldest tissue at the tip of the leaf (FIG. 20). It appears from these results that the CslH1 gene is preferentially (although not exclusively) expressed in cells that have stopped dividing and elongating and are thus differentiating. Cells in the maturing endosperm would be in a similar phase of development, ie. cell division would have stopped, cell enlargement would be slowing with the cells differentiating into specialised starch storage parenchyma.

Figure 21:
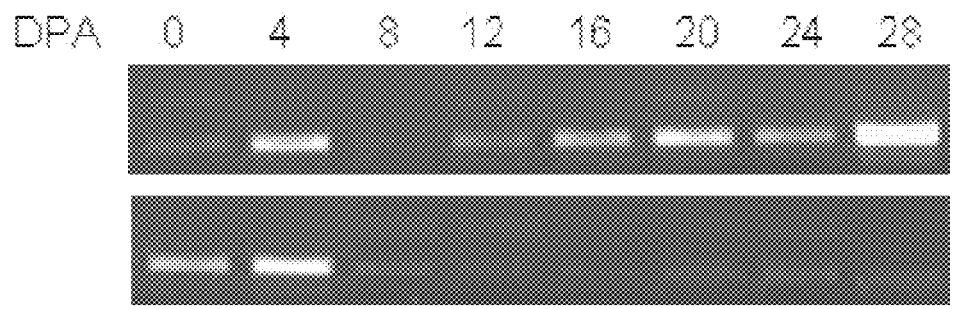
FIG. 21 shows the results of semi quantitative RT-PCR expression analysis of the barley cv. Himalaya and wheat CslH1 genes during endosperm development. Semi quantitative RT-PCR showing the difference in expression pattern of the CslH1 gene in the developing endosperm of barley cv. Himalaya gene (upper panel) compared to wheat cv. Westonia (lower panel). DPA=days post anthesis.

In barley endosperm tissue, CslH1 gene expression peaked around 4 days post anthesis and then increased during later stages to reach a maximum at 28 days (FIG. 21).

Figure 22:
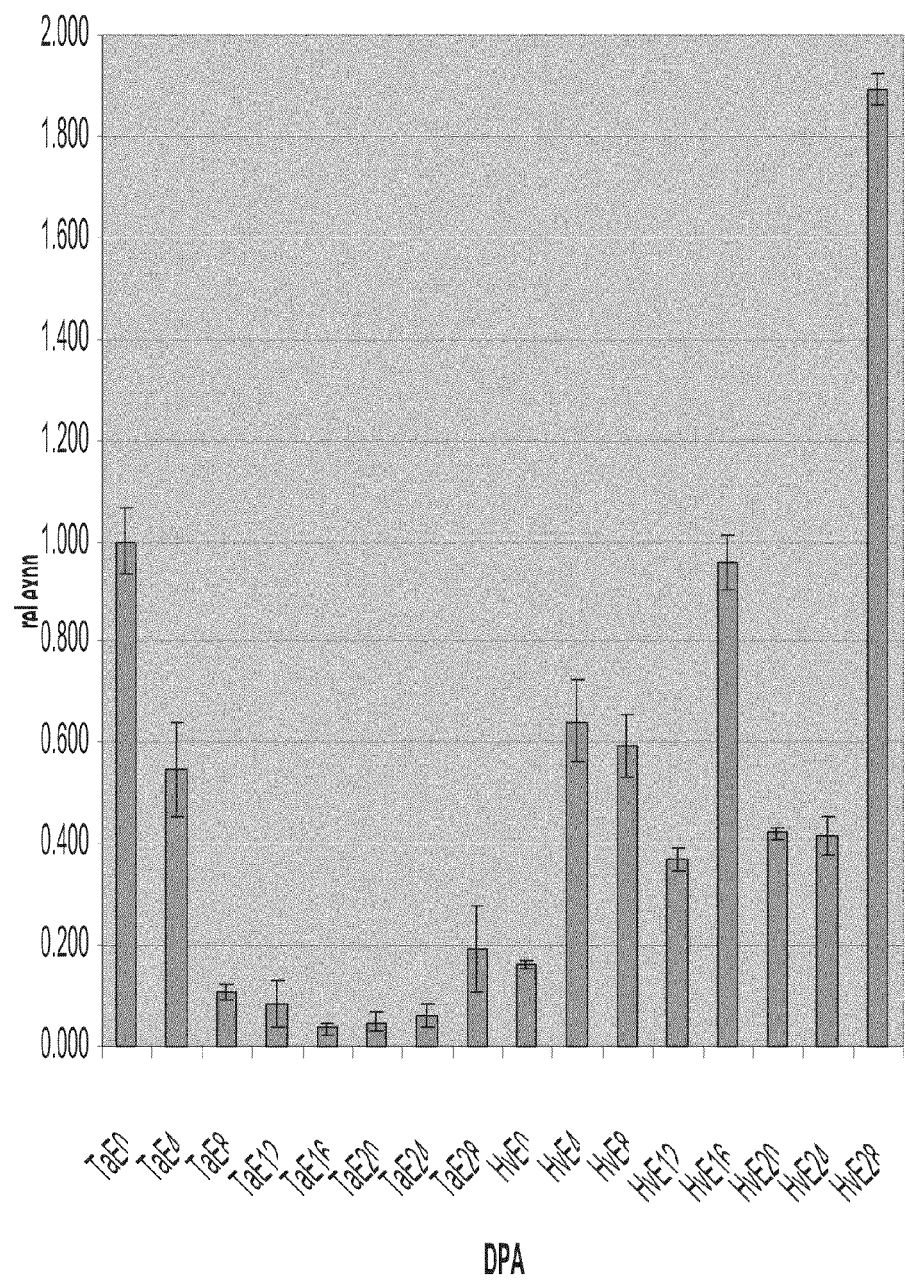
FIG. 22 shows the results of quantitative RT-PCR expression analysis of the barley cv. Himalaya and wheat CslH1 genes during endosperm development. Quantitative real time RT-PCR showing the difference in expression pattern of the barley CslH1 gene compared to wheat CslH1 gene in developing endosperm. The Ta0 dpa sample has been set to one and the other expression levels are relative to this.

There was a large difference in CslH1 gene expression in wheat where expression peaked at 4 days post anthesis after which expression was very low. These results were confirmed by real time PCR which showed that at 28 days post anthesis, the CslH gene was expressed about 10 fold higher levels in barley than in wheat (FIG. 22).

EXAMPLE 11

Overexpression of the Barley CslH Gene in Wheat Grain

Figure 23:
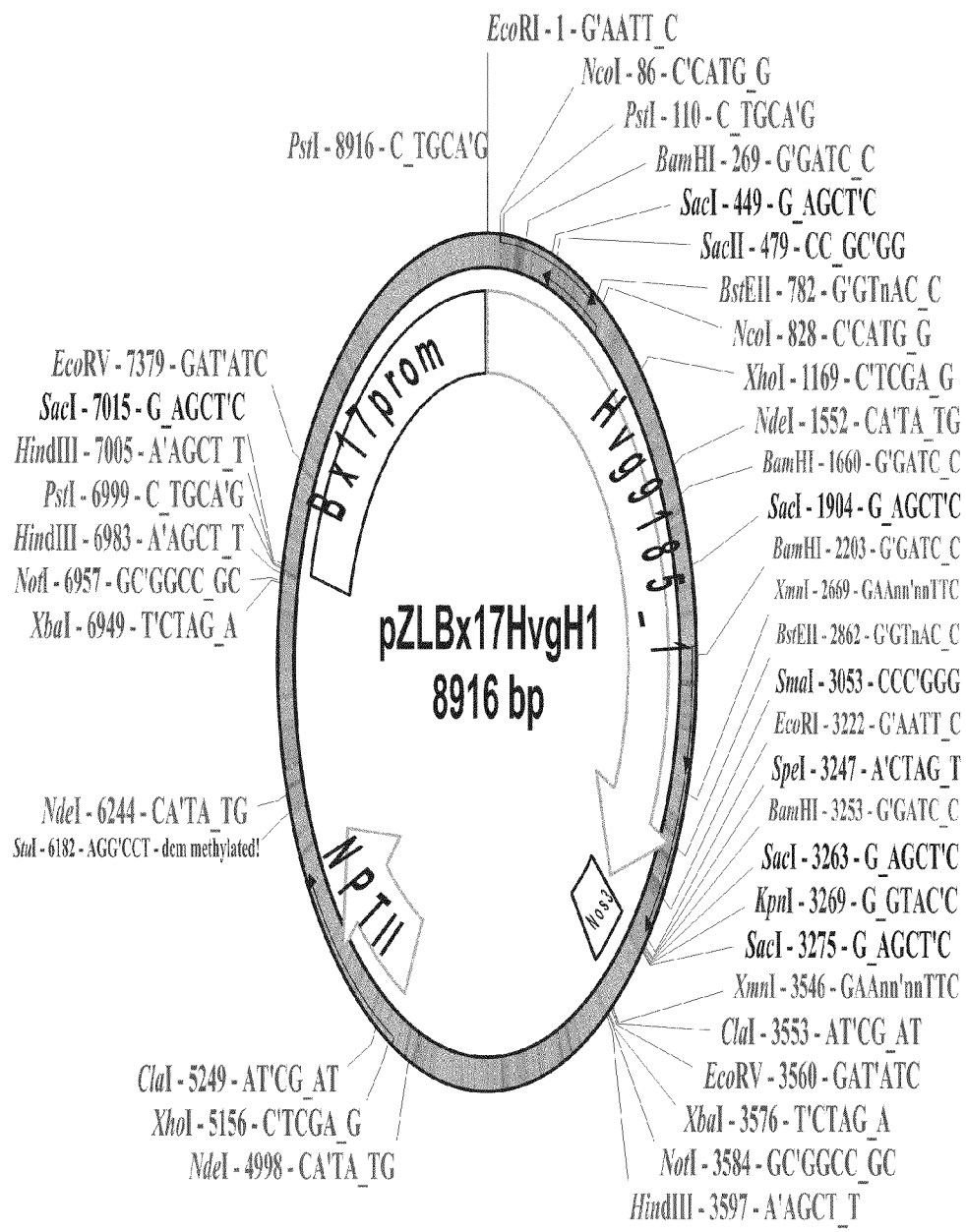
FIG. 23 shows a plasmid map of the plant transformation vector used to express the barley cv. Himalaya CslH1 genomic sequence under control of the Bx17 promoter. A schematic representation of the plant transformation vector designated pZLBx17HvgH1. The boxes inside the circular plasmid represent various genetic elements: Bx17prom=Bx17 promoter driving expression of the barley HvCslH1 genomic sequence; Hvg9185_1=HvCslH1 genomic clone number 1 isolated with primer pair SJ91 and SJ85; Nos3'=nopaline synthase polyadenylation sequence; NPTII=bacterial kanamycin resistance gene. The position of selected restriction sites is indicated outside of the plasmid map.

Transgenic wheat plants were generated by biolistics transformation with the full length genomic HvCslH1 (cv. Himalaya) gene under control of the glutenin promoter such that expression should only occur in endosperm tissues (FIG. 23). Lines were screened for the presence or absence of the transgene by PCR of young leaf material. Twelve PCR positive lines and three PCR negative lines (H1-2, -7 and -11) were grown to maturity in the glasshouse. RNA was isolated from developing grain at approximately 15 days post anthesis and cDNA was made using Superscript III. Expression of the barley transgene was then analysed by real time PCR. Table 5 shows the relative expression levels compared to the endogenous wheat CslH gene as the primers used amplify both the wheat and barley genes.

TABLE 5

Relative expression of CslH gene in wheat endosperm

| Line | Run 1 | Run 2 | Run 3 |
|---|---|---|---|
| H1-1 | 468 | 225 | |
| H1-2 | | 2 | |
| H1-3 | 206 | | |
| H1-4 | 620 | 497 | 243 |
| H1-5 | 299 | 411 | |
| H1-6 | 952 | | |
| H1-7 | 63 | | |
| H1-8 | 140 | | 230 |
| H1-9 | | 1771 | |
| H1-10 | | 4396 | 4052 |
| H1-11 | 26 | | 6 |
| H1-12 | 10 | 1103 | |
| H1-14 | 1013 | 352 | |
| H1-15 | 10 | | |
| H1-13 | 1 | 1 | |

Most of the lines expressed the barley CslH gene at several hundred fold higher levels than the controls with line 9, 10, 12 and 14 showing the highest expression (greater than one thousand fold higher).

At maturity, single grains from were analysed for beta glucan content and a summary of the results are shown in Table 6:

TABLE 6

Beta glucan content of transgenic wheat flour

| Transgenic line | Average Beta glucan | std dev | Max beta glucan |
|---|---|---|---|
| H1-1 | 0.81 | 0.08 | .8 |
| H1-2 | 0.68 | 0.02 | .7 |
| H1-3 | 0.89 | 0.05 | .9 |
| H1-4 | 0.82 | 0.05 | .8 |
| H1-5 | 0.83 | 0.21 | 1.1 |
| H1-6 | 0.91 | 0.09 | 1.0 |
| H1-7 | 0.65 | 0.05 | .7 |
| H1-8 | 0.87 | 0.15 | 1.1 |
| H1-9 | 1.17 | 0.33 | 1.9 |
| H1-10 | 1.12 | 0.39 | 1.9 |
| H1-11 | 0.82 | 0.14 | 1.0 |
| H1-12 | 1.23 | 0.26 | 1.7 |
| H1-14 | 0.99 | 0.19 | 1.4 |
| H1-15 | 0.60 | 0.26 | .8 |
| H1-16 | 1.00 | 0.11 | 1.2 |
| PCR – (2, 7, 11) average | 0.69 | 0.10 | 1.0 |
| PCR + (rest) average | 0.97 | 0.11 | 1.9 |

The PCR negative lines all had the lowest beta glucan contents averaging 0.69% of grain weight, whereas grain from the PCR positive lines had an increased average beta glucan content of 0.97%. The last column of Table 6 shows the maximum beta glucan content of any single grain from a given line—the highest PCR negative line was 1.0% (and most grains were much lower than this) but several of the PCR positive lines had grains with significantly increased beta glucan levels with line 9 and line 10 (the highest expressers) having grains with up to 1.9% beta glucan. These levels of beta glucan have never been seen before in wheat.

Figure 25:
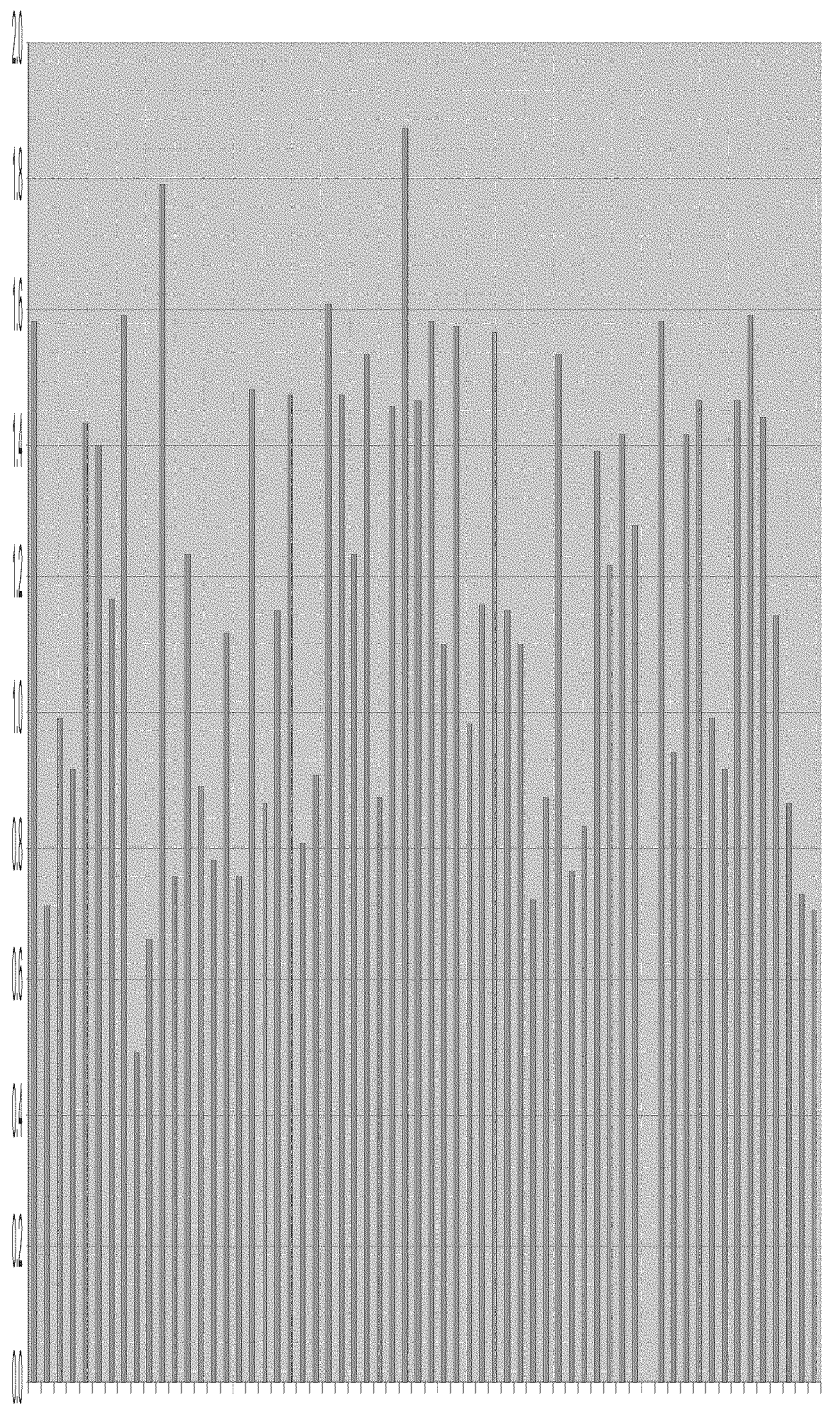
FIG. 25 shows the beta glucan contents of single wheat grains from T0 plant line 10 expressing the barley cv. Himalaya CslH1 gene. Graph showing beta glucan content of individual wheat grains from a T0 line number 10. Beta glucan is given as a percentage of flour weight.

The heads from these T0 plants contain T1 seed which are segregating for the transgene. If the DNA is inserted at a single locus a ratio of three transgenic to one wild type seed should be observed. FIG. 25 shows the beta glucan levels of individual T1 seeds from the H1 transgenic line 10 from which it can be seen that approximately three quarters (47/61) have higher beta glucan levels than the average of the PCR negative lines (0.7%). From the ratio of the highest beta glucan level (1.9%) to the average PCR negative level (0.7%) the increase in beta glucan content is 2.7 times that normally seen in wild type wheat grains. A further significant observation is that a high proportion of the grains have at least 1.4% beta glucan.

It is expected that further increases in beta glucan will be seen in these grains when the lines are made homozygous and gene dosage increases.

EXAMPLE 12

Materials and Methods for Examples 9 to 11

Plant Material

Barley (*Hordeum vulgare*) cultivar Himalaya and wheat (*Triticum aestivum*) cultivar Chinese Spring, Westonia and Bob White26, were grown under standard glasshouse conditions.

Primer Sequences

The primer sequences referred to in Examples 9 to 11 and this example are shown below in Table 7:

TABLE 7

Primer sequences for Examples 9 to 12

| Primer | Target gene | Sequence (5'- 3') | Sequence Identifier |
|---|---|---|---|
| SJ27 | Cs1H1 | AGGCGTGGTTCGCGTTCG | SEQ ID NO: 44 |
| SJ28 | Cs1H1 | CAGCGCGTAGTACGTCAC | SEQ ID NO: 45 |
| SJ72 | Cs1H1 | CAGCCGTGATGACCAACG | SEQ ID NO: 46 |
| SJ73 | Cs1H1 | GTTGCCAAAGGGATCGTC | SEQ ID NO: 47 |
| SJ79 | Cs1H1 | GCGGTCGTGACGAACATGTCCAC | SEQ ID NO: 48 |
| SJ75 | Cs1H1 | GACGCTCCACGGGATTC | SEQ ID NO: 49 |
| SJ85 | Cs1H1 | GGTTAGTTCCTTGTGCAGAGGT | SEQ ID NO: 50 |
| SJ91 | Cs1H1 | GAGCTGTGTTCGTGGAGCTTAG | SEQ ID NO: 51 |
| SJ163 | Cs1H1 | CTGCTCTCGGCCACGGCCAT | SEQ ID NO: 52 |
| SJ164 | Cs1H1 | CCGCCGGTTAGTTCCTTGTGCAGA | SEQ ID NO: 53 |
| SJ183 | Cs1H1 | GGAGAGTTCGTGTGCTGTGG | SEQ ID NO: 54 |
| SJ204 | Cs1H1 | CACCATGAGCCCCGTCCGGTTCGACA | SEQ ID NO: 55 |
| TUB | Alpha tubulin | CAAACCTCAGGGAAGCAGTCA | SEQ ID NO: 56 |
| TUB2F | Alpha tubulin | AGTGTCCTGTCCACCCACTC | SEQ ID NO: 57 |
| SJ107 | Cs1F6 | GCATCGTACTGGTGCTGCT | SEQ ID NO: 58 |
| SJ82 | Cs1F6 | GCGCTTCTCACGGGACACGTACA | SEQ ID NO: 59 |
| SJ94 | Cs1F4 | GATGCGTACAACTCGAGCAA | SEQ ID NO: 60 |
| SJ95 | Cs1F4 | CGTTGCTGAAGTCAAGTGGA | SEQ ID NO: 61 |
| SJ97 | Cs1F9 | CGCTGCAAACGAGAAAGAAGG | SEQ ID NO: 62 |
| SJ93 | Cs1F9 | GGCGCTGAAATCCAGAGG | SEQ ID NO: 63 |
| SJ44 | Cs1F3 | CGGAAATCCATAGGAAAGG | SEQ ID NO: 64 |
| SJ38 | Cs1F3 | CGGCGGAACATGCAAC | SEQ ID NO: 65 |
| SJ96 | Cs1F8 | GGATTGACCCAGCTGAAAAC | SEQ ID NO: 66 |
| SJ37 | Cs1F8 | GAGTTGTTGACGTAGTGGTC | SEQ ID NO: 67 |
| SJ244 | Bx17 prom | CGAGCACCCCAATCTACAGA | SEQ ID NO: 68 |

DNA, RNA Isolation and cDNA Synthesis

Plant DNA was isolated from fully expanded leaf tissue using a CTAB based method (Murray and Thompson, Nucleic Acids Res. 8: 4321-4325, 1980). Total RNA was isolated from leaf and coleoptile tissues using an RNAeasy kit from Qiagen. RNA was isolated from developing endosperm using a phenol SDS method and LiCl precipitation (Clarke et al., *Functional and Integrative Genomics* 8, 211-221, 2007). RNA was treated with DNAse using a "DNA-free" kit from Ambion and then cDNA was synthesised using SuperscriptIII reverse transcriptase according to the manufacturer's instructions (Clontech).

Cloning of CslH Genes

The methods for cloning CslH genes were similar to those described in the cloning and characterisation of CslF genes (Burton et al., *Plant Physiol* 146: 1821-1833, 2008). A 1.8 kb tentative consensus sequence (TC140327) of a barley homolog of the rice Cellulose synthase like H1 gene (LOC_Os10g20090) was identified in the TIGR database. PCR primer pairs (SJ27-SJ73 and SJ72-SJ75) were designed based on the rice CslH1 sequence and used to amplify sequences from cDNA. The 5' end of the gene was then amplified by 5'RACE using a SMART cDNA library and nested CslH1 primers SJ28 and SJ79 according to the manufacturer's instructions (Clontech).

A full length genomic clone was isolated by amplification with primers SJ91 and SJ85 and Phusion Taq polymerase (Finnzymes) according to the manufacturers recommend cycling conditions (denature 30 sec at 98° C. followed by 35 cycles of 98° C. for 5 sec, 63° C. for 7 sec and 72° C. for 3 m) and cloned into the pCRBluntII TOPO cloning vector (Invitrogen).

Wheat CslH genomic clones were isolated by PCR with Phusion polymerase from the cultivar Chinese Spring using primers SJ163 and SJ164 and an annealing temperature of 70° C. A genome walking kit was used according to the manufacturers instructions (Clontech) to obtain sequences extending upstream of the coding region of all three wheat CslH homeologs from the variety Bob White (data not shown). A primer (SJ204) was designed that was specific to the third homeolog and used with SJ164 to isolate the third full length genomic clone. It was confirmed that the predicted exon/intron boundaries could be spliced correctly by sequencing cDNA fragments (data not shown).

Expression Analysis of CSLH Gene in Wheat and Barley by RT-PCR

Total RNA was isolated from sections of the first leaf of a 7 day old plant, from dark grown coleoptiles of different ages, and from developing grain collected at 4 day intervals post anthesis (DPA), DNAse treated and reverse transcribed with Superscript III according to the manufacturer's instructions (Invitrogen). PCR reactions were performed using HotStarTaq (Qiagen). The cDNA was diluted and used in PCR reactions at a level equivalent to 1 ng of original RNA per microlitre. For semi-quantitative RT-PCR, CslH1 primers 972 and 5J74, for the CslF genes, primer pairs were as follows; (CslF6; SJ107-SJ82), (CslF4; SJ94-SJ95), (CslF9; SJ97-SJ93), (CslF3; SJ44-SJ38), (CslF8; SJ96-SJ37). An annealing temperature of 59° C. was used. Test amplifications were performed to ensure that the amplification was not saturated (approx 32-35 cycles except tubulin 24 cycles) and the products were analysed by ethidium bromide staining after agarose gel electrophoresis. Real time PCR was performed on triplicate samples on a Rotorgene 6000 machine (Corbett Life Sciences, AU) using HotStarTaq (Qiagen), SybrGreen and primers SJ183 and SJ164 and an annealing temperature of 60° C. Relative expression levels were calculated using the machine software with wheat 0 dpa samples as the comparator (set to one). The Ct value of this sample was 25.5 cycles. For analysis of transgenic grain at 15 dpa, the relative expression values were normalised against tubulin and compared to the lowest expression line (H1-13).

Expression Analysis of CslH Gene in Barley by Q-PCR

HvCslH1 transcript was measured in developing coleoptile 0.5 to 7 days post germination. HvCslH1 transcript was shown to accumulate only after the completion of the elongation phase and the emergence of the leaf. Highest levels of expression were seen at 7 days when the coleoptile is senescing (twisting and shrinking) (Gibeaut et al., *Planta* 221:729-738, 2005).

Production of Transgenic Wheat Plants Overexpressing the Barley CslH Gene in Endosperm The full length barley cv. Himalaya genomic CslH sequence (SEQ ID NO: 71) was amplified using primers SJ91 and SJ85, was inserted as an EcoRI fragment between a 1.9 kb fragment of the high molecular weight glutenin Bx17 promoter and the nopaline synthase terminator (FIG. 23). The Bx17 promoter confers high level expression in developing endosperm (Reddy and Appels, *Theor Appl Genet*. 85: 616-624, 1993).

Figure 24:
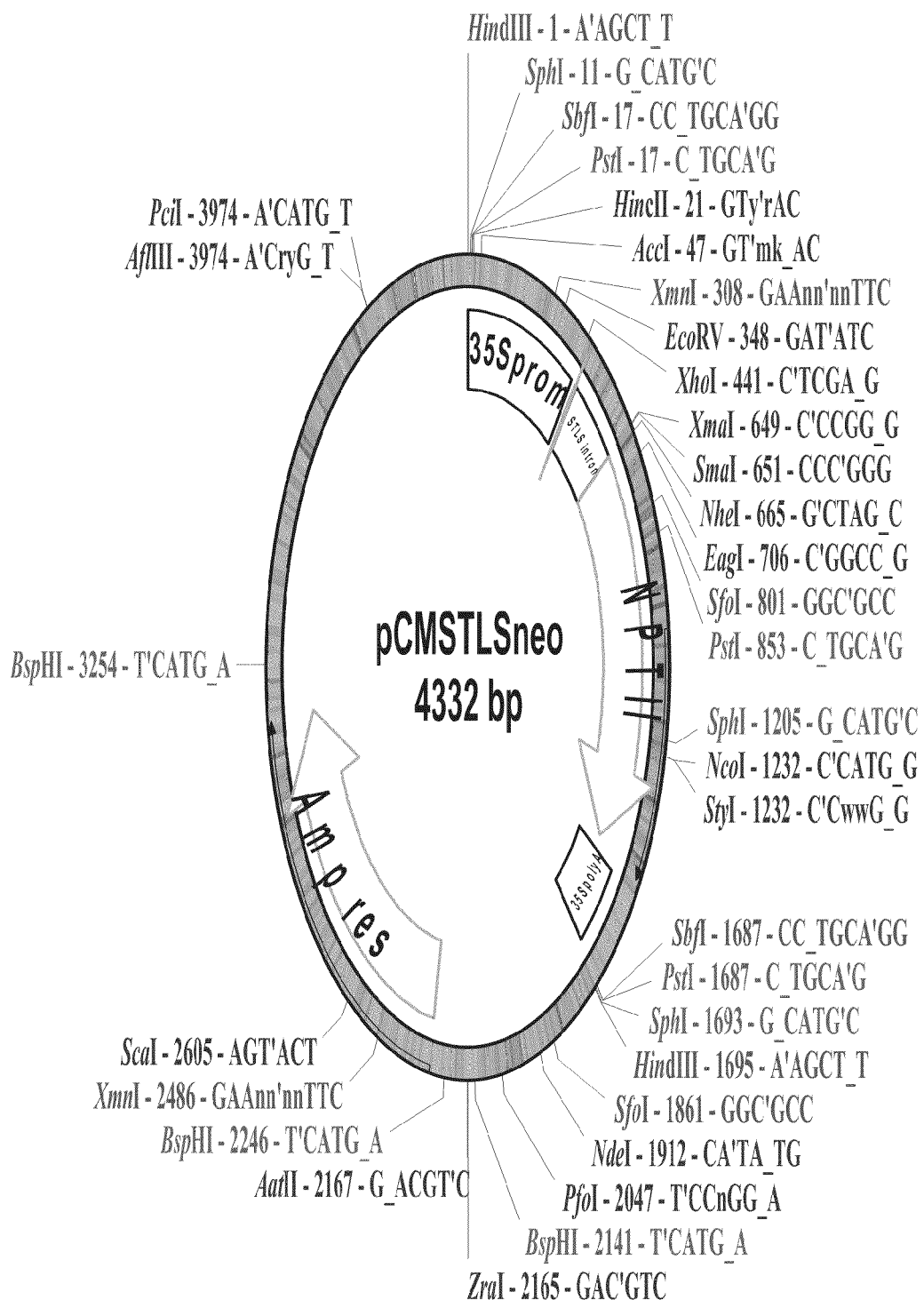
FIG. 24 shows a plasmid map of the plant selectable marker plasmid conferring kanamycin resistance. A schematic representation of the plant transformation vector designated pCMSTLSneo. The boxes inside the circular plasmid represent various genetic elements: 35Sprom=CaMV 35S promoter driving expression of the plant selectable marker gene; NPTII=plant kanamycin resistance gene; STLS intron=*Solanum tuberosum* large subunit intron; 35S polyA=CaMV 35S polyadenylation sequence; Amp res=bacterial ampicillin resistance gene. The position of selected restriction sites is indicated outside of the plasmid map.

Bob White 26 wheat plants were transformed using the biolistics method (Pellegrineschi et al., Genome 45: 421-430, 2002) with 50 mg/L G418 as the selection agent. The HvCslH expression vector (pZLBx17HvgH1 and a second plasmid with the CaMV 35S promoter driving expression of the NPTII selectable marker (pCMSTLSneo, FIG. 24) were mixed in equimolar amounts and co bombarded into immature embryos.

Transgenic plants were screened for the presence of the transgene using young leaf tissue and the RedExtractnAmp™ kit from Sigma with primers SJ244 and SJ79.

At anthesis (emergence of the anthers and shedding of pollen) heads were tagged to enable grain to be sampled at approximately 15 dpa. Three grains from a head were pooled, RNA extracted and reverse transcribed and levels of transgene expression were analysed by real time PCR using primers SJ183 and SJ85. Expression levels were normalised against alpha tubulin (primers TUB and TUB2F) and finally expressed as a ratio compared to the lowest expresser.

Flour from mature single grains was analysed for beta glucan content using a scaled down version of the lichenase enzymatic method (AACC Method 32-33, Megazyme assay kit, McCleary and Glennie-Holmes, *J. Inst Brewing* 91: 285-295, 1985). Beta glucan contents are expressed as a percentage (w/w) of the milled whole grain flour.

EXAMPLE 13

Overexpression of the Barley CslH Gene in Barley cv. Golden Promise

The full-length coding region of the barley CslH cDNA (SEQ ID NO: 1) was transferred into two Gateway-enabled barley transformation vectors. The vector pRB474 contains the oat globulin promoter (Vickers et al., *Plant Mol Biol* 62: 195-214, 2006) which provides endosperm specific expression and the vector pMDC32 (Curtis and Grossniklaus, *Plant Physiol.* 133: 462-9, 2003) contains a double 35S promoter which drives constitutive expression in all plant tissues.

Barley Transformation

The vectors were transferred into *Agrobacterium tumefaciens* and immature scutella of the barley cultivar Golden Promise were transformed using established protocols to produce two populations of transgenic plants. Insertion of the transgene was confirmed by Southern blotting. Plants 236-1 to 236-18 contain the barley CslH gene driven by the oat globulin promoter. Plants 237-1 and -2 contain the barley CslH gene driven by the 35S promoter. Plants 208-2, -3, -5 and -7 are control plants and are transgenic for the empty vector pRB474 carrying the oat globulin promoter only.

Transcript Analysis

Leaf and developing grain samples, from 7 and 14 days after pollination (DAP) were collected from the 236 plants. Total RNA was extracted using TRIzol reagent (Invitrogen) following a standard protocol and cDNA was synthesized according to Burton et al., (*Plant Physiol* 146: 1821-1833, 2008). Quantitative real-time PCR (QPCR) was carried out according to Burton et al. (2008, supra). The transcript levels of the CslH gene were compared in the endosperm of the transgenic grain to wild type endosperm levels which are generally very low.

Figure 26:
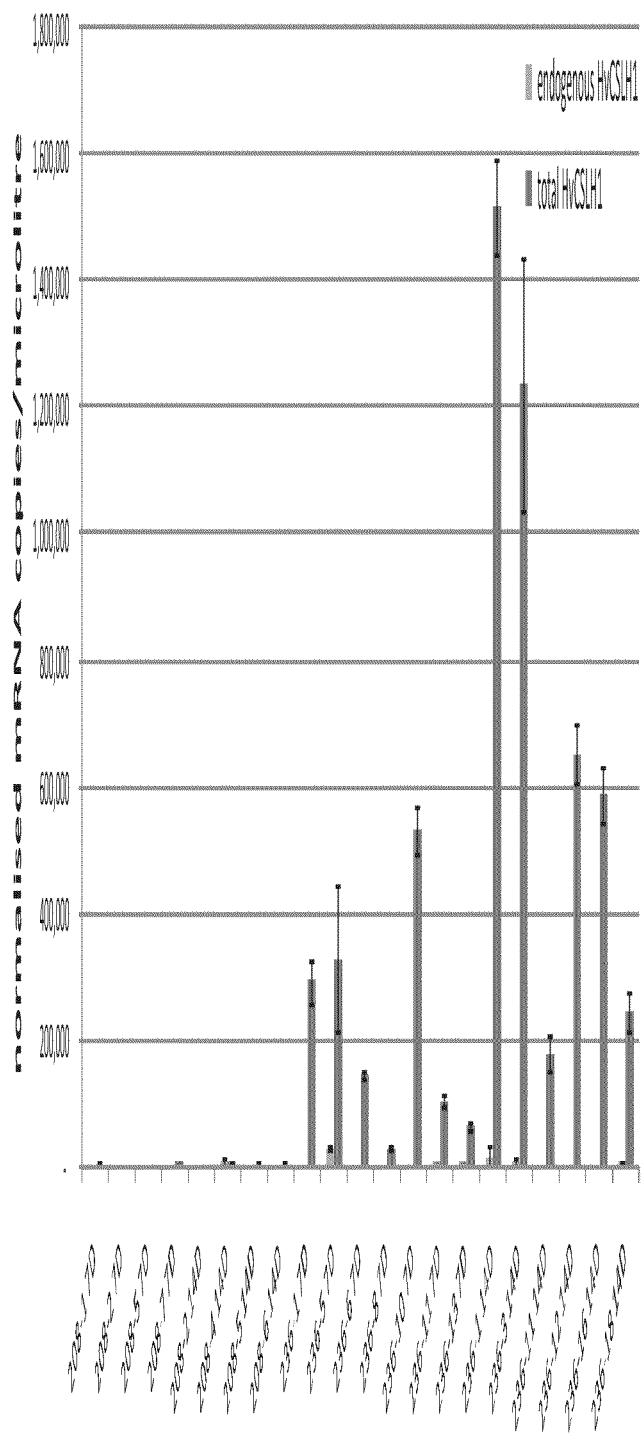
FIG. 26 shows a quantitative RT-PCR expression analysis of CslH1 genes in empty vector control (208) and transgenic (236) barley. Expression is shown in leaf and developing grain at 7 days after pollination (7D) and 14 days after pollination (14D).

As shown in FIG. 26, the empty vector control lines (208) have typical wild type levels of CslH transcript. The transgenic lines (236) show significantly increased HvCslH1 mRNA levels at 7 days (7D) and further increases at 14 days (14D) after pollination.

Beta-Glucan Analysis

The T1 seed from the transgenic plants were collected. A sample of the bulked T1 grain from each individual plant was ground to flour and the amount of beta-glucan present was assayed using Megazyme method (described supra). The data from each plant are presented as the mean value of two replicates and the amount of beta-glucan as a percentage of grain weight is shown in Table 8, below:

TABLE 8

(1,3;1,4)-β-D-glucan content of bulked transgenic barley flour

| Plant Line | (1,3;1,4)-β-D-glucan as % of grain weight |
|---|---|
| 208-2 (empty vector control) | 3.9 |
| 208-3 (empty vector control) | 4.4 |
| 208-5 (empty vector control) | 3.0 |
| 208-7 (empty vector control) | 4.3 |
| 236-1 | 5.0 |
| 236-2 | 5.6 |
| 236-3 | 4.4 |
| 236-4 | 5.2 |
| 236-5 | 5.9 |
| 236-6 | 3.3 |
| 236-7 | 4.5 |
| 236-8 | 4.2 |
| 236-9 | 3.2 |
| 236-10 | 5.3 |
| 236-11 | 5.4 |
| 236-13 | 4.7 |
| 236-14 | 4.7 |
| 236-15 | 3.4 |
| 236-16 | 3.4 |
| 236-17 | 4.4 |
| 236-18 | 3.7 |
| 237-1 | 4.6 |
| 237-2 | 3.0 |

The empty vector control lines (208) have a (1,3;1,4)-β-D-glucan content around 4% which is typical for wild type Golden Promise grain. Even though the T1 grain is bulked (and therefore contains null-segregant grains) a significant number of the transgenic lines (shaded) show an overall (1,3;1,4)-β-D-glucan content greater than the control, with the highest value at 5.9%.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a transgene" includes a single transgene as well as two or more transgenes; "a plant cell" includes a single cell as well as two or more cells; and so forth.

The invention claimed is:

1. A method for modulating the level of (1,3;1,4)-β-D-glucan produced by a plant or fungal cell, the method comprising modulating the level and/or activity of a CslH-encoded (1,3;1,4)-β-D-glucan synthase in the cell, wherein the level and/or activity of the CslH-encoded (1,3;1,4)-β-D-glucan synthase is modulated by modulating the expression of a CslH nucleic acid in the cell, and wherein modulating the expression of a CslH nucleic acid in the cell results in modulation of the level of (1,3;1,4)-β-D-glucan produced by the cell compared to a wild-type cell of the same taxon, and wherein the CslH nucleic acid comprises:
   (i) a nucleotide sequence set forth in SEQ ID NO: 1;
   (ii) a nucleotide sequence encoding the amino acid sequence set forth in SEQ ID NO: 2; or
   (iii) a nucleotide sequence encoding an amino acid sequence which is at least 95% identical to the amino acid sequence set forth in SEQ ID NO: 2.

2. The method of claim 1 wherein the cell is a plant cell.

3. The method of claim 2 wherein the cell is a monocot plant cell.

4. The method of claim 2 wherein the cell is a cereal crop plant cell.

5. A plant or fungal cell comprising any one or more of:
   a modulated level and/or activity of CslH-encoded (1,3;1,4)-β-D-glucan synthase relative to a wild type cell of the same taxon; and/or
   modulated expression of a CslH nucleic acid relative to a wild type cell of the same taxon,
   wherein the cell comprises a modulated level of (1,3;1,4)-β-D-glucan relative to a wild-type cell of the same taxon,
   wherein the CslH nucleic acid comprises:
   (i) a nucleotide sequence set forth in SEQ ID NO: 1;
   (ii) a nucleotide sequence encoding the amino acid sequence set forth in SEQ ID NO: 2; or
   (iii) a nucleotide sequence encoding an amino acid sequence which is at least 95% identical to the amino acid sequence set forth in SEQ ID NO: 2.

6. The cell of claim 5 wherein the cell is produced according to the method of claim 1.

7. The cell of claim 5 wherein the cell is a plant cell.

8. The cell of claim 7 wherein the cell is a monocot plant cell.

9. The cell of claim 7 wherein the cell is a cereal crop plant cell.

10. A multicellular structure comprising one or more cells according to claim 5.

11. The multicellular structure of claim 10 wherein the multicellular structure is selected from the list consisting of a whole plant, a plant tissue, a plant organ, a plant part, plant reproductive material or cultured plant tissue.

12. The multicellular structure of claim 10 wherein the multicellular structure comprises a cereal crop plant or a tissue, organ or part thereof.

13. The multicellular structure of claim 12 wherein the multicellular structure comprises a cereal grain.

14. The multicellular structure of claim 11 wherein the multicellular structure comprises a cell having modulated dietary fibre content relative to a wild type cell of the same taxon.

15. The multicellular structure of claim 14 wherein the multicellular structure comprises a cell having an increased level of (1,3;1,4)-β-D-glucan relative to a wild type cell of the same taxon and an increased dietary fibre content relative to a wild type cell of the same taxon.

* * * * *